United States Patent
Norris et al.

(10) Patent No.: US 7,230,165 B2
(45) Date of Patent: Jun. 12, 2007

(54) TOCOPHEROL BIOSYNTHESIS RELATED GENES AND USES THEREOF

(75) Inventors: Susan R. Norris, University City, MO (US); Kim Lincoln, Somerville, MA (US); Mark S. Abad, Webster Groves, MO (US); Robert J. Eilers, Edwardsville, IL (US); Karen Kindle Hartsuyker, Kirkwood, MO (US); Joseph Hirschberg, Jerusalem (IL); Balasulojini Karunanandaa, Creve Coeur, MO (US); Farhad Moshiri, Chesterfield, MO (US); Joshua C. Stein, Acton, MA (US); Henry E. Valentin, Wildwood, MO (US); Tyamagondlu V. Venkatesh, St. Louis, MO (US)

(73) Assignee: Monsanto Technology LLC, St. Louis, MO (US)

(*) Notice: Subject to any disclaimer, the term of this patent is extended or adjusted under 35 U.S.C. 154(b) by 379 days.

(21) Appl. No.: 10/634,548

(22) Filed: Aug. 5, 2003

(65) Prior Publication Data

US 2004/0045051 A1    Mar. 4, 2004

Related U.S. Application Data

(60) Provisional application No. 60/400,689, filed on Aug. 5, 2002.

(51) Int. Cl.
*A01H 1/00* (2006.01)
*C07K 14/415* (2006.01)
*C12N 5/14* (2006.01)
*C12N 9/00* (2006.01)

(52) U.S. Cl. .................. 800/295; 435/6; 435/69.1; 435/183; 435/468; 435/419; 530/370; 536/23.1; 800/278

(58) Field of Classification Search ............... 435/69.1, 435/183, 410, 419, 320.1; 530/370; 536/23.1, 536/23.2, 23.6; 800/278, 295
See application file for complete search history.

(56) References Cited

U.S. PATENT DOCUMENTS

| | | |
|---|---|---|
| 4,727,219 A | 2/1988 | Brar et al. |
| 5,304,478 A | 4/1994 | Bird et al. |
| 5,429,939 A | 7/1995 | Misawa et al. |
| 5,432,069 A | 7/1995 | Grüninger et al. |
| 5,545,816 A | 8/1996 | Ausich et al. |
| 5,618,988 A | 4/1997 | Hauptmann et al. |
| 5,684,238 A | 11/1997 | Ausich et al. |
| 5,693,507 A | 12/1997 | Daniell et al. |
| 5,750,865 A | 5/1998 | Bird et al. |
| 5,792,903 A | 8/1998 | Hirschberg et al. |
| 5,876,964 A | 3/1999 | Croteau et al. |
| 5,908,940 A | 6/1999 | Lane et al. |
| 6,281,017 B1 | 8/2001 | Croteau et al. |
| 6,303,365 B1 | 10/2001 | Martin et al. |
| 6,541,259 B1 | 4/2003 | Lassner et al. |
| 2002/0069426 A1 | 6/2002 | Boronat et al. |
| 2002/0108148 A1 | 8/2002 | Boronat et al. |
| 2003/0148300 A1 | 8/2003 | Valentin et al. |
| 2003/0150015 A1 | 8/2003 | Norris et al. |
| 2003/0154513 A1 | 8/2003 | van Eenennaam et al. |
| 2003/0166205 A1 | 9/2003 | van Eenennaam et al. |
| 2003/0170833 A1 | 9/2003 | Lassner et al. |
| 2003/0176675 A1 | 9/2003 | Valentin et al. |
| 2003/0213017 A1 | 11/2003 | Valentin et al. |
| 2004/0018602 A1 | 1/2004 | Lassner et al. |
| 2004/0045051 A1 | 3/2004 | Norris et al. |

FOREIGN PATENT DOCUMENTS

| | | |
|---|---|---|
| CA | 2339519 | 2/2000 |
| CA | 2343919 | 3/2000 |
| CA | 2372332 | 11/2000 |
| DE | 198 35 219 A1 | 8/1998 |
| EP | 0 531 639 A2 | 3/1993 |
| EP | 0 531 639 A3 | 3/1993 |
| EP | 0 674 000 A2 | 9/1995 |
| EP | 0 723 017 A2 | 7/1996 |
| EP | 0 763 542 A2 | 3/1997 |
| EP | 1 033 405 A2 | 9/2000 |
| EP | 1 063 297 A1 | 12/2000 |
| FR | 2 778 527 | 11/1999 |
| GB | 560529 | 4/1944 |
| WO | WO 91/02059 | 2/1991 |

(Continued)

OTHER PUBLICATIONS

N_Geneseq_21 Database, Accession No. AAC36634, EP1033405A2, SEQ ID No. 14519, Sep. 6, 2000.*

(Continued)

*Primary Examiner*—Phuong T. Bui
(74) *Attorney, Agent, or Firm*—Fulbright & Jaworski L.L.P.

(57) ABSTRACT

The present invention relates to genes associated with the tocopherol biosynthesis pathway. More particularly, the present invention provides and includes nucleic acid molecules and proteins associated with genes that encode polypeptides associated with the tocopherol biosynthesis pathway. The present invention also provides methods for utilizing such agents, for example in gene isolation, gene analysis, and the production of transgenic plants. Moreover, the present invention includes transgenic plants modified to express the aforementioned polypeptides. In addition, the present invention includes methods for the production of products from the tocopherol biosynthesis pathway as well as in production of plants that are drought resistant.

17 Claims, 13 Drawing Sheets

FOREIGN PATENT DOCUMENTS

| | | |
|---|---|---|
| WO | WO 91/09128 | 6/1991 |
| WO | WO 91/13078 | 9/1991 |
| WO | WO 93/18158 | 9/1993 |
| WO | WO 94/11516 | 5/1994 |
| WO | WO 94/12014 | 6/1994 |
| WO | WO 94/18337 | 8/1994 |
| WO | WO 95/08914 | 4/1995 |
| WO | WO 95/18220 | 7/1995 |
| WO | WO 95/23863 | 9/1995 |
| WO | WO 95/34668 | 12/1995 |
| WO | WO 96/02650 | 2/1996 |
| WO | WO 96/06172 | 2/1996 |
| WO | WO 96/13149 | 5/1996 |
| WO | WO 96/13159 | 5/1996 |
| WO | WO 96/36717 A2 | 11/1996 |
| WO | WO 96/36717 A3 | 11/1996 |
| WO | WO 96/38567 | 12/1996 |
| WO | WO 97/17447 | 5/1997 |
| WO | WO 97/27285 | 7/1997 |
| WO | WO 97/49816 | 12/1997 |
| WO | WO 98/04685 | 2/1998 |
| WO | WO 98/06862 | 2/1998 |
| WO | WO 98/18910 | 5/1998 |
| WO | WO 99/04021 | 1/1999 |
| WO | WO 99/04622 | 2/1999 |
| WO | WO 99/06580 | 2/1999 |
| WO | WO 99/07867 | 2/1999 |
| WO | WO 99/11757 | 3/1999 |
| WO | WO 99/19460 | 4/1999 |
| WO | WO 99/55889 | 11/1999 |
| WO | WO 99/58649 | 11/1999 |
| WO | WO 00/01650 | 1/2000 |
| WO | WO 00/08169 | 2/2000 |
| WO | WO 00/08187 | 2/2000 |
| WO | WO 00/10380 | 3/2000 |
| WO | WO 00/11165 | 3/2000 |
| WO | WO 00/14207 | 3/2000 |
| WO | WO 00/17233 | 3/2000 |
| WO | WO 00/22150 A3 | 4/2000 |
| WO | WO 00/28005 | 5/2000 |
| WO | WO 00/32757 A2 | 6/2000 |
| WO | WO 00/32757 A3 | 6/2000 |
| WO | WO 00/34448 | 6/2000 |
| WO | WO 00/42205 A2 | 7/2000 |
| WO | WO 00/42205 A3 | 7/2000 |
| WO | WO 00/46346 | 8/2000 |
| WO | WO 00/61770 | 10/2000 |
| WO | WO 00/63389 | 10/2000 |
| WO | WO 00/63391 | 10/2000 |
| WO | WO 00/65036 A2 | 11/2000 |
| WO | WO 00/65036 A3 | 11/2000 |
| WO | WO 00/68393 | 11/2000 |
| WO | WO 01/04330 | 1/2001 |
| WO | WO 01/09341 | 2/2001 |
| WO | WO 01/12827 | 2/2001 |
| WO | WO 01/21650 | 3/2001 |
| WO | WO 01/44276 | 6/2001 |
| WO | WO 01/62781 | 8/2001 |
| WO | WO 01/79472 | 10/2001 |
| WO | WO 01/88169 A2 | 11/2001 |
| WO | WO 01/88169 A3 | 11/2001 |
| WO | WO 02/00901 A1 | 1/2002 |
| WO | WO 02/12478 | 2/2002 |
| WO | WO 02/26933 | 4/2002 |
| WO | WO 02/29022 | 4/2002 |
| WO | WO 02/31173 | 4/2002 |
| WO | WO 02/33060 | 4/2002 |
| WO | WO 02/46441 | 6/2002 |
| WO | WO 02/072848 | 9/2002 |
| WO | WO 02/089561 | 11/2002 |
| WO | WO 03/034812 | 5/2003 |
| WO | WO 03/047547 | 6/2003 |

OTHER PUBLICATIONS

N_Geneseq_8 Database, Accession No. AAC36634, EP1033405A2, SEQ ID No. 14519, Sep. 6, 2000.*

International Search Report, PCT/03/25276, pp. 1-5 (Jan. 10, 2005).

Bevan et al., Database NCBI, Accession No. ATT32M21 (Mar. 2000).

Bowie et al., "Deciphering the Message in Protein Sequences: Tolerance to Amino Acid Substitutions", Science, 247:1306-1310 (1990).

McConnell et al., "Role of *Phabulosa* and *Phavoluta* in determining radial patterning in shoots", Nature, 411(6838): 709-713 (2001).

Baker et al., NCBI Accession No. X64451 (Dec. 1993).

Addlesee et al., "Cloning, sequencing and functional assignment of the chlorophyll biosyntheses gene, *chlP*, of *Synechocystis* sp. PCC 6803", FEBS Letters 389 (1996) 126-130.

Arango et al., "Tocopherol synthesis from homogentisate in *Capsicum anuum* L. (yellow pepper) chromoplast membranes: evidence for tocopherol cyclase", Biochem J., 336:531-533 (1998).

Arigoni et al., "Terpenoid biosynthesis from 1-doxy-D-xylulose in higher plants by intramolecular skeletal rearrangement", Proc. Natl. Acad. Sci. USA, 94:10600-10605 (1997).

Baker et al., "Sequence and characterization of the *gcpE* gene of *Escherichia coli*", FEMS Microbiology Letters, 94:175-180 (1992).

Bayley et al., "Engineering 2,4-D resistance into cotton," Theor Appl Genet, 83:645-649 (1992).

Bentley, R., "The Shikimate Pathway—A Metabolic Tree with Many Branches," Critical Reviews™ in Biochemistry and Molecular Biology; vol. 25, Issue 5, 307-384 (1990).

Bevan, M., "Binary *Agrobacterium* vectors for plant transformation", Nucleic Acids Research, 12:8711-8721 (1984).

Beyer et al., "Phytoene-forming activities in wild-type and transformed rice endosperm," IRRN 21:2-3, p. 44-45 (Aug.-Dec. 1996).

Bork et al., "Go hunting in sequence database but watch out for the traps", TIG 12, 10:425-427 (Oct. 1996).

Bouvier et al., "Dedicated Roles of Plastid Transketolases during the Early Onset of Isoprenoid Biogenesis in Pepper Fruits", Plant Physiol., 117:1423-1431 (1998).

Bramley et al., "Biochemical characterization of transgenic tomato plants in which carotenoid synthesis has been inhibited through the expression of antisense RNA to pTOM5," The Plant Journal, 2(3), 343-349 (1992).

Breitenbach et al., "Expression in *Escherichia coli* and properties of the carotene ketolase from *Haematococcus pluvialis*," FEMS Microbiology Letters 140, 241-246 (1996).

Broun et al., "Catalytic Plasticity of Fatty Acid Modification Enzymes Underlying Chemical Diversity of Plant Lipids," Science, 282:1315-1317 (1998).

Buckner et al., "The *y1* Gene of Maize Codes for Phytoene Synthase," Genetics 143:479-488 (May1996).

Burkhardt et al., "Genetic engineering of provitamin A biosynthesis in rice endosperm," Experientia, 818-821.

Burkhardt et al., "Transgenic rice (*Oryza sativa*) endosperm expressing daffodil (*Narcissus pseudonarcissus*) phytoene synthase accumulates phytoene, a key intermediate of provitamin A biosynthesis" The Plant Journal, 11(5), 1071-1078 (1997).

Cohoon et al., "Production of Fatty Acid Components of Meadowfoam Oil in Somatic Soybean Embryos," Plant Physiology, 124:243-251 (2000).

Chaudhuri et al., "The purification of shikimate dehydrogenase from *Escherichia coli*," Biochem. J., 226:217-223 (1985).

Cheng et al., "Highly Divergent Methyltransferases Catalyze a Conserved Reaction in Tocopherol and Plastoquinone Synthesis in Cyanobacteria and Photosynthetic Eukaryotes", The Plant Cell, 15:2343-2356 (2003).

Collakova et al., "Isolation and Functional Analysis of Homogentisate Phytyltransferase from *Synechocystis* sp. PCC 6803 and *Arabidopsis*", Plant Physiology, 127:1113-1124 (2001).

Collakova et al., "Homogentisate Phytyltransferase Activity is Limiting for Tocopherol Biosynthesis in *Arabidopsis*", Plant Physiology, 131:632-642 (Feb. 2003).

Collakova et al., "Isolation and Characterization of Tocopherol Prenyl Transferase From Synechocyslis and *Arabidopsis*", Poster Abstract see REN-01-026.

Cook et al., "Nuclear Mutations affecting plastoquinone accumulation in maize", Photosynthesis Research, 31:99-111 (1992).

Cunillera et al., "Characterization of dehydrodolichyl diphosphate synthase of *Arabidopsis thaliana*, a key enzyme in dolichol biosynthesis", FEBS Letters, 477:170-174 (2000).

d'Amato et al., "Subcellular localization of chorismate-mutase isoenzymes in protoplasts from mesophyll and suspension-cultured cells of *Nicotiana silvestris*," Planta, 162:104-108 (1984).

Doerks et al., "Protein annotation: detective work for function prediction", TIG, 14:248-250 (1998).

d'Harlingue et al., "Plastid Enzymes of Terpenoid Biosynthesis, Purification and Characterization of $_\gamma$-Tocopherol Methyltransferase from *Capsicum* Chromoplasts," The Journal of Biological Chemistry, vol. 260, No. 28, pp. 15200-15203, Dec. 5, 1985.

De Luca, Vincenzo, "Molecular characterization of secondary metabolic pathways", AgBiotech News and Information, 5(6):225N-229N (1993).

Duncan et al., "The overexpression and complete amino acid sequence of *Escherichia coli* 3-dehydroquinase", Biochem. J., 238:475-483 (1986).

Duvold et al., "Incorporation of 2-C-Methyl-D-erythritol, a Putative Isoprenoid Precursor in the Mevalonate-Independent Pathway, into Ubiquinone and Menaquinone of *Escherichia coli*", Tetrahedron Letters, 38(35):6181-6184 (1997).

Elliott, Thomas, "A Method for Constructing Single-Copy *lac* Fusions in *Salmonella typhimurium* and Its Application to the *hemA-prfA* Operon", Journal of Bacteriology, 174:245-253 (1992).

Eisenreich et al., "The deoxyxylulose phosphate pathway of terpenoid biosynthesis in plants and microorganisms", Chemistry & Biology, 5(9):R221-R233 (1998).

Ericson et al., "Analysis of the promoter region of napin genes from *Brassica napus* demonstrates binding of nuclear protein in vitro to a conserved sequence motif", Eur. J. Biochem., 197:741-746 (1991).

Estévez et al., "1-Deoxy-D-xylulose-5-phosphate Synthase, a Limiting Enzyme for Plastidic Isoprenoid Biosynthesis in Plants", The Journal of Biological Chemistry, 276(25):22901-22909 (2001).

Fellermeier et al., "Cell-free conversion of 1-deoxyl-D-xylulose 5-phosphate and 2-*C*-methyl-D-erythritol 4-phosphate into β-carotene in higher plants and its inhibition by fosmidomycin", Tetrahedron Letters, 40:2743-2746 (1999).

Fiedler et al., "The formation of homogentisate in the biosynthesis of tocopherol and plastoquinone in spinach chloroplasts", Planta, 155:511-515 (1982).

Fourgoux-Nicol et al., "Isolation of rapeseed genes expressed early and specifically during development of the male gametophyte", Plant Molecular Biology, 40:857-872 (1999).

Fraser et al., "Enzymic confirmation of reactions involved in routes to astaxanthin formation, elucidated using a direct substrate in vitro assay", Eur. J. Biochem., 252:229-236 (1998).

Fraser et al., "In Vitro Characterization of Astaxanthin Biosynthetic Enzymes", The Journal of Biological Chemistry, 272(10)6128-6135 (1997).

Fray et al., "Constitutive expression of a fruit phytoene synthase gene in transgenic tomatoes causes dwarfism by redirecting metabolites from the gibberellin pathway", The Plant Journal, 8(5):639-701 (1995).

Fray et al., "Identification and genetic analysis of normal and mutant phytoene synthase genes of tomato by sequencing complementation and co-suppression", Plant Molecular Biology, 22:589-602 (1993).

Fuqua et al., "Characterization of *melA*: a gene encoding melanin biosythesis from the marine bacterium *Shewanella colwelliana*", Gene, 109:131-136 (1991).

Furuya et al., "Production of Tocopherols by Cell Culture of Safflower", Phytochemistry, 26(10):2741-2747 (1987).

Garcia et al., "Subcellular localization and purification of a *p*-hydroxyphenylpyruvate dioxygenase from cultured carrot cells and characterization of the corresponding cDNA", Biochem. J., 325:761-769 (1997).

Gaubier et al., "A chlorophyll synthetase gene from *Arabidopsis thaliana*", Mol. Gen. Genet., 249:58-64 (1995).

Goers et al., "Separation and characterization of two chorismate-mutase isoenzymes from *Nicotiana silvestris*", Planta, 162:109-116 (1984).

Grabse et al., "Loss of α-tocopherol in tobacco plants with decreased geranylgeranyl reductase activity does not modify photosynthesis in optimal growth conditions but increases sensitivity to high-light stress", Planta, 213:620-628 (2001).

Harker et al., "Biosynthesis of ketocarotenoids in transgenic cyanobacteria expressing the algal gene for β-C-4-oxygenase, *crtO*", FEBS Letters, 404:129-134 (1997).

Harker et al., "Expression of prokaryotic 1-deoxy-D-xylulose-5-phosphatases in *Escherichia coli* increases carotenoid and ubiquinone biosynthesis", FEBS Letters, 448:115-119 (1999).

Hecht et al., "Studies of the nonmevalonate pathway to terpenes: The role of the GcpE (IspG) protein", PNAS, 98(26):14837-14842 (2001).

Herrmann, K.M., "The Shikimate Pathway as an Entry to Aromatic Secondary Metabolism", Plan Physiol., 107:7-12 (1995).

Herz et al., "Biosynthesis of terpenoids: YgbB protein converts 4-diphosphocytidyl-2C-methyl-D-erythritol 2-phosphate to 2C-methyl-D-erythritol 2,4-cyclodiphosphate", Proc. Natl. Acad. Sci. USA, 97(6):2486-2490 (2000).

Kajiwara et al., "Isolation and functional identification of a novel cDNA for astaxanthin biosynthesis from *Haematococcus pluvialis*, and astaxanthin synthesis in *Escherichia coli*", Plant Molecular Biology, 29:343-352 (1995).

Kaneko et al., "Complete Genomic Sequence of the Filamentous Nitrogen-fixing Cyanobacterium *Anabaena* sp. Strain PCC 7120", DNA Research, 8(5):205-213 (2001).

Keegstra, K., "Transport and Routing of Proteins into Chloroplasts", Cell, 56(2):247-253 (1989).

Keller et al., "Metabolic compartmentation of plastid prenyllipid biosynthesis Evidence for the involvement of a multifunctional geranylgeranyl reductase", Eur. J. Biochem., 251:413-417 (1998).

Kishore et al., "Amino Acid Biosynthesis Inhibitors as Herbicides", Ann. Rev. Biochem., 57:627-663 (1988).

Koziel et al., "Optimizing expression of transgenes with an emphasis on post-transcriptional events", Plant Molecular Biology, 32:393-405 (1996).

Kumagai et al., "Cytoplasmic inhibition of carotenoid biosynthesis with virus-derived RNA", Proc. Natl. Acad. Sci. USA, 92:1679-1683 (1995).

Kuntz et al., "Identification of a cDNA for the plastid-located geranylgeranyl pyrophosphate synthase from *Capsicum annuum*: correlative increase in enzyme activity and transcript level during fruit ripening", The Plant Journal, 2(1):25-34 (1992).

Lange et al., "A Family of transketolases that directs isoprenoid biosynthesis via a mevalonate-independent pathway", Proc. Natl. Acad. Sci. USA, 95:2100-2104 (1998).

Lange et al., "Isoprenoid Biosyntheis via a Mevalonate-Independent Pathway in Plants: Cloning and Heterologous Expression of 1-Deoxy-D-xylulose-5-phosphate Reductoisomerase from Peppermint", Archives of Biochemistry and Biophysics, 365(1):170-174 (1999).

Li et al., "Identification of a maize endosperm-specific cDNA encoding farnesyl pyrophosphate synthetase", Gene, 171:193-196 (1996).

Linthorst et al., "Constitutive Expression of Pathogenesis-Related Proteins PR-1,GRP, and PR-S in Tobacco Has No Effect on Virus Infection", The Plant Cell, 1:285-291 (1989).

Lois et al., "Cloning and characterization of a gene from *Escherichia coli* encoding a transketolase-like enzyme that catalyzes the synthesis of D-1-deoxyxylulose 5-phosphate, a common precursor for isoprenoid, thiamin, and pyridoxol biosynthesis", Proc. Natl. Acad. Sci. USA, 95(5):2105-2110 (1998).

Lopez et al., "Sequence of the *bchG* Gene from *Chloroflexus aurantiacus*: Relationship between Chlorophyll Synthase and other Polyprenyltransferases", Journal of Bacteriology, 178(11):3369-3373 (1996).

Lotan et al., "Cloning and expression in *Escherichia coli* of the gene encoding β-C-4-oxygenase, that converts β-carotene to the ketocarotenoid canthaxanthin in *Haematococcus pluvialis*", FEBS Letters, 364:125-128 (1995).

Mahmoud et al., "Metabolic engineering of essential oil yield and composition in mint by altering expression of deoxyxylulose phosphate reductoisomerase and menthofuran synthase", PNAS, 98(15):8915-8920 (2001).

Mandel et al., "*CLA1*, a novel gene required for chloroplast development, is highly conserved in evolution", The Plant Journal, 9(5):649-658 (1996).

Marshall et al., "Biosynthesis of Tocopherols: A Re-Examination of the Biosynthesis and Metabolism of 2-Methyl-6-Phytyl-1,4-Benzoquinol", Phytochemistry, 24 (8):1705-1711 (1985).

Misawa et al., "Expression of an *Erwinia* phytoene desaturase gene not only confers multiple resistance to herbicides interfering with carotenoid biosynthesis but also alters xanthophyll metabolism in transgenic plants", The Plant Journal, 6(4):481-489 (1994).

Misawa et al., "Elucidation of the *Erwinia uredovora* Carotenoid Biosynthetic Pathway by Functional Analysis of Gene Products Expressed in *Escherichia coli*", Journal of Bacteriology, 172(12):6704-6712 (1990).

Misawa et al., "Functional expression of the *Erwinia uredovora* carotenoid biosynthesis gene *crtI* in transgenic plants showing an increase of β-carotene biosynthesis activity and resistance to the bleaching herbicide norflurazon", The Plant Journal, 4(5):833-840 (1993).

Misawa et al., "Structure and Functional Analysis of a Marine Bacterial Carotenoid Biosynthesis Gene Cluster and Astaxanthin Biosynthetic Pathway Proposed at the Gene Level", Journal of Bacteriology, 177(22):6575-6584 (1995).

Nakamura et al., "Structural Analysis of *Arabidopsis thaliana* Chromosome 5. III. Sequence Features of the Regions of 1,191,918 bp Covered by Seventeen Physically Assigned P1 Clones", DNA Research, 4(6):401-414 (1997).

Nawrath et al., "Targeting of the polyhydroxybutyrate biosynthetic pathway to the plastids of *Arabidopsis thaliana* results in high levels of polymer accumulation", Proc. Natl. Acad. Sci. USA, 91:12760-12764 (1994).

Norris et al., "Genetic Dissection of Carotenoid Synthesis in *Arabidopsis* Defines Plastoquinone as an Essential Component of Phytoene Desaturation", The Plant Cell, 7:2139-2149 (1995).

Norris et al., "Complementation of the *Arabidopsis pds1* Mutation with the Gene Encoding *p*-Hydroxyphenylpyruvate Dioxygenase", Plant Physiol., 117:1317-1323 (1998).

Oh et al., "Molecular Cloning, Expression, and Functional Analysis of a *cis*-Prenyltransferase from *Arabidopsis thaliana*", The Journal of Biological Chemistry, 275(24):18482-18488 (2000).

Okada et al., "Five Geranylgeranyl Diphosphate Synthases Expressed in Different Organs Are Localized into Three Subcellular Compartments in *Arabidopsis*", Plant Physiology, 122:1045-1056 (2000).

Oommen et al., "The Elicitor-Inducible Alfalfa Isoflavone Reductase Promoter Confers Different Patterns of Developmental Expression in Homologous and Heterologous Transgenic Plants", The Plant Cell, 6:1789-1803 (1994).

Oster et al., "The G4 Gene of *Arabidopsis thaliana* Encodes a Chlorophyll Synthase of Etiolated Plants", Bot. Acta, 110:420-423 (1997).

Peisker et al., "Phytol and the Breakdown of Chlorophyll in Senescent Leaves", J. Plant Physiol., 135:428-432 (1989).

Pompliano et al., "Probing Lethal Metabolic Perturbations in Plants with Chemical Inhibition of Dehydroquinate Synthase", J. Am. Chem. Soc., 111:1866-1871 (1989).

Porfirova et al., "Isolation of an *Arabidopsis* mutant lacking vitamin E and identification of a cyclase essential for all tocopherol biosynthesis", PNAS, 99(19):12495-12500 (2002).

Querol et al., "Functional analysis of the *Arabidopsis thaliana* GCPE protein involved in plastid isoprenoid biosynthesis", FEBS Letters, 514:343-346 (2002).

Rippert et al., "Molecular and biochemical characterization of an *Arabidopsis thaliana* arogenate dehydrogenase with two highly similar and active protein domains", Plant Mol. Biol., 48:361-368 (2002).

Rippert et al., "Engineering Plant Shikimate Pathway for Production of Tocotrienol and Improving Herbicide Resistance", Plant Physiology, 134:92-100 (2004).

Rodriguez-Concepción et al., "Elucidation of the Methylerythritol Phosphate Pathway for Isoprenoid Biosynthesis in Bacteria and Plastids. A Metabolic Milestone Achieved through Genomics", Plant Physiology, 130:1079-1089 (2002).

Rodriguez-Concepción et al., "1-Deoxy-D-xylulose 5-phosphate reductoisomerase and plastid isoprenoid biosynthesis during tomato fruit ripening", The Plant Journal, 27(3):213-222 (2001).

Rohdich et al., "Cytidine 5'-triphosphate-dependent biosynthesis of isoprenoids: YgbP protein of *Escherichia coli* catalyzes the formation of 4-diphosphocytidyl-2-C-methylerythritol", Proc. Natl. Acad. Sci. USA, 96(21):11758-11763 (1999).

Rohmer et al., "Glyceraldehyde 3-Phosphate and Pyruvate as Precursors of Isopenic Units in an Alternative Non-mevalonate Pathway for Terpenoid Biosynthesis", J. Am. Chem. Soc., 118:2564-2566 (1996).

Rohmer et al., "Isoprenoid biosynthesis in bacteria: a novel pathway for the early steps leading to isopentenyl diphosphate", Biochem. J., 295:517-524 (1993).

Rohmer, M., "A Mevalonate-independent Route to Isopentenyl Diphosphate", Comprehensive Natural Products Chemistry, 2:45-67 (1999).

Rohmer, M., "Isoprenoid biosynthesis via the mevalonate-independent route, a novel target for antibacterial drugs?", Progress in Drug Research, 50:136-154 (1998).

Römer et al., "Expression of the Genes Encoding the Early Carotenoid Biosynthetic Enzymes in *Capsicum annuum*", Biochemical and Biophysical Research Communications, 196(3):1414-1421 (1993).

Ruzafa et al., "The protein encoded by the *Shewanella colwelliana melA* gene is a *p*-hydroxyphenylpyruvate dioxygenase", FEMS Microbiology Letters, 124:179-184 (1994).

Saint-Guily et al., "Complementary DNA Sequence of an Adenylate Translocator from *Arabidopsis thaliana*", Plant Physiol., 100(2):1069-1071 (1992).

Sandmann et al., "New functional assignment of the carotenogenic genes *crtB* and *crtE* with constructs of these genes from *Erwinia* species", FEMS Microbiology Letters, 90:253-258 (1992).

Sato et al., "Structural Analysis of *Arabidopsis thaliana* Chromosome 5. X. Sequence Features of the Regions of 3,076,755 bp Covered by Sixty P1 and TAC Clones", DNA Research, 7(1):31-63 (2000).

Sato et al., "Structural Analysis of *Arabidopsis thaliana* Chromosome 5. IV. Sequence Features of the Regions of 1,456,315 bp Covered by Nineteen Physically Assigned P1 and TAC Clones", DNA Research, 5:41-54 (1998).

Savidge et al., "Isolation and Characterization of Homogentisate Phytyltransferase Genes from *Synechocystis* sp. PCC 6803 and *Arabidopsis*", Plant Physiology, 129:321-322 (2002).

Schwender et al., "Cloning and heterologous expression of a cDNA encoding 1-deoxy-D-xylulose-5-phosphate reductoisomerase of *Arabidopsis thaliana*", FEBS Letters, 455:140-144 (1999).

Scolnik et al., "Nucleotide Sequence of an *Arabidopsis* cDNA for Geranylgeranyl Pyrophosphate Synthase", Plant Physiol., 104(4):1469-1470 (1994).

Shewmaker et al., "Seed-specific overexpression of phytoene synthase: increase in carotenoids and other metabolic effects", The Plant Journal, 20(4):401-412 (1999).

Shigeoka et al., "Isolation and properties of γ-tocopherol methyltransferase in *Euglena gracilis*", Biochimica et Biophysica Acta, 1128:220-226 (1992).

Shintani et al., "Elevating the Vitamin E Content of Plants Through Metabolic Engineering", SCIENCE, 282:2098-2100 (1998).

Singh et al., "Chorismate Mutase Isoenzymes from *Sorghum bicolor*: Purification and Properties", Archives of Biochemistry and Biophysics, 243(2):374-384 (1985).

Smith, F.W. et al., "The cloning of two *Arabidopsis* genes belonging to a phosphate transporter family", Plant Journal, 11(1):83-92 (1997).

Smith, C.J.S. et al., "Antisense RNA inhibition of polygalacturonase gene expression in transgenic tomatoes", Nature, 334:724-726 (1998).

Smith, T.F. et al., "The challenges of genome sequence annotation or the devil is in the details", Nature Biotechnology, 15:1222-1223 (1997).

Soll et al., "Hydrogenation of Geranylgeraniol", Plant Physiol., 71:849-854 (1983).

Soll et al., "Tocopherol and Plastoquinone Synthesis in Spinach Chloroplasts Subfractions", Archives of Biochemistry and Biophysics, 204(2):544-550 (1980).

Soll et al., "2-Methyl-6-Phytylquinol and 2,3-Dimethyl-5-Phytylquinol as Precursors of Tocopherol Synthesis in Spinach Chloroplasts", Phytochemistry, 19:215-218 (1980).

Sprenger et al., "Identification of a thiamin-dependent synthase in *Escherichia coli* required for the formation of the 1-deoxy-D-xylulose 5-phosphate precursor to isoprenoids, thiamin, and pyridoxol", Proc. Natl. Acad. Sci. USA, 94:12857-12862 (1997).

Spurgeon et al., "Biosynthesis of Isoprenoid Compounds", 1:1-45 (1981).

Stam et al., "The Silence of Genes in Transgenic Plants", Annals of Botany, 79:3-12 (1997).

Stocker et al., "Identification of the Tocopherol-Cyclase in the Blue-Green Algae *Anabaena variabilis* Kützing (Cyanobacteria)", Helvetica Chimica Acta, 76:1729-1738 (1993).

Stocker et al., "The Substrate Specificity of Tocopherol Cyclase", Bioorganic & Medicinal Chemistry, 4(7):1129-1134 (1996).

Sun et al., "Cloning and Functional Analysis of the β-Carotene Hydroxylase of *Arabidopsis thaliana*", The Journal of Biological Chemistry, 271(40):24349-24352 (1996).

Suzich et al., "3-Deoxy-D-*arabino*-Heptulosonate 7-Phosphate Synthase from Carrot Root (*Daucus carota*) Is a Hysteretic Enzyme", Plant Physiol., 79:765-770 (1985).

Svab et al., "High-frequency plastid transformation in tobacco by selection for a chimeric *aadA* gene", Proc. Natl. Acad. Sci. USA, 90:913-917 (1993).

Svab et al., "Stable transformation of plastids in higher plants", Proc. Natl. Acad. Sci. USA, 87:8526-8530 (1990).

Takahashi et al., "A 1-deoxy-D-xylulose 5-phosphate reductoisomerase catalyzing the formation of 2-*C*-methyl-D-erythritol 4-phosphate in an alternative nonmevalonate pathway for terpenoid biosynthesis", Proc. Natl. Acad. Sci. USA, 95:9879-9884 (1998).

Takatsuji, H., "Zinc-finger transcription factors in plants", CMLS Cell. Mol. Life Sci., Birkhauser Vertag Basel CH, 54(6):582-596 (1998).

Tjaden et al., "Altered plastidic ATP/ADP-transporter activity influences potato (*Solanum tubersomum* L.) tuber morphology, yield and composition of tuber starch", The Plant Journal, 16(5):531-540 (1998).

Town et al., "Whole genome shotgun sequencing of *Brassica oleracea*, BOGKS71TR BOGK *Brassica oleracea* genomic clone BOGKS71, DNA sequence", Database EMBL Accession No. BH534089 (Dec. 2001).

Town et al, "Whole genome shotgun sequencing of *Brassica oleracea*, BOGAU46TR BOGA *Brassica oleracea* genomic clone BOGAU46, DNA sequence", Database EMBL Accession No. BH248880 (Nov. 2001).

Verwoert et al., "Developmental specific expression and organelle tarteting of the *Escherichia coli fabD* gene, encoding malonyl coenzyme A-acyl carrier protein transacylase in transgenic rape and tobacco seeds", Plant Molecular Biology, 26:189-202 (1994).

Xia et al., "A monofunctional prephenate dehydrogenase created by cleavage of the 5' 109 bp of the *tyrA* gene from *Erwinia herbicola*", Journal of General Microbiology, 138(7):1309-1316 (1992).

Xia et al., "The *pheAl tyrAl aroF* Region from *Erwinia herbicola*: An Emerging Comparative Basis for Analysis of Gene Organization and Regulation in Enteric Bacteria", Database GENBANK on STN, GenBank ACC. No. (GBN): M74133, J. Mol. Evol., 36(2):107-120 Abstract (1993).

Yamamoto, E., "Purification and Metal Requirements of 3-Dehydroquinate Synthase from *Phaseolus mungo* Seedlings", Phytochemistry, 19:779-781 (1980).

Zaka et al., "Changes in Carotenoids and Tocopherols During Maturation of *Cassia* Seeds", Pakistan J. Sci. Ind. Res., 30(11):812-814 (1987).

Zeidler et al., "Inhibition of the Non-Mevalonate 1-Deoxy-D-xylulose-5-phosphate Pathway of Plant Isoprenoid Biosynthesis by Fosmidomycin", A Journal of Biosciences, Zeitschrift fuer Naturforschung, Section C, 53(11/12):980-986 (Nov./Dec. 1998).

Zhu et al., "Geranylgeranyl pyrophosphate synthase encoded by the newly isolated gene *GGPS6* from *Arabidopsis thaliana* is localized in mitochondria", Plant Molecular Biology, 35:331-341 (1997).

Zhu et al., "Cloning and Functional Expression of a Novel Geranylgeranyl Pyrophosphate Synthase Gene from *Arabidopsis thaliana* in *Escherichia coli*", Plant Cell Physiol., 38(3):357-361 (1997).

Kaneko et al., NCBI General Identifier No. 1653572, Accession No. BAA18485 (Jul. 2001).

Kaneko et al., NCBI General Identifier No. 1001725, Accession No. BAA10562 (Feb. 2003).

Alcala et al., Genbank Accession No. AI 897027 (Jul. 1999).

Bevan et al., Database EMBL, Accession No. AL035394 (Feb. 1999).

Bevan et al., TREMBL Database Accession No. O65524 (Aug. 1998).

Campos et al., NCBI General Identifier BAA 18485, Database EMBL, Accession No. AF148852, (2000).

Chen et al., EMBL Sequence Database Accession No. AI995392 (Sep. 1999).

Desprez et al., Database EMBL, Accession No. Z34566 (Jun. 1994).

Fedenko et al., Abstract: RU 2005353, Derwent Accession No. 1994-253787.

Gaubier et al., Database EMBL, Accession No. Q38833 (Nov. 1996).

Kaneko et al., Database EMBL, Accession No. P73726 (Feb. 1997).

Kaneko et al., Database EMBL, Accession No. P73962 (Jul. 1998).

Kaneko et al., EMBL Sequence Database Accession No. D90909 (Oct. 1996).

Kaneko et al., TREMBL Database Accession No. P73727 (Feb. 1997).

Lange et al., "Mentha x Piperita 1-deoxy-D-xylulose-5-phosphate Reductoisomerase (DXR) mRNA", complete cds, Entrez Report, Accession No. AF116825 (Apr. 1999).

Lin et al., Database EMBL, Accession No. AC003672 (Dec. 1997).

Lin et al., Database EMBL, Accession No. AC003673 (Dec. 1997).

Lin et al., Database EMBL, Accession No. AC004077 (Feb. 1998).

Malakhov et al., Database TREMBL, Accession No. Q55207 (Nov. 1996).

Murata et al., EMBL Sequence Database Accession No. D13960 (Mar. 1996).

Nakamura et al., Database EMBL, Accession No. AB009053, Abstract (Dec. 1997) (1998)(2000).

Nakamura et al., Database EMBL, Accession No. AB005246 (Jul. 1997).

Newman et al., Database EMBL, Accession No. AA586087, Abstract (Sep. 1997).

Newman et al., Database EMBL, Accession No. R30625 (Aug. 1995).

Newman et al., Database EMBL, Accession No. T44803 (Feb. 1995).

Newman et al., DEBEST ID:1262303, Entrez Report, Accession No. AA586087 (Sep. 1997).

Oster et al., Database Biosis, Accession No. PREV199800047824 (Oct. 1997).

Ouyang et al., Database EMBL, Accession No. AF381248 (Jan. 2003).

Rounsley et al., Database EMBL, Accession No. B24116 (Oct. 1997).

Rounsley et al., Database EMBL, Accession No. B29398 (Oct. 1997).

Rounsley et al., Database TREMBL, Accession No. O64684 (Aug. 1998).

Schwender et al., *Arabidopsis thaliana* mRNA for Partial 1-deoxyl-d-xylulose-5-phosphate Reductoisomerase (dxr gene), Entrez Report, Accession No. AJ242588 (Aug. 1999).

Scolnik et al., Database EMBL, Accession No. L40577 (Apr. 1995).

Shintani et al., Database NCBI, Accession No. AF104220 (Jan. 1999).

Shoemaker et al., Database EMBL, Accession No. AI748688 (Jun. 1999).

Shoemaker et al., Database EMBL, Accession No. AI938569 (Aug. 1999).

Shoemaker et al., Database EMBL, Accession No. AI988542 (Sep. 1999).

Shoemaker et al., Database EMBL, Accession No. AW306617 (Jan. 2000).

Tabata et al., Database EMBL, Accession No. D64001 (Sep. 1995).

Tabata et al., Database EMBL, Accession No. D64006 (Sep. 1995).

Tabata et al., Database EMBL, Accession No. D90909 (Oct. 1996).

Tabata et al., Database EMBL, Accession No. D90911 (Oct. 1996).

Tabata et al., Database EMBL, Accession No. Q55145 (Nov. 1996).

Tabata et al., Database EMBL, Accession No. Q55500 (Nov. 1996).

Walbot, V., Database EMBL, Accession No. AI795655 (Jul. 1999).

Wing et al., Database EMBL, Accession No. AQ690643 (Jul. 1999).

Xia et al., Database EMBL, Accession No. M74133 (Jun. 1993).

Bevan et al., Accession T4 8445.

International Search Report, PCT/US00/10367, pp. 1-5 (Sep. 15, 2000).

International Search Report, PCT/US00/10368, pp. 1-14 (Jun. 15, 2001).

Written Opinion, PCT/US00/10368, pp. 1-6 (May 9, 2002).

IPER, PCT/US00/10368, pp. 1-5 (Aug. 16, 2002).

Examination Report, New Zealand Patent Application No. 514600, based on PCT/US/00/10368, pp. 1-2 (Apr. 24, 2003).

Communication pursuant to Article 96(2) EPC, EP Application 00922287.8, based on PCT/US00/10368, pp. 1-6 (Oct. 17, 2003).

Examiner's Report No. 2, Australia Patent Application No. 42492/00, based on PCT/US00/10368, pp. 1-4 (Nov. 12, 2003).

International Search Report, PCT/US01/12334, pp. 1-5 (Apr. 5, 2002).

International Search Report, PCT/US01/24335, pp. 1-8 (Mar. 6, 2003).

International Search Report, PCT/US01/42673, pp. 1-4.

International Search Report, PCT/US02/03294, pp. 1-4 (Mar. 19, 2003).

International Search Report, PCT/US02/13898, pp. 1-3 (Sep. 13, 2002).

IPER, PCT/US02/13898, pp. 1-4 (Apr. 24, 2003).

International Search Report, PCT/US02/14445, pp. 1-6 (Oct. 30, 2003).

International Search Report, PCT/US02/26047, pp. 1-5 (Dec. 5, 2003).

International Search Report, PCT/US02/34079, pp. 1-5 (Jul. 28, 2003).

Written Opinion, PCT/US02/34079, pp. 1-4 (Oct. 23, 2003).

Response to Written Opinion, PCT/US02/34079, pp. 1-6 (Dec. 22, 2003).

sir 1736 cyanobase www.kazusa.com.

GenBank Accession No. AY085036.

SWISSPROT Accession No. Q9LZ76.

SWISSPROT Accession No. P20048.

Karunanandaa et al., "Metabolically enhanced oilseed crops with enhanced seed tocopherol", *Metabol. Eng.* 7:384-400, 2005.

Valentin et al., "The *Arabidopsis* vitamin E pathway gene5-1 Mutant Reveals a Critical Role for Phytol Kinase in Seed Tocopherol Biosynthesis", *Plant Cell* 18:212-224; 2005.

Database UniProt, Database Accession No. PHYKI_ARATH, Oct. 1, 2000.

Database UniProt, Database Accession No. SEC59_YEAST, Feb. 1, 1991.

European Patent Office Supplementary Search Report of PCT/US0325276, Dec. 27, 2006.

Kaneko et al., "Sequence analysis of the genome of the unicellular cyanobacterium synechocystis sp strain PCC6803. I. sequence features in the 1 mb region from map positions 64% to 92% of the genome," *DNA Research*, 2:153-166, 1995.

Kaneko et al., "Sequence analysis of the genome of the unicellular cyanobacterium synechocystis sp. strain PCC6803. II. Sequence determination of the entire genome and assignment of potential protein-coding regions (supplement)," *DNA Research*, 3 (Supp.):185-209, 1996.

\* cited by examiner

Cy-motif1 (Syn-43 to66) (SEQ ID NO: 69)

```
                       *          20
CySynechoS  :  EVTRKIVHIGAGQVVLIAWWLSIP  : 24
CyNostoc2   :  DLTRKAIHIGAGMWVFGVLLLFNR  : 24
CyNosttoc1  :  EIVRKIVHIGTGNVILLAWWLDIP  : 24
CyAnabena   :  EIVRKIVHIGAGHVILLAWWLDIP  : 24
CyTricho    :  EISRKVVHIGTGNVILFAWWLEIP  : 24
CyThermoS   :  EWSRKVVHIGAGQVILIAYALGVP  : 24
CyProchlor  :  ELSRKIVHIGTGPVIPLAWWLGIP  : 24
CySynechoC  :  ELSRKIIHIGTGAVVPLAWFFAIP  : 24
CyProchlor  :  ELSRKIVHMGSGPIIPLAYWLNIS  : 24
```

Figure 11

Cy-motif2 (Syn-89 to118) (SEQ ID NO: 70)

```
                       *          20       *
CySynechoS  :  ILPSLESVGRHSMGTLFYALSIGLLVGGFF  : 30
CyNostoc2   :  FIGAMDTQDSS-PGTVYFAISVTLLFGLLW  : 29
CyNosttoc1  :  ILPGINSVGRQSFGTFFYSVSFGILVASFW  : 30
CyAnabena   :  LLPGINSVGRQSLGTFFYAVSVGILVAWFW  : 30
CyTricho    :  ILPSVNSVGRKSLGTFFYAVSIGILIGWFW  : 30
CyThermoS   :  IFPSISGVGRQSWGTFFYAVSIGILMALFW  : 30
CYProchlor  :  LLPAIEDVNRHSYGTMAYALTITLLLIFFW  : 30
CySynechoC  :  IVPAVEDVNRNSYGTMAYGLAITMLLILCW  : 30
CyProchlor  :  LLTSIENIERKSFGTIAYGISITLLLILFW  : 30
```

Figure 12

Cy-motif3 (Syn-129 to144) (SEQ ID NO: 71)

```
                       *
CySynechoS  :  GILVMAWGDGLAALVG  : 16
CyNostoc2   :  GIMAMTWGDALAALIG  : 16
CyNosttoc1  :  GILIMTWGDGLAALIG  : 16
CyAnabena   :  GMMVMAWGDGLAALVG  : 16
CyTricho    :  GILTMAWGDGFAAIIG  : 16
CyThermoS   :  GILVMAWGDGLAALVG  : 16
CYProchlor  :  GVLVMAFGDGLAGLIG  : 16
CySynechoC  :  GVLVMALGDGLAGLIG  : 16
CyProchlor  :  GVLVMAFGDGLAGFIG  : 16
```

Figure 13

Cy-motif4 (Syn-156 to174)   (SEQ ID NO: 72)

```
                             *
CySynechoS : GFRKSWEGTLTMVEASFLV : 19
CyNostoc2  : NSVRSWEGSAAMFVASTVV : 19
CyNosttoc1 : GTQKSWEGSLTMMFVSYFI : 19
CyAnabena  : GAQKSWEGSLTMALASYLV : 19
CyTricho   : GMNKSWEGSLGMCLVSYTV : 19
CyThermoS  : GTSKSWEGTLTMFWVSTLV : 19
CYProchlor : GQRKSIAGTLTMAVITLII : 19
CySynechoC : GQTKSVAGTLTMALVSTLV : 19
CyProchlor : GQRKSLIGTLTMGFVSALI : 19
```

Figure 14

Cy-motif5 (Syn-203 to 225)   (SEQ ID NO: 73)

```
                           *
CySynechoS : LESFSRWGIDNLTVPLG : 17
CyNostoc2  : AEAVSPHGTDNLSVPLV : 17
CyNosttoc1 : LEAFSFLGIDNLTVPLG : 17
CyAnabena  : LEAFSLLGVDNLTVPLG : 17
CyTricho   : LETISKVGLDNLTVPLG : 17
CyThermoS  : LELIAWRGMDNLTVPIG : 17
CYProchlor : LEQISRWGIDNLTVPIG : 17
CySynechoC : LEQVSPAGVDNLSVPLL : 17
CyProchlor : LEQVSTLGIDNITVPIG : 17
```

Figure 15

Pl-motif1 ltt1 (101 to 122)  (SEQ ID NO: 74)

```
                          *        20
ltt1        : LSRKLVHILSGLLFVLAWPIFS : 22
ltt1_r      : LIRKLVHINIGLVFMLCWPLFS : 22
Sorghum_2   : LSRKLVHISVGLVFLLXWPLFS : 22
Wheat_1     : LNRKLVHITIGMVFLLFWPLFS : 22
Rice_5      : LNRKLVHITIGMVFLLFWPLFS : 22
Maize_6     : LSRKLVHISVGLVFMLFWPLFS : 22
Maize_7     : LSRKLVHISVGLVFMLFWPLFS : 22
Sorghum_4   : LSRKLVHISVGLVFLLFWPLFS : 22
Leek        : LNRKLVHILVGLVFMLFWPIFS : 22
Maize_8     : LIRKLVHINIGLVFMLCWPLFS : 22
Brassica_1  : LIRKLVHINIGLVFMLCWPLFS : 22
Cotton_1    : LNRKLVHISIGLVFMLCWPLFS : 22
Soy_1       : LNRKLVHISIGLIFMLC-PLFS : 21
Rice_6      : LCRKLVHITVGLVYFLMWPLFS : 22
Wheat_2     : LCRKLVHISVGLVYFLMWPLFS : 22
Maize_9     : LCRKLVHITVGLVFFLMWPLFS : 22
Brassica_2  : LSRKLVHILSGLLFALSWPIFS : 22
Cotton_2    : LSRKLVHILSGLLFAISWPIFS : 22
Soy_4       : LSRKLVHILSGLLFLVSWPIFS : 22
Sorghum_1   : LSRKVVHVLSGVLFMSSWPLFS : 22
Maize_3     : LSRKVVHVLSGVLFMSSWPLFS : 22
Soy_3       : LSRKVVHVLSGVLFMSSWPLFS : 22
Maize_4     : LSRKVVHVLSGVLFMSSWPLVS : 22
Rice_2      : LSRKIVHVLSGVLFMSSWPLFS : 22
Wheat_3     : LSRKVVHVLSGVFFMASWPLFS : 22
```

Figure 16

Pl-motif2 ltt1 (131 to175)  (SEQ ID NO: 75)

```
                    *        20         *        40
ltt1        : AAFVPLVNGLRLVINGLSISPNSMLIKSVTREGRAEELLKGPLFY : 45
ltt1_r      : ASLVPGLNIVRMLLLGLGVYHDEGTIKSMSRHGDRRELLKGPLYY : 45
Sorghum_2   : AALAPGVNVIRMLLLGLGLMKNEAMVKSISRSGDYRELLKGPLYY : 45
Wheat_1     : AALAPGINIIRMLLLGLGIMKNEAMVKSMSRSGDHRELLKGPLYY : 45
Rice_5      : AAVAPGINIIRMLLLGLGVMKNEAMVKSMSRSGDPRELLKGPLYY : 45
Maize_6     : AALAPGVNIIRMLLLGLGLMKNEAMVKSMSRSGDYRELLKGPLYY : 45
Maize_7     : AALAPGVNIIRMLLLGLGLMKNEAMVKSMSRSGDYRELLKGPLYY : 45
Leek        : AALAPGINIFRMLFMGLGIIKNEAMVQSISRHGDYRELLKGPLYY : 45
Maize_8     : ASLVPGLNIVRMLLLGLGVYHDEGTIKSMSRHGDRRELLKGPLYY : 45
Brassica_1  : ASLVPGLNIVRMLLLGLGVYQDEGTIKSMSRHGDRRELLKGPLYY : 45
Cotton_1    : AAITPGVNIIRMLLIGSGIWKDEATVKSMSRYGNYRELLKGPLYY : 45
Soy_1       : AALIPGINIFRMLVIGLGILKDEATVKSMSRFGDYRELLKGPLYY : 45
Rice_6      : ASIVIAFNIIKVTLIGLGIVKDDGVINSMTRNGDPRELLKGPLYY : 45
Wheat_2     : ASIVIALNIIKVILIGSGVVKDDGVVNSMTRNGDYRELLKGPLYY : 45
Maize_9     : APLIIININMKVTVIGLGFVKAEGVVNSMTRHGDRRELLKGPLYY : 45
Brassica_2  : AAFVPLVNGLRLVVNGLSVSPNSTLIQSVTREGRPEELLKGPLFY : 45
Cotton_2    : ASLMPLFNCLRLVIHGLSLTDDQSLIKSVTREGNPKELLRGPLYY : 45
Soy_4       : AAFVPLVNCLRLLVNGLSLASDEGLIKSVTREGDPLELLRGPLYY : 45
Sorghum_1   : AAVMPLLNSIRLLIYGLRLYTDEALVKSVTREGKPEELLRGPLYY : 45
Maize_3     : AAVMPFLNSMRLLIYGLRLYTDEALVKSVTREGKPEELLRGPLYY : 45
Maize_4     : AAVMPFLNSMRLLIYGLRLYTDEALVKSVTREGKPEELLR-PLYY : 44
Sorghum_3   : AAVMPLLNSIRLLIYGLRLYTDEALVKSVTREGKPEELLRGPLYY : 45
Rice_2      : AAIMPLLNCIRLLTYGLRLSTDEALVKSVTREGKPEELLRGPLYY : 45
Wheat_3     : AAVMPFLNCVRLLTYGLGFYSDEALVKSVTREGKREELLRGPLYY : 45
```

Figure 17

Pl-motif3 ltt1 (187 to 222) (SEQ ID NO: 76)

```
                          *          20         *
ltt1       : WRESPIGMISLAMMCGGDGIADIMGRKFGSTKIPYN : 36
ltt1_r     : WKSSPIAIAVICNLCAGDGMADIVGRRFGTEKLPYN : 36
Sorghum_2  : WRTSPVAIALICNLCAGDGIADVVGRRLGKEKLPYN : 36
Wheat_1    : WRTSPIAIALVCNLCAGDGIADVVGRRLGKEKLPYN : 36
Rice_5     : WRTSPIAIALICNLCAGDGIADIVGRRLGQEKLPYN : 36
Maize_6    : WRTSPVAIALICNLCAGDGIADVVGRRLGKEKLPYN : 36
Maize_7    : WRTSPVAIALICNLCAGDGIADVVGRRLGKEKLPYN : 36
Leek       : WRTSPVGMAAVCNLCAGDGLADIIGRRFGKHKLTYN : 36
Maize_8    : WKSSPIAIAVICNLCAGDGMADIVGRRFGTEKLPYN : 36
Brassica_1 : WKTSPIAIAVICNLCAGDGMADIVGRRLGTEKLPYN : 36
Cotton_1   : WRTSPIGIAALCNLCAGDGLADVVGRRLGRKKLPYN : 36
Soy_1      : WRTSPISIAAICNLCAGDGMADIVGRRLGGEKIPYN : 36
Rice_6     : WRTSPISIAVICNLCAGDGVADIAGRQLGRIKLPYN : 36
Wheat_2    : WRTSPISIAVICNLCAGDGVADIAGRRFGHVKLPHN : 36
Maize_9    : WRTSPISIAVICNLCAGDGVADIAGRRFGHVKLPHN : 36
Brassica_2 : WRDSPTGMISLAMMCGGDGIADIMGRKYGSYKIPYN : 36
Cotton_2   : WRESPVGVICLAMMCGGDGVADIIGRKYGSSKIPYN : 36
Soy_4      : WRESPIGVISLAMMCAGDGIADIIGRRYGSMKIPYN : 36
Maize_3    : WRESPIGIVSLSMMSGGDGFADIVGRRYGSAKLPFN : 36
Soy_3      : WRESPIGIVSLSMMSGGDGFADIVGRRYGSAKLPFN : 36
Maize_4    : WRESPIGIVSLSMMSGGDGFADIVGRRYGSAKLPFN : 36
Sorghum_3  : WRESPVGIVSLSMMSGGDGFADIVGRRYGSVKLPFN : 36
Rice_2     : WRQSPIGIVSLSMMSGGDGFADIVGRRYGSAKLPFN : 36
Wheat_3    : WRDSPIGIVSLSMMSGGDGFADIVGRRFGSLKLPFN : 36
```

Figure 18

Pl-motif4 ltt1 (225 to 254)   (SEQ ID NO: 77)

```
                      *         20          *
ltt1       : KSWAGSISMFIFGFFISIALLYYYSSLGYL : 30
ltt1_r     : KSFAGSIGMATAGFLASVAYMYYFASFGYI : 30
Sorghum_2  : KSYAGSIAMAVAGFLASVGYMHYFHTFGFI : 30
Wheat_1    : KSYAGSIAMAVAGFLASIGYMHYFHSFGLM : 30
Rice_5     : KSYAGSIAMALAGFMASIGYMHYFQSFGFI : 30
Maize_6    : KSYAGSIAMAVAGFLASVGYMHYFHTFGFI : 30
Maize_7    : KSYAGSIAMAVAGFLASVGYMHYFHTFGFI : 30
Leek       : KSIEGSAAMALAGFVASVLYMHYFAIFGFI : 30
Maize_8    : KSFAGSIGMATAGFLASVGYMYYFASFGYI : 30
Brassica_1 : KSLAGSIGMAIAGFLASVGYMYYFSSFGYM : 30
Cotton_1   : KSVAGSVAMATAGFLSSVGYMYYFSYFGYI : 30
Soy_1      : KSFAGSIAMATAGFLTSIGYMWYFSSFGFI : 30
Rice_6     : KSYAGSIAMFLAGFLASILYMCYFHLFGFV : 30
Wheat_2    : KSYAGSIAMFFAGFVASILFMCYFHLFGFV : 30
Maize_9    : KSYAGSIAMFLAGFIASVLFMCYFNIFGFV : 30
Brassica_2 : KSLAGSISMFIFGFFISIGLLYYSSLGYL : 30
Cotton_2   : KSWVGSISMFVSGFIISIGMLYYYSALGYL : 30
Soy_4      : KSLAGSMSMLVFGFLVSIGMLYYYSVLGHV : 30
Maize_3    : KSWAGSISMFISGFLLSAMMLYFSSLGYI : 30
Soy_3      : KSWAGSISMFISGFLLSAMMLYFSSLGYI : 30
Maize_4    : KSWAGSISMFISGFLLSAMMLYFSSLGYI : 30
Sorghum_3  : KSWAGSISMFISGFLLSAMMFYFSSLGYI : 30
Rice_2     : KSWIGSISMFISGFLLSALMLFYFSCLGYF : 30
Wheat_3    : KSWVGSAAMFISGFLLSALMLSYFSWLGYI : 30
```

Figure 19

Pl-motif5 ltt1 (267 to 285)   (SEQ ID NO: 78)

```
                              *
ltt1       : MVSMVATVVESLPITDQLD : 19
ltt1_r     : VISIASALVESLPISTDID : 19
Sorghum_2  : VVSVAATLVESHPISTELD : 19
Wheat_1    : VVSVAAALVESHPISTELD : 19
Rice_5     : VVSVTAALVESHPISTHLD : 19
Maize_6    : VVSVAAALVESHPISTELD : 19
Maize_7    : VVSVAAALVESHPISTELD : 19
Leek       : LLSFASAVVESLPISSELD : 19
Maize_8    : VISIASALVESLPISTDID : 19
Brassica_1 : VISIASALIESLPISTDID : 19
Cotton_1   : VVSLASALVESLPISTELD : 19
Soy_1      : LVSIVTAFVESLPISTELD : 19
Rice_6     : VTSLSAAIVESLPISTRLD : 19
Wheat_2    : VTSLAAAIVESLPVSTLLD : 19
Maize_9    : VISLAAAVVESLPISTRLD : 19
Brassica_2 : IVSLVATLVESLPITDQID : 19
Cotton_2   : FISLVATVVESLPISMLID : 19
Soy_4      : FISFVATLVESLPITKVVD : 19
Maize_3    : LVALAATVVECVPVTEVVD : 19
Soy_3      : LVALAATVVECVPVTEVVD : 19
Maize_4    : LVALAATVVECVPVTEVVD : 19
Sorghum_3  : LVALAATVVECIPVTEVVD : 19
Rice_2     : LVALAATVVECIPVNDVVD : 19
Wheat_3    : LVALAATVVECIPVTDVVD : 19
```

Figure 20

SEQUENCE LISTING

<160> NUMBER OF SEQ ID NOS: 79

<210> SEQ ID NO 1
<211> LENGTH: 1091
<212> TYPE: DNA
<213> ORGANISM: Arabidopsis thaliana

<400> SEQUENCE: 1

```
aaaaaaagat aaattacaaa atatcatttt ccttatctta ttgacttgtc aagattctct      60
tcttcttctt cttcttcctc ctcctccaaa ctcagttccc tccgtccatg gcagcaacct     120
tacctctatc tccgatcaat catcagttgt gtcggttcgg gaacaactct ttgacgactc     180
accggttctg ttctcctggc ttcttgattt cttctccttg tttcattggt ttgaccggaa     240
tgggctctgc tactcagtta cgtgctcgtc gttctctgat ctcttcagca gttgcgacga     300
attcgctgtt gcatgacgtc ggagccaccg tggcagtgct tggtggagca tacgcgcttg     360
tcttaagctt cgagagtctc accaagcgaa acgtcattca acagagtttg agcagaaagc     420
ttgtgcatat actctcaggt ctgcttttcg tacttgcgtg gccaatcttc agcggatcga     480
ccgaggctcg atactttgct gcttttgttc cgttagtgaa tggcttaagg cttgttatta     540
acggactatc catttcccca aattcgatgc taatcaaatc cgtcacaaga gaagggagag     600
cagaagagtt gcttaaaggt cctttgttct acgttctagc tcttcttttc tctgcggttt     660
tcttctggag agagtctcct atcggtatga tctcgttagc aatgatgtgt ggtggcgatg     720
gaatagctga tataatggga cgtaagtttg ggtcaactaa gatacttac aacccaagaa      780 agagttgggc aggaagcatc tccatgttca tcttcggctt cttcatctcc atcgcattac     840
tttactatta ctcaagcctt gggtaccttg acatgaactg ggaaacgacc ttgcagagag     900
tagcaatggt ctcaatggtc gccacggtag tcgagtcgct acccatcacc gatcaattag     960
```

```
acgacaatat tcggttcct ctggctacta ttttagctgc ttatttaagt ttcggatatt      1020
agattaatcc ctcataaacc gaatgtgtat atacgtattt ttttaatgaa tccgaccta      1080 caaatgtttc c                                                          1091
```

<210> SEQ ID NO 2
<211> LENGTH: 304
<212> TYPE: PRT
<213> ORGANISM: Arabidopsis thaliana

<400> SEQUENCE: 2

```
Met Ala Ala Thr Leu Pro Leu Ser Pro Ile Asn His Gln Leu Cys Arg
1               5                   10                  15

Phe Gly Asn Asn Ser Leu Thr Thr His Arg Phe Cys Ser Pro Gly Phe
            20                  25                  30

Leu Ile Ser Ser Pro Cys Phe Ile Gly Leu Thr Gly Met Gly Ser Ala
        35                  40                  45

Thr Gln Leu Arg Ala Arg Arg Ser Leu Ile Ser Ser Ala Val Ala Thr
    50                  55                  60

Asn Ser Leu Leu His Asp Val Gly Ala Thr Val Ala Val Leu Gly Gly
65                  70                  75                  80

Ala Tyr Ala Leu Val Leu Ser Phe Glu Ser Leu Thr Lys Arg Asn Val
                85                  90                  95

Ile Gln Gln Ser Leu Ser Arg Lys Leu Val His Ile Leu Ser Gly Leu
            100                 105                 110

Leu Phe Val Leu Ala Trp Pro Ile Phe Ser Gly Ser Thr Glu Ala Arg
        115                 120                 125

Tyr Phe Ala Ala Phe Val Pro Leu Val Asn Gly Leu Arg Leu Val Ile
    130                 135                 140

Asn Gly Leu Ser Ile Ser Pro Asn Ser Met Leu Ile Lys Ser Val Thr
145                 150                 155                 160

Arg Glu Gly Arg Ala Glu Glu Leu Leu Lys Gly Pro Leu Phe Tyr Val
                165                 170                 175

Leu Ala Leu Leu Phe Ser Ala Val Phe Phe Trp Arg Glu Ser Pro Ile
            180                 185                 190

Gly Met Ile Ser Leu Ala Met Met Cys Gly Gly Asp Gly Ile Ala Asp
        195                 200                 205

Ile Met Gly Arg Lys Phe Gly Ser Thr Lys Ile Pro Tyr Asn Pro Arg
    210                 215                 220

Lys Ser Trp Ala Gly Ser Ile Ser Met Phe Ile Phe Gly Phe Phe Ile
225                 230                 235                 240

Ser Ile Ala Leu Leu Tyr Tyr Tyr Ser Ser Leu Gly Tyr Leu His Met
                245                 250                 255

Asn Trp Glu Thr Thr Leu Gln Arg Val Ala Met Val Ser Met Val Ala
            260                 265                 270

Thr Val Val Glu Ser Leu Pro Ile Thr Asp Gln Leu Asp Asp Asn Ile
        275                 280                 285

Ser Val Pro Leu Ala Thr Ile Leu Ala Ala Tyr Leu Ser Phe Gly Tyr
    290                 295                 300
```

<210> SEQ ID NO 3
<211> LENGTH: 1897
<212> TYPE: DNA
<213> ORGANISM: Arabidopsis thaliana

<400> SEQUENCE: 3

```
aaaaaaagat aaattacaaa atatcatttt ccttatctta ttgacttgtc aagattctct      60
tcttcttctt cttcttcctc ctcctccaaa ctcagttccc tccgtccatg gcagcaacct     120
tacctctatc tccgatcaat catcagttgt gtcggttcgg gaacaactct ttgacgactc     180
accggttctg ttctcctggc ttcttgattt cttctccttg tttcattggt ttgaccggaa     240
tgggctctgc tactcagtta cgtgctcgtc gttctctgat ctcttcagca gttgcgacga     300
attcgctgtt gcatgacgtc ggagccaccg tggcagtgct ggtggagca tacgcgcttg      360 tcttaagctt cgagagtctc accaagcgaa acgtcattca acaggtctct taataatcgt     420
tttagttatc cacacaattt ctccgtttac aattccagtt ttattcgaac cactactat      480 gttgaaagaa gtttctcaag ttgtgtttgc agtagtactc attagaaaca atgataagcc     540
taggaaattt tgttgtgaat tagtttttc attctgaatt tttataagaa ttggtaacac      600
cttagtaagc agtataccac tttatcatga ccaatcggta aagcggacaa gaacaaagtg     660
gtccaaaaat atttaccgct ttatatgtta ccactttcc taacctccct tttaactatc      720
cgtaatcgcc taccgctaaa acatatacc gttcctttgt gttaacaaag taagaaaagg      780
aagaaacaat aactttgatt gttttatggt gagcagagtt tgagcagaaa gcttgtgcat     840
atactctcag gtctgctttt cgtacttgcg tggccaatct tcaggtattg ctttctctct     900
atgtttgtaa atctctctgt acctttaaaa catgtatagc attctgattt cttttactc      960 atctttaagt ttagcggatc gaccgaggct cgatactttg ctgcttttgt tccgttagtg    1020
aatggcttaa ggcttgttat taacggacta tccatttccc caaattcgat gctaatcaaa    1080
tccgtcacaa gagaagggag agcagagtaa gttgtctagt tttttttcc aactttgata     1140 tgatttttca acaatctgat tacacatttc ttgttttcca accatcacag agagttgctt    1200
aaaggtcctt tgttctacgt tctagctctt cttttctctg cggttttctt ctggagagag    1260
tctcctatcg gtatgatctc gttagcaatg atgtgtggtg gcgatggtaa attttctgtc    1320
aagtactact gtataactat tactacaatt tacaaaatgc gcataaatgt actaactaag    1380
tgctgcatca atatgtctat gtaggaatag ctgatataat gggacgtaag tttgggtcaa    1440
ctaagatacc ttacaaccca agaaagagtt aggcaggaag catctccatg ttcatcttcg    1500
gcttcttcat ctccatcgcg taaaaatatt accaatccca ctattaatca tcaaaatgtc    1560
tccttcttga cgacgaacaa gtcttaagaa ctgagatgag tttgctacta aacctaaccg    1620
ttttcttttg taattttgca gattacttta ctattactca agccttgggt accttcacat    1680
gaactgggaa acgaccttgc agagagtagc aatggtctca atggtcgcca cggtagtcga    1740
gtcgctaccc atcaccgatc aattagacga caatatttcg gttcctctgg ctactatttt    1800
agctgcttat ttaagtttcg gatattagat taatccctca taaaccgaat gtgtatatac    1860 gtatttttt aatgaatccg accttacaaa tgtttcc                               1897
```

<210> SEQ ID NO 4
<211> LENGTH: 226
<212> TYPE: PRT
<213> ORGANISM: Arabidopsis thaliana

<400> SEQUENCE: 4

```
Met Ala Ala Thr Leu Pro Leu Ser Pro Ile Asn His Gln Leu Cys Arg
1               5                   10                  15

Phe Gly Asn Asn Ser Leu Thr Thr His Arg Phe Cys Ser Pro Gly Phe
            20                  25                  30

Leu Ile Ser Ser Pro Cys Phe Ile Gly Leu Thr Gly Met Gly Ser Ala
```

```
             35                  40                  45
Thr Gln Leu Arg Ala Arg Arg Ser Leu Ile Ser Ser Ala Val Ala Thr
         50                  55                  60
Asn Ser Leu Leu His Asp Val Gly Ala Thr Val Ala Val Leu Gly Gly
 65                  70                  75                  80
Ala Tyr Ala Leu Val Leu Ser Phe Glu Ser Leu Thr Lys Arg Asn Val
                 85                  90                  95
Ile Gln Gln Ser Leu Ser Arg Lys Leu Val His Ile Leu Ser Gly Leu
            100                 105                 110
Leu Phe Val Leu Ala Trp Pro Ile Phe Ser Gly Ser Thr Glu Ala Arg
        115                 120                 125
Tyr Phe Ala Ala Phe Val Pro Leu Val Asn Gly Leu Arg Leu Val Ile
    130                 135                 140
Asn Gly Leu Ser Ile Ser Pro Asn Ser Met Leu Ile Lys Ser Val Thr
145                 150                 155                 160
Arg Glu Gly Arg Ala Glu Glu Leu Leu Lys Gly Pro Leu Phe Tyr Val
                165                 170                 175
Leu Ala Leu Leu Phe Ser Ala Val Phe Phe Trp Arg Glu Ser Pro Ile
            180                 185                 190
Gly Met Ile Ser Leu Ala Met Met Cys Gly Gly Asp Gly Ile Ala Asp
        195                 200                 205
Ile Met Gly Arg Lys Phe Gly Ser Thr Lys Ile Pro Tyr Asn Pro Arg
    210                 215                 220
Lys Ser
225

<210> SEQ ID NO 5
<211> LENGTH: 1162
<212> TYPE: DNA
<213> ORGANISM: Arabidopsis thaliana

<400> SEQUENCE: 5
gtgttttcta gtgttgcaga aaatggcaac tactagtact actacaaagc tctccgttct      60
ctgctgctct ttcatttcat ctcctctcgt tgactctcct ccttctctcg ccttcttctc     120
tccgattcca cgattcctca ctgtccgaat cgcgactagc tttagatcga gctctaggtt     180
tccggccacc aaaatccgca agtcttcact cgccgccgtg atgtttccgg aaaattcggt     240
tttatcagat gtctgcgcgt ttggagtcac tagcatcgtt gcgttctcgt gcctcggttt     300
ctggggagag attggcaaac gtggcatctt cgaccagaaa ctcatccgga agcttgtgca     360
tataaatatt gggctagttt ttatgctttg ctggccgctg ttcagttctg aatccaagg      420
agcactttc gcatctcttg tacctggact caatatagta aggatgctat tgctgggct      480
tggagtgtac cacgacgaag gaacaatcaa gtcaatgagc agacatggag atcgcaggga     540
actacttaag gggccgcttt actatgtact gtcaatcaca tcagcctgca tctactattg     600
gaaatcatcc ccaatcgcga ttgcggtgat atgcaacctt tgcgcaggag atggtatggc     660
tgacattgtg ggtcggcggt ttggaacaga gaagcttcct tacaacaaaa acaaatcatt     720
tgctggtagc attggaatgg ccaccgccgg gtttctagca tctgttgcgt atatgtacta     780
ctttgcttca tttggttaca tcgaggatag cgggggaatg attcttcgtt tcctcgtcat     840
ctctatagca tcagctcttg tggaatcact cccaataagc accgacattg acgacaatct     900
caccatttcc ttaacctctg ccttggccgg attcttactc ttctaataat accctctcgt     960
tgttatgtat catcaaataa agggtcgagc ttgattgctg atatgagggt aaaactgcat    1020
```

```
tcattgttcc catcttcttc tgtatgtacg tattagtgaa acatctcata ttgttgttgt    1080
ccacaaatct tatttttcag ctgcaattgc agttgggtac aatgttgtaa tgttctatcc    1140
attagtgaga catatgatga cg                                             1162
```

<210> SEQ ID NO 6
<211> LENGTH: 307
<212> TYPE: PRT
<213> ORGANISM: Arabidopsis thaliana

<400> SEQUENCE: 6

```
Met Ala Thr Thr Ser Thr Thr Thr Lys Leu Ser Val Leu Cys Cys Ser
1               5                   10                  15

Phe Ile Ser Ser Pro Leu Val Asp Ser Pro Ser Leu Ala Phe Phe
            20                  25                  30

Ser Pro Ile Pro Arg Phe Leu Thr Val Arg Ile Ala Thr Ser Phe Arg
        35                  40                  45

Ser Ser Ser Arg Phe Pro Ala Thr Lys Ile Arg Lys Ser Ser Leu Ala
    50                  55                  60

Ala Val Met Phe Pro Glu Asn Ser Val Leu Ser Asp Val Cys Ala Phe
65                  70                  75                  80

Gly Val Thr Ser Ile Val Ala Phe Ser Cys Leu Gly Phe Trp Gly Glu
                85                  90                  95

Ile Gly Lys Arg Gly Ile Phe Asp Gln Lys Leu Ile Arg Lys Leu Val
            100                 105                 110

His Ile Asn Ile Gly Leu Val Phe Met Leu Cys Trp Pro Leu Phe Ser
        115                 120                 125

Ser Gly Ile Gln Gly Ala Leu Phe Ala Ser Leu Val Pro Gly Leu Asn
    130                 135                 140

Ile Val Arg Met Leu Leu Leu Gly Leu Gly Val Tyr His Asp Glu Gly
145                 150                 155                 160

Thr Ile Lys Ser Met Ser Arg His Gly Asp Arg Arg Glu Leu Leu Lys
                165                 170                 175

Gly Pro Leu Tyr Tyr Val Leu Ser Ile Thr Ser Ala Cys Ile Tyr Tyr
            180                 185                 190

Trp Lys Ser Ser Pro Ile Ala Ile Ala Val Ile Cys Asn Leu Cys Ala
        195                 200                 205

Gly Asp Gly Met Ala Asp Ile Val Gly Arg Arg Phe Gly Thr Glu Lys
    210                 215                 220

Leu Pro Tyr Asn Lys Asn Lys Ser Phe Ala Gly Ser Ile Gly Met Ala
225                 230                 235                 240

Thr Ala Gly Phe Leu Ala Ser Val Ala Tyr Met Tyr Tyr Phe Ala Ser
                245                 250                 255

Phe Gly Tyr Ile Glu Asp Ser Gly Gly Met Ile Leu Arg Phe Leu Val
            260                 265                 270

Ile Ser Ile Ala Ser Ala Leu Val Glu Ser Leu Pro Ile Ser Thr Asp
        275                 280                 285

Ile Asp Asp Asn Leu Thr Ile Ser Leu Thr Ser Ala Leu Ala Gly Phe
    290                 295                 300

Leu Leu Phe
305
```

<210> SEQ ID NO 7
<211> LENGTH: 22
<212> TYPE: DNA

<213> ORGANISM: Artificial sequence - Primer 404
<220> FEATURE:
<223> OTHER INFORMATION: An artificial polynucleotide sequence

<400> SEQUENCE: 7
gtggctcggc ttcactttt ac                                    22

<210> SEQ ID NO 8
<211> LENGTH: 20
<212> TYPE: DNA
<213> ORGANISM: Artificial sequence - Primer 405
<220> FEATURE:
<223> OTHER INFORMATION: An artificial polynucleotide sequence

<400> SEQUENCE: 8
ccacactcat atcaccgtgg                                      20

<210> SEQ ID NO 9
<211> LENGTH: 31
<212> TYPE: DNA
<213> ORGANISM: Artificial sequence - Primer 1652-e-1-f
<220> FEATURE:
<223> OTHER INFORMATION: An artificial polynucleotide sequence

<400> SEQUENCE: 9
ccgagcggcc gcattatccc aagatcactg g                         31

<210> SEQ ID NO 10
<211> LENGTH: 28
<212> TYPE: DNA
<213> ORGANISM: Artificial sequence - primer 1652-i-2-r
<220> FEATURE:
<223> OTHER INFORMATION: An artificial polynucleotide sequence

<400> SEQUENCE: 10
gccgaggatc caccaagcaa tcagcacc                             28

<210> SEQ ID NO 11
<211> LENGTH: 27
<212> TYPE: DNA
<213> ORGANISM: Artificial sequence - Primer 1652-i-3-f
<220> FEATURE:
<223> OTHER INFORMATION: An artificial polynucleotide sequence

<400> SEQUENCE: 11
gccgaggatc ctggtgggac aaaggtg                              27

<210> SEQ ID NO 12
<211> LENGTH: 29
<212> TYPE: DNA
<213> ORGANISM: Artificial sequence
<220> FEATURE:
<223> OTHER INFORMATION: An artificial polynucleotide sequence

<400> SEQUENCE: 12
gccgagctcg agcccaattc cgggtattg                            29

<210> SEQ ID NO 13
<211> LENGTH: 1404
<212> TYPE: DNA
<213> ORGANISM: Arabidopsis thaliana

<400> SEQUENCE: 13
atggcgacga cggttacact caaatccttc accggacttc gtcaatcatc aacggagcaa     60
acaaacttcg tctctcatgt accgtcatca ctttctctcc ctcaacgacg gacctctctc    120

```
cgagtaaccg cagccagggc cactcccaaa ctctccaacc gtaaactccg tgtcgccgtc      180
atcggtggtg gaccagcagg cggggcagct gcagagactc tagcacaagg aggaatcgag      240
acgattctca tcgagcgtaa gatggacaat tgcaagcctt gcgtggcgc gattcctctc       300
tgtatggtcg gagaattcaa cttgccgttg atattattg atcggagagt gacgaagatg       360
aagatgattt cgccgtcgaa cattgctgtt gatattggtc gtacgcttaa ggagcatgag       420
tatataggta tggtgagaag agaagttctt gatgcttatc tgagagagag agctgagaag      480
agtggagcca ctgtgattaa cggtctcttc cttaagatgg atcatccgga gaattgggac      540
tcgccgtaca ctttgcatta cactgagtac gatggtaaaa ctggagctac agggacgaag      600
aaaacaatgg aggttgatgc tgtcattgga gctgatggag ctaactctag ggttgctaaa      660
tctattgatg ctggtgatta cgactacgca attgcatttc aggagaggat taggattcct      720
gatgagaaaa tgacttacta tgaggattta gctgagatgt atgttggaga tgatgtgtcg      780
ccggatttct atggttgggt gttccctaag tgcgaccatg tagctgttgg aacaggtact      840
gtgactcaca aagtgacat caagaagttc agctcgcga ccagaaacag agctaaggac        900
aagattcttg gagggaagat catccgtgtg gaggctcatc cgattcctga acatccgaga      960
ccacgtaggc tctcgaaacg tgtggctctt gtaggtgatg ctgcaggta tgtgactaaa       1020
tgctctggtg aagggatcta ctttgctgct aagagtggaa gaatgtgtgc tgaagccatt      1080
gtcgaaggtt cacagaatgg taagaagatg attgacgaag gggacttgag gaagtacttg      1140
gagaaatggg ataagacata cttgcctacc tacagggtac ttgatgtgtt gcagaaagtg      1200
ttttacagat caaatccggc tagagaagcg tttgtggaga tgtgtaatga tgagtatgtt      1260
cagaagatga cattcgatag ctatctgtac aagcgggttg cgccgggtag tcctttggag      1320
gatatcaagt tggctgtgaa caccattgga agtttggtta gggctaatgc tctaaggaga      1380
gagattgaga agcttagtgt ttaa                                             1404
```

<210> SEQ ID NO 14
<211> LENGTH: 1338
<212> TYPE: DNA
<213> ORGANISM: Arabidopsis thaliana

<400> SEQUENCE: 14

```
atgggccacc aaaacgccgc cgtttcagag aatcaaaacc atgatgacgg cgctgcgtcg      60
tcgccgggat tcaagctcgt cggattttcc aagttcgtaa gaaagaatcc aaagtctgat      120
aaattcaagg ttaagcgctt ccatcacatc gagttctggt gcggcgacgc aaccaacgtc      180
gctcgtcgct ctcctgggg tctggggatg agattctccg ccaaatccga tctttccacc      240
ggaaacatgg ttcacgcctc ttacctactc acctccggtg acctccgatt cctttttcact      300
gctccttact ctccgtctct ctccgccgga gagattaaac cgacaaccac agcttctatc      360
ccaagtttcg atcacggctc ttgtcgttcc ttcttctctt cacatggtct cggtgttaga      420
gccgttgcga ttgaagtaga agacgcagag tcagctttct ccatcagtgt agctaatggc      480
gctattcctt cgtcgcctcc tatcgtcctc aatgaagcag ttacgatcgc tgaggttaaa      540
ctatacggcg atgttgttct ccgatatgtt agttacaaag cagaagatac cgaaaaatcc      600
gaattcttgc cagggttcga gcgtgtagag gatgcgtcgt cgttcccatt ggattatggt      660
atccggcggc ttgaccacgc cgtgggaaac gttcctgagc ttggtccggc tttaacttat      720
gtagcggggt tcactggttt tcaccaattc gcagagttca cagcagacga cgttggaacc      780
```

```
gccgagagcg gtttaaattc agcggtcctg gctagcaatg atgaaatggt tcttctaccg    840
attaacgagc cagtgcacgg aacaaagagg aagagtcaga ttcagacgta tttggaacat    900
aacgaaggcg cagggctaca acatctggct ctgatgagtg aagacatatt caggaccctg    960
agagagatga ggaagaggag cagtattgga ggattcgact tcatgccttc tcctccgcct   1020
acttactacc agaatctcaa gaaacgggtc ggcgacgtgc tcagcgatga tcagatcaag   1080
gagtgtgagg aattagggat tcttgtagac agagatgatc aagggacgtt gcttcaaatc   1140
ttcacaaaac cactaggtga caggccgacg atatttatag agataatcca gagagtagga   1200
tgcatgatga agatgagga agggaaggct taccagagtg gaggatgtgg tggttttggc   1260
aaaggcaatt tctctgagct cttcaagtcc attgaagaat acgaaaagac tcttgaagcc   1320
aaacagttag tgggatga                                                 1338

<210> SEQ ID NO 15
<211> LENGTH: 1182
<212> TYPE: DNA
<213> ORGANISM: Arabidopsis thaliana

<400> SEQUENCE: 15
atggagtctc tgctctctag ttcttctctt gtttccgctg ctggtgggtt ttgttggaag     60
aagcagaatc taaagctcca ctcttttatca gaaatccgag ttctgcgttg tgattcgagt    120
aaagttgtcg caaaccgaa gtttaggaac atcttgtta ggcctgatgg tcaaggatct     180
tcattgttgt tgtatccaaa acataagtcg agatttcggg ttaatgccac tgcgggtcag    240
cctgaggctt tcgactcgaa tagcaaacag aagtcttta gagactcgtt agatgcgttt    300
tacaggtttt ctaggcctca tacagttatt ggcacagtgc ttagcatttt atctgtatct    360
ttcttagcag tagagaaggt ttctgatata tctccttac ttttcactgg catcttggag    420
gctgttgttg cagctctcat gatgaacatt tacatagttg ggctaaatca gttgtctgat    480
gttgaaatag ataaggttaa caagccctat cttccattgg catcaggaga atattctgtt    540
aacaccggca ttgcaatagt agcttccttc tccatcatga gtttctggct tgggtggatt    600
gttggttcat ggccattgtt ctgggctctt tttgtgagtt tcatgctcgg tactgcatac    660
tctatcaatt tgccacttt acggtggaaa agatttgcat tggttgcagc aatgtgtatc    720
ctcgctgtcc gagctattat tgttcaaatc gcctttatc tacatattca gacacatgtg    780
tttggaagac caatcttgtt cactaggcct cttatttcg ccactgcgtt tatgagcttt    840
ttctctgtcg ttattgcatt gttaaggat atacctgata tcgaagggga taagatattc    900
ggaatccgat cattctctgt aactctgggt cagaaacggg tgttttggac atgtgttaca    960
ctacttcaaa tggcttacgc tgttgcaatt ctagttggag ccacatctcc attcatatgg   1020
agcaaagtca tctcggttgt gggtcatgtt atactcgcaa caactttgtg ggctcgagct   1080
aagtccgttg atctgagtag caaaaccgaa ataacttcat gttatatgtt catatggaag   1140 ctctttatg cagagtactt gctgttacct ttttgaagt ga                       1182

<210> SEQ ID NO 16
<211> LENGTH: 1122
<212> TYPE: DNA
<213> ORGANISM: Erwinia herbicola

<400> SEQUENCE: 16
atggtggctg aactgaccgc gttacgcgat caaattgaca gtgtagataa agcgctgctg     60
gatctgctgg ctaagcgact ggaactggtg gccgaggtag gtgaggtgaa gagccgttac    120
```

-continued

```
ggcctgccta tctatgtgcc tgagcgtgag gcgtcgatgc tggcttcgcg tcgcaaagag      180
gccgaagcgc tcggcgtacc accggatctg attgaggatg tgctgcgtcg cgtgatgcgg      240
gaatcctata ccagcgagaa tgataaaggc tttaaaaccc tctgtcctga actgcgcccg      300
gtggtgattg tcggtggtaa gggccagatg ggccggctgt ttgaaaaaat gctcgggcta      360
tcaggctaca cggttaaaac gctggataaa gaggactggc tcaggctga gactctgctc       420 agcgatgccg gaatggtgat cattagcgtg ccgattcacc tgaccgagca ggtgattgcc      480
caactgccac cactgccgga agattgtatt ctggtcgatc tggcgtcagt caaaaaccgg      540
cctctgcagg caatgctggc tgcccataac gggcctgtac tgggtctgca tccgatgttt      600
ggcccggaca gcggcagcct ggcaaaacag gtggtggtct ggtgtgatgg aagacaaccg      660
gaagcgtatc agtggttcct ggagcagatt caggtctggg gtgcgcgtct gcatcgtatc      720
agcgctgttg agcatgacca gaacatggca ttcattcagg cgctgcgtca ctttgctacc      780
ttcgcttatg gtctgcattt agccgaagag aacgtcaatc tggatcagct gctggcgctc      840
tcgtcgccca tttaccggct tgaactggcg atggtgggc ggttgttcgc tcaggatccg       900
caactctatg cggatatcat catgtcttca gagagtaatc tggcgctgat aaaacgctat      960
taccagcggt ttggtgaagc gattgcgctg ctggagcagg cgacaagca ggcgtttatc      1020 gccagctttta accgggttga acagtggttt ggcgatcacg caaaacgctt cctggtcgaa   1080
agccgaagcc tgttgcgatc ggccaatgac agccgcccat aa                        1122
```

<210> SEQ ID NO 17
<211> LENGTH: 702
<212> TYPE: DNA
<213> ORGANISM: Synechocystis PCC6803

<400> SEQUENCE: 17

```
atgggcattg agcaaaataa tcctatggct ttgcccctct ggattgcggt ggggctggcg      60
gcgacctacc tagggctgt ggtgttaacc gcggaactgc ttaaccgcct ttccctcagt       120
ccggcggagg taactcgtaa aattgtccac atcggagcgg ggcaagtggt gctgattgct      180
tggtggttga gtattcctgg ttgggtgggg gcgatcgccg gggttttttgc cgctggcatt    240 gcagtgctct cctatcgttt gccgattttg cccagcttag aaagtgttgg ccgccacagt     300
tacggcactt tgttttacgc ccttagcatt ggtctattgg tgggggatt tttctcccctt    360 ggactgccga tatttgcggc gatcggtatt ttagtcatgg cctggggcga tggactggcg     420
gccctggtgg gacaaggtg gggcgtcac cgctaccaag tctttggttt ccgcaaaagt       480
tgggagggca ctctccaccat ggtgttggcc agttttttgg tcacggttgt atttcttagt    540
tacaccttcg gcttcacagt tattgtcctt gttgtggctg ggacggtggc gatcgccagt     600
gctggactgg agagcttttc ccgctgggc attgataact taactgttcc cctgggcagt    660
gctttgattg cttgggctgg tagctatctt tggttgggat ag                        702
```

<210> SEQ ID NO 18
<211> LENGTH: 1188
<212> TYPE: DNA
<213> ORGANISM: Synechocystis PCC6803

<400> SEQUENCE: 18

```
gatacataaa tcttcaacac aactctttaa ttatctagtt taatacaaat ggcggcgata     60
gaggacagtc caacgttttc ctctgtggta actccggcgg cttttgagat aggcagcctc    120
```

```
ccgacaaccg agataccggt ggatccggtg gaaaatgatt caacagcacc gccaaaaccg      180
gtgagaatca cctgtccaac agtcgccgga acttatcccg tcgttttatt cttccatggc      240
ttttatcttc gcaactactt ctactctgac gttcttaacc acatcgcttc gcatggttac      300
attcttgtag ccccacagtt gtgcaaatta ttgccgccgg gagggcaagt ggaagtggac      360
gatgctggaa gtgtgataaa ctgggcatcg gaaaacctca agctcacct accaacttcg       420 gtaaatgcta atggaaaata cacctcactc gtgggccaca gccgcggtgg gaaaacggcg      480
tttgcggttg cgctaggcca tgccgcaaca ttagacccat ccatcacgtt ttcagctcta      540
ataggaattg atccagtcgc aggaactaac aaatacatta gaaccgatcc gcatatctta      600
acgtataaac cggaatcttt cgagctggac ataccggttg cagtggtggg aaccggactc      660
ggaccgaagt ggaacaacgt gatgccacca tgcgcaccaa cggacttaaa ccatgaggag      720
ttttacaaag agtgtaaggc gacgaaagcc catttcgtgg ctgcggatta cggacatatg      780
gatatgttgg acgatgattt gcccggtttt gttgggttta tggccggttg tatgtgtaag      840
aatgggcaaa gaaaaaagtc tgagatgagg agctttgtag gtggaattgt ggttgcgttt      900
ctcaagtata gtttgtgggg tgaaaaagcg gagattcgat tgattgtgaa ggatccttcc      960
gtttctccgg ccaagcttga tccttcacct gagttggaag aagcttctgg tatcttcgtc      1020
tagatttgtg ttatgtacta ttatcagagg ggtcttgaat atttgaaaaa cctatcaatg      1080
ttttctagct ccaagctagc tattgttcat gtcctaagtt gcatgtgtat ttttattaaa      1140
ctcgatcaaa acatttgtta tagttttacc ccaaaaaaaa aaaaaaa                    1188

<210> SEQ ID NO 19
<211> LENGTH: 1135
<212> TYPE: DNA
<213> ORGANISM: Arabidopsis thaliana

<400> SEQUENCE: 19
aaaaaaagta agaaaagaa aaactaataa agaacaaaaa aaatgtcctc ttcttcatca       60
agaaacgcct ttgaagatgg caaatacaaa tcaaatctct taaccttgga ctcatcatct      120
cgttgctgca aaataacacc gtcttctaga gcttcaccgt ctccgccaaa gcagctgttg      180
gtggctacgc cggtggagga aggagattat ccggtggtga tgctcctcca tggttacctt      240
ctctacaact ccttctattc tcagcttatg ttgcatgtct cttctcatgg cttcatcctc      300
atcgctcctc agttatatag tatcgccgga ccagacacaa tggatgagat taaatcaacg      360
gcggagatta tggattggtt atcagtagga cttaatcact ttcttccagc gcaagtaaca      420
ccaaacctat ccaaatttgc cctctccggc catagccgcg gtggcaaaac gcgtttgcg       480 gtcgccttaa agaaatttgg gtactcctcg aatctaaaga tctcgacatt gatcggtata      540
gatccagtcg atggaacagg gaaagggaaa caaacccctc ctccggtgtt ggcttacctt      600
ccaaactcat ttgacctaga caaaacgcct atacttgtga tcggttcggg gcttggtgaa      660
accgctcgga acccattatt cccaccgtgt gcacctcccg gagtgaatca ccgagagttc      720
tttcgggaat gtcaaggtcc agcatggcat ttcgttgcga aggattatgg gcatttggac      780
atgcttgatg atgatacaaa agggattaga gggaagagtt cttattgttt gtgtaagaat      840
ggtgaagaga ggagaccaat gaggagattc gttggtggac ttgttgtatc attttttgaag      900 gcttatttgg aaggagatga tcgtgaatta gttaagatca agatgggtg tcacgaggat      960 gttcccgttg aaattcaaga gtttgaggtt atcatgtaaa cataagtttt tctttagggg      1020
ctggtttttc tattgtcaat atcatcagct tttgttgctt atggttttac aaacttatat      1080
```
tgtacaactc tttaagtcac ctctttgctt acaaaaaaaa aaaaaaaaaa aaaaa    1135

<210> SEQ ID NO 20
<211> LENGTH: 190
<212> TYPE: PRT
<213> ORGANISM: Aquifex aeolicus

<400> SEQUENCE: 20

```
Met Asn Leu Glu Arg Gly Asn Met Leu Glu Leu Arg Arg Lys Leu Phe
1               5                   10                  15

His Phe Leu Ser Ile Leu Leu Ile Ile Pro Val Lys Phe Phe Pro
            20                  25                  30

Phe Trp Leu Asn Val Phe Leu Phe Leu Ser Ala Ile Leu Leu Asn Leu
        35                  40                  45

Leu Ile Ile Phe Arg Val Ser Pro Phe Tyr Asn Ile Phe Glu Val Phe
    50                  55                  60

Ile Lys Leu Phe Glu Arg Glu Lys Asn Leu Glu Thr Pro Gly Ile Gln
65                  70                  75                  80

Ser Leu Trp Ala Ile Leu Gly Val Phe Ile Ser Tyr Leu Leu Phe Gly
                85                  90                  95

Glu Asn Ala Val Val Gly Ile Val Leu Ala Leu Gly Asp Gly Phe
            100                 105                 110

Ser Gly Leu Val Gly Tyr Tyr Phe Gly Arg Arg Lys Leu Phe Tyr Asn
        115                 120                 125

Pro Lys Lys Ser Leu Glu Gly Thr Leu Ala Phe Phe Thr Ala Ser Phe
    130                 135                 140

Leu Gly Leu Leu Leu Phe Thr Asp Phe Cys Glu Ala Phe Val Ile Ser
145                 150                 155                 160

Leu Ile Cys Ala Val Leu Glu Ser Leu Pro Leu Lys Leu Asp Asp Asn
                165                 170                 175

Phe Tyr Ile Pro Val Leu Ala Ser Phe Leu Gly Glu Val Leu
            180                 185                 190
```

<210> SEQ ID NO 21
<211> LENGTH: 237
<212> TYPE: PRT
<213> ORGANISM: Chlorobium tepidum

<400> SEQUENCE: 21

```
Met Thr Ala Ile Ala Pro Thr Phe Phe Asp Leu Pro Val Val Trp His
1               5                   10                  15

Asn Val Leu Val Met Leu Leu Thr Ile Ala Tyr Val Phe Ser Val Pro
            20                  25                  30

Leu Leu Met Asp Trp Leu Val Thr Asn His Gly Leu Pro Arg Asp Ile
        35                  40                  45

Ser Arg Lys Ile Thr His Ile Cys Ala Gly Ser Val Ile Val Phe Leu
    50                  55                  60

Pro Leu Phe Arg Asp Gly Asp Trp Ser His Tyr Leu Asn Ile Thr Val
65                  70                  75                  80

Phe Ala Val Trp Thr Val Leu Ile Gln Lys Gly Leu Phe Ala Ala
                85                  90                  95

Asp Asp Asp Gln Ala Val Lys Thr Met Thr Arg Thr Gly Asp Lys Arg
            100                 105                 110

Glu Leu Leu Lys Gly Pro Leu Tyr Phe Val Ile Val Ala Met Ile Cys
        115                 120                 125
```

```
Gly Thr Leu Tyr Tyr Lys Gln Phe Ala Gly Val Leu Ala Met Ala Ile
            130                 135                 140

Leu Gly Trp Gly Asp Gly Leu Ala Pro Ile Val Gly Thr Arg Met Gly
145                 150                 155                 160

Lys Met Lys Tyr Lys Val Phe Cys Glu Arg Ser Val Glu Gly Ser Ile
                165                 170                 175

Ala Phe Leu Ala Gly Ser Leu Ala Gly Leu Phe Phe Val Trp Leu
            180                 185                 190

Ile Val Pro Gln Ala Phe Asn Pro Ala Lys Ile Ala Met Ile Ala Val
                195                 200                 205

Ala Ala Thr Val Ile Glu Ala Leu Ser Pro Lys Glu Val Asp Asn Ile
            210                 215                 220

Leu Ile Pro Ala Glu Val Ile Ala Leu Ala Ala Val Leu
225                 230                 235

<210> SEQ ID NO 22
<211> LENGTH: 477
<212> TYPE: PRT
<213> ORGANISM: Chlorobium tepidum

<400> SEQUENCE: 22

Met Gly Val Val Met Phe Phe Ile Pro Ser Tyr Phe Ser Asn Phe
1               5                   10                  15

Tyr Pro Leu Ala Ala Ala Phe Leu Phe Ala Val Val Gly Leu Val Ser
            20                  25                  30

Leu Lys Ala Gly Ile Leu Gln Ser Leu His Gly Glu Pro Val Val Thr
        35                  40                  45

Gln Glu Gly Glu Arg Val Ile Ser Tyr Gly Pro Val Leu Phe Pro Leu
    50                  55                  60

Val Phe Phe Leu Gln Ala Leu Phe Leu Trp Gly Glu His Val Trp Ile
65                  70                  75                  80

Leu Gln Ile Ser Met Leu Val Leu Gly Ile Gly Asp Ala Leu Ala Ala
                85                  90                  95

Leu Val Gly Thr Ala Ala Gly Gly Arg His Ile Glu Asn Leu Thr Lys
            100                 105                 110

Ser Arg Lys Ser Ile Glu Gly Ser Met Ala Met Phe Ile Ser Ser Leu
        115                 120                 125

Val Ile Leu Ser Val Ser Ile Phe Val Phe Arg Asp Ala Phe Thr Gly
130                 135                 140

Gly Leu Val Gly Gln Pro Ile Trp Lys Leu Leu Ala Leu Ala Leu Leu
145                 150                 155                 160

Leu Ala Leu Leu Val Thr Ala Val Glu Ala Leu Leu Ser Trp Gly Leu
                165                 170                 175

Asp Asn Leu Phe Ile Pro Leu Ala Ile Ala Tyr Val Leu Tyr Val Val
            180                 185                 190

Asp Val Asn Ser Met Val Thr Ile Asp Gly Leu Leu Leu Gly Gly Leu
        195                 200                 205

Phe Ala Leu Phe Ile Ala Ile Phe Ser Ile Lys Val Lys Phe Leu Asn
    210                 215                 220

Asn Ser Gly Ala Thr Ala Thr Phe Leu Leu Gly Thr Thr Ile Phe Gly
225                 230                 235                 240

Val Gly Gly Met Val Trp Thr Val Pro Met Leu Thr Phe Tyr Leu Leu
                245                 250                 255

Ser Ser Ile Leu Ser Lys Leu Gly His Lys Arg Lys Ala Lys Phe Asp
            260                 265                 270
```

```
Leu Val Phe Glu Lys Gly Ser Gln Arg Asp Ala Gly Gln Val Tyr Ala
            275                 280                 285
Asn Gly Gly Val Ala Trp Ile Met Met Val Ile Tyr Ser Leu Thr Gly
        290                 295                 300
Asp Pro Tyr Ile Phe Phe Ala Tyr Leu Gly Thr Leu Ala Ala Val Gln
305                 310                 315                 320
Ala Asp Thr Trp Ala Thr Glu Ile Gly Thr Met Trp Pro Asn Ala Lys
                325                 330                 335
Ala Arg Leu Ile Thr Thr Phe Lys Asp Val Pro Val Gly Thr Ser Gly
            340                 345                 350
Gly Val Ser Ile Pro Gly Thr Leu Ala Ser Phe Leu Gly Ser Leu Leu
        355                 360                 365
Ile Cys Ser Ser Ala Val Leu Met Asn Val Ser Trp Ile Asp Gln Val
        370                 375                 380
Gly Ile Val Thr Ser Leu Leu Val Ile Gly Val Ser Gly Leu Phe Ala
385                 390                 395                 400
Ser Leu Val Asp Ser Phe Phe Gly Ala Thr Val Gln Ala Gln Tyr Tyr
                405                 410                 415
Asp Pro Ile Arg Gln Lys Val Thr Glu Arg Thr His Ser Ile Ala Ser
            420                 425                 430
Asp Gly Ser Arg Val Ala Asn Glu Leu Leu Lys Gly Tyr Asp Phe Val
        435                 440                 445
Asn Asn Asp Leu Val Asn Thr Leu Cys Ala Ile Ser Gly Ser Ala Val
        450                 455                 460
Ala Tyr Leu Val Val Arg Asn Leu Val Ser Leu Ser Leu
465                 470                 475

<210> SEQ ID NO 23
<211> LENGTH: 236
<212> TYPE: PRT
<213> ORGANISM: Chloroflexus aurantiacus

<400> SEQUENCE: 23

Met Ser Thr Arg Asp Leu Ile Gly Leu Ile Val Ser Phe Gly Tyr Ala
1               5                   10                  15
Phe Gly Leu Leu Ile Ile Ala Glu Val Ile Arg Arg Trp Arg Gly Tyr
            20                  25                  30
Pro Gln Asp Phe Thr Arg Lys Phe Val His Ile Gly Ala Gly Met Trp
        35                  40                  45
Val Phe Gly Val Leu Ala Leu Phe Glu Asn Trp Thr Ile Gly Ile Ile
    50                  55                  60
Pro Phe Ala Thr Phe Ile Val Leu Asn Phe Ile Phe Tyr Arg Phe Arg
65                  70                  75                  80
Leu Leu Ala Ala Ile Asp Ala Pro Asp Ser Thr Pro Gly Thr Val Tyr
                85                  90                  95
Phe Ala Leu Ser Ile Thr Ile Leu Phe Leu Ile Phe Trp Arg Thr Asn
            100                 105                 110
Ser Pro Asp Asp Arg Gly Tyr Ile Ala Ala Gly Thr Met Ala Met
        115                 120                 125
Thr Trp Gly Asp Ala Leu Ala Ile Val Gly Lys Arg Trp Gly Arg
        130                 135                 140
His Tyr Tyr Gln Ile Gly Gln Gly Arg Arg Ser Phe Glu Gly Ser Ala
145                 150                 155                 160
Ala Met Phe Ile Ala Ser Thr Val Ala Ile Leu Leu Thr Leu Leu Phe
```

```
                    165                 170                 175
Thr Pro Gly Ser Ala Leu Ser Pro Gln Ser Ser Pro Ile Asp Val Gly
            180                 185                 190

Ala Ala Leu Ile Thr Ser Ile Val Ala Gly Leu Val Ala Thr Ile Ala
            195                 200                 205

Glu Gly Val Ser Pro His Gly Thr Asp Asn Ile Ser Val Pro Leu Leu
            210                 215                 220

Ala Gly Ala Val Ile Ala Val Met Leu Gly Val Val
225                 230                 235

<210> SEQ ID NO 24
<211> LENGTH: 209
<212> TYPE: PRT
<213> ORGANISM: Nostoc punctiforme

<400> SEQUENCE: 24

Met Leu Leu Ile Leu Val Ile Ala Trp Val Val Asn Arg Phe Ala Asp
1               5                   10                  15

Glu Pro Glu Ile Val Arg Lys Ile Val His Ile Gly Thr Gly Asn Val
            20                  25                  30

Ile Leu Leu Ala Trp Trp Leu Asp Ile Pro Ala Ser Val Gly Ile Thr
        35                  40                  45

Ala Ser Ile Leu Ala Ser Ala Ile Thr Leu Leu Ser Tyr Arg Leu Pro
    50                  55                  60

Ile Leu Pro Gly Ile Asn Ser Val Gly Arg Gln Ser Phe Gly Thr Phe
65                  70                  75                  80

Phe Tyr Ser Val Ser Phe Gly Ile Leu Val Ala Ser Phe Trp Tyr Leu
                85                  90                  95

Gln Gln Pro Gln Tyr Ala Ala Leu Gly Ile Leu Ile Met Thr Trp Gly
            100                 105                 110

Asp Gly Leu Ala Ala Leu Ile Gly Gln Arg Phe Gly Thr His Lys Tyr
        115                 120                 125

Lys Val Phe Gly Thr Gln Lys Ser Trp Glu Gly Ser Leu Thr Met Met
    130                 135                 140

Phe Val Ser Tyr Phe Ile Ser Ile Leu Ile Leu Val Gly Thr Gln Gly
145                 150                 155                 160

Asn Ser Trp Gln Thr Trp Val Ile Ser Leu Ala Val Ala Phe Ile Ala
                165                 170                 175

Thr Val Leu Glu Ala Phe Ser Phe Leu Gly Ile Asp Asn Leu Thr Val
            180                 185                 190

Pro Leu Gly Ser Ala Ala Leu Ala Phe Phe Leu Ser Gln Leu Val Tyr
        195                 200                 205

Phe

<210> SEQ ID NO 25
<211> LENGTH: 239
<212> TYPE: PRT
<213> ORGANISM: Nostoc punctiforme

<400> SEQUENCE: 25

Met Thr Asn Asp Phe Ile Gly Leu Ala Ile Ser Tyr Ile Tyr Ala Ile
1               5                   10                  15

Ser Leu Leu Val Ile Gly Glu Gly Leu Arg Arg Leu Phe Gly Val Lys
            20                  25                  30

Pro Asp Leu Thr Arg Lys Ala Ile His Ile Gly Ala Gly Met Trp Val
        35                  40                  45
```

```
Phe Gly Val Leu Leu Leu Phe Asn Arg Trp Glu Ile Gly Ile Ile Pro
     50                  55                  60

Phe Ala Thr Phe Ile Gly Leu Asn Tyr Leu Phe Tyr Arg Tyr Arg Phe
 65                  70                  75                  80

Ile Gly Ala Met Asp Thr Gln Asp Ser Ser Pro Gly Thr Val Tyr Phe
                 85                  90                  95

Ala Ile Ser Val Thr Leu Leu Phe Gly Leu Leu Trp Arg Pro Asp Gly
            100                 105                 110

Pro Val Asp Ser Val Ala Ile Ala Val Ala Gly Ile Met Ala Met Thr
            115                 120                 125

Trp Gly Asp Ala Leu Ala Ala Leu Ile Gly Arg Arg Phe Gly Gln His
130                 135                 140

Lys Tyr Gln Val Gly Asn Ser Val Arg Ser Trp Glu Gly Ser Ala Ala
145                 150                 155                 160

Met Phe Val Ala Ser Thr Val Val Ile Phe Leu Val Leu Leu Leu Leu
                165                 170                 175

Pro Gly Ser Ser Leu Ser Pro Leu Gly Thr Pro Leu Ser Phe Gly Leu
                180                 185                 190

Ala Leu Leu Thr Ala Val Val Ala Ala Thr Phe Ala Thr Leu Ala Glu
            195                 200                 205

Ala Val Ser Pro His Gly Thr Asp Asn Leu Ser Val Pro Leu Val Thr
            210                 215                 220

Ala Gly Val Val Trp Val Ile Lys Gln Asn Leu His Leu Phe Phe
225                 230                 235

<210> SEQ ID NO 26
<211> LENGTH: 235
<212> TYPE: PRT
<213> ORGANISM: Nostoc sp.-pcc 7120

<400> SEQUENCE: 26

Met Leu Asn Leu Val Ser Glu Leu Ile Ser Thr Pro Pro Leu Trp Leu
 1               5                  10                  15

Gln Ile Thr Ile Val Ala Ala Trp Val Phe Phe Ile Leu Ala Ile Ala
             20                  25                  30

Gly Leu Val Asn Arg Phe Ala Thr Ser Asp Ser Glu Ile Val Arg Lys
         35                  40                  45

Ile Val His Ile Gly Ala Gly His Val Ile Leu Leu Ala Trp Trp Leu
     50                  55                  60

Asp Ile Pro Ala Ser Val Gly Ile Gly Ala Ser Val Ala Ser Ile
 65                  70                  75                  80

Val Thr Leu Leu Ser Tyr Ile Phe Pro Leu Pro Gly Ile Asn Ser
                 85                  90                  95

Val Gly Arg Gln Ser Leu Gly Thr Phe Phe Tyr Ala Val Ser Val Gly
            100                 105                 110

Ile Leu Val Ala Trp Phe Trp His Ile Gln Gln Pro Gln Tyr Ala Ala
            115                 120                 125

Ile Gly Met Met Val Met Ala Trp Gly Asp Gly Leu Ala Ala Leu Val
            130                 135                 140

Gly Gln Arg Phe Gly Lys His Lys Tyr Lys Leu Leu Gly Ala Gln Lys
145                 150                 155                 160

Ser Trp Glu Gly Ser Leu Thr Met Ala Leu Ala Ser Tyr Leu Val Cys
                165                 170                 175

Ser Leu Ile Leu Leu Gly Val Leu Gly Asn Val Trp Gln Thr Trp Leu
```

```
                180               185               190
Val Ser Leu Ala Val Ala Phe Val Ala Thr Ser Leu Glu Ala Phe Ser
        195               200               205

Leu Leu Gly Val Asp Asn Leu Thr Val Pro Leu Gly Ser Ala Ala Ile
    210               215               220

Ala Phe Ala Leu Ile Gln Phe Trp Pro Leu His
225               230               235

<210> SEQ ID NO 27
<211> LENGTH: 201
<212> TYPE: PRT
<213> ORGANISM: Prochlorococcus marinus-MIT9313

<400> SEQUENCE: 27

Met Leu Ser Ala Ala Val Val Cys Arg Val Arg Trp Pro Asn Gln Arg
1               5                   10                  15

Glu Leu Ser Arg Lys Ile Val His Ile Gly Thr Gly Pro Val Ile Pro
            20                  25                  30

Leu Ala Trp Trp Leu Gly Ile Pro Ser Asp Trp Ala Ile Pro Met Ala
        35                  40                  45

Ile Leu Ile Thr Ile Gly Ile Leu Ile Asn His Arg Trp Arg Leu Leu
    50                  55                  60

Pro Ala Ile Glu Asp Val Asn Arg His Ser Tyr Gly Thr Val Ala Tyr
65                  70                  75                  80

Ala Leu Thr Ile Thr Leu Leu Leu Ile Phe Phe Trp Pro Glu Asn Ala
                85                  90                  95

Ala Ala Val Cys Ser Gly Val Leu Val Met Ala Phe Gly Asp Gly Leu
            100                 105                 110

Ala Gly Leu Ile Gly Arg Lys Val Arg Ser Pro Asn Trp Leu Ile Trp
        115                 120                 125

Gly Gln Arg Lys Ser Ile Ala Gly Thr Leu Thr Met Ala Val Ile Thr
    130                 135                 140

Leu Ile Ile Leu Phe Thr Leu Ser Leu Leu Ile Asp Ala Ser Phe His
145                 150                 155                 160

Pro Leu Arg Ile Phe Ala Val Thr Gly Leu Ala Val Gly Leu Glu Gln
                165                 170                 175

Leu Ser Arg Trp Gly Ile Asp Asn Leu Thr Val Pro Ile Gly Val Ala
            180                 185                 190

Val Ala Trp Ser Trp Met Thr Ala Ile
        195                 200

<210> SEQ ID NO 28
<211> LENGTH: 217
<212> TYPE: PRT
<213> ORGANISM: Prochlorococcus marinus-CCMP-1375

<400> SEQUENCE: 28

Met Ile Asn Ala Tyr Ser Phe Ile Leu Ile Ser Gly Trp Leu Ile Ile
1               5                   10                  15

Val Leu Ser Thr Ser Tyr Phe Cys Asn Lys Leu Phe Pro Glu Glu Lys
            20                  25                  30

Glu Leu Ser Arg Lys Ile Val His Met Gly Ser Gly Pro Ile Ile Pro
        35                  40                  45

Leu Ala Tyr Trp Leu Asn Ile Ser Ala Gln Ile Ala Ile Pro Ile Ala
    50                  55                  60

Ser Val Ile Thr Leu Ala Leu Leu Ile Asn Tyr Arg Phe Lys Leu Leu
```

```
                65                  70                  75                  80
        Thr Ser Ile Glu Asn Ile Glu Arg Lys Ser Phe Gly Thr Ile Ala Tyr
                        85                  90                  95

Gly Ile Ser Ile Thr Leu Leu Ile Leu Phe Trp Thr Asp Asn Pro
                    100                 105                 110

Ser Ala Val Ile Ser Gly Val Leu Val Met Ala Phe Gly Asp Gly Leu
                    115                 120                 125

Ala Gly Phe Ile Gly Arg Lys Val Lys Ser Pro Gln Trp Ile Leu Phe
            130                 135                 140

Gly Gln Arg Lys Ser Leu Ile Gly Thr Leu Thr Met Gly Phe Val Ser
        145                 150                 155                 160

Ala Leu Ile Leu Thr Ile Val Asn Gln Ser Thr Ala Met Gln Leu Gly
                        165                 170                 175

Pro Ile Ala Ile Leu Ser Ile Thr Ser Ile Ala Val Ala Leu Glu Gln
                    180                 185                 190

Val Ser Thr Leu Gly Ile Asp Asn Ile Thr Val Pro Ile Gly Val Ala
                    195                 200                 205

Leu Ser Trp Gln Ile Met Ser Phe Arg
            210                 215

<210> SEQ ID NO 29
<211> LENGTH: 204
<212> TYPE: PRT
<213> ORGANISM: Rickettsia conorii

<400> SEQUENCE: 29

Met Glu Ile Lys Asp Phe Asp Phe Glu Lys Lys Arg Lys Ile Phe His
        1               5                   10                  15

Leu Ser Ala Ile Ile Phe Pro Leu Leu Tyr Leu Phe Ile Pro Arg Thr
                        20                  25                  30

Ala Met Thr Leu Leu Leu Phe Ile Ile Thr Ala Ile Thr Leu Tyr Leu
                    35                  40                  45

Asp Val Ser Arg His Asn Asn Ala Thr Ile Ser Glu Phe Val Thr Arg
            50                  55                  60

Phe Phe Ser Lys Val Ile Arg Leu Glu Glu Asn Asn Gly Ser Phe Ala
        65                  70                  75                  80

Leu Ser Gly Val Ser Phe Met Met Ile Gly Phe Leu Thr Ala Leu
                        85                  90                  95

Leu Phe Pro Lys Asn Leu Val Ile Cys Ser Trp Leu Ile Leu Ile Ile
                    100                 105                 110

Ser Asp Cys Leu Ala Ala Leu Val Gly Val Lys Ile Gly Asn Ser Leu
                    115                 120                 125

Gly Asn Gly Lys Ser Ile Ala Gly Ser Ile Thr Phe Leu Ala Ser Ala
            130                 135                 140

Ile Phe Ile Ser Ile Leu Val Tyr Phe Tyr Leu Gly Tyr Asn Thr Ser
        145                 150                 155                 160

Phe Ile Ile Ile Ile Ser Cys Ile Gly Ala Thr Val Ala Glu Phe
                        165                 170                 175

Tyr Ser Lys Asp Leu Arg Ile Asn Asp Asn Leu Ser Ile Pro Leu Ser
                    180                 185                 190

Tyr Cys Leu Ser Thr Ala Ile Leu Ser Tyr Ile Leu
                    195                 200

<210> SEQ ID NO 30
<211> LENGTH: 204
```

```
<212> TYPE: PRT
<213> ORGANISM: Rickettsia prowazekii

<400> SEQUENCE: 30

Met Lys Thr Glu Asp Phe Asp Ph

Ile Phe Ile Ser Ile Leu Val Tyr Phe Tyr Leu Gly Tyr Asn Thr Ser
145                 150                 155                 160

Phe Ile Ile Ile Ile Ser Cys Ile Gly Ala Thr Val Ala Glu Phe
            165                 170                 175

Tyr Ser Lys Asp Leu Arg Ile Asn Asp Asn Leu Ser Ile Pro Leu Ser
        180                 185                 190

Tyr Cys Leu Ser Thr Ala Ile Leu Ser Tyr Ile Leu
        195                 200

<210> SEQ ID NO 32
<211> LENGTH: 216
<212> TYPE: PRT
<213> ORGANISM: Synechococcus sp.-WH-8102

<400> SEQUENCE: 32

Met Val His Leu Ile Gly Pro Ile Ala Ile Ser Leu Trp Leu Gly Ile
1               5                   10                  15

Val Val Leu Ile Ala Val Leu Thr Arg Gln Arg Trp Pro Asp Gln Gln
            20                  25                  30

Glu Leu Ser Arg Lys Ile Ile His Ile Gly Thr Gly Ala Val Val Pro
        35                  40                  45

Leu Ala Trp Phe Phe Ala Ile Pro Ala Trp Ile Ala Val Pro Phe Ala
    50                  55                  60

Val Leu Val Thr Leu Ala Thr Ala Ile Asn His Arg Trp Arg Ile Val
65                  70                  75                  80

Pro Ala Val Glu Asp Val Asn Arg Asn Ser Tyr Gly Thr Val Ala Tyr
                85                  90                  95

Gly Leu Ala Ile Thr Met Leu Leu Ile Leu Cys Trp Pro Ala Arg Ala
            100                 105                 110

Asp Ala Val Cys Ala Gly Val Leu Val Met Ala Leu Gly Asp Gly Leu
        115                 120                 125

Ala Gly Leu Ile Gly Arg Ser Val Asn Ser Ala Arg Trp Thr Val Leu
    130                 135                 140

Gly Gln Thr Lys Ser Val Ala Gly Thr Leu Thr Met Ala Leu Val Ser
145                 150                 155                 160

Thr Leu Val Leu Val Gly Leu Met Leu Val Ser Gly Asn Ala Ile Gly
                165                 170                 175

Trp Arg Val Ala Leu Gly Ile Ser Thr Met Ala Thr Ala Leu Glu Gln
            180                 185                 190

Val Ser Pro Ala Gly Val Asp Asn Leu Ser Val Pro Leu Leu Val Gly
        195                 200                 205

Leu Thr Trp Val Leu Leu Ile Ser
    210                 215

<210> SEQ ID NO 33
<211> LENGTH: 214
<212> TYPE: PRT
<213> ORGANISM: Thermosynechococcus elongatus BP-1

<400> SEQUENCE: 33

Met Phe Trp Ala Gly Ile Trp Val Thr Gly Trp Leu Gly Leu Val Leu
1               5                   10                  15

Leu Ile Ala Glu Leu Ile His Ala Trp Phe Pro Asn Ala Lys Glu Trp
            20                  25                  30

Ser Arg Lys Val Val His Ile Gly Ala Gly Gln Val Ile Leu Ile Ala
        35                  40                  45

```
Tyr Ala Leu Gly Val Pro Thr Arg Trp Gly Ile Ile Ala Ala Ile
    50                  55                  60

Ala Gly Met Val Thr Leu Leu Ser Tyr Arg Val Ser Ile Phe Pro Ser
65              70                  75                  80

Ile Ser Gly Val Gly Arg Gln Ser Trp Gly Thr Phe Phe Tyr Ala Val
                85                  90                  95

Ser Ile Gly Ile Leu Met Ala Leu Phe Trp Lys Thr Leu Pro Glu Leu
                100                 105                 110

Ala Val Leu Gly Ile Leu Val Met Ala Trp Gly Asp Gly Leu Ala Ala
            115                 120                 125

Leu Val Gly Ile His Trp Gly Arg His Pro Leu Pro Gly Thr Ser Lys
    130                 135                 140

Ser Trp Glu Gly Thr Leu Thr Met Phe Trp Val Ser Thr Leu Val Ala
145                 150                 155                 160

Ala Leu Ser Leu Thr Pro Ile Ala Ala Leu Glu Ser Leu Trp Ile Ala
                165                 170                 175

Pro Phe Val Gly Val Gly Ala Thr Leu Leu Glu Leu Ile Ala Trp Arg
            180                 185                 190

Gly Met Asp Asn Leu Thr Val Pro Ile Gly Ser Ala Leu Leu Ala Tyr
    195                 200                 205

Gly Leu Leu Asn Leu Ser
    210

<210> SEQ ID NO 34
<211> LENGTH: 244
<212> TYPE: PRT
<213> ORGANISM: Trichodesmium erythraeum-IMS101

<400> SEQUENCE: 34

Met Tyr Ile Leu Leu Leu Asn Ala Ile Leu Phe Ser Phe Leu Ile
1               5                   10                  15

Val Ser Ile Ile Ser Thr Phe Pro Asn Ile Trp Leu Gln Val Phe Leu
                20                  25                  30

Val Gly Gly Trp Leu Gly Ile Ile Leu Ile Phe Ala Glu Ala Leu Asn
            35                  40                  45

Arg Phe Ala Lys Val Asp Pro Glu Ile Ser Arg Lys Val His Ile
    50                  55                  60

Gly Thr Gly Asn Val Ile Leu Phe Ala Trp Trp Leu Glu Ile Pro Pro
65              70                  75                  80

Trp Ile Gly Ile Thr Ala Gly Ile Ile Ser Ala Ile Ala Leu Ile
                85                  90                  95

Ser Tyr Arg Leu Pro Ile Leu Pro Ser Val Asn Ser Val Gly Arg Lys
            100                 105                 110

Ser Leu Gly Thr Phe Phe Tyr Ala Val Ser Ile Gly Ile Leu Ile Gly
            115                 120                 125

Trp Phe Trp Ser Ile Gln Gln Pro Gln Tyr Ala Ala Ile Gly Ile Leu
    130                 135                 140

Thr Met Ala Trp Gly Asp Gly Phe Ala Ala Ile Ile Gly Gln Asn Phe
145                 150                 155                 160

Gly Lys His Pro Tyr Gln Val Trp Gly Met Asn Lys Ser Trp Glu Gly
            165                 170                 175

Ser Leu Gly Met Cys Leu Val Ser Tyr Thr Val Cys Ser Leu Ile Leu
            180                 185                 190

Leu Ala Val Gln Gly Asn Ile Trp Gln Thr Trp Ile Val Ala Ile Pro
    195                 200                 205
```

```
Val Ala Leu Ala Ala Thr Ala Leu Glu Thr Leu Ser Lys Val Gly Leu
        210                 215                 220

Asp Asn Leu Thr Val Pro Leu Gly Ser Ala Ala Leu Cys Phe Phe Leu
225                 230                 235                 240

Asn Gln Phe Phe

<210> SEQ ID NO 35
<211> LENGTH: 519
<212> TYPE: PRT
<213> ORGANISM: Saccharomyces cerevisiae

<400> SEQUENCE: 35

Met Val Ala Ile Ile Pro His Ala Ser Phe Thr Thr Ile Lys Leu Thr
1               5                   10                  15

Gln Lys Thr Glu Gly Ser Gln Met Pro Thr Glu Ile Cys Lys Ile
            20                  25                  30

Asn Met Arg Thr Arg Lys Phe Asp Val Gly Gly Asn Ser Arg Asp Phe
            35                  40                  45

Glu Cys Phe Tyr Ser Asn Phe Val Gln Thr Val Ile Leu Leu Gly Thr
    50                  55                  60

Phe Phe Tyr Cys Val Glu Arg Leu Gln Pro Trp Ser Ile Val Thr Ala
65              70                  75                  80

Asp Ile Ser Tyr Lys Gln Ile Phe Val Asn Val Phe Val Cys Leu
                85                  90                  95

Ile Met Val Gly Leu Ile Phe Thr Lys Tyr Trp Gln His Gly Tyr Lys
            100                 105                 110

Ser Leu Pro Lys Phe Asp Thr Ile Tyr Ser Leu Tyr Leu Pro Phe Met
        115                 120                 125

Val Ser Leu Leu Phe Asp Thr Ser Ser Thr Val Ile Asn Thr Ile Leu
130                 135                 140

Ile Leu Ser Val Leu Asn Ser Tyr Arg Trp Arg Thr Gln Leu Val Val
145                 150                 155                 160

Ile Ile Leu Gln Leu Cys Leu Ile Phe Phe Asn Phe Glu Ala Gly Asp
                165                 170                 175

Arg Leu Lys Asn Ile Ile Ser Ile Val Ile Asn Ser Leu Leu Ser Leu
            180                 185                 190

Ile Leu Lys Tyr Ile Gly Gln Leu Lys Ser Leu Asp Asn Ile Asp Ser
        195                 200                 205

Asn Leu Phe Ser Ile Leu Leu Thr Asn Ile Leu Tyr Val Ser Glu Ala
    210                 215                 220

Gly Thr Val His Phe Arg Ile Leu Lys Gly Ile Ile Leu Ala Leu Thr
225                 230                 235                 240

Thr Ile Ile Ser Ile Asn Tyr Val Leu Lys Lys Val Met His Phe Lys
                245                 250                 255

Pro Phe Met Leu Ser Ile Ser Phe Ala Ile Gly Leu Pro Leu Phe Ala
            260                 265                 270

Asn Thr Phe Ile His Leu Glu Asp Gly Glu Asn Pro Leu Leu Trp Leu
        275                 280                 285

Val Lys Tyr Ile Leu Glu Ser Thr Ile Arg Gln Lys Ile Leu Phe Ala
    290                 295                 300

Trp Ser Ser Ile Leu Ile Leu Ser Ile Pro Ser Ile Leu Ile Glu Lys
305                 310                 315                 320

Asp Ser Leu Ser Leu Asn Thr Ser Arg Lys Leu Trp His Phe Ile Ile
                325                 330                 335
```

```
Phe Leu Leu Ile Ile Pro Ser Phe Gln Met Asp Ser Asn Phe Val Lys
                340                 345                 350

Ile Ala Leu Ser Gly Thr Ile Pro Val Phe Leu Ser Ile Glu Tyr Ile
            355                 360                 365

Arg Phe Gln Asn Leu Pro Pro Leu Gly Ser Ala Ile Glu Leu Gln Leu
        370                 375                 380

Arg Arg Phe Ala Asp Asp Arg Asp His Ser Gly Pro Leu Ile Ile Ser
385                 390                 395                 400

Tyr Leu Tyr Leu Leu Phe Gly Ile Ser Thr Pro Leu Leu Met Asn Asn
                405                 410                 415

Ser Pro Met Gly Leu Ile Gly Leu Gly Ile Gly Asp Ser Leu Ala Ser
            420                 425                 430

Ile Ile Gly Lys Arg Tyr Gly Arg Ile Arg Trp Lys Gly Thr Gln Lys
        435                 440                 445

Thr Leu Glu Gly Thr Leu Ala Phe Ile Val Thr Ser Phe Ile Val Cys
    450                 455                 460

Leu Val Leu Leu Arg Phe Asp Lys Ala Ala Ile Phe Asn His Leu Thr
465                 470                 475                 480

Thr Leu Gln Leu Leu Thr Leu Cys Thr Leu Ser Gly Val Leu Glu Gly
                485                 490                 495

Asn Ser Val Leu Asn Asp Asn Ile Leu Ile Pro Ala Phe Met Met Ile
            500                 505                 510

Cys Glu Lys Leu Ile Thr Leu
        515
```

<210> SEQ ID NO 36
<211> LENGTH: 290
<212> TYPE: PRT
<213> ORGANISM: Saccharomyces cerevisiae

<400> SEQUENCE: 36

```
Met Gly Thr Glu Asp Ala Ile Ala Leu Pro Asn Ser Thr Leu Glu Pro
1               5                   10                  15

Arg Thr Glu Ala Lys Gln Arg Leu Ser Ser Lys Ser His Gln Val Ser
            20                  25                  30

Ala Lys Val Thr Ile Pro Ala Lys Glu Glu Ile Ser Ser Ser Asp Asp
        35                  40                  45

Asp Ala His Val Pro Val Thr Glu Ile His Leu Lys Ser His Glu Trp
    50                  55                  60

Phe Gly Asp Phe Ile Thr Lys His Glu Ile Pro Arg Lys Val Phe His
65                  70                  75                  80

Ser Ser Ile Gly Phe Ile Thr Leu Tyr Leu Tyr Thr Gln Gly Ile Asn
                85                  90                  95

Tyr Lys Asn Val Leu Trp Pro Leu Ile Tyr Ala Phe Ile Ile Leu Phe
            100                 105                 110

Ile Leu Asp Leu Ile Arg Leu Asn Trp Pro Phe Phe Asn Met Leu Tyr
        115                 120                 125

Cys Arg Thr Val Gly Ala Leu Met Arg Lys Glu Ile His Thr Tyr
    130                 135                 140

Asn Gly Val Leu Trp Tyr Ile Leu Gly Leu Ile Phe Ser Phe Asn Phe
145                 150                 155                 160

Phe Ser Lys Asp Val Thr Leu Ile Ser Leu Phe Leu Ser Trp Ser
                165                 170                 175

Asp Thr Ala Ala Ala Thr Ile Gly Arg Lys Tyr Gly His Leu Thr Pro
```

```
                  180                 185                 190
Lys Val Ala Arg Asn Lys Ser Leu Ala Gly Ser Ile Ala Ala Phe Thr
            195                 200                 205
Val Gly Val Ile Thr Cys Trp Val Phe Tyr Gly Tyr Phe Val Pro Ala
            210                 215                 220
Tyr Ser Tyr Val Asn Lys Pro Gly Glu Ile Gln Trp Ser Pro Glu Thr
225                 230                 235                 240
Ser Arg Leu Ser Leu Asn Met Leu Ser Leu Leu Gly Gly Val Ala
                245                 250                 255
Ala Leu Ser Glu Gly Ile Asp Leu Phe Asn Trp Asp Asp Asn Phe Thr
            260                 265                 270
Ile Pro Val Leu Ser Ser Leu Phe Met Asn Ala Val Ile Lys Thr Phe
            275                 280                 285
Lys Lys
    290

<210> SEQ ID NO 37
<211> LENGTH: 288
<212> TYPE: PRT
<213> ORGANISM: Allium porrum

<400> SEQUENCE: 37

Thr Gly Pro Pro Leu Val Pro Leu Thr Pro His Leu Thr Thr Val Lys
1               5                   10                  15
Ser Thr Asn Thr Thr Val Thr Thr Arg Pro Ala Asn Phe Pro Thr Arg
            20                  25                  30
Ile His Ile Asp Arg Ser Ala Ala Lys Leu Ser Leu Arg Asn Gln Trp
        35                  40                  45
Ser Leu Thr Ala Ser Ile Leu Pro Val Asn Pro Leu Ala Gln Asp Ala
    50                  55                  60
Cys Ala Ala Val Ile Thr Ala Gly Ala Ala Leu Gly Leu Leu Arg Phe
65                  70                  75                  80
Phe Glu Glu Leu Ala Lys Arg Gln Thr Phe Asp Gln Lys Leu Asn Arg
                85                  90                  95
Lys Leu Val His Ile Leu Val Gly Leu Val Phe Met Leu Phe Trp Pro
            100                 105                 110
Ile Phe Ser Ser Glu Trp Gln Ala Pro Leu Leu Ala Ala Leu Ala Pro
            115                 120                 125
Gly Ile Asn Ile Phe Arg Met Leu Phe Met Gly Leu Gly Ile Ile Lys
        130                 135                 140
Asn Glu Ala Met Val Gln Ser Ile Ser Arg His Gly Asp Tyr Arg Glu
145                 150                 155                 160
Leu Leu Lys Gly Pro Leu Tyr Tyr Ala Cys Thr Ile Thr Leu Ala Thr
                165                 170                 175
Ser Val Phe Trp Arg Thr Ser Pro Val Gly Met Ala Ala Val Cys Asn
            180                 185                 190
Leu Cys Ala Gly Asp Gly Leu Ala Asp Ile Ile Gly Arg Arg Phe Gly
            195                 200                 205
Lys His Lys Leu Thr Tyr Asn Pro Asp Lys Ser Ile Glu Gly Ser Ala
        210                 215                 220
Ala Met Ala Leu Ala Gly Phe Val Ala Ser Val Leu Tyr Met His Tyr
225                 230                 235                 240
Phe Ala Ile Phe Gly Phe Ile Glu Glu Ser Leu Gly Met Val Val Arg
                245                 250                 255
```

```
Phe Phe Leu Leu Ser Phe Ala Ser Ala Val Val Glu Ser Leu Pro Ile
            260                 265                 270

Ser Ser Glu Leu Asp Asp Asn Leu Thr Val Pro Leu Thr Ser Pro Arg
        275                 280                 285
```

<210> SEQ ID NO 38
<211> LENGTH: 289
<212> TYPE: PRT
<213> ORGANISM: Brassica napus

<400> SEQUENCE: 38

```
Asp Ser Ser Cys Phe Phe Ser Pro Ile Pro Arg Phe Leu Thr Leu
1               5                   10                  15

Arg Ile Ala Thr Thr Thr Ala Leu Arg Ser Ala Ala Thr Phe Thr Leu
            20                  25                  30

Arg Arg Ser Pro Ser His Arg Ser Leu Thr Pro Ser Leu Ala Val Met
        35                  40                  45

Phe Pro Asp Asn Ser Val Leu Ser Asp Val Cys Ala Ser Gly Ile Thr
    50                  55                  60

Ser Val Val Ala Val Ser Cys Leu Gly Phe Trp Gly Glu Ile Gly Lys
65                  70                  75                  80

Arg Gly Phe Phe Asp Gln Lys Leu Ile Arg Lys Leu Val His Ile Asn
                85                  90                  95

Ile Gly Leu Val Phe Met Leu Cys Trp Pro Leu Phe Ser Ser Gly Arg
            100                 105                 110

Gln Gly Ala Leu Leu Ala Ser Leu Val Pro Gly Leu Asn Ile Val Arg
        115                 120                 125

Met Leu Leu Leu Gly Leu Gly Val Tyr Gln Asp Glu Gly Thr Ile Lys
130                 135                 140

Ser Met Ser Arg His Gly Asp Arg Arg Glu Leu Leu Lys Gly Pro Leu
145                 150                 155                 160

Tyr Tyr Ala Leu Ser Ile Thr Ser Ala Cys Phe Phe Tyr Trp Lys Thr
                165                 170                 175

Ser Pro Ile Ala Ile Ala Val Ile Cys Asn Leu Cys Ala Gly Asp Gly
            180                 185                 190

Met Ala Asp Ile Val Gly Arg Arg Leu Gly Thr Glu Lys Leu Pro Tyr
        195                 200                 205

Asn Arg Asn Lys Ser Leu Ala Gly Ser Ile Gly Met Ala Ile Ala Gly
    210                 215                 220

Phe Leu Ala Ser Val Gly Tyr Met Tyr Tyr Phe Ser Ser Phe Gly Tyr
225                 230                 235                 240

Met Glu Ser Thr Gly Trp Asp Met Ile Leu Arg Phe Leu Val Ile Ser
                245                 250                 255

Ile Ala Ser Ala Leu Ile Glu Ser Leu Pro Ile Ser Thr Asp Ile Asp
            260                 265                 270

Asp Asn Leu Thr Ile Pro Leu Thr Ser Ala Leu Val Gly Thr Leu Leu
        275                 280                 285

Phe
```

<210> SEQ ID NO 39
<211> LENGTH: 304
<212> TYPE: PRT
<213> ORGANISM: Brassica napus

<400> SEQUENCE: 39

Met Ala Ala Ala Leu Pro Leu Ser Pro Val Ser His Gln Leu Cys Arg

```
              1               5                  10                 15
Ile Ser Asn Arg Phe Trp Tyr Asn Ala Met Thr Pro Arg Phe Cys Ser
                    20                  25                  30

Pro Val Ser Ser Pro Cys Tyr Ile Gly Val Lys Gly Ile Gly Ser Ser
                35                  40                  45

Ser Gln Leu Arg Ala Arg His Pro Leu Ile Ser Ser Ala Ala Ser Thr
        50                  55                  60

Asp Tyr Leu Leu His Asp Val Gly Ala Thr Val Ala Val Leu Ser Gly
65                  70                  75                  80

Ala Tyr Ala Leu Val Leu Leu Phe Glu Ser Leu Thr Lys Arg Asp Val
                    85                  90                  95

Ile Pro Gln Arg Leu Ser Arg Lys Leu Val His Ile Leu Ser Gly Leu
                100                 105                 110

Leu Phe Ala Leu Ser Trp Pro Ile Phe Ser Ala Ser Thr Glu Ala Arg
                115                 120                 125

Tyr Phe Ala Ala Phe Val Pro Leu Val Asn Gly Leu Arg Leu Val Val
                130                 135                 140

Asn Gly Leu Ser Val Ser Pro Asn Ser Thr Leu Ile Gln Ser Val Thr
145                 150                 155                 160

Arg Glu Gly Arg Pro Glu Leu Leu Lys Gly Pro Leu Phe Tyr Val
                    165                 170                 175

Leu Ala Leu Leu Val Ala Ala Val Phe Phe Trp Arg Asp Ser Pro Thr
                180                 185                 190

Gly Met Ile Ser Leu Ala Met Met Cys Gly Gly Asp Gly Ile Ala Asp
                195                 200                 205

Ile Met Gly Arg Lys Tyr Gly Ser Tyr Lys Ile Pro Tyr Asn Pro Arg
            210                 215                 220

Lys Ser Leu Ala Gly Ser Ile Ser Met Phe Ile Phe Gly Phe Phe Ile
225                 230                 235                 240

Ser Ile Gly Leu Leu Tyr Tyr Tyr Ser Ser Leu Gly Tyr Leu His Met
                    245                 250                 255

Asn Trp Glu Thr Thr Phe Thr Arg Val Ala Ile Val Ser Leu Val Ala
                260                 265                 270

Thr Leu Val Glu Ser Leu Pro Ile Thr Asp Gln Ile Asp Asp Asn Val
                275                 280                 285

Ser Val Pro Leu Ala Thr Ile Leu Ala Ala Tyr Leu Ser Phe Gly Tyr
                290                 295                 300

<210> SEQ ID NO 40
<211> LENGTH: 240
<212> TYPE: PRT
<213> ORGANISM: Gossypium hirsutum-LIB3165

<400> SEQUENCE: 40

Met Leu Tyr Glu Asn Ser Leu Val Ser Asp Leu Phe Ala Ala Val Val
1               5                   10                  15

Cys Cys Gly Val Ile Phe Ala Phe Leu Leu Leu Trp Gln Val Thr Ala
                20                  25                  30

Lys Cys Gly Val Asp Gln Lys Leu Asn Arg Lys Leu Val His Ile Ser
            35                  40                  45

Ile Gly Leu Val Phe Met Leu Cys Trp Pro Leu Phe Ser Ala Gly Tyr
        50                  55                  60

Arg Gly Ala Ile Leu Ala Ala Ile Thr Pro Gly Val Asn Ile Ile Arg
65                  70                  75                  80
```

-continued

```
Met Leu Leu Ile Gly Ser Gly Ile Trp Lys Asp Glu Ala Thr Val Lys
                85                  90                  95

Ser Met Ser Arg Tyr Gly Asn Tyr Arg Glu Leu Leu Lys Gly Pro Leu
            100                 105                 110

Tyr Tyr Ala Ile Thr Val Thr Leu Ala Cys Val Val Tyr Trp Arg Thr
        115                 120                 125

Ser Pro Ile Gly Ile Ala Ala Leu Cys Asn Leu Cys Ala Gly Asp Gly
130                 135                 140

Leu Ala Asp Val Val Gly Arg Leu Gly Arg Lys Lys Leu Pro Tyr
145                 150                 155                 160

Asn Arg Asn Lys Ser Val Ala Gly Ser Val Ala Met Ala Thr Ala Gly
                165                 170                 175

Phe Leu Ser Ser Val Gly Tyr Met Tyr Tyr Phe Ser Tyr Phe Gly Tyr
            180                 185                 190

Ile Gln Glu Gly Trp Gly Met Ile Leu Arg Phe Leu Val Val Ser Leu
        195                 200                 205

Ala Ser Ala Leu Val Glu Ser Leu Pro Ile Ser Thr Glu Leu Asp Asp
210                 215                 220

Asn Leu Thr Val Ser Leu Thr Ser Ile Phe Ile Gly Ser Leu Ile Phe
225                 230                 235                 240

<210> SEQ ID NO 41
<211> LENGTH: 298
<212> TYPE: PRT
<213> ORGANISM: Gossypium hirsutum

<400> SEQUENCE: 41

Met Ser Leu Ser Leu Ser Phe Thr His Pro Ile Leu Ser Arg His Val
1               5                   10                  15

Tyr Ser Ala Val Phe Pro Pro Arg Phe Leu Phe Leu Ser Pro Leu
            20                  25                  30

Ile Pro Thr Thr Ser Arg Phe Pro Ile Leu Tyr Arg Ala Pro Gln Arg
        35                  40                  45

Ala Thr Ala Leu Ser Ala Thr Ala Val Thr Ala Ser Ile Phe Arg Asp
50                  55                  60

Thr Ala Ala Ser Ala Ser Val Phe Ala Gly Ala Tyr Ala Leu Val Phe
65                  70                  75                  80

Thr Phe Asp Ile Leu Thr Gln Lys Glu Leu Ile Gln Gln Asn Leu Ser
                85                  90                  95

Arg Lys Leu Val His Ile Leu Ser Gly Leu Leu Phe Ala Ile Ser Trp
            100                 105                 110

Pro Ile Phe Ser Asn Ala Asp Glu Ala Arg Tyr Phe Ala Ser Leu Val
        115                 120                 125

Pro Leu Phe Asn Cys Leu Arg Leu Val Ile His Gly Leu Ser Leu Thr
130                 135                 140

Asp Asp Gln Ser Leu Ile Lys Ser Val Thr Arg Glu Gly Asn Pro Lys
145                 150                 155                 160

Glu Leu Leu Arg Gly Pro Leu Tyr Tyr Val Ala Met Leu Met Leu Cys
                165                 170                 175

Ala Leu Val Phe Trp Arg Glu Ser Pro Val Gly Val Ile Cys Leu Ala
            180                 185                 190

Met Met Cys Gly Gly Asp Gly Val Ala Asp Ile Ile Gly Arg Lys Tyr
        195                 200                 205

Gly Ser Ser Lys Ile Pro Tyr Asn Gln Ser Lys Ser Trp Val Gly Ser
210                 215                 220
```

-continued

Ile Ser Met Phe Val Ser Gly Phe Ile Ile Ser Ile Gly Met Leu Tyr
225                 230                 235                 240

Tyr Tyr Ser Ala Leu Gly Tyr Leu Gln Leu Asp Trp Gly Tyr Thr Leu
            245                 250                 255

His Arg Val Ala Phe Ile Ser Leu Val Ala Thr Val Val Glu Ser Leu
            260                 265                 270

Pro Ile Ser Met Leu Ile Asp Asp Asn Ile Ser Val Pro Leu Ala Ser
            275                 280                 285

Met Leu Ala Ala Tyr Leu Thr Phe Gly His
        290                 295

<210> SEQ ID NO 42
<211> LENGTH: 318
<212> TYPE: PRT
<213> ORGANISM: Glycine max

<400> SEQUENCE: 42

Met Met Phe Leu Ser Phe Asn Met Ile Ser Gly Gly Asn Thr Leu Gln
1               5                   10                  15

Arg Phe Asp Pro Val Ala Cys Val Ser Ser Val Pro Leu Leu Leu Ala
            20                  25                  30

Pro Thr Thr Arg Pro Thr Phe His Phe Pro Ser Pro Phe Leu Ser Lys
        35                  40                  45

Pro Lys Pro Thr Tyr Leu Phe Thr Ser Phe Ser Ser Ser Ser Ser Ser
    50                  55                  60

Ser Ser Ser Phe Phe Ser Ser Thr Thr Pro Pro Arg Ser Thr Met Leu
65                  70                  75                  80

His His Asp Pro Leu Val Ser Asp Val Tyr Ala Thr Ala Ile Ser Gly
                85                  90                  95

Val Val Ala Leu Ser Phe Leu Arg Leu Phe Gln Glu Thr Ala Lys Arg
            100                 105                 110

Asp Leu Phe Asp Gln Lys Leu Asn Arg Lys Leu Val His Ile Ser Ile
        115                 120                 125

Gly Leu Ile Phe Met Leu Cys Pro Leu Phe Ser Thr Glu Thr Trp Ala
    130                 135                 140

Ser Phe Ala Ala Leu Ile Pro Gly Ile Asn Ile Phe Arg Met Leu
145                 150                 155                 160

Val Ile Gly Leu Gly Ile Leu Lys Asp Glu Ala Thr Val Lys Ser Met
                165                 170                 175

Ser Arg Phe Gly Asp Tyr Arg Glu Leu Leu Lys Gly Pro Leu Tyr Tyr
            180                 185                 190

Ala Ala Thr Ile Thr Leu Ala Ala Ile Ile Tyr Trp Arg Thr Ser Pro
        195                 200                 205

Ile Ser Ile Ala Ala Ile Cys Asn Leu Cys Ala Gly Asp Gly Met Ala
    210                 215                 220

Asp Ile Val Gly Arg Arg Leu Gly Gly Glu Lys Ile Pro Tyr Asn Lys
225                 230                 235                 240

Asn Lys Ser Phe Ala Gly Ser Ile Ala Met Ala Thr Ala Gly Phe Leu
                245                 250                 255

Thr Ser Ile Gly Tyr Met Trp Tyr Phe Ser Ser Phe Gly Phe Ile Glu
            260                 265                 270

Gly Ser Trp Lys Leu Val Leu Gly Phe Leu Leu Val Ser Ile Val Thr
        275                 280                 285

Ala Phe Val Glu Ser Leu Pro Ile Ser Thr Glu Leu Asp Asp Asn Leu

```
            290                 295                 300
Thr Val Pro Leu Thr Ser Ile Leu Val Gly Ser Ile Ile Leu
305                 310                 315
```

<210> SEQ ID NO 43
<211> LENGTH: 319
<212> TYPE: PRT
<213> ORGANISM: Glycine max
<220> FEATURE:
<221> NAME/KEY: misc_feature
<222> LOCATION: (158)..(158)
<223> OTHER INFORMATION: Xaa can be any naturally occurring amino acid

<400> SEQUENCE: 43

```
Met Met Phe Leu Ser Phe Asn Met Ile Ser Gly Gly Asn Thr Leu Gln
1               5                  10                  15

Arg Phe Asp Pro Val Ala Cys Val Ser Ser Val Pro Leu Leu Leu Ala
            20                  25                  30

Pro Thr Thr Arg Pro Thr Phe His Phe Pro Ser Pro Phe Leu Ser Lys
        35                  40                  45

Pro Lys Pro Thr Tyr Leu Phe Thr Ser Phe Ser Ser Ser Ser Ser
50                  55                  60

Ser Ser Ser Phe Phe Ser Ser Thr Thr Pro Pro Arg Ser Thr Met Leu
65                  70                  75                  80

His His Asp Pro Leu Val Ser Asp Val Tyr Ala Thr Ala Ile Ser Gly
                85                  90                  95

Val Val Ala Leu Ser Phe Leu Arg Leu Phe Gln Glu Thr Ala Lys Arg
            100                 105                 110

Asp Leu Phe Asp Gln Lys Leu Asn Arg Lys Leu Val His Ile Ser Ile
        115                 120                 125

Gly Leu Ile Phe Met Leu Cys Trp Pro Leu Phe Ser Thr Glu Thr Trp
    130                 135                 140

Ala Ser Phe Phe Ala Ala Leu Ile Pro Gly Ile Asn Ile Xaa Arg Met
145                 150                 155                 160

Leu Val Ile Gly Leu Gly Ile Leu Lys Asp Glu Ala Thr Val Lys Ser
                165                 170                 175

Met Ser Arg Phe Gly Asp Tyr Arg Glu Leu Leu Lys Gly Pro Leu Tyr
            180                 185                 190

Tyr Ala Ala Thr Ile Thr Leu Ala Ala Ile Ile Tyr Trp Arg Thr Ser
        195                 200                 205

Pro Ile Ser Ile Ala Ala Ile Cys Asn Leu Cys Ala Gly Asp Gly Met
    210                 215                 220

Ala Asp Ile Val Gly Arg Arg Leu Gly Gly Glu Lys Ile Pro Tyr Asn
225                 230                 235                 240

Lys Asn Lys Ser Phe Ala Gly Ser Ile Ala Met Ala Thr Ala Gly Phe
                245                 250                 255

Leu Thr Ser Ile Gly Tyr Met Trp Tyr Phe Ser Ser Phe Gly Phe Ile
            260                 265                 270

Glu Gly Ser Trp Lys Leu Val Leu Gly Phe Leu Leu Val Ser Ile Val
        275                 280                 285

Thr Ala Phe Val Glu Ser Leu Pro Ile Ser Thr Glu Leu Asp Asp Asn
    290                 295                 300

Leu Thr Val Pro Leu Thr Ser Ile Leu Val Gly Ser Ile Ile Leu
305                 310                 315
```

<210> SEQ ID NO 44

<211> LENGTH: 292
<212> TYPE: PRT
<213> ORGANISM: Glycine max
<220> FEATURE:
<221> NAME/KEY: misc_feature
<222> LOCATION: (148)..(148)
<223> OTHER INFORMATION: Xaa can be any naturally occurring amino acid

<400> SEQUENCE: 44

```
Met Ala Ala Ala Ala Trp Thr Gly Ala Ser Pro Asn Ser Leu
1               5                   10                  15

Leu Leu Ser Arg Ser Pro Pro His Ala Ala Leu Ala Pro Ser Pro
                20                  25                  30

Gly Ser Ser Met Arg Arg Arg Leu Leu Leu Gly Val Gly Thr Pro Ala
            35                  40                  45

Val Ala Ala Leu Ala Ala Ala Pro Pro Ala Val Leu Gln Asp Gly
        50                  55                  60

Ala Val Thr Val Leu Ile Thr Ala Gly Ala Tyr Ser Leu Val Arg Val
65                  70                  75                  80

Phe Asp Glu Leu Thr Glu Arg Arg Leu Ile Glu Lys Ser Leu Ser Arg
                85                  90                  95

Lys Val Val His Val Leu Ser Gly Val Leu Phe Met Ser Ser Trp Pro
                100                 105                 110

Leu Phe Ser Asn Ser Thr Glu Ala Arg Tyr Phe Ala Ala Val Val Pro
                115                 120                 125

Phe Leu Asn Ser Met Arg Leu Leu Ile Tyr Gly Leu Arg Leu Tyr Thr
            130                 135                 140

Asp Glu Ala Xaa Glu Leu Leu Arg Gly Pro Leu Tyr Tyr Val Leu Val
145                 150                 155                 160

Leu Leu Phe Ser Val Leu Val Phe Trp Arg Glu Ser Pro Ile Gly Ile
                165                 170                 175

Val Ser Leu Ser Met Met Ser Gly Gly Asp Gly Phe Ala Asp Ile Val
                180                 185                 190

Gly Arg Arg Tyr Gly Ser Ala Lys Leu Pro Phe Asn Arg Lys Lys Ser
            195                 200                 205

Trp Ala Gly Ser Ile Ser Met Phe Ile Ser Gly Phe Leu Leu Ser Ala
210                 215                 220

Met Met Met Leu Tyr Phe Ser Ser Leu Gly Tyr Ile Asp Val Ile Trp
225                 230                 235                 240

Glu Glu Ala Leu Gly Lys Leu Ala Leu Val Ala Leu Ala Ala Thr Val
                245                 250                 255

Val Glu Cys Val Pro Val Thr Glu Val Val Asp Asp Asn Ile Ser Val
                260                 265                 270

Pro Leu Ala Thr Met Leu Val Ala Phe Leu Leu Phe Ser Ser Asn Arg
            275                 280                 285

Thr Ile Val Asn
        290
```

<210> SEQ ID NO 45
<211> LENGTH: 302
<212> TYPE: PRT
<213> ORGANISM: Glycine max

<400> SEQUENCE: 45

```
Met Thr Leu Leu Ser Ser His Leu Leu Val Phe Ser Ala Val His His
1               5                   10                  15

Arg Ala Pro Pro Thr Thr Thr Thr Arg Asn Ser Pro Thr Thr Asn His
```

-continued

```
                    20                  25                  30
Thr Val Arg Phe Leu Cys Ser Pro Gly Val Pro Ala Val Arg Leu
         35                  40                  45
Asp Gln Arg Leu Pro Arg Phe Val Pro Gly Ala Gly Ala Glu Asp
 50                  55                  60
Leu Leu Tyr Asn Ala Gly Ala Thr Val Gly Val Leu Gly Gly Tyr
 65                  70                  75                  80
Ala Leu Val Arg Ala Phe Asp Glu Leu Thr Arg Arg Asn Ile Leu Gln
                 85                  90                  95
Gln Gly Leu Ser Arg Lys Leu Val His Ile Leu Ser Gly Leu Leu Phe
            100                 105                 110
Leu Val Ser Trp Pro Ile Phe Ser Asn Ser Pro Lys Ala Arg Tyr Phe
            115                 120                 125
Ala Ala Phe Val Pro Leu Val Asn Cys Leu Arg Leu Leu Val Asn Gly
            130                 135                 140
Leu Ser Leu Ala Ser Asp Glu Gly Leu Ile Lys Ser Val Thr Arg Glu
145                 150                 155                 160
Gly Asp Pro Leu Glu Leu Leu Arg Gly Pro Leu Tyr Tyr Val Leu Ile
                165                 170                 175
Leu Ile Leu Ser Ala Leu Val Phe Trp Arg Glu Ser Pro Ile Gly Val
            180                 185                 190
Ile Ser Leu Ala Met Met Cys Ala Gly Asp Gly Ile Ala Asp Ile Ile
            195                 200                 205
Gly Arg Arg Tyr Gly Ser Met Lys Ile Pro Tyr Asn Glu His Lys Ser
            210                 215                 220
Leu Ala Gly Ser Met Ser Met Leu Val Phe Gly Phe Leu Val Ser Ile
225                 230                 235                 240
Gly Met Leu Tyr Tyr Tyr Ser Val Leu Gly His Val Gln Leu Asp Trp
                245                 250                 255
Ala Ser Thr Leu Pro Arg Val Ala Phe Ile Ser Phe Val Ala Thr Leu
            260                 265                 270
Val Glu Ser Leu Pro Ile Thr Lys Val Val Asp Asp Asn Ile Ser Val
            275                 280                 285
Pro Leu Ala Thr Met Ala Val Ala Phe Phe Thr Phe His His
            290                 295                 300

<210> SEQ ID NO 46
<211> LENGTH: 314
<212> TYPE: PRT
<213> ORGANISM: Oryza sativa

<400> SEQUENCE: 46

Met Ala Ala Ala Ala Arg Pro Val Asp Val Arg His Phe Pro Cys
 1               5                  10                  15
Ser Ser Ser Val Ala Ala Ser Ser Ser Leu Leu Leu Ser Arg Ser Lys
                 20                  25                  30
Ser Arg Leu Ala Ser Pro Ala Ala Ala Ala Ser Ser Met Arg Arg
             35                  40                  45
Arg Leu Val Leu Gly Val Gly Ala Ala Ala Pro Ala Val Ala Ala
     50                  55                  60
Leu Ala Ala Ser Ala Thr Pro Ala Ala Leu Arg Asp Cys Ala Ala Thr
 65                  70                  75                  80
Leu Leu Ile Thr Ala Gly Ala Tyr Ser Leu Val Arg Ala Phe Asp Gly
                 85                  90                  95
```

```
Leu Thr Ala Arg Arg Leu Ile Glu Gln Asn Leu Ser Arg Lys Ile Val
            100                 105                 110

His Val Leu Ser Gly Val Leu Phe Met Ser Ser Trp Pro Leu Phe Ser
        115                 120                 125

Asn Ser Thr Glu Ala Arg Phe Phe Ala Ala Ile Val Pro Leu Leu Asn
    130                 135                 140

Cys Ile Arg Leu Leu Thr Tyr Gly Leu Arg Leu Ser Thr Asp Glu Ala
145                 150                 155                 160

Leu Val Lys Ser Val Thr Arg Glu Gly Lys Pro Glu Leu Leu Arg
                165                 170                 175

Gly Pro Leu Tyr Tyr Val Ile Val Leu Val Ser Val Leu Val Phe
            180                 185                 190

Trp Arg Gln Ser Pro Ile Gly Ile Val Ser Leu Ser Met Met Ser Gly
        195                 200                 205

Gly Asp Gly Phe Ala Asp Ile Val Gly Arg Arg Tyr Gly Ser Ala Lys
    210                 215                 220

Leu Pro Phe Asn Glu Asn Lys Ser Trp Ile Gly Ser Ile Ser Met Phe
225                 230                 235                 240

Ile Ser Gly Phe Leu Leu Ser Ala Leu Met Leu Phe Tyr Phe Ser Cys
                245                 250                 255

Leu Gly Tyr Phe Thr Val Cys Trp Asp Leu Ala Leu Gly Lys Leu Ala
            260                 265                 270

Leu Val Ala Leu Ala Ala Thr Val Val Glu Cys Ile Pro Val Asn Asp
        275                 280                 285

Val Val Asp Asp Asn Ile Ser Val Pro Leu Ala Thr Met Leu Ala Ala
    290                 295                 300

Tyr Leu Leu Phe Gly Tyr Ser Ser Cys Cys
305                 310

<210> SEQ ID NO 47
<211> LENGTH: 269
<212> TYPE: PRT
<213> ORGANISM: Oryza sativa

<400> SEQUENCE: 47

Met Arg Arg Arg Leu Val Leu Gly Val Gly Ala Ala Ala Ala Pro Ala
1               5                   10                  15

Val Ala Ala Leu Ala Ala Ser Ala Thr Pro Ala Ala Leu Arg Asp Cys
                20                  25                  30

Ala Ala Thr Leu Leu Ile Thr Ala Gly Ala Tyr Ser Leu Val Arg Ala
            35                  40                  45

Phe Asp Gly Leu Thr Ala Arg Arg Leu Ile Glu Gln Asn Leu Ser Arg
        50                  55                  60

Lys Ile Val His Val Leu Ser Gly Val Leu Phe Met Ser Ser Trp Pro
65                  70                  75                  80

Leu Phe Ser Asn Ser Thr Glu Ala Arg Phe Phe Ala Ala Ile Val Pro
                85                  90                  95

Leu Leu Asn Cys Ile Arg Leu Leu Thr Tyr Gly Leu Arg Leu Ser Thr
            100                 105                 110

Asp Glu Ala Leu Val Lys Ser Val Thr Arg Glu Gly Lys Pro Glu Glu
        115                 120                 125

Leu Leu Arg Gly Pro Leu Tyr Tyr Val Ile Val Leu Val Ser Val
    130                 135                 140

Leu Val Phe Trp Arg Gln Ser Pro Ile Gly Ile Val Ser Leu Ser Met
145                 150                 155                 160
```

```
Met Ser Gly Gly Asp Gly Phe Ala Asp Ile Val Gly Arg Arg Tyr Gly
            165                 170                 175

Ser Ala Lys Leu Pro Phe Asn Glu Asn Lys Ser Trp Ile Gly Ser Ile
            180                 185                 190

Ser Met Phe Ile Ser Gly Phe Leu Leu Ser Ala Leu Met Leu Phe Tyr
            195                 200                 205

Phe Ser Cys Leu Gly Tyr Phe Thr Val Cys Trp Asp Leu Ala Leu Gly
            210                 215                 220

Lys Leu Ala Leu Val Ala Leu Ala Ala Thr Val Val Glu Cys Ile Pro
225                 230                 235                 240

Val Asn Asp Val Val Asp Asp Asn Ile Ser Val Pro Leu Ala Thr Met
            245                 250                 255

Leu Ala Ala Tyr Leu Leu Phe Gly Tyr Ser Ser Cys Cys
            260                 265
```

<210> SEQ ID NO 48
<211> LENGTH: 803
<212> TYPE: PRT
<213> ORGANISM: Oryza sativa

<400> SEQUENCE: 48

```
Met Ala Gly Gly Gly Lys Ser Val Ala Ala Leu Ala Met Ala
1               5                   10                  15

Cys Phe Leu Leu Ile Leu Ala Ala Phe Ala Pro Ala Ala Ala
            20                  25                  30

Pro Pro Asp Ile Met Ser Ile Ile Arg Tyr Asn Ala Glu His Gly Val
            35                  40                  45

Arg Gly Leu Glu Arg Thr Glu Ala Glu Ala Arg Ala Ala Tyr Asp Leu
50                  55                  60

Trp Leu Ala Arg His Arg Gly Gly Gly Gly Ser Arg Asn Gly
65                  70                  75                  80

Phe Ile Gly Glu His Glu Arg Arg Phe Arg Val Phe Trp Asp Asn Leu
            85                  90                  95

Lys Phe Val Asp Ala His Asn Ala Arg Ala Asp Glu Arg Gly Gly Phe
            100                 105                 110

Arg Leu Gly Met Asn Arg Phe Ala Asp Leu Thr Asn Gly Glu Phe Arg
            115                 120                 125

Ala Thr Tyr Leu Gly Thr Thr Pro Ala Gly Arg Gly Arg Arg Val Gly
            130                 135                 140

Glu Ala Tyr Arg His Asp Gly Val Glu Ala Leu Pro Asp Ser Val Asp
145                 150                 155                 160

Trp Arg Asp Lys Gly Ala Val Val Ala Pro Val Lys Asn Gln Gly Gln
            165                 170                 175

Cys Gly Ser Cys Trp Ala Phe Ser Ala Val Ala Ala Val Glu Gly Ile
            180                 185                 190

Asn Lys Ile Val Thr Gly Glu Leu Val Ser Leu Ser Glu Gln Glu Leu
            195                 200                 205

Val Glu Cys Ala Arg Asn Gly Gln Asn Ser Gly Cys Asn Gly Gly Ile
            210                 215                 220

Met Asp Asp Ala Phe Ala Phe Ile Ala Arg Asn Gly Gly Leu Asp Thr
225                 230                 235                 240

Glu Glu Asp Tyr Pro Tyr Thr Ala Met Asp Gly Lys Cys Asn Leu Ala
            245                 250                 255

Lys Arg Ser Arg Lys Val Val Ser Ile Asp Gly Phe Glu Asp Val Pro
```

```
                    260                 265                 270
Glu Asn Asp Glu Leu Ser Leu Gln Lys Ala Val Ala His Gln Pro Val
                275                 280                 285

Ser Val Ala Ile Asp Ala Gly Gly Arg Glu Phe Gln Leu Tyr Asp Ser
290                 295                 300

Gly Val Phe Thr Gly Arg Cys Gly Thr Asn Leu Asp His Gly Val Val
305                 310                 315                 320

Ala Val Gly Tyr Gly Thr Asp Ala Ala Thr Gly Ala Ala Tyr Trp Thr
                325                 330                 335

Val Arg Asn Ser Trp Gly Pro Asp Trp Gly Glu Asn Gly Tyr Ile Arg
                340                 345                 350

Met Glu Arg Asn Val Thr Ala Arg Thr Gly Lys Cys Gly Ile Ala Met
                355                 360                 365

Met Ala Ser Tyr Pro Ile Lys Lys Gly Pro Asn Pro Lys Pro Ser Pro
                370                 375                 380

Pro Ser Pro Ala Pro Ser Pro Pro Gln Gln Cys Asp Arg Tyr Ser Lys
385                 390                 395                 400

Cys Pro Ala Gly Thr Thr Cys Cys Asn Tyr Gly Ile Arg Asn His
                    405                 410                 415

Cys Ile Val Trp Gly Cys Cys Pro Val Glu Gly Ala Thr Cys Cys Lys
                420                 425                 430

Asp His Ser Thr Cys Cys Pro Lys Glu Tyr Pro Val Cys Asn Ala Lys
                435                 440                 445

Ala Arg Thr Cys Ser Lys Ser Lys Asn Ser Pro Tyr Asn Val Glu Ala
                450                 455                 460

Leu Ile Arg Thr Pro Ala Ala Met Ala Arg Ser Val Pro Glu Gln Pro
465                 470                 475                 480

Asp Ser Ile Ser Phe Ser Val Tyr Arg Met Ala Ala Ala Arg Pro
                    485                 490                 495

Val Asp Val Val Arg His Phe Pro Cys Ser Ser Ser Val Ala Ala Ser
                500                 505                 510

Ser Ser Leu Leu Leu Ser Arg Ser Lys Ser Arg Leu Ala Ser Pro Ala
                515                 520                 525

Ala Ala Ala Ala Ser Ser Met Arg Arg Arg Leu Val Leu Gly Val Gly
                530                 535                 540

Ala Ala Ala Ala Pro Ala Val Ala Ala Leu Ala Ala Ser Ala Thr Pro
545                 550                 555                 560

Ala Ala Leu Arg Asp Cys Ala Ala Thr Leu Leu Ile Thr Ala Gly Ala
                565                 570                 575

Tyr Ser Leu Val Arg Ala Phe Asp Gly Leu Thr Ala Arg Arg Leu Ile
                580                 585                 590

Glu Gln Asn Leu Ser Arg Lys Ile Val His Val Leu Ser Gly Val Leu
                595                 600                 605

Phe Met Ser Ser Trp Pro Leu Phe Ser Asn Ser Thr Glu Ala Arg Phe
                610                 615                 620

Phe Ala Ala Ile Val Pro Leu Leu Asn Cys Ile Arg Leu Leu Thr Tyr
625                 630                 635                 640

Gly Leu Arg Leu Ser Thr Asp Glu Ala Leu Val Lys Ser Val Thr Arg
                    645                 650                 655

Glu Gly Lys Pro Glu Glu Leu Leu Arg Gly Pro Leu Tyr Tyr Val Ile
                660                 665                 670

Val Leu Leu Val Ser Val Leu Val Phe Trp Arg Gln Ser Pro Ile Gly
                675                 680                 685
```

```
Ile Val Ser Leu Ser Met Met Ser Gly Gly Asp Gly Phe Ala Asp Ile
    690             695             700
Val Gly Arg Arg Tyr Gly Ser Ala Lys Leu Pro Phe Asn Glu Asn Lys
705             710             715             720
Ser Trp Ile Gly Ser Ile Ser Met Phe Ile Ser Gly Phe Leu Leu Ser
            725             730             735
Ala Leu Met Leu Phe Tyr Phe Ser Cys Leu Gly Tyr Phe Thr Val Cys
            740             745             750
Trp Asp Leu Ala Leu Gly Lys Leu Ala Leu Val Ala Leu Ala Ala Thr
            755             760             765
Val Val Glu Cys Ile Pro Val Asn Asp Val Val Asp Asp Asn Ile Ser
    770             775             780
Val Pro Leu Ala Thr Met Leu Ala Ala Tyr Leu Leu Phe Gly Tyr Ser
785             790             795             800
Ser Cys Cys

<210> SEQ ID NO 49
<211> LENGTH: 657
<212> TYPE: PRT
<213> ORGANISM: Oryza sativa

<400> SEQUENCE: 49

Met Asn Arg Phe Ala Asp Leu Thr Asn Gly Glu Phe Arg Ala Thr Tyr
1               5                   10                  15
Leu Gly Thr Thr Pro Ala Gly Arg Gly Arg Val Gly Glu Ala Tyr
            20                  25                  30
Arg His Asp Gly Val Glu Ala Leu Pro Asp Ser Val Asp Trp Arg Asp
            35                  40                  45
Lys Gly Ala Val Val Ala Pro Val Lys Asn Gln Gly Gln Cys Gly Ser
    50                  55                  60
Cys Trp Ala Phe Ser Ala Val Ala Ala Val Glu Gly Ile Asn Lys Ile
65                  70                  75                  80
Val Thr Gly Glu Leu Val Ser Leu Ser Glu Gln Glu Leu Val Glu Cys
                85                  90                  95
Ala Arg Asn Gly Gln Asn Ser Gly Cys Asn Gly Gly Ile Met Asp Asp
            100                 105                 110
Ala Phe Ala Phe Ile Ala Arg Asn Gly Gly Leu Asp Thr Glu Glu Asp
            115                 120                 125
Tyr Pro Tyr Thr Ala Met Asp Gly Lys Cys Asn Leu Ala Lys Arg Ser
            130                 135                 140
Arg Lys Val Val Ser Ile Asp Gly Phe Glu Asp Val Pro Glu Asn Asp
145                 150                 155                 160
Glu Leu Ser Leu Gln Lys Ala Val Ala His Gln Pro Val Ser Val Ala
                165                 170                 175
Ile Asp Ala Gly Gly Arg Glu Phe Gln Leu Tyr Asp Ser Gly Val Phe
            180                 185                 190
Thr Gly Arg Cys Gly Thr Asn Leu Asp His Gly Val Val Ala Val Gly
            195                 200                 205
Tyr Gly Thr Asp Ala Ala Thr Gly Ala Ala Tyr Trp Thr Val Arg Asn
            210                 215                 220
Ser Trp Gly Pro Asp Trp Gly Glu Asn Gly Tyr Ile Arg Met Glu Arg
225                 230                 235                 240
Asn Val Thr Ala Arg Thr Gly Lys Cys Gly Ile Ala Met Met Ala Ser
                245                 250                 255
```

-continued

```
Tyr Pro Ile Lys Lys Gly Pro Asn Pro Lys Pro Ser Pro Pro Ser Pro
        260                 265                 270

Ala Pro Ser Pro Pro Gln Gln Cys Asp Arg Tyr Ser Lys Cys Pro Ala
        275                 280                 285

Gly Thr Thr Cys Cys Asn Tyr Gly Ile Arg Asn His Cys Ile Val
        290                 295             300

Trp Gly Cys Cys Pro Val Glu Gly Ala Thr Cys Cys Lys Asp His Ser
305             310                 315                 320

Thr Cys Cys Pro Lys Glu Tyr Pro Val Cys Asn Ala Lys Ala Arg Thr
                325                 330                 335

Cys Ser Lys Ser Val Tyr Arg Met Ala Ala Ala Arg Pro Val Asp
            340                 345                 350

Val Val Arg His Phe Pro Cys Ser Ser Val Ala Ser Ser Ser
            355                 360                 365

Leu Leu Leu Ser Arg Ser Lys Ser Arg Leu Ala Ser Pro Ala Ala Ala
        370                 375                 380

Ala Ala Ser Ser Met Arg Arg Arg Leu Val Leu Gly Val Gly Ala Ala
385                 390                 395                 400

Ala Ala Pro Ala Val Ala Ala Leu Ala Ala Ser Ala Thr Pro Ala Ala
                405                 410                 415

Leu Arg Asp Cys Ala Ala Thr Leu Leu Ile Thr Ala Gly Ala Tyr Ser
            420                 425                 430

Leu Val Arg Ala Phe Asp Gly Leu Thr Ala Arg Arg Leu Ile Glu Gln
            435                 440                 445

Asn Leu Ser Arg Lys Ile Val His Val Leu Ser Gly Val Leu Phe Met
        450                 455                 460

Ser Ser Trp Pro Leu Phe Ser Asn Ser Thr Glu Ala Arg Phe Phe Ala
465                 470                 475                 480

Ala Ile Val Pro Leu Leu Asn Cys Ile Arg Leu Leu Thr Tyr Gly Leu
                485                 490                 495

Arg Leu Ser Thr Asp Glu Ala Leu Val Lys Ser Val Thr Arg Glu Gly
            500                 505                 510

Lys Pro Glu Glu Leu Leu Arg Gly Pro Leu Tyr Tyr Val Ile Val Leu
        515                 520                 525

Leu Val Ser Val Leu Val Phe Trp Arg Gln Ser Pro Ile Gly Ile Val
        530                 535                 540

Ser Leu Ser Met Met Ser Gly Asp Gly Phe Ala Asp Ile Val Gly
545                 550                 555                 560

Arg Arg Tyr Gly Ser Ala Lys Leu Pro Phe Asn Glu Asn Lys Ser Trp
                565                 570                 575

Ile Gly Ser Ile Ser Met Phe Ile Ser Gly Phe Leu Leu Ser Ala Leu
            580                 585                 590

Met Leu Phe Tyr Phe Ser Cys Leu Gly Tyr Phe Thr Val Cys Trp Asp
        595                 600                 605

Leu Ala Leu Gly Lys Leu Ala Leu Val Ala Leu Ala Ala Thr Val Val
        610                 615                 620

Glu Cys Ile Pro Val Asn Asp Val Val Asp Asp Asn Ile Ser Val Pro
625                 630                 635                 640

Leu Ala Thr Met Leu Ala Ala Tyr Leu Leu Phe Gly Tyr Ser Ser Cys
                645                 650                 655

Cys
```

```
<210> SEQ ID NO 50
<211> LENGTH: 246
<212> TYPE: PRT
<213> ORGANISM: Oryza sativa

<400> SEQUENCE: 50

Met Ala Ala Ala Ile Pro Pro Glu Ala Ser Gly Leu Ala His Asp Leu
1               5                   10                  15

Gly Ser Ala Ala Val Thr Ala Gly Val Ala Leu Ala Leu Leu Arg Phe
            20                  25                  30

Phe Glu Glu Leu Ala Lys Arg Gly Val Phe Glu Gln Lys Leu Asn Arg
        35                  40                  45

Lys Leu Val His Ile Thr Ile Gly Met Val Phe Leu Leu Phe Trp Pro
    50                  55                  60

Leu Phe Ser Ser Gly Ser Tyr Ala Pro Phe Leu Ala Ala Val Ala Pro
65                  70                  75                  80

Gly Ile Asn Ile Ile Arg Met Leu Leu Gly Leu Gly Val Met Lys
                85                  90                  95

Asn Glu Ala Met Val Lys Ser Met Ser Arg Ser Gly Asp Pro Arg Glu
            100                 105                 110

Leu Leu Lys Gly Pro Leu Tyr Tyr Ala Thr Thr Ile Thr Phe Ala Thr
        115                 120                 125

Ser Ile Phe Trp Arg Thr Ser Pro Ile Ala Ile Ala Leu Ile Cys Asn
    130                 135                 140

Leu Cys Ala Gly Asp Gly Ile Ala Asp Ile Val Gly Arg Arg Leu Gly
145                 150                 155                 160

Gln Glu Lys Leu Pro Tyr Asn Pro Asn Lys Ser Tyr Ala Gly Ser Ile
                165                 170                 175

Ala Met Ala Leu Ala Gly Phe Met Ala Ser Ile Gly Tyr Met His Tyr
            180                 185                 190

Phe Gln Ser Phe Gly Phe Ile Glu Glu Ser Trp Ser Leu Ala Phe Gly
        195                 200                 205

Phe Leu Val Val Ser Val Thr Ala Ala Leu Val Glu Ser His Pro Ile
    210                 215                 220

Ser Thr His Leu Asp Asp Asn Leu Thr Val Pro Leu Thr Ser Phe Leu
225                 230                 235                 240

Val Gly Ser Leu Val Phe
                245

<210> SEQ ID NO 51
<211> LENGTH: 271
<212> TYPE: PRT
<213> ORGANISM: Oryza sativa

<400> SEQUENCE: 51

Met Glu Ser Pro Val Leu Arg Asp Ala Gly Ala Ala Val Leu Thr Gly
1               5                   10                  15

Ala Thr Ala Leu Ala Val Leu Arg Phe Trp Glu Glu Val Gly Asn Arg
            20                  25                  30

Ala Leu Leu Asp Gln Lys Leu Cys Arg Lys Leu Val His Ile Thr Val
        35                  40                  45

Gly Leu Val Tyr Phe Leu Met Trp Pro Leu Phe Ser Ala Asp Asp Val
    50                  55                  60

Tyr Ala Pro Phe Leu Ala Ser Ile Val Ile Ala Phe Asn Ile Ile Lys
65                  70                  75                  80

Val Thr Leu Ile Gly Leu Gly Ile Val Lys Asp Asp Gly Val Ile Asn
```

```
                      85                  90                  95
Ser Met Thr Arg Asn Gly Asp Pro Arg Glu Leu Leu Lys Gly Pro Leu
            100                 105                 110

Tyr Tyr Ala Cys Ala Met Thr Leu Ala Thr Val Ile Phe Trp Arg Thr
        115                 120                 125

Ser Pro Ile Ser Ile Ala Val Ile Cys Asn Leu Cys Ala Gly Asp Gly
    130                 135                 140

Val Ala Asp Ile Ala Gly Arg Gln Leu Gly Arg Ile Lys Leu Pro Tyr
145                 150                 155                 160

Asn Pro Asp Lys Ser Tyr Ala Gly Ser Ile Ala Met Phe Leu Ala Gly
                165                 170                 175

Phe Leu Ala Ser Ile Leu Tyr Met Cys Tyr Phe His Leu Phe Gly Phe
            180                 185                 190

Val Glu Glu Ser Trp Thr Met Val Ile Ala Phe Gly Val Thr Ser Leu
        195                 200                 205

Ser Ala Ala Ile Val Glu Ser Leu Pro Ile Ser Thr Arg Leu Asp Asp
    210                 215                 220

Asn Leu Thr Val Pro Leu Ala Ser Val Leu Ile Gly Val Leu Val Phe
225                 230                 235                 240

Tyr Tyr Ile Gly Ala Arg Asn Leu Cys Cys Met Ser Ala Asp Ser Ser
                245                 250                 255

Asp Ile Ser Ala Leu Val Gln Asn Gln Met Phe Leu Gly Arg Phe
            260                 265                 270

<210> SEQ ID NO 52
<211> LENGTH: 271
<212> TYPE: PRT
<213> ORGANISM: Oryza sativa

<400> SEQUENCE: 52

Met Glu Ser Gln Val Leu Arg Asp Ala Gly Ala Val Leu Thr Gly
1               5                   10                  15

Ala Thr Ala Leu Ala Val Leu Arg Phe Trp Glu Glu Val Gly Asn Arg
            20                  25                  30

Ala Leu Leu Asp Gln Lys Leu Cys Arg Lys Leu Val His Ile Thr Val
        35                  40                  45

Gly Leu Val Tyr Phe Leu Met Trp Pro Leu Phe Ser Ala Asp Asp Val
    50                  55                  60

Tyr Ala Pro Phe Leu Ala Ser Ile Val Ile Ala Phe Asn Ile Ile Lys
65                  70                  75                  80

Val Thr Leu Ile Gly Leu Gly Ile Val Lys Asp Asp Gly Val Ile Asn
                85                  90                  95

Ser Met Thr Arg Asn Gly Asp Pro Arg Glu Leu Leu Lys Gly Pro Leu
            100                 105                 110

Tyr Tyr Ala Cys Ala Met Thr Leu Ala Thr Val Ile Phe Trp Arg Thr
        115                 120                 125

Ser Pro Ile Ser Ile Ala Val Ile Cys Asn Leu Cys Ala Gly Asp Gly
    130                 135                 140

Val Ala Asp Ile Ala Gly Arg Gln Leu Gly Arg Ile Lys Leu Pro Tyr
145                 150                 155                 160

Asn Pro Asp Lys Ser Tyr Ala Gly Ser Ile Ala Met Phe Leu Ala Gly
                165                 170                 175

Phe Leu Ala Ser Ile Leu Tyr Met Cys Tyr Phe His Leu Phe Gly Phe
            180                 185                 190
```

```
Val Glu Glu Ser Trp Thr Met Val Ile Ala Phe Gly Val Thr Ser Leu
        195                 200                 205

Ser Ala Ala Ile Val Glu Ser Leu Pro Ile Ser Thr Arg Leu Asp Asp
        210                 215                 220

Asn Leu Thr Val Pro Leu Ala Ser Val Leu Ile Gly Val Leu Val Phe
225                 230                 235                 240

Tyr Tyr Ile Gly Ala Arg Asn Leu Cys Cys Met Ser Ala Asp Ser Ser
                245                 250                 255

Asp Ile Ser Ala Leu Val Gln Asn Gln Met Phe Leu Gly Arg Phe
        260                 265                 270

<210> SEQ ID NO 53
<211> LENGTH: 205
<212> TYPE: PRT
<213> ORGANISM: Sorghum bicolor

<400> SEQUENCE: 53

Met Ala Ala Ala Thr Ala Trp Pro Gly Ala Ala Ser Asn Ser Leu
1               5                   10                  15

Leu Leu Ser Arg Ser Pro Pro His Ala Ala Ala Ala Leu Ala Leu
            20                  25                  30

Ala Pro Ser Pro Gly Ser Ser Met Arg Arg Arg Leu Ile Leu Gly Val
        35                  40                  45

Gly Thr Pro Ala Val Ala Ala Leu Ala Ala Ala Pro Pro Ala Val
    50                  55                  60

Leu Gln Asp Gly Ala Val Thr Val Leu Ile Thr Ala Gly Ala Tyr Ser
65                  70                  75                  80

Leu Val Arg Val Phe Asp Glu Leu Thr Glu Arg Arg Leu Ile Glu Lys
                85                  90                  95

Ser Leu Ser Arg Lys Val Val His Val Leu Ser Gly Val Leu Phe Met
                100                 105                 110

Ser Ser Trp Pro Leu Phe Ser Asn Ser Thr Glu Ala Arg Tyr Phe Ala
            115                 120                 125

Ala Val Val Pro Leu Leu Asn Ser Ile Arg Leu Leu Ile Tyr Gly Leu
        130                 135                 140

Arg Leu Tyr Thr Asp Glu Ala Leu Val Lys Ser Val Thr Arg Glu Gly
145                 150                 155                 160

Lys Pro Glu Glu Leu Leu Arg Gly Pro Leu Tyr Tyr Val Leu Val Leu
                165                 170                 175

Leu Phe Ser Val Leu Val Phe Trp Arg Glu Ser Pro Val Gly Ile Val
            180                 185                 190

Ser Leu Ser Met Met Ser Gly Gly Asp Gly Phe Ala Asp
        195                 200                 205

<210> SEQ ID NO 54
<211> LENGTH: 202
<212> TYPE: PRT
<213> ORGANISM: Sorghum bicolor
<220> FEATURE:
<221> NAME/KEY: misc_feature
<222> LOCATION: (18)..(18)
<223> OTHER INFORMATION: Xaa can be any naturally occurring amino acid

<400> SEQUENCE: 54

Lys Leu Ser Arg Lys Leu Val His Ile Ser Val Gly Leu Val Phe Leu
1               5                   10                  15

Leu Xaa Trp Pro Leu Phe Ser Ser Gly Trp Tyr Ala Pro Phe Leu Ala
            20                  25                  30
```

```
Ala Leu Ala Pro Gly Val Asn Val Ile Arg Met Leu Leu Gly Leu
        35                  40                  45

Gly Leu Met Lys Asn Glu Ala Met Val Lys Ser Ile Ser Arg Ser Gly
 50                  55                  60

Asp Tyr Arg Glu Leu Leu Lys Gly Pro Leu Tyr Tyr Ala Thr Thr Ile
 65                  70                  75                  80

Thr Phe Ala Thr Ser Val Leu Trp Arg Thr Ser Pro Val Ala Ile Ala
                 85                  90                  95

Leu Ile Cys Asn Leu Cys Ala Gly Asp Gly Ile Ala Asp Val Val Gly
            100                 105                 110

Arg Arg Leu Gly Lys Glu Lys Leu Pro Tyr Asn Pro Asn Lys Ser Tyr
            115                 120                 125

Ala Gly Ser Ile Ala Met Ala Val Ala Gly Phe Leu Ala Ser Val Gly
        130                 135                 140

Tyr Met His Tyr Phe His Thr Phe Gly Phe Ile Glu Glu Thr Trp Tyr
145                 150                 155                 160

Met Ala Leu Gly Phe Leu Val Val Ser Val Ala Ala Thr Leu Val Glu
                165                 170                 175

Ser His Pro Ile Ser Thr Glu Leu Asp Asp Asn Leu Thr Val Pro Leu
            180                 185                 190

Thr Ser Phe Leu Val Gly Ser Leu Ile Phe
            195                 200

<210> SEQ ID NO 55
<211> LENGTH: 191
<212> TYPE: PRT
<213> ORGANISM: Sorghum bicolor

<400> SEQUENCE: 55

Ser Thr Ser Thr Cys Ser Asn Ser Thr Glu Ala Arg Tyr Phe Ala Ala
 1               5                  10                  15

Val Val Pro Leu Leu Asn Ser Ile Arg Leu Leu Ile Tyr Gly Leu Arg
                20                  25                  30

Leu Tyr Thr Asp Glu Ala Leu Val Lys Ser Val Thr Arg Glu Gly Lys
            35                  40                  45

Pro Glu Glu Leu Leu Arg Gly Pro Leu Tyr Tyr Val Leu Val Leu Leu
        50                  55                  60

Phe Ser Val Leu Val Phe Trp Arg Glu Ser Pro Val Gly Ile Val Ser
 65                  70                  75                  80

Leu Ser Met Met Ser Gly Gly Asp Gly Phe Ala Asp Ile Val Gly Arg
                85                  90                  95

Arg Tyr Gly Ser Val Lys Leu Pro Phe Asn Lys Lys Ser Trp Ala
            100                 105                 110

Gly Ser Ile Ser Met Phe Ile Ser Gly Phe Leu Leu Ser Ala Met Met
        115                 120                 125

Met Phe Tyr Phe Ser Ser Leu Gly Tyr Ile Asp Val Ile Trp Gln Glu
130                 135                 140

Ala Leu Gly Lys Leu Ala Leu Val Ala Leu Ala Thr Val Val Glu
145                 150                 155                 160

Cys Ile Pro Val Thr Glu Val Asp Asp Asn Ile Ser Val Pro Leu
                165                 170                 175

Ala Thr Met Leu Val Ala Phe Leu Leu Phe Ser Ser Asn Ala Gln
            180                 185                 190
```

```
<210> SEQ ID NO 56
<211> LENGTH: 296
<212> TYPE: PRT
<213> ORGANISM: Triticum aestivum

<400> SEQUENCE: 56

Leu His Thr Arg Leu Arg Ser Arg Pro Leu Cys Ser Pro Thr Ser Ser
1               5                   10                  15

Ala Pro Thr Val Ser Ser Ser Ala Pro Pro Ser Leu Arg Phe Arg
            20                  25                  30

Phe Gly Phe Pro Arg Arg Gly Cys Ala Ala Asp Arg Ser Arg Arg Ala
            35                  40                  45

Thr Thr Met Ala Ala Val Val Ser Pro Gly Asp Gly Leu Val His
50                  55                  60

Asp Leu Val Ser Ser Gly Val Thr Ala Ala Ile Ala Leu Gly Leu Leu
65                  70                  75                  80

Arg Phe Phe Glu Glu Leu Ala Lys Arg Gly Val Cys Asp Gln Lys Leu
                85                  90                  95

Asn Arg Lys Leu Val His Ile Thr Ile Gly Met Val Phe Leu Leu Phe
            100                 105                 110

Trp Pro Leu Phe Ser Ser Gly Arg Tyr Ala Pro Phe Phe Ala Ala Leu
            115                 120                 125

Ala Pro Gly Ile Asn Ile Ile Arg Met Leu Leu Leu Gly Leu Gly Ile
        130                 135                 140

Met Lys Asn Glu Ala Met Val Lys Ser Met Ser Arg Ser Gly Asp His
145                 150                 155                 160

Arg Glu Leu Leu Lys Gly Pro Leu Tyr Tyr Ala Thr Thr Ile Thr Leu
                165                 170                 175

Ala Thr Ser Val Leu Trp Arg Thr Ser Pro Ile Ala Ile Ala Leu Val
            180                 185                 190

Cys Asn Leu Cys Ala Gly Asp Gly Ile Ala Asp Val Val Gly Arg Arg
        195                 200                 205

Leu Gly Lys Glu Lys Leu Pro Tyr Asn Pro Asn Lys Ser Tyr Ala Gly
    210                 215                 220

Ser Ile Ala Met Ala Val Ala Gly Phe Leu Ala Ser Ile Gly Tyr Met
225                 230                 235                 240

His Tyr Phe His Ser Phe Gly Leu Met Glu Lys Ser Trp Tyr Met Thr
                245                 250                 255

Leu Gly Phe Leu Val Val Ser Val Ala Ala Ala Leu Val Glu Ser His
            260                 265                 270

Pro Ile Ser Thr Glu Leu Asp Asp Asn Leu Thr Val Pro Leu Thr Ser
        275                 280                 285

Phe Leu Val Gly Ser Leu Ile Leu
    290                 295

<210> SEQ ID NO 57
<211> LENGTH: 292
<212> TYPE: PRT
<213> ORGANISM: Triticum aestivum

<400> SEQUENCE: 57

Leu Cys Glu Ser Val Cys Glu Leu Arg Gly Ala Ser Val Gly Gly Ser
1               5                   10                  15

Met Trp Pro Glu Ser Pro Pro Leu Arg Asp Ala Gly Ala Ala Val Leu
            20                  25                  30

Thr Gly Cys Val Ala Met Ala Val Leu Arg Phe Trp Glu Glu Val Gly
```

```
                35                  40                  45
Asn Arg Ala Leu Leu Asp Gln Lys Leu Cys Arg Lys Leu Val His Ile
         50                  55                  60
Ser Val Gly Leu Val Tyr Phe Leu Met Trp Pro Leu Phe Ser Ala Asp
 65                  70                  75                  80
Asp Val Tyr Ala Pro Phe Leu Ala Ser Ile Val Ala Leu Asn Ile
                 85                  90                  95
Ile Lys Val Ile Leu Ile Gly Ser Gly Val Val Lys Asp Asp Gly Val
                100                 105                 110
Val Asn Ser Met Thr Arg Asn Gly Asp Tyr Arg Glu Leu Leu Lys Gly
            115                 120                 125
Pro Leu Tyr Tyr Ala Cys Thr Ile Thr Leu Thr Thr Val Ile Phe Trp
        130                 135                 140
Arg Thr Ser Pro Ile Ser Ile Ala Val Ile Cys Asn Leu Cys Ala Gly
145                 150                 155                 160
Asp Gly Val Ala Asp Ile Ala Gly Arg Arg Phe Gly His Val Lys Leu
                165                 170                 175
Pro His Asn Pro Asp Lys Ser Tyr Ala Gly Ser Ile Ala Met Phe Phe
            180                 185                 190
Ala Gly Phe Val Ala Ser Ile Leu Phe Met Cys Tyr Phe His Leu Phe
        195                 200                 205
Gly Phe Val Glu Gln Ser Trp Thr Met Val Ala Ala Phe Gly Val Thr
    210                 215                 220
Ser Leu Ala Ala Ala Ile Val Glu Ser Leu Pro Val Ser Thr Leu Leu
225                 230                 235                 240
Asp Asp Asn Leu Thr Thr Pro Ile Ala Ser Ala Leu Val Gly Ser Leu
                245                 250                 255
Val Phe Tyr Tyr Val Gly Gly Gly Gly Ala Gly Ser Gly Asp Gly
            260                 265                 270
Thr Ser Ile Ser Ala Thr Ala Ala Met Val Phe Ala Gly Ser Ser Tyr
        275                 280                 285
Tyr Ser Glu Gly
    290

<210> SEQ ID NO 58
<211> LENGTH: 300
<212> TYPE: PRT
<213> ORGANISM: Triticum aestivum

<400> SEQUENCE: 58

Met Ala Ala Ala Arg Pro Ala Leu Pro Ser Ser Pro Thr Ser Leu Leu
 1                   5                  10                  15
Leu Ala Arg Ser Thr Ser Ala Pro Asp Leu Ala Ala Arg Pro Arg
             20                  25                  30
Arg Trp Leu Val Ala Ala Ala Gly Val Pro Ala Val Ala Gly Ala Leu
         35                  40                  45
Ala Ala Ser Ala Ser Thr Pro Ala Ala Ser Met Leu Leu Arg Asp Gly
     50                  55                  60
Gly Ala Thr Leu Leu Val Thr Ala Gly Ala Tyr Ser Leu Val Arg Ala
 65                  70                  75                  80
Phe Asp Ala Leu Thr Glu Arg Arg Leu Val Gln Gln Ser Leu Ser Arg
                 85                  90                  95
Lys Val Val His Val Leu Ser Gly Val Phe Phe Met Ala Ser Trp Pro
                100                 105                 110
```

```
Leu Phe Ser Asn Ser Thr Ser Ala Arg Phe Ala Ala Val Val Pro
            115                 120                 125

Phe Leu Asn Cys Val Arg Leu Leu Thr Tyr Gly Leu Gly Phe Tyr Ser
130                 135                 140

Asp Glu Ala Leu Val Lys Ser Val Thr Arg Glu Gly Lys Arg Glu Glu
145                 150                 155                 160

Leu Leu Arg Gly Pro Leu Tyr Tyr Val Ile Val Leu Ile Ile Val
            165                 170                 175

Leu Val Phe Trp Arg Asp Ser Pro Ile Gly Ile Val Ser Leu Ser Met
            180                 185                 190

Met Ser Gly Gly Asp Gly Phe Ala Asp Ile Val Gly Arg Arg Phe Gly
            195                 200                 205

Ser Leu Lys Leu Pro Phe Asn Lys Lys Ser Trp Val Gly Ser Ala
            210                 215                 220

Ala Met Phe Ile Ser Gly Phe Leu Ser Ala Leu Met Leu Ser Tyr
225                 230                 235                 240

Phe Ser Trp Leu Gly Tyr Ile His Val Ser Trp Asp Gln Ala Leu Gly
            245                 250                 255

Lys Leu Val Leu Val Ala Leu Ala Thr Val Val Glu Cys Ile Pro
            260                 265                 270

Val Thr Asp Val Val Asp Asp Asn Ile Ser Val Pro Leu Ala Thr Met
            275                 280                 285

Leu Val Ala Phe Leu Leu Phe Gly Asn Thr Ala Asn
            290                 295                 300

<210> SEQ ID NO 59
<211> LENGTH: 157
<212> TYPE: PRT
<213> ORGANISM: Zea mays

<400> SEQUENCE: 59

Leu Ala Ala Leu Thr Ile Thr Thr Leu Leu Leu Tyr Arg Glu Leu Leu
1               5                   10                  15

Arg Gly Pro Leu Tyr Tyr Val Leu Val Leu Leu Phe Ser Val Leu Val
            20                  25                  30

Phe Trp Arg Glu Ser Pro Ile Gly Ile Val Ser Leu Ser Met Met Ser
            35                  40                  45

Gly Gly Asp Gly Phe Ala Asp Ile Val Gly Arg Arg Tyr Gly Ser Ala
        50                  55                  60

Lys Leu Pro Phe Asn Arg Lys Lys Ser Trp Ala Gly Ser Ile Ser Met
65                  70                  75                  80

Phe Ile Ser Gly Phe Leu Leu Ser Ala Met Met Met Leu Tyr Phe Ser
            85                  90                  95

Ser Leu Gly Tyr Ile Asp Val Ile Trp Glu Glu Ala Leu Gly Lys Leu
            100                 105                 110

Ala Leu Val Ala Leu Ala Thr Val Val Glu Cys Val Pro Val Thr
            115                 120                 125

Glu Val Val Asp Asp Asn Ile Ser Val Pro Leu Ala Thr Met Leu Val
130                 135                 140

Ala Phe Leu Leu Phe Ser Ser Asn Arg Thr Ile Val Asn
145                 150                 155

<210> SEQ ID NO 60
<211> LENGTH: 188
<212> TYPE: PRT
<213> ORGANISM: Zea mays
```

```
<400> SEQUENCE: 60

Ala Pro Pro Ala Ala Leu Gln Asp Gly Ala Val Thr Val Leu Ile Thr
1               5                   10                  15

Ala Gly Ala Tyr Ser Leu Val Arg Val Phe Asp Glu Leu Thr Glu Arg
                20                  25                  30

Arg Leu Ile Glu Lys Ser Leu Ser Arg Lys Val Val His Val Leu Ser
            35                  40                  45

Gly Val Leu Phe Met Ser Ser Trp Pro Leu Phe Ser Asn Ser Thr Glu
        50                  55                  60

Ala Arg Tyr Phe Ala Ala Val Val Pro Phe Leu Asn Ser Met Arg Leu
65                  70                  75                  80

Leu Ile Tyr Gly Leu Arg Leu Tyr Thr Asp Glu Ala Leu Val Lys Ser
                85                  90                  95

Val Thr Arg Glu Gly Lys Pro Glu Glu Leu Leu Arg Gly Pro Leu Tyr
                100                 105                 110

Tyr Val Leu Val Leu Leu Phe Ser Val Leu Val Phe Trp Arg Glu Ser
            115                 120                 125

Pro Ile Gly Ile Val Ser Leu Ser Met Met Ser Gly Gly Asp Gly Phe
        130                 135                 140

Ala Asp Ile Val Gly Arg Arg Tyr Gly Ser Ala Lys Leu Pro Phe Asn
145                 150                 155                 160

Arg Lys Lys Ser Trp Gly Arg Ser Ile Ser Met Phe Ile Ser Cys Phe
                165                 170                 175

Leu Leu Ser Ala Met Met Met Leu Tyr Phe Ser Ser
                180                 185

<210> SEQ ID NO 61
<211> LENGTH: 303
<212> TYPE: PRT
<213> ORGANISM: Zea mays

<400> SEQUENCE: 61

Met Ala Ala Ala Ala Trp Thr Gly Ala Ala Ser Pro Asn Ser Leu
1               5                   10                  15

Leu Leu Ser Arg Ser Pro Pro His Ala Ala Leu Ala Pro Ser Pro
                20                  25                  30

Gly Ser Ser Met Arg Arg Arg Leu Leu Leu Gly Val Gly Thr Pro Ala
            35                  40                  45

Val Ala Ala Leu Ala Ala Ala Pro Pro Ala Val Leu Gln Asp Gly
        50                  55                  60

Ala Val Thr Val Leu Ile Thr Ala Gly Ala Tyr Ser Leu Val Arg Val
65                  70                  75                  80

Phe Asp Glu Leu Thr Glu Arg Leu Ile Glu Lys Ser Leu Ser Arg
                85                  90                  95

Lys Val Val His Val Leu Ser Gly Val Leu Phe Met Ser Ser Trp Pro
                100                 105                 110

Leu Phe Ser Asn Ser Thr Glu Ala Arg Tyr Phe Ala Ala Val Val Pro
            115                 120                 125

Phe Leu Asn Ser Met Arg Leu Leu Ile Tyr Gly Leu Arg Leu Tyr Thr
        130                 135                 140

Asp Glu Ala Leu Val Lys Ser Val Thr Arg Glu Gly Lys Pro Glu Glu
145                 150                 155                 160

Leu Leu Arg Gly Pro Leu Tyr Tyr Val Leu Val Leu Leu Phe Ser Val
                165                 170                 175
```

-continued

```
Leu Val Phe Trp Arg Glu Ser Pro Ile Gly Ile Val Ser Leu Ser Met
                180                 185                 190

Met Ser Gly Gly Asp Gly Phe Ala Asp Ile Val Gly Arg Arg Tyr Gly
            195                 200                 205

Ser Ala Lys Leu Pro Phe Asn Arg Lys Ser Trp Ala Gly Ser Ile
    210                 215                 220

Ser Met Phe Ile Ser Gly Phe Leu Ser Ala Met Met Leu Tyr
225                 230                 235                 240

Phe Ser Ser Leu Gly Tyr Ile Asp Val Ile Trp Glu Ala Leu Gly
                245                 250                 255

Lys Leu Ala Leu Val Ala Leu Ala Thr Val Glu Cys Val Pro
            260                 265                 270

Val Thr Glu Val Val Asp Asp Asn Ile Ser Val Pro Leu Ala Thr Met
            275                 280                 285

Leu Val Ala Phe Leu Leu Phe Ser Ser Asn Arg Thr Ile Val Asn
    290                 295                 300
```

<210> SEQ ID NO 62
<211> LENGTH: 267
<212> TYPE: PRT
<213> ORGANISM: Zea mays

<400> SEQUENCE: 62

```
Met Arg Arg Arg Leu Leu Leu Gly Val Gly Thr Pro Ala Val Ala Ala
1               5                   10                  15

Leu Ala Ala Ala Pro Pro Ala Val Leu Gln Asp Gly Ala Val Thr
            20                  25                  30

Val Leu Ile Thr Ala Gly Ala Tyr Ser Leu Val Arg Val Phe Asp Glu
        35                  40                  45

Leu Thr Glu Arg Arg Leu Ile Glu Lys Ser Leu Ser Arg Lys Val Val
    50                  55                  60

His Val Leu Ser Gly Val Leu Phe Met Ser Ser Trp Pro Leu Val Ser
65              70                  75                  80

Asn Ser Thr Glu Ala Arg Tyr Phe Ala Ala Val Pro Phe Leu Asn
                85                  90                  95

Ser Met Arg Leu Leu Ile Tyr Gly Leu Arg Leu Tyr Thr Asp Glu Ala
            100                 105                 110

Leu Val Lys Ser Val Thr Arg Glu Gly Lys Pro Glu Glu Leu Leu Arg
        115                 120                 125

Pro Leu Tyr Tyr Val Leu Val Leu Phe Ser Val Leu Val Phe Trp
    130                 135                 140

Arg Glu Ser Pro Ile Gly Ile Val Ser Leu Ser Met Met Ser Gly Gly
145                 150                 155                 160

Asp Gly Phe Ala Asp Ile Val Gly Arg Arg Tyr Gly Ser Ala Lys Leu
                165                 170                 175

Pro Phe Asn Arg Lys Ser Trp Ala Gly Ser Ile Ser Met Phe Ile
            180                 185                 190

Ser Gly Phe Leu Leu Ser Ala Met Met Met Leu Tyr Phe Ser Ser Leu
        195                 200                 205

Gly Tyr Ile Asp Val Ile Trp Glu Glu Ala Leu Gly Lys Leu Ala Leu
    210                 215                 220

Val Ala Leu Ala Ala Thr Val Glu Cys Val Pro Val Thr Glu Val
225                 230                 235                 240

Val Asp Asp Asn Ile Ser Val Pro Leu Ala Thr Met Leu Val Ala Phe
```

```
                    245                 250                 255
Leu Leu Phe Ser Ser Asn Arg Thr Ile Val Asn
            260                 265

<210> SEQ ID NO 63
<211> LENGTH: 236
<212> TYPE: PRT
<213> ORGANISM: Zea mays

<400> SEQUENCE: 63

Ala Arg Gly Thr Ala Gly Ala Tyr Ser Leu Val Arg Val Phe Asp Glu
1               5                   10                  15

Leu Thr Glu Arg Arg Leu Ile Glu Lys Ser Leu Ser Arg Lys Val Val
            20                  25                  30

His Val Leu Ser Gly Val Leu Phe Met Ser Ser Trp Pro Leu Phe Ser
        35                  40                  45

Asn Ser Thr Glu Ala Arg Tyr Phe Ala Ala Val Val Pro Phe Leu Asn
    50                  55                  60

Ser Met Arg Leu Leu Ile Tyr Gly Leu Arg Leu Tyr Thr Asp Glu Ala
65                  70                  75                  80

Leu Val Lys Ser Val Thr Arg Glu Gly Lys Pro Glu Glu Leu Leu Arg
                85                  90                  95

Gly Pro Leu Tyr Tyr Val Leu Val Leu Phe Ser Val Leu Val Phe
            100                 105                 110

Trp Arg Glu Ser Pro Ile Gly Ile Val Ser Leu Ser Met Met Ser Gly
        115                 120                 125

Gly Asp Gly Phe Ala Asp Ile Val Gly Arg Arg Tyr Gly Ser Ala Lys
    130                 135                 140

Leu Pro Phe Asn Arg Lys Lys Ser Trp Ala Gly Ser Ile Ser Met Phe
145                 150                 155                 160

Ile Ser Gly Phe Leu Leu Ser Ala Met Met Met Leu Tyr Phe Ser Ser
                165                 170                 175

Leu Gly Tyr Ile Asp Val Ile Trp Glu Glu Ala Leu Gly Lys Leu Ala
            180                 185                 190

Leu Val Ala Leu Ala Ala Thr Val Val Glu Cys Val Pro Val Thr Glu
        195                 200                 205

Val Val Asp Asp Asn Ile Ser Val Pro Leu Ala Thr Met Leu Val Ala
    210                 215                 220

Phe Leu Leu Phe Ser Ser Asn Arg Thr Ile Val Asn
225                 230                 235

<210> SEQ ID NO 64
<211> LENGTH: 302
<212> TYPE: PRT
<213> ORGANISM: Zea mays

<400> SEQUENCE: 64

Leu Ser Tyr Ser Thr His Arg Ala His Leu Leu Gln Ser Arg Pro Leu
1               5                   10                  15

Ser Pro Ser Pro Thr Val Pro Ala Gly Ala Ala Ser Ala Ser Cys Ala
            20                  25                  30

Pro Arg Ser Leu Cys Phe Arg Arg Arg Ser Ser Arg Leu Ala Ala
        35                  40                  45

Glu Arg Thr Arg Arg Pro Thr Met Ala Ala Ala Ile Ser Leu Glu Ala
    50                  55                  60

Gly Gly Ala Leu Ala His Asp Leu Gly Ser Ala Val Val Thr Gly Gly
```

```
                65                  70                  75                  80
Val Ala Leu Ala Leu Leu Lys Phe Phe Glu Glu Leu Ala Lys Arg Gly
                    85                  90                  95

Val Phe Glu Gln Lys Leu Ser Arg Lys Leu Val His Ile Ser Val Gly
                100                 105                 110

Leu Val Phe Met Leu Phe Trp Pro Leu Phe Ser Ser Gly Trp Tyr Thr
                115                 120                 125

Pro Phe Leu Ala Ala Leu Ala Pro Gly Val Asn Ile Ile Arg Met Leu
                130                 135                 140

Leu Leu Gly Leu Gly Leu Met Lys Asn Glu Ala Met Val Lys Ser Met
145                 150                 155                 160

Ser Arg Ser Gly Asp Tyr Arg Glu Leu Leu Lys Gly Pro Leu Tyr Tyr
                165                 170                 175

Ala Ala Thr Ile Thr Phe Ala Thr Ser Leu Leu Trp Arg Thr Ser Pro
                180                 185                 190

Val Ala Ile Ala Leu Ile Cys Asn Leu Cys Ala Gly Asp Gly Ile Ala
                195                 200                 205

Asp Val Val Gly Arg Arg Leu Gly Lys Glu Lys Leu Pro Tyr Asn Pro
210                 215                 220

Asn Lys Ser Tyr Ala Gly Ser Ile Ala Met Ala Val Ala Gly Phe Leu
225                 230                 235                 240

Ala Ser Val Gly Tyr Met His Tyr Phe His Thr Phe Gly Phe Ile Glu
                245                 250                 255

Glu Thr Trp Tyr Met Ala Leu Ser Phe Leu Val Val Ser Val Ala Ala
                260                 265                 270

Ala Leu Val Glu Ser His Pro Ile Ser Thr Glu Leu Asp Asp Asn Leu
                275                 280                 285

Thr Val Leu Leu Thr Ser Phe Leu Val Gly Ser Leu Ile Phe
                290                 295                 300

<210> SEQ ID NO 65
<211> LENGTH: 312
<212> TYPE: PRT
<213> ORGANISM: Zea mays

<400> SEQUENCE: 65

Met Leu Ser Leu Ala Ala His Ile Thr Pro Leu Ser Tyr Ser Thr His
1               5                   10                  15

Arg Ala His Leu Leu Gln Ser Arg Pro Leu Ser Pro Ser Pro Thr Val
                20                  25                  30

Pro Ala Gly Ala Ala Ser Ala Ser Cys Ala Pro Arg Ser Leu Cys Phe
                35                  40                  45

Arg Arg Arg Arg Ser Ser Arg Leu Ala Ala Glu Arg Thr Arg Arg Pro
            50                  55                  60

Thr Met Ala Ala Ala Ile Ser Leu Glu Ala Gly Gly Ala Leu Ala His
65                  70                  75                  80

Asp Leu Gly Ser Ala Val Val Thr Gly Gly Val Ala Leu Ala Leu Leu
                85                  90                  95

Lys Phe Phe Glu Glu Leu Ala Lys Arg Gly Val Phe Glu Gln Lys Leu
                100                 105                 110

Ser Arg Lys Leu Val His Ile Ser Val Gly Leu Val Phe Met Leu Phe
                115                 120                 125

Trp Pro Leu Phe Ser Ser Gly Trp Tyr Thr Pro Phe Leu Ala Ala Leu
            130                 135                 140
```

```
Ala Pro Gly Val Asn Ile Ile Arg Met Leu Leu Leu Gly Leu Gly Leu
145                 150                 155                 160

Met Lys Asn Glu Ala Met Val Lys Ser Met Ser Arg Ser Gly Asp Tyr
            165                 170                 175

Arg Glu Leu Leu Lys Gly Pro Leu Tyr Tyr Ala Ala Thr Ile Thr Phe
            180                 185                 190

Ala Thr Ser Leu Leu Trp Arg Thr Ser Pro Val Ala Ile Ala Leu Ile
        195                 200                 205

Cys Asn Leu Cys Ala Gly Asp Gly Ile Ala Asp Val Val Gly Arg Arg
    210                 215                 220

Leu Gly Lys Glu Lys Leu Pro Tyr Asn Pro Asn Lys Ser Tyr Ala Gly
225                 230                 235                 240

Ser Ile Ala Met Ala Val Ala Gly Phe Leu Ala Ser Val Gly Tyr Met
                245                 250                 255

His Tyr Phe His Thr Phe Gly Phe Ile Glu Glu Thr Trp Tyr Met Ala
            260                 265                 270

Leu Ser Phe Leu Val Val Ser Val Ala Ala Ala Leu Val Glu Ser His
        275                 280                 285

Pro Ile Ser Thr Glu Leu Asp Asp Asn Leu Thr Val Pro Leu Thr Ser
    290                 295                 300

Phe Leu Val Gly Ser Leu Ile Phe
305                 310

<210> SEQ ID NO 66
<211> LENGTH: 307
<212> TYPE: PRT
<213> ORGANISM: Zea mays

<400> SEQUENCE: 66

Met Ala Thr Thr Ser Thr Thr Thr Lys Leu Ser Val Leu Cys Cys Ser
1               5                   10                  15

Phe Ile Ser Ser Pro Leu Val Asp Ser Pro Pro Ser Leu Ala Phe Phe
            20                  25                  30

Ser Pro Ile Pro Arg Phe Leu Thr Val Arg Ile Ala Thr Ser Phe Arg
        35                  40                  45

Ser Ser Ser Arg Phe Pro Ala Thr Lys Ile Arg Lys Ser Ser Leu Ala
    50                  55                  60

Ala Val Met Phe Pro Glu Asn Ser Val Leu Ser Asp Val Cys Ala Phe
65                  70                  75                  80

Gly Val Thr Ser Ile Val Ala Phe Ser Cys Leu Gly Phe Trp Gly Glu
                85                  90                  95

Ile Gly Lys Arg Gly Ile Phe Asp Gln Lys Leu Ile Arg Lys Leu Val
            100                 105                 110

His Ile Asn Ile Gly Leu Val Phe Met Leu Cys Trp Pro Leu Phe Ser
        115                 120                 125

Ser Gly Ile Gln Gly Ala Leu Phe Ala Ser Leu Val Pro Gly Leu Asn
    130                 135                 140

Ile Val Arg Met Leu Leu Leu Gly Leu Val Tyr His Asp Glu Gly
145                 150                 155                 160

Thr Ile Lys Ser Met Ser Arg His Gly Asp Arg Arg Glu Leu Leu Lys
                165                 170                 175

Gly Pro Leu Tyr Tyr Val Leu Ser Ile Thr Ser Ala Cys Ile Tyr Tyr
            180                 185                 190

Trp Lys Ser Ser Pro Ile Ala Ile Ala Val Ile Cys Asn Leu Cys Ala
        195                 200                 205
```

```
Gly Asp Gly Met Ala Asp Ile Val Gly Arg Arg Phe Gly Thr Glu Lys
        210                 215                 220

Leu Pro Tyr Asn Lys Asn Lys Ser Phe Ala Gly Ser Ile Gly Met Ala
225                 230                 235                 240

Thr Ala Gly Phe Leu Ala Ser Val Gly Tyr Met Tyr Phe Ala Ser
                245                 250                 255

Phe Gly Tyr Ile Glu Asp Ser Gly Gly Met Ile Leu Arg Phe Leu Val
            260                 265                 270

Ile Ser Ile Ala Ser Ala Leu Val Glu Ser Leu Pro Ile Ser Thr Asp
        275                 280                 285

Ile Asp Asp Asn Leu Thr Ile Ser Leu Thr Ser Ala Leu Ala Gly Phe
290                 295                 300

Leu Leu Phe
305

<210> SEQ ID NO 67
<211> LENGTH: 298
<212> TYPE: PRT
<213> ORGANISM: Zea mays

<400> SEQUENCE: 67

Arg Thr Ala Glu Leu Gln His Pro Val Gln Gln Asp Gln Arg Gly
1               5                   10                  15

Cys Thr Ser Ala Ser Arg Val Gly Thr Met Trp Thr Gly Ser Pro Leu
            20                  25                  30

Leu Arg Asp Val Gly Ala Ala Val Leu Thr Gly Val Ala Ala Ala
        35                  40                  45

Val Leu Arg Phe Trp Glu Glu Ile Ala Asn Arg Ala Leu Leu Asp Gln
50                  55                  60

Lys Leu Cys Arg Lys Leu Val His Ile Thr Val Gly Leu Val Phe Phe
65                  70                  75                  80

Leu Met Trp Pro Leu Phe Ser Ser Asp Asp Val Phe Ala Pro Ser Leu
                85                  90                  95

Ala Pro Leu Ile Ile Ile Asn Ile Met Lys Val Thr Val Ile Gly
            100                 105                 110

Leu Gly Phe Val Lys Ala Glu Gly Val Val Asn Ser Met Thr Arg His
        115                 120                 125

Gly Asp Arg Arg Glu Leu Leu Lys Gly Pro Leu Tyr Tyr Ala Cys Ala
130                 135                 140

Ile Thr Leu Thr Thr Ile Val Phe Trp Arg Thr Ser Pro Ile Ser Ile
145                 150                 155                 160

Ala Val Ile Cys Asn Leu Cys Ala Gly Asp Val Ala Asp Ile Ala
            165                 170                 175

Gly Arg Arg Phe Gly His Val Lys Leu Pro His Asn Pro Glu Lys Ser
            180                 185                 190

Tyr Ala Gly Ser Ile Ala Met Phe Leu Ala Gly Phe Ile Ala Ser Val
        195                 200                 205

Leu Phe Met Cys Tyr Phe Asn Ile Phe Gly Phe Val Glu Lys Ser Trp
        210                 215                 220

Ser Met Val Ala Ala Phe Gly Val Ile Ser Leu Ala Ala Ala Val Val
225                 230                 235                 240

Glu Ser Leu Pro Ile Ser Thr Arg Leu Asp Asp Asn Leu Thr Val Ser
                245                 250                 255

Val Ala Ser Val Leu Val Gly Ala Leu Val Phe Tyr Ser Ile Gly Ala
```

```
                          260                 265                 270
Arg Asn Leu Cys Cys Met Ser Ser Glu Val Arg Ser Ile Pro Ala
            275                 280                 285
Thr Val Gly Met Val Phe Ala Gly Ser Ser
        290                 295

<210> SEQ ID NO 68
<211> LENGTH: 166
<212> TYPE: PRT
<213> ORGANISM: Sorghum bicolor

<400> SEQUENCE: 68

Met Phe Ser Leu Gly Pro Leu Gly Ala His Thr Ser Pro Leu Ser Cys
1               5                   10                  15

Ser Thr Tyr His Ala Pro Leu Leu Gln Ser Arg Arg Leu Ser Pro Ser
            20                  25                  30

Pro Thr Ala Pro Ala Ser Ala Ala Ala Ser Cys Ala Pro Arg Ser
        35                  40                  45

Leu Cys Phe Leu Arg Arg Arg Ser Ser Arg Phe Ala Ala Glu Arg Asn
50                  55                  60

Arg Arg Pro Thr Met Ala Ala Ile Ser Leu Glu Ala Gly Gly Gly
65                  70                  75                  80

Leu Ala His Asp Leu Gly Ser Ala Ala Val Thr Ala Gly Val Ala Leu
                85                  90                  95

Ala Leu Leu Lys Phe Phe Glu Glu Ile Ala Lys Arg Gly Val Phe Glu
            100                 105                 110

Gln Lys Leu Ser Arg Lys Leu Val His Ile Ser Val Gly Leu Val Phe
        115                 120                 125

Leu Leu Phe Trp Pro Leu Phe Ser Ser Gly Trp Tyr Ala Pro Phe Leu
    130                 135                 140

Ala Ala Leu Ala Pro Gly Val Asn Val Ile Arg Met Leu Leu Leu Gly
145                 150                 155                 160

Leu Gly Leu Met Lys Asn
                165

<210> SEQ ID NO 69
<211> LENGTH: 24
<212> TYPE: PRT
<213> ORGANISM: Artificial Sequence
<220> FEATURE:
<223> OTHER INFORMATION: Conserved Motif
<220> FEATURE:
<221> NAME/KEY: MISC_FEATURE
<222> LOCATION: (1)..(1)
<223> OTHER INFORMATION: x = e or d
<220> FEATURE:
<221> NAME/KEY: MISC_FEATURE
<222> LOCATION: (2)..(2)
<223> OTHER INFORMATION: x = v, l, i, or w
<220> FEATURE:
<221> NAME/KEY: MISC_FEATURE
<222> LOCATION: (3)..(3)
<223> OTHER INFORMATION: x = t, v, or s
<220> FEATURE:
<221> NAME/KEY: MISC_FEATURE
<222> LOCATION: (6)..(6)
<223> OTHER INFORMATION: x = i, a, or v
<220> FEATURE:
<221> NAME/KEY: MISC_FEATURE
<222> LOCATION: (7)..(7)
<223> OTHER INFORMATION: x = v or i
<220> FEATURE:
<221> NAME/KEY: MISC_FEATURE
<222> LOCATION: (9)..(9)
```

```
<223> OTHER INFORMATION: x = i or m
<220> FEATURE:
<221> NAME/KEY: MISC_FEATURE
<222> LOCATION: (11)..(11)
<223> OTHER INFORMATION: x = a, t, or s
<220> FEATURE:
<221> NAME/KEY: MISC_FEATURE
<222> LOCATION: (13)..(13)
<223> OTHER INFORMATION: x = q, m, n, h, p, or a
<220> FEATURE:
<221> NAME/KEY: MISC_FEATURE
<222> LOCATION: (14)..(14)
<223> OTHER INFORMATION: x = v, w, or i
<220> FEATURE:
<221> NAME/KEY: MISC_FEATURE
<222> LOCATION: (15)..(15)
<223> OTHER INFORMATION: x = v or i
<220> FEATURE:
<221> NAME/KEY: MISC_FEATURE
<222> LOCATION: (16)..(16)
<223> OTHER INFORMATION: x = l, f, or p
<220> FEATURE:
<221> NAME/KEY: MISC_FEATURE
<222> LOCATION: (17)..(17)
<223> OTHER INFORMATION: x = i, g, l, or f
<220> FEATURE:
<221> NAME/KEY: MISC_FEATURE
<222> LOCATION: (18)..(18)
<223> OTHER INFORMATION: x = a or v
<220> FEATURE:
<221> NAME/KEY: MISC_FEATURE
<222> LOCATION: (19)..(19)
<223> OTHER INFORMATION: x = w, l, or y
<220> FEATURE:
<221> NAME/KEY: MISC_FEATURE
<222> LOCATION: (20)..(20)
<223> OTHER INFORMATION: x = w, l, a, or f
<220> FEATURE:
<221> NAME/KEY: MISC_FEATURE
<222> LOCATION: (21)..(21)
<223> OTHER INFORMATION: x = l or f
<220> FEATURE:
<221> NAME/KEY: MISC_FEATURE
<222> LOCATION: (22)..(22)
<223> OTHER INFORMATION: x = s, f, d, e, g, a, or n
<220> FEATURE:
<221> NAME/KEY: MISC_FEATURE
<222> LOCATION: (23)..(23)
<223> OTHER INFORMATION: x = i, n, or v
<220> FEATURE:
<221> NAME/KEY: MISC_FEATURE
<222> LOCATION: (24)..(24)
<223> OTHER INFORMATION: x = p, r, or s

<400> SEQUENCE: 69

Xaa Xaa Xaa Arg Lys Xaa Xaa His Xaa Gly Xaa Gly Xaa Xaa Xaa Xaa
1               5                   10                  15

Xaa Xaa Xaa Xaa Xaa Xaa Xaa Xaa
            20

<210> SEQ ID NO 70
<211> LENGTH: 30
<212> TYPE: PRT
<213> ORGANISM: Artificial Sequence
<220> FEATURE:
<223> OTHER INFORMATION: Conserved Motif
<220> FEATURE:
<221> NAME/KEY: MISC_FEATURE
<222> LOCATION: (1)..(1)
<223> OTHER INFORMATION: x = i, f, or l
<220> FEATURE:
<221> NAME/KEY: MISC_FEATURE
<222> LOCATION: (2)..(2)
<223> OTHER INFORMATION: x = l, i, f, or v
<220> FEATURE:
<221> NAME/KEY: MISC_FEATURE
```

```
<222> LOCATION: (3)..(3)
<223> OTHER INFORMATION: x = p, g, or t
<220> FEATURE:
<221> NAME/KEY: MISC_FEATURE
<222> LOCATION: (4)..(4)
<223> OTHER INFORMATION: x = s, a, or g
<220> FEATURE:
<221> NAME/KEY: MISC_FEATURE
<222> LOCATION: (5)..(5)
<223> OTHER INFORMATION: x = l, m, i, or v
<220> FEATURE:
<221> NAME/KEY: MISC_FEATURE
<222> LOCATION: (6)..(6)
<223> OTHER INFORMATION: x = e, d, n, or s
<220> FEATURE:
<221> NAME/KEY: MISC_FEATURE
<222> LOCATION: (7)..(7)
<223> OTHER INFORMATION: x = s, t, g, d, or n
<220> FEATURE:
<221> NAME/KEY: MISC_FEATURE
<222> LOCATION: (8)..(8)
<223> OTHER INFORMATION: x = v, q, or i
<220> FEATURE:
<221> NAME/KEY: MISC_FEATURE
<222> LOCATION: (9)..(9)
<223> OTHER INFORMATION: x = g, d, n, or e
<220> FEATURE:
<221> NAME/KEY: MISC_FEATURE
<222> LOCATION: (10)..(10)
<223> OTHER INFORMATION: x = r or s
<220> FEATURE:
<221> NAME/KEY: MISC_FEATURE
<222> LOCATION: (11)..(11)
<223> OTHER INFORMATION: x = h, s, q, k, or n
<220> FEATURE:
<221> NAME/KEY: MISC_FEATURE
<222> LOCATION: (12)..(12)
<223> OTHER INFORMATION: x = s or none
<220> FEATURE:
<221> NAME/KEY: MISC_FEATURE
<222> LOCATION: (13)..(13)
<223> OTHER INFORMATION: x = y, p, f, l, or w
<220> FEATURE:
<221> NAME/KEY: MISC_FEATURE
<222> LOCATION: (16)..(16)
<223> OTHER INFORMATION: x = l, v, f, or i
<220> FEATURE:
<221> NAME/KEY: MISC_FEATURE
<222> LOCATION: (17)..(17)
<223> OTHER INFORMATION: x = f, y, or a
<220> FEATURE:
<221> NAME/KEY: MISC_FEATURE
<222> LOCATION: (18)..(18)
<223> OTHER INFORMATION: x = y or f
<220> FEATURE:
<221> NAME/KEY: MISC_FEATURE
<222> LOCATION: (19)..(19)
<223> OTHER INFORMATION: x = a, s, or g
<220> FEATURE:
<221> NAME/KEY: MISC_FEATURE
<222> LOCATION: (20)..(20)
<223> OTHER INFORMATION: x = l, i, or v
<220> FEATURE:
<221> NAME/KEY: MISC_FEATURE
<222> LOCATION: (21)..(21)
<223> OTHER INFORMATION: x = s, t, or a
<220> FEATURE:
<221> NAME/KEY: MISC_FEATURE
<222> LOCATION: (22)..(22)
<223> OTHER INFORMATION: x = i, v, or f
<220> FEATURE:
<221> NAME/KEY: MISC_FEATURE
<222> LOCATION: (23)..(23)
<223> OTHER INFORMATION: x = g or t
<220> FEATURE:
<221> NAME/KEY: MISC_FEATURE
<222> LOCATION: (24)..(24)
<223> OTHER INFORMATION: x = l, i, or m
<220> FEATURE:
```

```
<221> NAME/KEY: MISC_FEATURE
<222> LOCATION: (26)..(26)
<223> OTHER INFORMATION: x = v, f, i, m, or l
<220> FEATURE:
<221> NAME/KEY: MISC_FEATURE
<222> LOCATION: (27)..(27)
<223> OTHER INFORMATION: x = g, a, or i
<220> FEATURE:
<221> NAME/KEY: MISC_FEATURE
<222> LOCATION: (28)..(28)
<223> OTHER INFORMATION: x = g, l, s, w, or f
<220> FEATURE:
<221> NAME/KEY: MISC_FEATURE
<222> LOCATION: (29)..(29)
<223> OTHER INFORMATION: x = f, l, or c
<220> FEATURE:
<221> NAME/KEY: MISC_FEATURE
<222> LOCATION: (30)..(30)
<223> OTHER INFORMATION: x = f or w

<400> SEQUENCE: 70

Xaa Xaa Xaa Xaa Xaa Xaa Xaa Xaa Xaa Xaa Xaa Xaa Xaa Gly Thr Xaa
1               5                   10                  15

Xaa Xaa Xaa Xaa Xaa Xaa Xaa Xaa Leu Xaa Xaa Xaa Xaa Xaa
            20                  25                  30

<210> SEQ ID NO 71
<211> LENGTH: 16
<212> TYPE: PRT
<213> ORGANISM: Artificial Sequence
<220> FEATURE:
<223> OTHER INFORMATION: Conserved Motif
<220> FEATURE:
<221> NAME/KEY: MISC_FEATURE
<222> LOCATION: (2)..(2)
<223> OTHER INFORMATION: x = i, m, or v
<220> FEATURE:
<221> NAME/KEY: MISC_FEATURE
<222> LOCATION: (3)..(3)
<223> OTHER INFORMATION: x = l or m
<220> FEATURE:
<221> NAME/KEY: MISC_FEATURE
<222> LOCATION: (4)..(4)
<223> OTHER INFORMATION: x = v, a, i, or t
<220> FEATURE:
<221> NAME/KEY: MISC_FEATURE
<222> LOCATION: (6)..(6)
<223> OTHER INFORMATION: x = a or t
<220> FEATURE:
<221> NAME/KEY: MISC_FEATURE
<222> LOCATION: (7)..(7)
<223> OTHER INFORMATION: x = w, f, or l
<220> FEATURE:
<221> NAME/KEY: MISC_FEATURE
<222> LOCATION: (10)..(10)
<223> OTHER INFORMATION: x = g or a
<220> FEATURE:
<221> NAME/KEY: MISC_FEATURE
<222> LOCATION: (11)..(11)
<223> OTHER INFORMATION: x = l or f
<220> FEATURE:
<221> NAME/KEY: MISC_FEATURE
<222> LOCATION: (13)..(13)
<223> OTHER INFORMATION: x = a or g
<220> FEATURE:
<221> NAME/KEY: MISC_FEATURE
<222> LOCATION: (14)..(14)
<223> OTHER INFORMATION: x = l, f, or i
<220> FEATURE:
<221> NAME/KEY: MISC_FEATURE
<222> LOCATION: (15)..(15)
<223> OTHER INFORMATION: x = v or i

<400> SEQUENCE: 71

Gly Xaa Xaa Xaa Met Xaa Xaa Gly Asp Xaa Xaa Ala Xaa Xaa Xaa Gly
```

-continued

```
1               5               10              15

<210> SEQ ID NO 72
<211> LENGTH: 19
<212> TYPE: PRT
<213> ORGANISM: Artificial Sequence
<220> FEATURE:
<223> OTHER INFORMATION: Conserved Motif
<220> FEATURE:
<221> NAME/KEY: MISC_FEATURE
<222> LOCATION: (1)..(1)
<223> OTHER INFORMATION: x = g or n
<220> FEATURE:
<221> NAME/KEY: MISC_FEATURE
<222> LOCATION: (2)..(2)
<223> OTHER INFORMATION: x = f, s, t, a, m, or q
<220> FEATURE:
<221> NAME/KEY: MISC_FEATURE
<222> LOCATION: (3)..(3)
<223> OTHER INFORMATION: x = r, v, q, n, s, or t
<220> FEATURE:
<221> NAME/KEY: MISC_FEATURE
<222> LOCATION: (4)..(4)
<223> OTHER INFORMATION: x = k or r
<220> FEATURE:
<221> NAME/KEY: MISC_FEATURE
<222> LOCATION: (6)..(6)
<223> OTHER INFORMATION: x = w, i, v, or l
<220> FEATURE:
<221> NAME/KEY: MISC_FEATURE
<222> LOCATION: (7)..(7)
<223> OTHER INFORMATION: x = e, a, or i
<220> FEATURE:
<221> NAME/KEY: MISC_FEATURE
<222> LOCATION: (9)..(9)
<223> OTHER INFORMATION: x = t or s
<220> FEATURE:
<221> NAME/KEY: MISC_FEATURE
<222> LOCATION: (10)..(10)
<223> OTHER INFORMATION: x = l or a
<220> FEATURE:
<221> NAME/KEY: MISC_FEATURE
<222> LOCATION: (11)..(11)
<223> OTHER INFORMATION: x = t, a, or g
<220> FEATURE:
<221> NAME/KEY: MISC_FEATURE
<222> LOCATION: (13)..(13)
<223> OTHER INFORMATION: x = v, f, m, a, c, or g
<220> FEATURE:
<221> NAME/KEY: MISC_FEATURE
<222> LOCATION: (14)..(14)
<223> OTHER INFORMATION: x = l, v, f, or w
<220> FEATURE:
<221> NAME/KEY: MISC_FEATURE
<222> LOCATION: (15)..(15)
<223> OTHER INFORMATION: x = a, v, or i
<220> FEATURE:
<221> NAME/KEY: MISC_FEATURE
<222> LOCATION: (16)..(16)
<223> OTHER INFORMATION: x = s or t
<220> FEATURE:
<221> NAME/KEY: MISC_FEATURE
<222> LOCATION: (17)..(17)
<223> OTHER INFORMATION: x = f, t, y, l, or a
<220> FEATURE:
<221> NAME/KEY: MISC_FEATURE
<222> LOCATION: (18)..(18)
<223> OTHER INFORMATION: x = l, v, f, t, or i
<220> FEATURE:
<221> NAME/KEY: MISC_FEATURE
<222> LOCATION: (19)..(19)
<223> OTHER INFORMATION: x = v or i

<400> SEQUENCE: 72

Xaa Xaa Xaa Xaa Ser Xaa Xaa Gly Xaa Xaa Xaa Met Xaa Xaa Xaa Xaa
1               5                   10                  15
```

Xaa Xaa Xaa

<210> SEQ ID NO 73
<211> LENGTH: 17
<212> TYPE: PRT
<213> ORGANISM: Artificial Sequence
<220> FEATURE:
<223> OTHER INFORMATION: Conserved Motif
<220> FEATURE:
<221> NAME/KEY: MISC_FEATURE
<222> LOCATION: (1)..(1)
<223> OTHER INFORMATION: x = l or a
<220> FEATURE:
<221> NAME/KEY: MISC_FEATURE
<222> LOCATION: (3)..(3)
<223> OTHER INFORMATION: x = s, a, t, l, or q
<220> FEATURE:
<221> NAME/KEY: MISC_FEATURE
<222> LOCATION: (4)..(4)
<223> OTHER INFORMATION: x = f, v, l, or i
<220> FEATURE:
<221> NAME/KEY: MISC_FEATURE
<222> LOCATION: (5)..(5)
<223> OTHER INFORMATION: x = s or a
<220> FEATURE:
<221> NAME/KEY: MISC_FEATURE
<222> LOCATION: (6)..(6)
<223> OTHER INFORMATION: x = r, p, f, l, k, w, or t
<220> FEATURE:
<221> NAME/KEY: MISC_FEATURE
<222> LOCATION: (7)..(7)
<223> OTHER INFORMATION: x = w, h, l, v, r, or a
<220> FEATURE:
<221> NAME/KEY: MISC_FEATURE
<222> LOCATION: (9)..(9)
<223> OTHER INFORMATION: x = i, t, v, l, or m
<220> FEATURE:
<221> NAME/KEY: MISC_FEATURE
<222> LOCATION: (12)..(12)
<223> OTHER INFORMATION: x = l or i
<220> FEATURE:
<221> NAME/KEY: MISC_FEATURE
<222> LOCATION: (13)..(13)
<223> OTHER INFORMATION: x = t or s
<220> FEATURE:
<221> NAME/KEY: MISC_FEATURE
<222> LOCATION: (16)..(16)
<223> OTHER INFORMATION: x = l or i
<220> FEATURE:
<221> NAME/KEY: MISC_FEATURE
<222> LOCATION: (17)..(17)
<223> OTHER INFORMATION: x = g, v, or l

<400> SEQUENCE: 73

Xaa Glu Xaa Xaa Xaa Xaa Xaa Gly Xaa Asp Asn Xaa Xaa Val Pro Xaa
1               5                   10                  15

Xaa

<210> SEQ ID NO 74
<211> LENGTH: 22
<212> TYPE: PRT
<213> ORGANISM: Artificial Sequence
<220> FEATURE:
<223> OTHER INFORMATION: Conserved Motif
<220> FEATURE:
<221> NAME/KEY: MISC_FEATURE
<222> LOCATION: (2)..(2)
<223> OTHER INFORMATION: x = s, i, n, or c
<220> FEATURE:
<221> NAME/KEY: MISC_FEATURE
<222> LOCATION: (5)..(5)
<223> OTHER INFORMATION: x = l, v, or i
<220> FEATURE:
<221> NAME/KEY: MISC_FEATURE
<222> LOCATION: (8)..(8)

```
<223> OTHER INFORMATION: x = i or v
<220> FEATURE:
<221> NAME/KEY: MISC_FEATURE
<222> LOCATION: (9)..(9)
<223> OTHER INFORMATION: x = l, n, s, or t
<220> FEATURE:
<221> NAME/KEY: MISC_FEATURE
<222> LOCATION: (10)..(10)
<223> OTHER INFORMATION: x = s, i, or v
<220> FEATURE:
<221> NAME/KEY: MISC_FEATURE
<222> LOCATION: (12)..(12)
<223> OTHER INFORMATION: x = l, m, or v
<220> FEATURE:
<221> NAME/KEY: MISC_FEATURE
<222> LOCATION: (13)..(13)
<223> OTHER INFORMATION: x = l, v, i, or f
<220> FEATURE:
<221> NAME/KEY: MISC_FEATURE
<222> LOCATION: (14)..(14)
<223> OTHER INFORMATION: x = f or y
<220> FEATURE:
<221> NAME/KEY: MISC_FEATURE
<222> LOCATION: (15)..(15)
<223> OTHER INFORMATION: x = v, m, l, f, or a
<220> FEATURE:
<221> NAME/KEY: MISC_FEATURE
<222> LOCATION: (16)..(16)
<223> OTHER INFORMATION: x = l, i, v, s, or a
<220> FEATURE:
<221> NAME/KEY: MISC_FEATURE
<222> LOCATION: (17)..(17)
<223> OTHER INFORMATION: Xaa can be any naturally occurring amino acid
<220> FEATURE:
<221> NAME/KEY: MISC_FEATURE
<222> LOCATION: (18)..(18)
<223> OTHER INFORMATION: x = w or none
<220> FEATURE:
<221> NAME/KEY: MISC_FEATURE
<222> LOCATION: (20)..(20)
<223> OTHER INFORMATION: x = i or l
<220> FEATURE:
<221> NAME/KEY: MISC_FEATURE
<222> LOCATION: (21)..(21)
<223> OTHER INFORMATION: x = f or v

<400> SEQUENCE: 74

Leu Xaa Arg Lys Xaa Val His Xaa Xaa Xaa Gly Xaa Xaa Xaa Xaa Xaa
1               5                   10                  15

Xaa Xaa Pro Xaa Xaa Ser
            20

<210> SEQ ID NO 75
<211> LENGTH: 45
<212> TYPE: PRT
<213> ORGANISM: Artificial Sequence
<220> FEATURE:
<223> OTHER INFORMATION: Conserved Motif
<220> FEATURE:
<221> NAME/KEY: MISC_FEATURE
<222> LOCATION: (2)..(2)
<223> OTHER INFORMATION: x = a, s, or p
<220> FEATURE:
<221> NAME/KEY: MISC_FEATURE
<222> LOCATION: (3)..(3)
<223> OTHER INFORMATION: x = f, l, v, or i
<220> FEATURE:
<221> NAME/KEY: MISC_FEATURE
<222> LOCATION: (4)..(4)
<223> OTHER INFORMATION: x = v, a, t, or i
<220> FEATURE:
<221> NAME/KEY: MISC_FEATURE
<222> LOCATION: (5)..(5)
<223> OTHER INFORMATION: x = p or i
<220> FEATURE:
<221> NAME/KEY: MISC_FEATURE
```

```
<222> LOCATION: (6)..(6)
<223> OTHER INFORMATION: x = l, g, a, i, or f
<220> FEATURE:
<221> NAME/KEY: misc_feature
<222> LOCATION: (7)..(7)
<223> OTHER INFORMATION: x = v, l, i, or f
<220> FEATURE:
<221> NAME/KEY: misc_feature
<222> LOCATION: (9)..(9)
<223> OTHER INFORMATION: x = g, i, v, c, or s
<220> FEATURE:
<221> NAME/KEY: misc_feature
<222> LOCATION: (10)..(10)
<223> OTHER INFORMATION: x = l, v, i, f, or m
<220> FEATURE:
<221> NAME/KEY: misc_feature
<222> LOCATION: (11)..(11)
<223> OTHER INFORMATION: x = r or k
<220> FEATURE:
<221> NAME/KEY: misc_feature
<222> LOCATION: (12)..(12)
<223> OTHER INFORMATION: x = l, m, or v
<220> FEATURE:
<221> NAME/KEY: misc_feature
<222> LOCATION: (13)..(13)
<223> OTHER INFORMATION: x = v, l, t, or i
<220> FEATURE:
<221> NAME/KEY: misc_feature
<222> LOCATION: (14)..(14)
<223> OTHER INFORMATION: x = i, l, f, v, or t
<220> FEATURE:
<221> NAME/KEY: misc_feature
<222> LOCATION: (15)..(15)
<223> OTHER INFORMATION: x = n, l, m, i, h, or y
<220> FEATURE:
<221> NAME/KEY: misc_feature
<222> LOCATION: (17)..(17)
<223> OTHER INFORMATION: x = l or s
<220> FEATURE:
<221> NAME/KEY: misc_feature
<222> LOCATION: (18)..(18)
<223> OTHER INFORMATION: x = s, g, or r
<220> FEATURE:
<221> NAME/KEY: misc_feature
<222> LOCATION: (19)..(19)
<223> OTHER INFORMATION: x = i, v, l, or f
<220> FEATURE:
<221> NAME/KEY: misc_feature
<222> LOCATION: (20)..(20)
<223> OTHER INFORMATION: x = s, y, m, i, w, l, v, t, or a
<220> FEATURE:
<221> NAME/KEY: misc_feature
<222> LOCATION: (21)..(21)
<223> OTHER INFORMATION: x = p, h, k, q, d, s, or t
<220> FEATURE:
<221> NAME/KEY: misc_feature
<222> LOCATION: (22)..(22)
<223> OTHER INFORMATION: x = n, d, or a
<220> FEATURE:
<221> NAME/KEY: misc_feature
<222> LOCATION: (23)..(23)
<223> OTHER INFORMATION: x = s, e, d, or q
<220> FEATURE:
<221> NAME/KEY: misc_feature
<222> LOCATION: (24)..(24)
<223> OTHER INFORMATION: x = m, g, a, t, or s
<220> FEATURE:
<221> NAME/KEY: misc_feature
<222> LOCATION: (25)..(25)
<223> OTHER INFORMATION: x = l, t, m, or v
<220> FEATURE:
<221> NAME/KEY: misc_feature
<222> LOCATION: (26)..(26)
<223> OTHER INFORMATION: x = i or v
<220> FEATURE:
<221> NAME/KEY: misc_feature
<222> LOCATION: (27)..(27)
<223> OTHER INFORMATION: x = k, q, or n
<220> FEATURE:
```

```
<221> NAME/KEY: misc_feature
<222> LOCATION: (29)..(29)
<223> OTHER INFORMATION: x = v, m, or i
<220> FEATURE:
<221> NAME/KEY: misc_feature
<222> LOCATION: (30)..(30)
<223> OTHER INFORMATION: x = t or s
<220> FEATURE:
<221> NAME/KEY: misc_feature
<222> LOCATION: (32)..(32)
<223> OTHER INFORMATION: x = e, h, s, y, f, or n
<220> FEATURE:
<221> NAME/KEY: misc_feature
<222> LOCATION: (34)..(34)
<223> OTHER INFORMATION: x = r, d, n, or k
<220> FEATURE:
<221> NAME/KEY: misc_feature
<222> LOCATION: (35)..(35)
<223> OTHER INFORMATION: x = a, r, y, h, or p
<220> FEATURE:
<221> NAME/KEY: misc_feature
<222> LOCATION: (36)..(36)
<223> OTHER INFORMATION: x = e, r, k, or l
<220> FEATURE:
<221> NAME/KEY: misc_feature
<222> LOCATION: (40)..(40)
<223> OTHER INFORMATION: x = k or r
<220> FEATURE:
<221> NAME/KEY: misc_feature
<222> LOCATION: (41)..(41)
<223> OTHER INFORMATION: x = g or none
<220> FEATURE:
<221> NAME/KEY: misc_feature
<222> LOCATION: (44)..(44)
<223> OTHER INFORMATION: x = f or y

<400> SEQUENCE: 75

Ala Xaa Xaa Xaa Xaa Xaa Xaa Asn Xaa Xaa Xaa Xaa Xaa Xaa Xaa Gly
1               5                   10                  15

Xaa Xaa Xaa Xaa Xaa Xaa Xaa Xaa Xaa Xaa Ser Xaa Xaa Arg Xaa
            20                  25                  30

Gly Xaa Xaa Xaa Glu Leu Leu Xaa Gly Pro Leu Xaa Tyr
        35                  40                  45

<210> SEQ ID NO 76
<211> LENGTH: 36
<212> TYPE: PRT
<213> ORGANISM: Artificial Sequence
<220> FEATURE:
<223> OTHER INFORMATION: Conserved Motif
<220> FEATURE:
<221> NAME/KEY: MISC_FEATURE
<222> LOCATION: (2)..(2)
<223> OTHER INFORMATION: x = r or k
<220> FEATURE:
<221> NAME/KEY: MISC_FEATURE
<222> LOCATION: (3)..(3)
<223> OTHER INFORMATION: x = e, s, t, d, or q
<220> FEATURE:
<221> NAME/KEY: MISC_FEATURE
<222> LOCATION: (6)..(6)
<223> OTHER INFORMATION: x = i, v, or t
<220> FEATURE:
<221> NAME/KEY: MISC_FEATURE
<222> LOCATION: (7)..(7)
<223> OTHER INFORMATION: x = g, a, or s
<220> FEATURE:
<221> NAME/KEY: MISC_FEATURE
<222> LOCATION: (8)..(8)
<223> OTHER INFORMATION: x = m, i, or v
<220> FEATURE:
<221> NAME/KEY: MISC_FEATURE
<222> LOCATION: (9)..(9)
<223> OTHER INFORMATION: x = i, a, or v
<220> FEATURE:
```

```
<221> NAME/KEY: MISC_FEATURE
<222> LOCATION: (10)..(10)
<223> OTHER INFORMATION: x = s, v, l, a, or c
<220> FEATURE:
<221> NAME/KEY: MISC_FEATURE
<222> LOCATION: (11)..(11)
<223> OTHER INFORMATION: x = l, i, or v
<220> FEATURE:
<221> NAME/KEY: MISC_FEATURE
<222> LOCATION: (12)..(12)
<223> OTHER INFORMATION: x = a, c, or s
<220> FEATURE:
<221> NAME/KEY: MISC_FEATURE
<222> LOCATION: (13)..(13)
<223> OTHER INFORMATION: x = m or n
<220> FEATURE:
<221> NAME/KEY: MISC_FEATURE
<222> LOCATION: (14)..(14)
<223> OTHER INFORMATION: x = m or l
<220> FEATURE:
<221> NAME/KEY: MISC_FEATURE
<222> LOCATION: (15)..(15)
<223> OTHER INFORMATION: x = c or s
<220> FEATURE:
<221> NAME/KEY: MISC_FEATURE
<222> LOCATION: (16)..(16)
<223> OTHER INFORMATION: x = g or a
<220> FEATURE:
<221> NAME/KEY: MISC_FEATURE
<222> LOCATION: (20)..(20)
<223> OTHER INFORMATION: x = i, m, l, v, or f
<220> FEATURE:
<221> NAME/KEY: MISC_FEATURE
<222> LOCATION: (23)..(23)
<223> OTHER INFORMATION: x = i or v
<220> FEATURE:
<221> NAME/KEY: MISC_FEATURE
<222> LOCATION: (24)..(24)
<223> OTHER INFORMATION: x = m, v, i, or a
<220> FEATURE:
<221> NAME/KEY: MISC_FEATURE
<222> LOCATION: (27)..(27)
<223> OTHER INFORMATION: x = k, r, or q
<220> FEATURE:
<221> NAME/KEY: MISC_FEATURE
<222> LOCATION: (28)..(28)
<223> OTHER INFORMATION: x = f, l, or y
<220> FEATURE:
<221> NAME/KEY: MISC_FEATURE
<222> LOCATION: (30)..(30)
<223> OTHER INFORMATION: x = s, t, k, q, r, g, or h
<220> FEATURE:
<221> NAME/KEY: MISC_FEATURE
<222> LOCATION: (31)..(31)
<223> OTHER INFORMATION: x = t, e, h, k, i, v, y, s, m, a, or l
<220> FEATURE:
<221> NAME/KEY: MISC_FEATURE
<222> LOCATION: (33)..(33)
<223> OTHER INFORMATION: x = i or l
<220> FEATURE:
<221> NAME/KEY: MISC_FEATURE
<222> LOCATION: (34)..(34)
<223> OTHER INFORMATION: x = p or t
<220> FEATURE:
<221> NAME/KEY: MISC_FEATURE
<222> LOCATION: (35)..(35)
<223> OTHER INFORMATION: x = y, h, or f

<400> SEQUENCE: 76

Trp Xaa Xaa Ser Pro Xaa Xaa Xaa Xaa Xaa Xaa Xaa Xaa Xaa Xaa
1               5                   10                  15

Gly Asp Gly Xaa Ala Asp Xaa Xaa Gly Arg Xaa Xaa Gly Xaa Xaa Lys
            20                  25                  30

Xaa Xaa Xaa Asn
    35
```

```
<210> SEQ ID NO 77
<211> LENGTH: 30
<212> TYPE: PRT
<213> ORGANISM: Artificial Sequence
<220> FEATURE:
<223> OTHER INFORMATION: Conserved Motif
<220> FEATURE:
<221> NAME/KEY: MISC_FEATURE
<222> LOCATION: (3)..(3)
<223> OTHER INFORMATION: x = w, f, y, i, l, or v
<220> FEATURE:
<221> NAME/KEY: MISC_FEATURE
<222> LOCATION: (4)..(4)
<223> OTHER INFORMATION: x = a, e, v, or i
<220> FEATURE:
<221> NAME/KEY: MISC_FEATURE
<222> LOCATION: (7)..(7)
<223> OTHER INFORMATION: x = i, a, v, or m
<220> FEATURE:
<221> NAME/KEY: MISC_FEATURE
<222> LOCATION: (8)..(8)
<223> OTHER INFORMATION: x = s, g, or a
<220> FEATURE:
<221> NAME/KEY: MISC_FEATURE
<222> LOCATION: (10)..(10)
<223> OTHER INFORMATION: x = f, a, or l
<220> FEATURE:
<221> NAME/KEY: MISC_FEATURE
<222> LOCATION: (11)..(11)
<223> OTHER INFORMATION: x = i, t, v, l, or f
<220> FEATURE:
<221> NAME/KEY: MISC_FEATURE
<222> LOCATION: (12)..(12)
<223> OTHER INFORMATION: x = f, a, or s
<220> FEATURE:
<221> NAME/KEY: MISC_FEATURE
<222> LOCATION: (15)..(15)
<223> OTHER INFORMATION: x = f, l, m, v, or i
<220> FEATURE:
<221> NAME/KEY: MISC_FEATURE
<222> LOCATION: (16)..(16)
<223> OTHER INFORMATION: x = i, a, s, t, v, or l
<220> FEATURE:
<221> NAME/KEY: MISC_FEATURE
<222> LOCATION: (18)..(18)
<223> OTHER INFORMATION: x = i, v, or a
<220> FEATURE:
<221> NAME/KEY: MISC_FEATURE
<222> LOCATION: (19)..(19)
<223> OTHER INFORMATION: x = a, g, l, or m
<220> FEATURE:
<221> NAME/KEY: MISC_FEATURE
<222> LOCATION: (20)..(20)
<223> OTHER INFORMATION: x = l, y, f, or m
<220> FEATURE:
<221> NAME/KEY: MISC_FEATURE
<222> LOCATION: (21)..(21)
<223> OTHER INFORMATION: x = l or m
<220> FEATURE:
<221> NAME/KEY: MISC_FEATURE
<222> LOCATION: (22)..(22)
<223> OTHER INFORMATION: x = y, h, w, c, l, f, or s
<220> FEATURE:
<221> NAME/KEY: MISC_FEATURE
<222> LOCATION: (24)..(24)
<223> OTHER INFORMATION: x = y or f
<220> FEATURE:
<221> NAME/KEY: MISC_FEATURE
<222> LOCATION: (25)..(25)
<223> OTHER INFORMATION: x = s, a, h, q, or n
<220> FEATURE:
<221> NAME/KEY: MISC_FEATURE
<222> LOCATION: (26)..(26)
<223> OTHER INFORMATION: x = s, t, i, y, l, a, v, c, or w
<220> FEATURE:
<221> NAME/KEY: MISC_FEATURE
<222> LOCATION: (27)..(27)
<223> OTHER INFORMATION: x = l or f
```

<220> FEATURE:
<221> NAME/KEY: MISC_FEATURE
<222> LOCATION: (29)..(29)
<223> OTHER INFORMATION: x = y, f, l, or h
<220> FEATURE:
<221> NAME/KEY: MISC_FEATURE
<222> LOCATION: (30)..(30)
<223> OTHER INFORMATION: x = l, i, m, v, or f

<400> SEQUENCE: 77

Lys Ser Xaa Xaa Gly Ser Xaa Xaa Met Xaa Xaa Gly Phe Xaa Xaa
1               5                   10                  15

Ser Xaa Xaa Xaa Xaa Xaa Tyr Xaa Xaa Xaa Xaa Gly Xaa Xaa
            20                  25                  30

<210> SEQ ID NO 78
<211> LENGTH: 19
<212> TYPE: PRT
<213> ORGANISM: Artificial Sequence
<220> FEATURE:
<223> OTHER INFORMATION: Conserved Motif
<220> FEATURE:
<221> NAME/KEY: MISC_FEATURE
<222> LOCATION: (1)..(1)
<223> OTHER INFORMATION: x = m, v, l, i, or f
<220> FEATURE:
<221> NAME/KEY: MISC_FEATURE
<222> LOCATION: (2)..(2)
<223> OTHER INFORMATION: x = v, i, l, or t
<220> FEATURE:
<221> NAME/KEY: MISC_FEATURE
<222> LOCATION: (3)..(3)
<223> OTHER INFORMATION: x = s or a
<220> FEATURE:
<221> NAME/KEY: MISC_FEATURE
<222> LOCATION: (4)..(4)
<223> OTHER INFORMATION: x = m, i, v, f, or l
<220> FEATURE:
<221> NAME/KEY: MISC_FEATURE
<222> LOCATION: (5)..(5)
<223> OTHER INFORMATION: x = v, a, t, or s
<220> FEATURE:
<221> NAME/KEY: MISC_FEATURE
<222> LOCATION: (6)..(6)
<223> OTHER INFORMATION: x = a, s, or t
<220> FEATURE:
<221> NAME/KEY: MISC_FEATURE
<222> LOCATION: (7)..(7)
<223> OTHER INFORMATION: x = t or a
<220> FEATURE:
<221> NAME/KEY: MISC_FEATURE
<222> LOCATION: (8)..(8)
<223> OTHER INFORMATION: x = v, l, f, or i
<220> FEATURE:
<221> NAME/KEY: MISC_FEATURE
<222> LOCATION: (9)..(9)
<223> OTHER INFORMATION: x = v or i
<220> FEATURE:
<221> NAME/KEY: MISC_FEATURE
<222> LOCATION: (11)..(11)
<223> OTHER INFORMATION: x = s or c
<220> FEATURE:
<221> NAME/KEY: MISC_FEATURE
<222> LOCATION: (12)..(12)
<223> OTHER INFORMATION: x = l, h, v, or i
<220> FEATURE:
<221> NAME/KEY: MISC_FEATURE
<222> LOCATION: (14)..(14)
<223> OTHER INFORMATION: x = i or v
<220> FEATURE:
<221> NAME/KEY: MISC_FEATURE
<222> LOCATION: (15)..(15)
<223> OTHER INFORMATION: x = t, s, or n
<220> FEATURE:
<221> NAME/KEY: MISC_FEATURE
<222> LOCATION: (16)..(16)

-continued

```
<223> OTHER INFORMATION: x = d, t, s, m, k, or e
<220> FEATURE:
<221> NAME/KEY: MISC_FEATURE
<222> LOCATION: (17)..(17)
<223> OTHER INFORMATION: x = q, d, e, h, r, l, or v
<220> FEATURE:
<221> NAME/KEY: MISC_FEATURE
<222> LOCATION: (18)..(18)
<223> OTHER INFORMATION: x = l, i, or v

<400> SEQUENCE: 78

Xaa Xaa Xaa Xaa Xaa Xaa Xaa Xaa Xaa Glu Xaa Xaa Pro Xaa Xaa Xaa
1               5                   10                  15

Xaa Xaa Asp

<210> SEQ ID NO 79
<211> LENGTH: 233
<212> TYPE: PRT
<213> ORGANISM: Synechococcus sp.

<400> SEQUENCE: 79

Met Gly Ile Glu Gln Asn Asn Pro Met Ala Leu Pro Leu Trp Ile Ala
1               5                   10                  15

Val Gly Leu Ala Ala Thr Tyr Leu Gly Ala Val Val Leu Thr Ala Glu
                20                  25                  30

Leu Leu Asn Arg Leu Ser Leu Ser Pro Ala Glu Val Thr Arg Lys Ile
            35                  40                  45

Val His Ile Gly Ala Gly Gln Val Val Leu Ile Ala Trp Trp Leu Ser
        50                  55                  60

Ile Pro Gly Trp Val Gly Ala Ile Ala Gly Val Phe Ala Ala Gly Ile
65                  70                  75                  80

Ala Val Leu Ser Tyr Arg Leu Pro Ile Leu Pro Ser Leu Glu Ser Val
                85                  90                  95

Gly Arg His Ser Tyr Gly Thr Leu Phe Tyr Ala Leu Ser Ile Gly Leu
            100                 105                 110

Leu Val Gly Gly Phe Phe Ser Leu Gly Leu Pro Ile Phe Ala Ala Ile
        115                 120                 125

Gly Ile Leu Val Met Ala Trp Gly Asp Gly Leu Ala Ala Leu Val Gly
130                 135                 140

Gln Arg Trp Gly Arg His Arg Tyr Gln Val Phe Gly Phe Arg Lys Ser
145                 150                 155                 160

Trp Glu Gly Thr Leu Thr Met Val Leu Ala Ser Phe Leu Val Thr Val
                165                 170                 175

Val Phe Leu Ser Tyr Thr Phe Gly Phe Thr Val Ile Val Leu Val Val
            180                 185                 190

Ala Gly Thr Val Ala Ile Ala Ser Ala Gly Leu Glu Ser Phe Ser Arg
        195                 200                 205

Trp Gly Ile Asp Asn Leu Thr Val Pro Leu Gly Ser Ala Leu Ile Ala
    210                 215                 220

Trp Ala Gly Ser Tyr Leu Trp Leu Gly
225                 230
```

TOCOPHEROL BIOSYNTHESIS RELATED GENES AND USES THEREOF

This application claims the benefit of U.S. Provisional Application No. 60/400,689 filed Aug. 5, 2002, which is incorporated herein by reference.

FIELD OF THE INVENTION

The present invention is in the field of plant genetics and biochemistry. More specifically, the invention relates to genes associated with the tocopherol biosynthesis pathway, and uses of such genes.

Tocopherols are an important component of mammalian diets. Epidemiological evidence indicates that tocopherol supplementation can result in decreased risk for cardiovascular disease and cancer, can aid in immune function, and is associated with prevention or retardation of a number of degenerative disease processes in humans (Traber and Sies, *Annu. Rev. Nutr.*, 16:321–347, 1996). Tocopherol functions, in part, by stabilizing the lipid bilayer of biological membranes (Skrypin and Kagan, *Biochim. Biophys. Acta.*, 815: 209, 1995); Kagan, *N.Y. Acad. Sci.*, p 121, 1989); Gomez-Fernandez et al., *Ann. N.Y. Acad. Sci.*, p 109, 1989), reducing polyunsaturated fatty acid (PUFA) free radicals generated by lipid oxidation (Fukuzawa et al., *Lipids*, 17:511–513, 1982), and scavenging oxygen free radicals, lipid peroxy radicals and singlet oxygen species (Diplock et al., *Ann. N Y Acad. Sci.*, 570:72, 1989); Fryer, *Plant Cell Environ.*, 15(4):381–392, 1992).

The compound α-tocopherol, which is often referred to as vitamin E, belongs to a class of lipid-soluble antioxidants that includes α, β, γ, and δ-tocopherols and α, β, γ, and δ-tocotrienols. α, β, γ, and δ-tocopherols and α, β, γ, and δ-tocotrienols are sometimes referred to collectively as "vitamin E". Vitamin E is more appropriately defined chemically as the beneficial activity for animals and humans which can be e.g., determined in the rat fetal absorption and hemolysis assays (Chow, Vitamin E, In: Handbook of Vitamins ISBN:0-8247-0428-2). α-Tocopherol has the highest vitamin E activity, in part because it is readily absorbed and retained by the body (Traber and Sies, *Annu. Rev. Nutr.*, 16:321–347, 1996). However, other tocopherols and tocotrienols such as β, γ, δ-tocopherols and tocotrienols also have significant health and nutritional benefits.

Tocopherols are synthesized only by plants and certain other photosynthetic organisms, including cyanobacteria. As a result, mammalian dietary tocopherols are obtained almost exclusively from these sources. Plant tissues vary considerably in total tocopherol content and tocopherol composition, with α-tocopherol the predominant tocopherol species found in green, photosynthetic plant tissues. Leaf tissue can contain from 10–50 μg of total tocopherols per gram fresh weight, but the edible parts of most of the world's major staple crops (e.g., rice, corn, wheat, potato) produce low to extremely low levels of total tocopherols, of which only a small percentage is α-tocopherol (Hess, Vitamin E, α-tocopherol, In *Antioxidants in Higher Plants*, R. Alscher and J. Hess, Eds., CRC Press, Boca Raton. pp. 111–134, 1993). Oil seed crops generally contain much higher levels of total tocopherols, but α-tocopherol is present only as a minor component in most oilseeds (Taylor and Barnes, *Chemy Ind.*, 722–726, October, 1981).

The recommended daily dietary intake of 15–30 mg of vitamin E is quite difficult to achieve from the average American diet. For example, it would take over 750 grams of spinach leaves, in which α-tocopherol comprises 60% of total tocopherols, or 200–400 grams of soybean oil to satisfy this recommended daily vitamin E intake. While it is possible to augment the diet with supplements, most of these supplements contain primarily synthetic vitamin E, having eight stereoisomers, whereas natural vitamin E is predominantly composed of only a single isomer. Furthermore, supplements tend to be relatively expensive, and the general population is disinclined to take vitamin supplements on a regular basis. Therefore, there is a need in the art for compositions and methods that either increase the total tocopherol production or increase the relative percentage of α-tocopherol produced by plants.

In addition to the health benefits of tocopherols, increased tocopherol levels in crops have been associated with enhanced stability and extended shelf life of plant products (Peterson, *Cereal-Chem.*, 72(1):21–24, 1995); Ball, *Fat-soluble vitamin assays in food analysis. A comprehensive review*, London, Elsevier Science Publishers Ltd. (1988). Further, tocopherol supplementation of swine, beef, and poultry feeds has been shown to significantly increase meat quality and extend the shelf life of post-processed meat products by retarding post-processing lipid oxidation, which contributes to the undesirable flavor components (Sante and Lacourt, *J. Sci. Food Agric.*, 65(4):503–507, 1994); Buckley et al., *J. of Animal Science*, 73:3122–3130, 1995).

There is a need in the art for nucleic acid molecules encoding enzymes involved in tocopherol biosysnthesis, as well as related enzymes and antibodies for the enhancement or alteration of tocopherol production in plants. There is a further need for transgenic organisms expressing those nucleic acid molecules involved in tocopherol biosynthesis, which are capable of nutritionally enhancing food and feed sources.

SUMMARY OF THE INVENTION

The present invention includes and provides substantially purified nucleic acid molecules encoding a polypeptide comprising an amino acid sequence selected from the group consisting of SEQ ID NOs: 20–41 and 53–68, encoding a phytol kinase polypeptide, or polypeptide having phytol kinase activity, encoding a yeast phytol kinase polypeptide, or a yeast polypeptide having phytol kinase activity, encoding a plant phytol kinase polypeptide, or a plant polypeptide having phytol kinase activity, encoding a cyanobacterial phytol kinase polypeptide, or a cyanobacterial polypeptide having phytol kinase activity, encoding a phytol kinase polypeptide or polypeptide having phytol kinase activity comprising an amino acid sequence selected from the group consisting of SEQ ID NOs: 69–78.

The present invention includes and provides plant specific phytol kinase motifs (SEQ ID NOs: 74, 77, and 78) and cyanobacterial specific motifs (SEQ ID NOs: 71–73) and nucleotides encoding the same.

The present invention includes and provides a DNA construct comprising a heterologous promoter that functions in plants operably linked to a nucleic acid molecule encoding a phytol kinase polypeptide, or a polypeptide having phytol kinase activity, comprising an amino acid sequence selected from the group consisting of SEQ ID NOs: 2, 6, 20–68, and 79 or comprising an amino acid sequence having at least about 70%, 80%, 90%, 95%, or 99% identity to such amino acid sequences.

The present invention includes and provides a transformed plant and progeny thereof comprising an introduced nucleic acid molecule comprising a nucleic acid sequence selected from the group consisting of: (1) SEQ ID NOs: 1, 5, and 17 and sequences having at least about 70, 80, 90, 95 or 99% identity to such sequences; (2) an introduced nucleic acid molecule encoding a polypeptide comprising an amino acid sequence having at least about 70, 80, 90, 95 or 99% identity to a sequence selected from the group consisting of SEQ ID NOs: 2, 6, 20–68, and 79; (3) an introduced nucleic acid molecule encoding a phytol kinase polypeptide, or a polypeptide having phytol kinase activity; (4) an introduced nucleic acid molecule encoding a plant phytol kinase polypeptide, or a plant polypeptide having phytol kinase activity; (5) an introduced nucleic acid molecule encoding a cyanobacterial phytol kinase polypeptide, or a cyanobacterial polypeptide having phytol kinase activity; (6) an introduced nucleic acid molecule encoding a phytol kinase polypeptide, or a polypeptide having phytol kinase activity comprising an amino acid sequence selected from the group consisting of SEQ ID NOs: 69–78; (7) an introduced nucleic acid molecule encoding a plant phytol kinase polypeptide, or a plant polypeptide having phytol kinase activity comprising an amino acid selected from the group consisting of SEQ ID NOs: 2, 6, and 37–68; (8) an introduced nucleic acid molecule encoding a cyanobacterial phytol kinase polypeptide, or a cyanobacterial polypeptide having phytol kinase activity, comprising an amino acid sequence selected from the group consisting of SEQ ID NOs: 20–27, and 29–34; (9) an introduced nucleic acid molecule encoding a plant phytol kinase polypeptide, or a plant polypeptide having phytol kinase activity, comprising an amino acid selected from the group consisting of SEQ ID NOs: 74, 77, and 78; (10) an introduced nucleic acid molecule encoding a plant phytol kinase polypeptide, or a plant polypeptide having phytol kinase activity, comprising an amino acid selected from the group consisting of SEQ ID NOs: 74, 77, and 78, wherein said polypeptide is not derived from *Allium porrum, Brassica napus,* Gossypium, *Glycine max, Oryza sativa, Sorghum bicolor, Triticum aestivum,* and *Zea mays;* (11) an introduced nucleic acid molecule encoding a plant phytol kinase polypeptide, or a plant polypeptide having phytol kinase activity, comprising an amino acid sequence selected from the group consisting of SEQ ID NOs: 74, 77, and 78 and further comprising an amino acid sequence comprising one or more of SEQ ID NOs: 75 and 76; (12) an introduced nucleic acid molecule encoding a plant phytol kinase polypeptide, or a plant polypeptide having phytol kinase activity, comprising an amino acid sequence selected from the group consisting of SEQ ID NOs: 74, 77, and 78 and further comprising an amino acid sequence comprising one or more of SEQ ID NOs: 75 and 76, wherein said polypeptide is not derived from *Allium porrum, Brassica napus,* Gossypium, *Glycine max, Oryza sativa, Sorghum bicolor, Triticum aestivum,* and *Zea mays;* (13) an introduced nucleic acid molecule encoding a cyanobacterial phytol kinase polypeptide, or a cyanobacterial polypeptide having phytol kinase activity, comprising an amino acid sequence selected from the group consisting of SEQ ID NOs: 71, 72, and 73; (14) an introduced nucleic acid molecule encoding a cyanobacterial phytol kinase polypeptide, or a cyanobacterial polypeptide having phytol kinase activity, comprising an amino acid sequence selected from the group consisting of SEQ ID NOs: 71, 72, and 73, wherein said polypeptide is not derived from Synechocystis, *Aquifex aeolicus, Chlorobium tepidum, Chloroflexus aurantiacus, Nostoc punctiforme, Prochlorococcus marinus, Rickettsia conorii, Rickettsia prowazekii, Rickettsia sibirica,* Synechoccus, *Thermosynechoccus elongatus, Trichodesmium erythraeum* and *Saccharomyces cerevisiae;* (15) an introduced nucleic acid molecule encoding a cyanobacterial phytol kinase polypeptide, or a cyanobacterial polypeptide having phytol kinase activity, comprising one or more amino acid sequences selected from the group consisting of SEQ ID NOs: 71, 72, and 73 and further comprising an amino acid sequence comprising one or more of SEQ ID NOs: 69 and 70; (16) an introduced nucleic acid molecule encoding a cyanobacterial phytol kinase polypeptide, or a cyanobacterial polypeptide having phytol kinase activity, comprising one or more amino acid sequences selected from the group consisting of SEQ ID NOs: 71, 72, and 73 and further comprising an amino acid sequence comprising one or more of SEQ ID NOs: 69 and 70, wherein said polypeptide is not derived from Synechocystis, *Aquifex aeolicus, Chlorobium tepidum, Chloroflexus aurantiacus, Nostoc punctiforme, Prochlorococcus marinus, Rickettsia conorii, Rickettsia prowazekii, Rickettsia sibirica,* Synechoccus, *Thermosynechoccus elongatus, Trichodesmium erythraeum* and *Saccharomyces cerevisiae;* (17) an introduced nucleic acid molecule encoding a yeast phytol kinase polypeptide, or a yeast polypeptide having phytol kinase activity; (18) an introduced nucleic acid molecule encoding a yeast phytol kinase polypeptide, or a yeast polypeptide having phytol kinase activity, comprising an amino acid sequence selected from the group consisting of SEQ ID NOs: 35 and 36; and, optionally, further comprising one or more additional introduced nucleic acid molecule(s) encoding enzyme(s) or coding region(s) of enzyme(s) of the tocopherol biosynthetic pathway, for example, MT1, tMT2, GMT, tyrA (e.g., SEQ ID NO: 16), HPT (e.g., SEQ ID NO: 15), tocopherol cyclase, dxs, dxr, GGPPS, HPPD (SEQ ID NO: 14), AANT1, IDI, chlorophyllase (SEQ ID NOs: 18 and 19), and GGH (SEQ ID NO: 13), as described in Table 1.

The present invention includes and provides methods for increasing at least one of tocopherol and tocotrienol levels in a plant relative to a plant of similar genetic background but lacking the introduced nucleic acid molecule(s).

In one embodiment, the transformed plant produces seed having at least one of increased tocopherol and tocotrienol levels relative to a seed having a similar genetic background but lacking the introduced nucleic acid molecule(s).

In one embodiment, the transformed plant is selected from the group consisting of alfalfa, *Arabidopsis thaliana,* barley, *Brassica campestris,* oilseed rape, broccoli, cabbage, citrus, canola, cotton, garlic, oat, Allium, flax, an ornamental plant, peanut, pepper, potato, rapeseed, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, chick peas, corn, Phaseolus, crambe, mustard, castor bean, sesame, cottonseed, linseed, safflower, and oil palm.

The present invention includes and provides a method for reducing tocopherol levels in a plant comprising: (a) transforming a plant cell with a nucleic acid molecule, the nucleic acid molecule having a promoter region which functions in plant cells to cause the production of an mRNA molecule, wherein the promoter region is linked to an inhibitory nucleic acid molecule complementary to at least a portion of SEQ ID NOs: 1, 5, and 17 or a sequence having at least about 70, 80, 90, 95, or 99% identity to such sequence; and (b) growing the transformed plant cell into a fertile plant; and (c) selecting for a plant with reduced tocopherol levels.

The present invention includes and provides a method of increasing the production of tocotrienols in a plant comprising (a) transforming a plant cell with a nucleic acid construct which causes the down regulation of SEQ ID NOs: 1, 5, or 17 or a nucleic acid sequence having at least about 70, 80, 90, 95, or 99% identity to such sequence; (b) growing the transformed plant cell into a fertile plant; and (c) selecting for a plant with increased tocotrienol levels.

The present invention includes and provides a method for screening for agents that alter tocopherol levels in a plant, comprising: (a) providing a plant lacking a polypeptide comprising the polypeptide sequence of SEQ ID NOs: 2, 6, 20–68, and 79; (b) exposing the plant to a test agent; and (c) assaying tocopherol levels in the plant.

In another preferred embodiment, expression or overexpression of a phytol kinase of the present invention in a transformed plant may provide tolerance to a variety of stresses.

DESCRIPTION OF THE NUCLEIC ACID AND AMINO ACID SEQUENCES

SEQ ID NO: 1 represents an LTT1 nucleic acid sequence from *Arabidopsis thaliana*.
SEQ ID NO: 2 represents a polypeptide sequence encoded by an LTT1 nucleic acid sequence from *Arabidopsis thaliana*.
SEQ ID NO: 3 represents a mutant LTT1 nucleic acid sequence from *Arabidopsis thaliana*.
SEQ ID NO: 4 represents a polypeptide sequence encoded by a mutant LTT1 nucleic acid sequence from *Arabidopsis thaliana*.
SEQ ID NO: 5 represents LTT1-r, a nucleic acid sequence related to LTT1 from *Arabidopsis thaliana*.
SEQ ID NO: 6 represents a polypeptide sequence encoded by an LTT1-r nucleic acid sequence from *Arabidopsis thaliana*.
SEQ ID NO: 7 represents nucleic acid sequence DNA primer 404.
SEQ ID NO: 8 represents nucleic acid sequence DNA primer 405.
SEQ ID NO: 9 represents nucleic acid sequence DNA primer 1652-e-1-f.
SEQ ID NO: 10 represents nucleic acid sequence DNA primer 1652-i-2-r.
SEQ ID NO: 11 represents nucleic acid sequence DNA primer 1652-i-3-f.
SEQ ID NO: 12 represents nucleic acid sequence DNA primer 1652-e-4-r.
SEQ ID NO: 13 represents a nucleic acid sequence of an *Arabidopsis thaliana* GGH.
SEQ ID NO: 14 represents a nucleic acid sequence of an *Arabidopsis thaliana* HPPD.
SEQ ID NO: 15 represents a nucleic acid sequence of an Arabidopsis HPT.
SEQ ID NO: 16 represents a nucleic acid sequence of an *Erwinia herbicola* TyrA.
SEQ ID NO: 17 represents a nucleic acid sequence of a Synechocystis LTT1.
SEQ ID NO: 18 represents a nucleic acid sequence of an *Arabidopsis thaliana* Chlorophyllase 1.
SEQ ID NO: 19 represents a nucleic acid sequence of an *Arabidopsis thaliana* Chlorophyllase 2.
SEQ ID NO: 20 represents a phytol kinase polypeptide sequence from *Aquifex aeolicus* VF5.
SEQ ID NO: 21 represents a phytol kinase polypeptide sequence from *Chlorobium tepidum* TLS 1.
SEQ ID NO: 22 represents a phytol kinase polypeptide sequence from *Chlorobium tepidum* TLS 2.
SEQ ID NO: 23 represents a phytol kinase polypeptide sequence from *Chloroflexus aurantiacus*.
SEQ ID NO: 24 represents a phytol kinase polypeptide sequence from *Nostoc punctiforme* 1.
SEQ ID NO: 25 represents a phytol kinase polypeptide sequence from *Nostoc punctiforme* 2.
SEQ ID NO: 26 represents a phytol kinase polypeptide sequence from *Nostoc punctiforme* 3.
SEQ ID NO: 27 represents a phytol kinase polypeptide sequence from *Prochlorococcus marinus* 1.
SEQ ID NO: 28 represents a dolichol kinase polypeptide sequence from *Prochlorococcus marinus* 2.
SEQ ID NO: 29 represents a phytol kinase polypeptide sequence from *Rickettsia conorii*.
SEQ ID NO: 30 represents a phytol kinase polypeptide sequence from *Rickettsia prowazekii*.
SEQ ID NO: 31 represents a phytol kinase polypeptide sequence from *Rickettsia sibirica*.
SEQ ID NO: 32 represents a phytol kinase polypeptide sequence from Synechococcus sp.
SEQ ID NO: 33 represents a phytol kinase polypeptide sequence from *Thermosynechococcus elongatus* BP-1.
SEQ ID NO: 34 represents a phytol kinase polypeptide sequence from *Trichodesmium erythraeum* IMS 101.
SEQ ID NO: 35 represents a dolichol kinase polypeptide sequence from *Saccharomyces cerevisiae*.
SEQ ID NO: 36 represents a Hsdl polypeptide sequence from *Saccharomyces cerevisiae*.
SEQ ID NO: 37 represents a phytol kinase polypeptide sequence from *Allium porrum*.
SEQ ID NO: 38 represents a phytol kinase polypeptide sequence from *Brassica napus* 1.
SEQ ID NO: 39 represents a phytol kinase polypeptide sequence from *Brassica napus* 2.
SEQ ID NO: 40 represents a phytol kinase polypeptide sequence from *Gossypium hirsutum* 1.
SEQ ID NO: 41 represents a phytol kinase polypeptide sequence from *Gossypium hirsutum* 2.
SEQ ID NO: 42 represents a phytol kinase polypeptide sequence from *Glycine max* 1.
SEQ ID NO: 43 represents a phytol kinase polypeptide sequence from *Glycine max* 2.
SEQ ID NO: 44 represents a phytol kinase polypeptide sequence from *Glycine max* 3.
SEQ ID NO: 45 represents a phytol kinase polypeptide sequence from *Glycine max* 4.
SEQ ID NO: 46 represents a phytol kinase polypeptide sequence from *Oryza sativa* 1.
SEQ ID NO: 47 represents a phytol kinase polypeptide sequence from *Oryza sativa* 2.
SEQ ID NO: 48 represents a phytol kinase polypeptide sequence from *Oryza sativa* 3.
SEQ ID NO: 49 represents a phytol kinase polypeptide sequence from *Oryza sativa* 4.
SEQ ID NO: 50 represents a phytol kinase polypeptide sequence from *Oryza sativa* 5.
SEQ ID NO: 51 represents a phytol kinase polypeptide sequence from *Oryza sativa* 6.
SEQ ID NO: 52 represents a phytol kinase polypeptide sequence from *Oryza sativa* 7.
SEQ ID NO: 53 represents a phytol kinase polypeptide sequence from *Sorghum bicolor* 1.
SEQ ID NO: 54 represents a phytol kinase polypeptide sequence from *Sorghum bicolor* 2.
SEQ ID NO: 55 represents a phytol kinase polypeptide sequence from *Sorghum bicolor* 3.
SEQ ID NO: 56 represents a phytol kinase polypeptide sequence from *Triticum aestivum* 1.
SEQ ID NO: 57 represents a phytol kinase polypeptide sequence from *Triticum aestivum* 2.

SEQ ID NO: 58 represents a phytol kinase polypeptide sequence from *Triticum aestivum* 3.
SEQ ID NO: 59 represents a phytol kinase polypeptide sequence from *Zea mays* 1.
SEQ ID NO: 60 represents a phytol kinase polypeptide sequence from *Zea mays* 2.
SEQ ID NO: 61 represents a phytol kinase polypeptide sequence from *Zea mays* 3.
SEQ ID NO: 62 represents a phytol kinase polypeptide sequence from *Zea mays* 4.
SEQ ID NO: 63 represents a phytol kinase polypeptide sequence from *Zea mays* 5.
SEQ ID NO: 64 represents a phytol kinase polypeptide sequence from *Zea mays* 6.
SEQ ID NO: 65 represents a phytol kinase polypeptide sequence from *Zea mays* 7.
SEQ ID NO: 66 represents a phytol kinase polypeptide sequence from *Zea mays* 8.
SEQ ID NO: 67 represents a phytol kinase polypeptide sequence from *Zea mays* 9.
SEQ ID NO: 68 represents a phytol kinase polypeptide sequence from *Sorghum bicolor* 4.
SEQ ID NO: 69 represents a cyanobacterial motif 1.
SEQ ID NO: 70 represents a cyanobacterial motif 2.
SEQ ID NO: 71 represents a cyanobacterial motif 3.
SEQ ID NO: 72 represents a cyanobacterial motif 4.
SEQ ID NO: 73 represents a cyanobacterial motif 5.
SEQ ID NO: 74 represents a plant motif 1.
SEQ ID NO: 75 represents a plant motif 2.
SEQ ID NO: 76 represents a plant motif 3.
SEQ ID NO: 77 represents a plant motif 4.
SEQ ID NO: 78 represents a plant motif 5.
SEQ ID NO: 79 represents represents a phytol kinase polypeptide sequence from *Synechocystis*.

BRIEF DESCRIPTION OF THE FIGURES

FIG. 11 illustrates cyanobacterial motif 1.
FIG. 12 illustrates cyanobacterial motif 2.
FIG. 13 illustrates cyanobacterial motif 3.
FIG. 14 illustrates cyanobacterial motif 4.
FIG. 15 illustrates cyanobacterial motif 5.
FIG. 16 illustrates plant motif 1.
FIG. 17 illustrates plant motif 2.
FIG. 18 illustrates plant motif 3.
FIG. 19 illustrates plant motif 4.
FIG. 20 illustrates plant motif 5.

DETAILED DESCRIPTION

Figure 1:
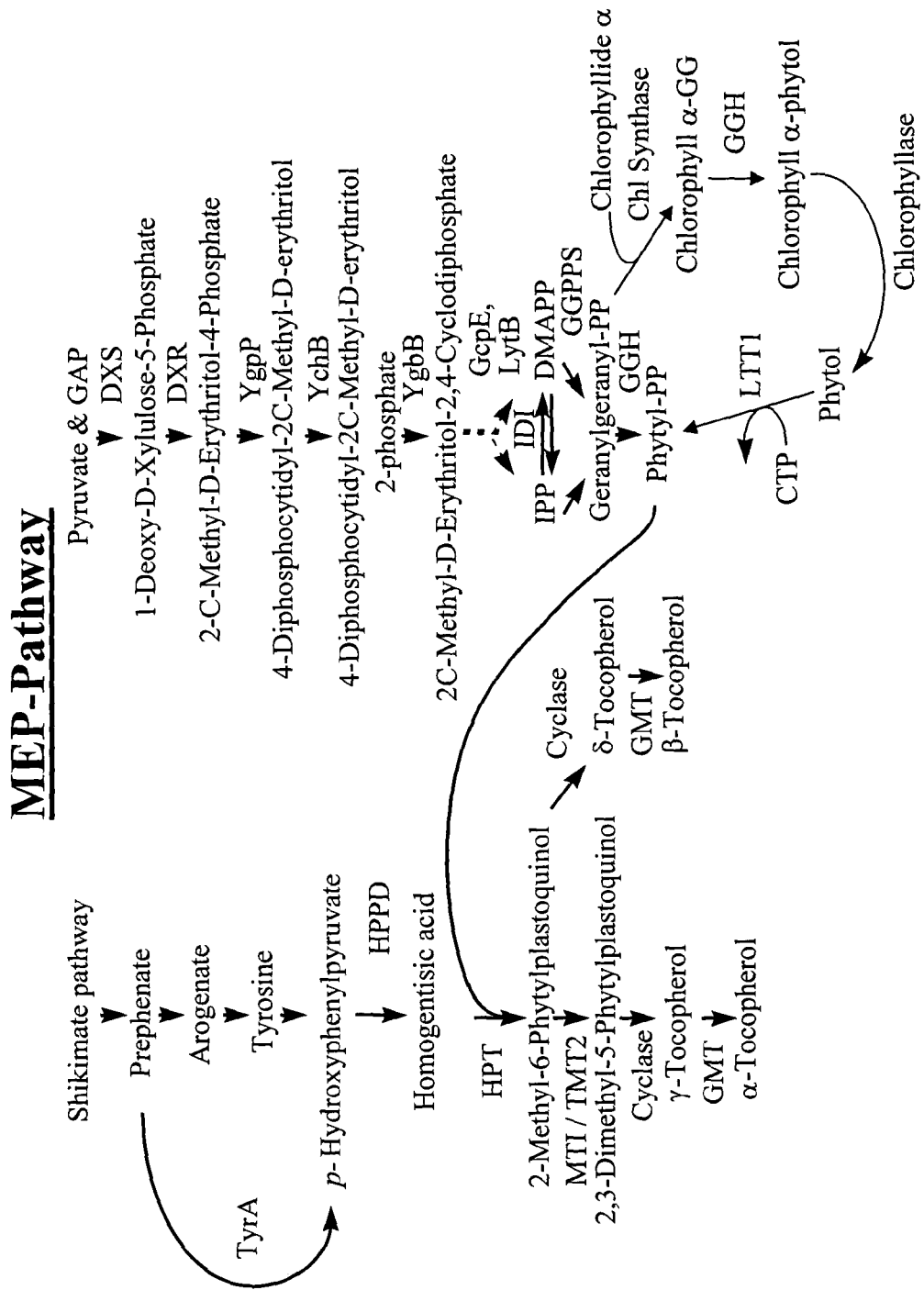
FIG. 1 illustrates a schematic representation of the tocopherol biosynthesis pathway.

The present invention provides a number of agents, for example, nucleic acid molecules and polypeptides associated with the synthesis of tocopherol, and provides uses of such agents.

Tocopherol Biosynthesis

The plastids of higher plants exhibit interconnected biochemical pathways leading to secondary metabolites including tocopherols. The tocopherol biosynthetic pathway in higher plants involves condensation of homogentisic acid and phytylpyrophosphate to form 2-methylphytylplastoquinol (Fiedler et al., *Planta*, 155:511–515 (1982); Soll et al., *Arch. Biochem. Biophys.*, 204:544–550 (1980); Marshall et al., *Phytochem.*, 24:1705–1711 (1985). This plant tocopherol pathway can be divided into four parts: 1) synthesis of homogentisic acid (HGA), which contributes to the aromatic ring of tocopherol; 2) synthesis of phytylpyrophosphate, which contributes to the side chain of tocopherol; 3) joining of HGA and phytylpyrophosphate via a prenyltransferase followed by a methylation reaction, a subsequent cyclization; 4) and another S-adenosyl methionine dependent methylation of an aromatic ring, which affects the relative abundance of each of the tocopherol species. See FIG. 1.

Various genes and their encoded proteins that are involved in tocopherol biosynthesis are listed in the table below.

TABLE 1

Tocopherol biosynthetic coding regions and enzymes

| Coding region or Enzyme Abbreviation | Enzyme name |
|---|---|
| tyrA | Mono or bifunctional prephenate dehydrogenase |
| HPT | Homogentisate prenyl transferase |
| DXS | 1-Deoxyxylulose-5-phosphate synthase |
| DXR | 1-Deoxyxylulose-5-phosphate reductoisomerase |
| GGPPS | Geranylgeranyl pyrophosphate synthase |
| HPPD | p-Hydroxyphenylpyruvate dioxygenase |
| AANT1 | Adenylate transporter |
| IDI | Isopentenyl diphosphate isomerase |
| MT1 | Bacterial 2-methylphytylplastoquinol methyltransferase |
| tMT2 | Plant 2-methylphytylplastoquinol methyltransferase |
| GGH | Geranylgeranyl diphosphate reductase |
| slr1737 | Tocopherol cyclase |
| GMT | Gamma Methyl Transferase |
| LTT1 | Phytol kinase |
| Chl1 and Chl2 | Chlorophyllase 1 and 2 |

As used herein, homogentisate prenyl transferase (HPT), phytylprenyl transferase (PPT), slr1736, and ATPT2, each refer to proteins or genes encoding proteins that have the same enzymatic activity.

As used herein, a phytol kinase is an enzyme that phosphorylates free phytol and/or phosphorylates phytol monophosphate. "Having phytol kinase activity" means that the enzyme phosphorylates free phytol and/or phosphorylates phytol monophosphate.

Synthesis of Homogentisic Acid

Homogentisic acid is the common precursor to both tocopherols and plastoquinones. In at least some bacteria, the synthesis of homogentisic acid is reported to occur via the conversion of chorismate to prephenate and then to p-hydroxyphenylpyruvate via a bifunctional prephenate dehydrogenase. Examples of bifunctional bacterial prephenate dehydrogenase enzymes include the proteins encoded by the tyrA genes of *Erwinia herbicola* and Escherichia coli. The tyrA gene product catalyzes the production of prephenate from chorismate, as well as the subsequent dehydrogenation of prephenate to form p-hydroxyphenylpyruvate (p-HPP), the immediate precursor to homogentisic acid. p-HPP is then converted to homogentisic acid by p-hydroxyphenylpyruvate dioxygenase (HPPD). In contrast, plants are believed to lack prephenate dehydrogenase activity, and it is generally believed that the synthesis of homogentisic acid from chorismate occurs via the synthesis and conversion of the intermediates arogenate, tyrosine, and p-hydroxyphenylpyruvate. Since pathways involved in homolentisic acid synthesis are also responsible for tyrosine formation, any alterations in these pathways can also result in the alteration in tyrosine synthesis and the synthesis of other aromatic amino acids.

Synthesis of Phytylpyrophosphate

Tocopherols are a member of the class of compounds referred to as the isoprenoids. Other isoprenoids include carotenoids, gibberellins, terpenes, chlorophyll and abscisic acid. A central intermediate in the production of isoprenoids is isopentenyl diphosphate (IPP). Cytoplasmic and plastid-based pathways to generate IPP have been reported. The cytoplasmic based pathway involves the enzymes acetoacetyl CoA thiolase, HMGCoA synthase, HMGCoA reductase, mevalonate kinase, phosphomevalonate kinase, and mevalonate pyrophosphate decarboxylase.

Recently, evidence for the existence of an alternative, plastid based, isoprenoid biosynthetic pathway emerged from studies in the research groups of Rohmer and Arigoni (Eisenreich et al., *Chem. Bio.*, 5:R221–R233, 1998); Rohmer, *Prog. Drug. Res.*, 50:135–154, 1998); Rohmer, *Comprehensive Natural Products Chemistry*, Vol. 2, pp. 45–68, Barton and Nakanishi (eds.), Pergamon Press, Oxford, England (1999), who found that the isotope labeling patterns observed in studies on certain eubacterial and plant terpenoids could not be explained in terms of the mevalonate pathway. Arigoni and coworkers subsequently showed that 1-deoxyxylulose, or a derivative thereof, serves as an intermediate of the novel pathway, now referred to as the MEP pathway (Rohmer et al., *Biochem. J.*, 295:517–524, 1993); Schwarz, Ph.D. thesis, Eidgenössiche Technische Hochschule, Zurich, Switzerland, 1994). Recent studies showed the formation of 1-deoxyxylulose 5-phosphate (Broers, Ph.D. thesis (Eidgenössiche Technische Hochschule, Zurich, Switzerland) (1994) from one molecule each of glyceraldehyde 3-phosphate (Rohmer, *Comprehensive Natural Products Chemistry*, Vol. 2, pp. 45–68, Barton and Nakanishi, eds., Pergamon Press, Oxford, England (1999) and pyruvate (Eisenreich et al., *Chem. Biol.*, 5:R223–R233, 1998); Schwarz supra; Rohmer et al., *J. Am. Chem. Soc.*, 118:2564–2566 (1996); and Sprenger et al., *Proc. Natl. Acad. Sci. (U.S.A.)*, 94:12857–12862, 1997) by an enzyme encoded by the dxs gene (Lois et al., *Proc. Natl. Acad. Sci. (U.S.A.)*, 95:2105–2110, 1997; U.S. Patent Publication 2003/0125573); and Lange et al., *Proc. Natl. Acad. Sci. (U.S.A.)*, 95:2100–2104, 1998). 1-Deoxyxylulose 5-phosphate can be further converted into 2-C-methylerythritol 4-phosphate (Arigoni et al., *Proc. Natl. Acad. Sci. (U.S.A.)*, 94:10600–10605, 1997) by a reductoisomerase encoded by the dxr gene (Bouvier et al., *Plant Physiol.*, 117:1421–1431, 1998); and Rohdich et al., *Proc. Natl. Acad. Sci. (U.S.A.)*, 96:11758–11763, 1999).

Genes reported to be in the MEP pathway also include ygbP, which catalyzes the conversion of 2-C-methyl-D-erythritol 4-phosphate into its respective cytidyl pyrophosphate derivative. The translation product of chB, in turn catalyzes the conversion of 4-phosphocytidyl-2C-methyl-D-erythritol into 4-diphosphocytidyl-2C-methyl-D-erythritol-2 phosphate. The latter compound is converted by the action of the translation product of ygbB into 2-C-methyl-D-erythritol, 2,4-cyclophosphate. Subsequently, 2C-methyl-D-erythritol, 2,4-cyclophosphate is converted by the translation product of gcpE to (E)-1-(4-hydroxy-3-methylbut-2-enyl) diphosphate. The latter compound is converted by the action of LytB to IPP and DMAPP (Herz et al., *Proc. Natl. Acad. Sci. (U.S.A.)*, 97(6):2485–2490, 2000).

Once IPP is formed by the MEP pathway, it is converted to GGDP by GGDP synthase, and then to phytylpyrophosphate, which is the central constituent of the tocopherol side chain.

Combination and Cyclization

Homogentisic acid is combined with either phytylpyrophosphate or solanylpyrophosphate by phytyl/prenyl transferase forming 2-methylphytyl plastoquinol or 2-methylsolanyl plastoquinol, respectively. 2-Methylsolanyl plastoquinol is a precursor to the biosynthesis of plastoquinones, while 2-methylphytyl plastoquinol is ultimately converted to tocopherol. It has been suggested that homogentisic acid, when combined with geranylgeranylpyrophosphate, will lead to the formation of tocotrienols.

Methylation of the Aromatic Ring

The major structural difference between each of the tocopherol subtypes is the position of the methyl groups around the phenyl ring. Both 2-methylphytyl plastoquinol and 2-methylsolanyl plastoquinol serve as substrates for the plant enzyme 2-methylphytylplastoquinol/2-methylsolanylplastoquinol methyltransferase (Tocopherol Methyl Transferase 2; Methyl Transferase 2; MT2; tMT2), which is capable of methylating a tocopherol precursor. Subsequent methylation of γ-tocopherol by γ-tocopherol methyl-transferase (GMT) generates the biologically active α-tocopherol.

A possible alternate pathway for the generation of α-tocopherol involves the generation of δ-tocopherol via the cyclization of 2-methylphytylplastoquinol by tocopherol cyclase. δ-tocopherol is then converted to β-tocopherol via the methylation of the 5 position by GMT. δ-tocopherol can be converted to α-tocopherol via methylation of the 3 position by tMT2, followed by methylation of the 5 position by GMT. In a possible alternative pathway, β-tocopherol is directly converted to α-tocopherol by tMT2 via the methylation of the 3 position (see, for example, *Biochemical Society Transactions*, 11:504–510 (1983); *Introduction to Plant Biochemistry*, 2nd edition, chapter 11 (1983); *Vitamin Hormone*, 29:153–200, 1971); *Biochemical Journal*, 109: 577 (1968); and, *Biochemical and Biophysical Research Communication*, 28(3):295 (1967). Since all potential mechanisms for the generation of α-tocopherol involve catalysis by tMT2, plants that are deficient in this activity accumulate δ-tocopherol and β-tocopherol. Plants that have increased tMT2 activity tend to accumulate γ-tocopherol and α-tocopherol. Since there is a low level of GMT activity in the seeds of many plants, these plants tend to accumulate γ-tocopherol.

The agents of the invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic and thus involve the capacity of the agent to mediate a chemical reaction or response. The agents will preferably be "substantially purified." The term "substantially purified," as used herein, refers to a molecule separated from substantially all other molecules normally associated with it in its native environmental conditions. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native environmental conditions.

The agents of the invention may also be recombinant. As used herein, the term recombinant means any agent (e.g., DNA, peptide, etc.), that is, or results, however indirectly, from human manipulation of a nucleic acid molecule.

It is understood that the agents of the invention may be labeled with reagents that facilitate detection of the agent (e.g., fluorescent labels, Prober et al., *Science,* 238:336–340 (1987); Albarella et al., EP 144914; chemical labels, Sheldon et al., U.S. Pat. No. 4,582,789; Albarella et al., U.S. Pat. No. 4,563,417; modified bases, Miyoshi et al., EP 119448).

Tocopherols are plant chloroplast lipophilic molecules involved in the response of plants to oxidative stresses (Porfirova et al, *PNAS,* 99(19):12495–12500, 2002). Therefore, in another preferred embodiment, expression or over-expression of a phytol kinase or polypeptide having phytol kinase activity (SEQ ID NOs: 2, 6, and 20–28) (FIG. 1) of the present invention in a transformed plant may provide tolerance to a variety of stresses, e.g., oxidative stress tolerance such as to drought, oxygen or ozone, UV tolerance, cold tolerance, or fungal/microbial pathogen tolerance. Environmental stresses, such as drought, increased salinity of soil, and extreme temperature, are major factors in limiting plant growth and productivity. The worldwide loss in yield of three major cereal crops, rice, maize (corn), and wheat due to water stress (drought) has been estimated to be over ten billion dollars annually. However, conventional breeding is a slow process for generating crop varieties with improved tolerance to stress conditions. Limited germplasm resources for stress tolerance and incompatibility in crosses between distantly related plant species are additional problems encountered in conventional breeding. Recent progress in plant genetic transformation and availability of potentially useful genes characterized from different sources make it possible to generate stress-tolerant crops using transgenic approaches (U.S. Pat. No. 5,981,842).

As used herein in a preferred aspect, a tolerance or resistance to stress is determined by the ability of a plant, when challenged by a stress such as drought to produce a plant having a higher yield or to a plant being less susceptible to an environmentally induced phenotype such as wilting, than one without such tolerance or resistance to stress. In a particularly preferred aspect of the present invention, the tolerance or resistance to stress is measured relative to a plant with a similar genetic background to the tolerant or resistance plant except that the plant expresses or over expresses a protein or fragment thereof of the present invention.

Nucleic Acid Molecules

The present invention includes and provides nucleic acid molecules encoding a polypeptide comprising an amino acid sequence selected from the group consisting of SEQ ID NOs: 30–41 and 53–68.

The present invention includes and provides nucleic acid molecules encoding a phytol kinase polypeptide, or a polypeptide having phytol kinase activity, comprising an amino acid sequence selected from the group consisting of SEQ ID NOs: 2, 6, 20–68, and 79 or comprising an amino acid sequence having at least about 70, 80, 90, 95, or 99% identity to such amino acid sequences.

The present invention includes and provides nucleic acid molecules comprising a nucleic acid sequence selected from the group consisting of SEQ ID NOs: 1, 5, and 17 and sequences having at least about 70, 90, 90, 95, or 99% identity to such sequences.

The present invention includes and provides nucleic acid molecules encoding a phytol kinase polypeptide, or a polypeptide having phytol kinase activity.

The present invention includes and provides nucleic acid molecules encoding a plant phytol kinase polypeptide, or a plant polypeptide having phytol kinase activity.

The present invention includes and provides nucleic acid molecules encoding a cyanobacterial phytol kinase polypeptide, or a cyanobacterial polypeptide having phytol kinase activity.

The present invention includes and provides nucleic acid molecules encoding a plant phytol kinase polypeptide, or a plant polypeptide having phytol kinase activity, comprising an amino acid sequence selected from the group consisting of SEQ ID NOs: 2, 6, and 37–68.

The present invention includes and provides nucleic acid molecules encoding cyanobacterial phytol kinase polypeptide, or a cyanobacterial polypeptide having phytol kinase activity, comprising an amino acid sequence selected from the group consisting of SEQ ID NOs: 20–27, 29–34, and 79.

The present invention includes and provides nucleic acid molecules encoding a yeast phytol kinase polypeptide, or a yeast polypeptide having phytol kinase activity.

The present invention includes and provides nucleic acid molecules encoding a yeast phytol kinase polypeptide, or a yeast polypeptide having phytol kinase activity, comprising an amino acid sequence selected from the group consisting of SEQ ID NOs: 35 and 36.

The present invention includes and provides nucleic acid molecules encoding a plant phytol kinase polypeptide, or a plant polypeptide having phytol kinase activity, comprising an amino acid selected from the group consisting of SEQ ID NOs: 74, 77, and 78.

The present invention includes and provides nucleic acid molecules encoding a plant phytol kinase polypeptide, or a plant polypeptide having phytol kinase activity, comprising an amino acid selected from the group consisting of SEQ ID NOs: 74, 77, and 78, wherein said polypeptide is not derived from *Allium porrum, Brassica napus,* Gossypium, *Glycine max, Oryza sativa, Sorghum bicolor, Triticum aestivum,* and *Zea mays*

The present invention includes and provides nucleic acid molecules encoding a plant phytol kinase polypeptide, or a plant polypeptide having phytol kinase activity, comprising an amino acid sequence selected from the group consisting of SEQ ID NOs: 74, 77, and 78 and further comprising an amino acid sequence comprising one or more of SEQ ID NOs: 75 and 76.

The present invention includes and provides nucleic acid molecules encoding a plant phytol kinase polypeptide, or a plant polypeptide having phytol kinase activity, comprising an amino acid sequence selected from the group consisting of SEQ ID NOs: 74, 77, and 78 and further comprising an amino acid sequence comprising one or more of SEQ ID NOs: 75 and 76, wherein said polypeptide is not derived from *Allium porrum, Brassica napus,* Gossypium, *Glycine max, Oryza sativa, Sorghum bicolor, Triticum aestivum,* and *Zea mays.*

The present invention includes and provides nucleic acid molecules encoding a cyanobacterial phytol kinase polypeptide, or a cyanobacterial polypeptide having phytol kinase activity, comprising an amino acid sequence selected from the group consisting of SEQ ID NOs: 71, 72, and 73.

The present invention includes and provides nucleic acid molecules encoding a cyanobacterial phytol kinase polypeptide, or a cyanobacterial polypeptide having phytol kinase activity, comprising an amino acid sequence selected from the group consisting of SEQ ID NOs: 71, 72, and 73, wherein said polypeptide is not derived from Synechocystis, *Aquifex aeolicus, Chlorobium tepidum, Chloroflexus aurantiacus, Nostoc punctiforme, Prochlorococcus marinus, Rickettsia conorii, Rickettsia prowazekii, Rickettsia sibirica,* Synechoccus, *Thermosynechoccus elongatus, Trichodesmium erythraeum* and *Saccharomyces cerevisiae.*

The present invention includes and provides nucleic acid molecules encoding a cyanobacterial phytol kinase polypeptide, or a cyanobacterial polypeptide having phytol kinase activity, comprising one or more amino acid sequences selected from the group consisting of SEQ ID NOs: 71, 72, and 73 and further comprising an amino acid sequence comprising one or more of SEQ ID NOs: 69 and 70.

The present invention includes and provides nucleic acid molecules encoding a cyanobacterial phytol kinase polypeptide, or a cyanobacterial polypeptide having phytol kinase activity, comprising one or more amino acid sequences selected from the group consisting of SEQ ID NOs: 71, 72, and 73 and further comprising an amino acid sequence comprising one or more of SEQ ID NOs: 69 and 70, wherein said polypeptide is not derived from Synechocystis, *Aquifex aeolicus, Chlorobium tepidum, Chloroflexus aurantiacus, Nostoc punctiforme, Prochlorococcus marinus, Rickettsia conorii, Rickettsia prowazekii, Rickettsia sibirica,* Synechoccus, *Thermosynechoccus elongatus, Trichodesmium erythraeum,* and *Saccharomyces cerevisiae.*

In another preferred aspect of the present invention a nucleic acid molecule comprises nucleotide sequences encoding a plastid transit peptide operably fused to a nucleic acid molecule that encodes a protein or fragment of the present invention.

It is understood that in a further aspect of nucleic acid sequences of the present invention, the nucleic acids can encode a protein that differs from any of the proteins in that one or more amino acids have been deleted, substituted or added without altering the function. For example, it is understood that codons capable of coding for such conservative amino acid substitutions are known in the art.

In one aspect of the present invention the nucleic acids of the present invention are said to be introduced nucleic acid molecules. A nucleic acid molecule is said to be "introduced" if it is inserted into a cell or organism as a result of human manipulation, no matter how indirect. Examples of introduced nucleic acid molecules include, without limitation, nucleic acids that have been introduced into cells via transformation, transfection, injection, and projection, and those that have been introduced into an organism via conjugation, endocytosis, phagocytosis, etc.

One subset of the nucleic acid molecules of the invention is fragment nucleic acids molecules. Fragment nucleic acid molecules may consist of significant portion(s) of, or indeed most of, the nucleic acid molecules of the invention, such as those specifically disclosed. Alternatively, the fragments may comprise smaller oligonucleotides (having from about 15 to about 400 nucleotide residues and more preferably, about 15 to about 30 nucleotide residues, or about 50 to about 100 nucleotide residues, or about 100 to about 200 nucleotide residues, or about 200 to about 400 nucleotide residues, or about 275 to about 350 nucleotide residues).

A fragment of one or more of the nucleic acid molecules of the invention may be a probe and specifically a PCR probe. A PCR probe is a nucleic acid molecule capable of initiating a polymerase activity while in a double-stranded structure with another nucleic acid. Various methods for determining the structure of PCR probes and PCR techniques exist in the art.

Nucleic acid molecules or fragments thereof of the present invention are capable of specifically hybridizing to other nucleic acid molecules under certain circumstances. Nucleic acid molecules of the present invention include those that specifically hybridize to nucleic acid molecules having a nucleic acid sequence selected from the group consisting of SEQ ID NOs: 1, 3, 5, 17, and complements thereof. Nucleic acid molecules of the present invention also include those that specifically hybridize to nucleic acid molecules encoding an amino acid sequence selected from SEQ ID NOs: 2, 6, 20–68, and 79, and fragments thereof.

As used herein, two nucleic acid molecules are said to be capable of specifically hybridizing to one another if the two molecules are capable of forming an anti-parallel, double-stranded nucleic acid structure.

A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., *Molecular Cloning, A Laboratory Manual,* 2nd Ed., Cold Spring Harbor Press, Cold Spring Harbor, N.Y. (2001), and by Haymes et al., *Nucleic Acid Hybridization, A Practical Approach,* IRL Press, Washington, D.C. (1985). Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization are, for example, 6.0×sodium chloride/sodium citrate (SSC) at about 45° C., followed by a wash of 2.0×SSC at 20–25° C., are known to those skilled in the art or can be found in *Current Protocols in Molecular Biology,* John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 65° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a nucleic acid of the present invention will specifically hybridize to one or more of the nucleic acid molecules set forth in SEQ ID NOs: 1, 3, 5, and 17, and complements thereof under moderately stringent conditions, for example at about 2.0×SSC and about 65° C.

In a particularly preferred embodiment, a nucleic acid of the present invention will include those nucleic acid molecules that specifically hybridize to one or more of the nucleic acid molecules set forth in SEQ ID NOs: 1, 3, 5, and 17, and complements thereof under high stringency conditions such as 0.2×SSC and about 65° C.

In one embodiment of a method of the present invention, any of the nucleic acid sequences or polypeptide sequences, or fragments of either, of the present invention can be used to search for related sequences. In a preferred embodiment, a member selected from the group consisting of SEQ ID NOs: 69–78 is used to search for related sequences. In another embodiment, any of the motifs or regions of conserved sequence shown in FIGS. 11–20 are used to search for related amino acid sequences. In one embodiment, one or more of SEQ ID NOs: 74, 77, and 78, and one or more of SEQ ID NOs: 75 and 76 are used to search for related sequences. In one embodiment, one or more of SEQ ID NOs: 71, 72 and 73 are used to search for related sequences. As used herein, "search for related sequences" means any method of determining relatedness between two sequences, including, but not limited to, searches that compare sequence homology: for example, a PBLAST search of a database for relatedness to a single amino acid sequence. Other searches may be conducted using profile based methods, such as the HMM (Hidden Markov model) META-MEME (http://metameme.sdsc.edu/mhmm-links.html), PSI-BLAST (http://www.ncbi.nlm.nih.gov/BLAST/). The present invention includes and provides for phytol kinases discovered using one or more of the alignments of FIGS. 11–20.

A polypeptide or polynucleotide molecule can be substantially identical or substantially homologous to related molecules. These homologues with substantial identity to a related molecule generally comprise at least one polypeptide sequence or one polynucleotide sequence that has at least seventy percent sequence identity compared to other polypeptide sequences or polynucleotide sequences. The Gap program in the WISCONSIN PACKAGE version 10.0-UNIX from Genetics Computer Group, Inc. based on the method of Needleman and Wunsch (J. Mol. Biol. 48:443–453, 1970) using the set of default parameters for pairwise comparison (for amino acid sequence comparison: Gap Creation Penalty=8, Gap Extension Penalty=2; for nucleotide sequence comparison: Gap Creation Penalty=50; Gap Extension Penalty=3) or using the TBLASTN program in the BLAST 2.2.1 software suite (Altschul et al., Nucleic Acids Res. 25:3389–3402), using BLOSUM62 matrix (Henikoff and Henikoff, Proc. Natl. Acad. Sci. U.S.A. 89:10915–10919, 1992) and the set of default parameters for pair-wise comparison (gap creation cost=11, gap extension cost=1.). In BLAST, the E-value, or expectation value, represents the number of different alignments with scores equivalent to or better than the raw alignment score, S, that are expected to occur in a database search by chance. The lower the E value, the more significant the match. Because database size is an element in E-value calculations, E-values obtained by "BLASTing" against public databases, such as GenBank, have generally increased over time for any given query/entry match. Percent identity refers to the percentage of identically matched amino acid residues that exist along the length of that portion of the sequences which is aligned by the BLAST algorithm. In a preferred embodiment the percent identity calculations are performed using BLASTN or BLASTP (default, parameters, version 2.0.8, Altschul etal., *Nucleic Acids Res.*, 25:3389–3402 (1997).

A nucleic acid molecule of the invention can also encode a homolog polypeptide. As used herein, a homolog polypeptide molecule or fragment thereof is a counterpart protein molecule or fragment thereof in a second species (e.g., corn rubisco small subunit is a homolog of Arabidopsis rubisco small subunit). A homolog can also be generated by molecular evolution or DNA shuffling techniques, so that the molecule retains at least one functional or structure characteristic of the original polypeptide (see, for example, U.S. Pat. No. 5,811,238).

Agents of the invention include nucleic acid molecules that encode having at least about a contiguous 10 amino acid region of a polypeptide of the present invention, more preferably having at least about a contiguous 25, 40, 50, 100, or 125 amino acid region of a polypeptide of the present invention, preferably a polypeptide comprising SEQ ID NO: 2, 6, or 20–68.

In a preferred embodiment, any of the nucleic acid molecules of the present invention can be operably linked to a promoter region that functions in a plant cell to cause the production of an mRNA molecule, where the nucleic acid molecule that is linked to the promoter is heterologous with respect to that promoter. As used herein, "heterologous" means not naturally occurring together.

Protein and Peptide Molecules

A class of agents includes one or more of the polypeptide molecules encoded by a nucleic acid agent of the invention. A particular preferred class of proteins is that having an amino acid sequence of SEQ ID NOs 2, 6, or 20–68, or a sequence having at least about 70, 80, 90, 95 or 99% identity to such sequences, or fragments thereof.

In another aspect of the present invention, the polypeptide is a phytol kinase or a polypeptide having phytol kinase activity. In another aspect of the present invention, the polypeptide is a plant, cyanobacterial, or yeast polypeptide. In still another aspect of the present invention, the phytol kinase polypeptide, or a polypeptide having phytol kinase activity, comprises an amino acid sequence selected from the group consisting of SEQ ID NOs: 2, 6, 20–68, and 79. In still another aspect of the present invention, the polypeptide is a plant phytol kinase polypeptide, or a plant polypeptide having phytol kinase activity, comprising an amino acid sequence selected from the group consisting of SEQ ID NOs: 2, 6, and 37–68.

In still another aspect of the present invention, the polypeptide is a yeast phytol kinase polypeptide, or a yeast polypeptide having phytol kinase activity, comprising an amino acid sequence selected from the group consisting of SDQ ID NOs: 35 and 36.

In one embodiment of the present invention, the polypeptide is a cyanobacterial phytol kinase polypeptide, or a cyanobacterial polypeptide having phytol kinase activity, comprising an amino acid sequence selected from the group consisting of SEQ ID NOs: 20–27, 29–34, and 79. The present invention includes and provides plant phytol kinase polypeptides, or plant polypeptides having phytol kinase activity, comprising an amino acid selected from the group consisting of SEQ ID NOs: 74, 77, and 78. In another aspect of the present invention, the plant phytol kinase polypeptide, or plant polypeptide having phytol kinase activity, comprises an amino acid selected from the group consisting of SEQ ID NOs: 74, 77, and 78, wherein said polypeptide is not derived from *Allium porrum*, *Brassica napus*, Gossypium, *Glycine max*, *Oryza sativa*, *Sorghum bicolor*, *Triticum aestivum*, and *Zea mays*.

In yet another aspect of the present invention, the plant phytol kinase polypeptide, or a plant polypeptide having phytol kinase activity, comprises an amino acid sequence selected from the group consisting of SEQ ID NOs: 74, 77, and 78 and further comprises an amino acid sequence comprising one or more of SEQ ID NOs: 75 and 76. The present invention includes and provides plant phytol kinase polypeptides, or plant polypeptides having phytol kinase activity, comprising an amino acid sequence selected from the group consisting of SEQ ID NOs: 74, 77, and 78 and further comprising an amino acid sequence comprising one or more of SEQ ID NOs: 75 and 76, wherein said polypeptide is not derived from *Allium porrum*, *Brassica napus*, Gossypium, *Glycine max*, *Oryza sativa*, *Sorghum bicolor*, *Triticum aestivum*, and *Zea mays*.

The present invention includes and provides cyanobacterial phytol kinase polypeptides, or cyanobacterial polypeptides having phytol kinase activity, comprising an amino acid sequence selected from the group consisting of SEQ ID NOs: 71, 72, and 73. The present invention includes and provides cyanobacterial phytol kinase polypeptides, or cyanobacterial polypeptides having phytol kinase activity, comprising an amino acid sequence selected from the group consisting of SEQ ID NOs: 71, 72, and 73, wherein said polypeptide is not derived from Synechocystis, *Aquifex aeolicus*, *Chlorobium tepidum*, *Chloroflexus aurantiacus*, *Nostoc punctiforme*, *Prochlorococcus marinus*, *Rickettsia conorii*, *Rickettsia prowazekii*, *Rickettsia sibirica*, Synechoccus, *Thermosynechoccus elongatus*, *Trichodesmium erythraeum* and *Saccharomyces cerevisiae*. In another aspect of the present invention, a class of proteins includes cyanobacterial phytol kinase polypeptides, or cyanobacterial polypeptides having phytol kinase activity, comprising one or more amino acid sequences selected from the group consisting of SEQ ID NOs: 71, 72, and 73 and further comprising an amino acid sequence comprising one or more of SEQ ID NOs: 69 and 70.

The present invention includes and provides cyanobacterial phytol kinase polypeptides, or cyanobacterial polypeptides having phytol kinase activity, comprising one or more amino acid sequences selected from the group consisting of SEQ ID NOs: 71, 72, and 73 and further comprising an amino acid sequence comprising one or more of SEQ ID NOs: 69 and 70, wherein said polypeptide is not derived from Synechocystis, *Aquifex aeolicus*, *Chlorobium tepidum*, *Chloroflexus aurantiacus*, *Nostoc punctiforme*, *Prochlorococcus marinus*, *Rickettsia conorii*, *Rickettsia prowazekii*, *Rickettsia sibirica*, Synechoccus, *Thermosynechoccus elongatus*, *Trichodesmium erythraeum*, and *Saccharomyces cerevisiae*.

Polypeptide agents may have C-terminal or N-terminal amino acid sequence extensions. One class of N-terminal extensions employed in a preferred embodiment are plastid transit peptides. When employed, plastid transit peptides can be operatively linked to the N-terminal sequence, thereby permitting the localization of the agent polypeptides to plastids. In an embodiment of the present invention, any suitable plastid targeting sequence can be used (see, e.g., U.S. Pat. Nos. 5,776,760; 6,489,542; and 5,717,084). Where suitable, a plastid targeting sequence can be substituted for a native plastid targeting sequence. In a further embodiment, any suitable, modified plastid targeting sequence can be used. In another embodiment, e.g., the plastid targeting sequence is a CTP1 sequence (U.S. Pat. No. 5,776,760).

As used herein, the term "protein," "peptide molecule," or "polypeptide" includes any molecule that comprises five or more amino acids. It is well known in the art that protein, peptide or polypeptide molecules may undergo modification, including post-translational modifications, such as, but not limited to, disulfide bond formation, glycosylation, phosphorylation, or oligomerization. Thus, as used herein, the term "protein," "peptide molecule," or "polypeptide" includes any protein that is modified by any biological or non-biological process. The terms "amino acid" and "amino acids" refer to all naturally occurring L-amino acids. This definition is meant to include norleucine, norvaline, ornithine, homocysteine, and homoserine.

A "protein fragment" is a peptide or polypeptide molecule whose amino acid sequence comprises a subset of the amino acid sequence of that protein. A protein or fragment thereof that comprises one or more additional peptide regions not derived from that protein is a "fusion" protein. Such molecules may be derivatized to contain carbohydrate or other moieties (such as keyhole limpet hemocyanin). Fusion protein or peptide molecules of the invention are preferably produced via recombinant means.

Plant Constructs and Plant Transformants

One or more of the nucleic acid molecules of the invention may be used in plant transformation or transfection. Exogenous genetic material may be transferred into a plant cell and the plant cell regenerated into a whole, fertile or sterile plant. Exogenous genetic material is any genetic material, whether naturally occurring or otherwise, from any source that is capable of being inserted into any organism.

In a preferred aspect of the present invention the exogenous genetic material comprises a nucleic acid sequence of SEQ ID NOs: 1, 5, 17, or nucleic acid sequences having at least about 70, 80, 90, 95, or 99% identity to such sequences or complements thereof and fragments of either. In a further aspect of the present invention the exogenous genetic material comprises a nucleic acid sequence encoding an amino acid sequence selected from the group consisting of SEQ ID NOs: 2, 6, 20–68, and 79, sequences having at least about 70, 80, 90, 95 or 99% identity to such sequences, or fragments thereof.

In another aspect of the present invention, the exogenous genetic material comprises nucleic acid molecules encoding a phytol kinase polypeptide or polypeptide having phytol kinase activity.

In another aspect of the present invention, the exogenous genetic material comprises nucleic acid molecules encoding a plant phytol kinase polypeptide, or a plant polypeptide having phytol kinase activity.

In another aspect of the present invention, the exogenous genetic material comprises nucleic acid molecules encoding a cyanobacterial phytol kinase polypeptide, or a cyanobacterial polypeptide having phytol kinase activity.

In another aspect of the present invention, the exogenous genetic material comprises nucleic acid molecules encoding a phytol kinase polypeptide, or a polypeptide having phytol kinase activity, comprising an amino acid sequence selected from the group consisting of SEQ ID NOs: 2, 6, 20–68, and 79.

In another aspect of the present invention, the exogeneous genetic material comprises nucleic acid molecules encoding a yeast phytol kinase polypeptide, or a yeast polypeptide having phytol kinase activity.

In another aspect of the present invention, the exogeneous genetic material comprises nucleic acid molecules encoding a yeast phytol kinase polypeptide, or a yeast polypeptide having phytol kinase activity, comprising an amino acid sequence selected from the group consisting of SEQ ID NOs: 35 and 36.

In another aspect of the present invention, the exogenous genetic material comprises nucleic acid molecules encoding a plant phytol kinase polypeptide, or a plant polypeptide having phytol kinase activity, comprising an amino acid sequence selected from the group consisting of SEQ ID NOs: 2, 6, and 37–68.

In another aspect of the present invention, the exogenous genetic material comprises nucleic acid molecules encoding cyanobacterial phytol kinase polypeptide, or a cyanobacterial polypeptide having phytol kinase activity, comprising an amino acid sequence selected from the group consisting of SEQ ID NOs: 20–27, 29–34, and 79.

In another aspect of the present invention, the exogenous genetic material comprises nucleic acid molecules encoding a plant phytol kinase polypeptide, or a plant polypeptide having phytol kinase activity, comprising an amino acid selected from the group consisting of SEQ ID NOs: 74, 77, and 78.

In another aspect of the present invention, the exogenous genetic material comprises nucleic acid molecules encoding a plant phytol kinase polypeptide, or a plant polypeptide having phytol kinase activity, comprising an amino acid selected from the group consisting of SEQ ID NOs: 74, 77, and 78, wherein said polypeptide is not derived from *Allium porrum, Brassica napus*, Gossypium, *Glycine max, Oryza sativa, Sorghum bicolor, Triticum aestivum*, and *Zea mays*.

In another aspect of the present invention, the exogenous genetic material comprises nucleic acid molecules encoding a plant phytol kinase polypeptide, or a plant polypeptide having phytol kinase activity, comprising an amino acid sequence selected from the group consisting of SEQ ID NOs: 74, 77, and 78 and further comprising an amino acid sequence comprising one or more of SEQ ID NOs: 75 and 76.

In another aspect of the present invention, the exogenous genetic material comprises nucleic acid molecules encoding a plant phytol kinase polypeptide, or a plant polypeptide having phytol kinase activity, comprising an amino acid sequence selected from the group consisting of SEQ ID NOs: 74, 77, and 78 and further comprising an amino acid sequence comprising one or more of SEQ ID NOs: 75 and 76, wherein said polypeptide is not derived from *Allium porrum, Brassica napus*, Gossypium, *Glycine max, Oryza sativa, Sorghum bicolor, Triticum aestivum*, and *Zea mays*.

In another aspect of the present invention, the exogenous genetic material comprises nucleic acid molecules encoding a cyanobacterial phytol kinase polypeptide, or a cyanobacterial polypeptide having phytol kinase activity, comprising an amino acid sequence selected from the group consisting of SEQ ID NOs: 71, 72, and 73.

In another aspect of the present invention, the exogenous genetic material comprises nucleic acid molecules encoding a cyanobacterial phytol kinase polypeptide, or a cyanobacterial polypeptide having phytol kinase activity, comprising an amino acid sequence selected from the group consisting of SEQ ID NOs: 71, 72, and 73, wherein said polypeptide is not derived from Synechocystis, *Aquifex aeolicus, Chlorobium tepidum, Chloroflexus aurantiacus, Nostoc punctiforme, Prochlorococcus marinus, Rickettsia conorii, Rickettsia prowazekii, Rickettsia sibirica*, Synechoccus, *Thermosynechoccus elongatus, Trichodesmium erythraeum* and *Saccharomyces cerevisiae*.

In another aspect of the present invention, the exogenous genetic material comprises a nucleic acid molecule encoding a cyanobacterial phytol kinase polypeptide, or a cyanobacterial polypeptide having phytol kinase activity, comprising one or more amino acid sequences selected from the group consisting of SEQ ID NOs: 71, 72, and 73 and further comprising an amino acid sequence comprising one or more of SEQ ID NOs: 69 and 70.

In another aspect of the present invention, the exogenous genetic material comprises a nucleic acid molecule encoding a cyanobacterial phytol kinase polypeptide, or a cyanobacterial polypeptide having phytol kinase activity, comprising one or more amino acid sequences selected from the group consisting of SEQ ID NOs: 71, 72, and 73 and further comprising an amino acid sequence comprising one or more of SEQ ID NOs: 69 and 70, wherein said polypeptide is not derived from Synechocystis, *Aquifex aeolicus, Chlorobium tepidum, Chloroflexus aurantiacus, Nostoc punctiforme, Prochlorococcus marinus, Rickettsia conorii, Rickettsia prowazekii, Rickettsia sibirica*, Synechoccus, *Thermosynechoccus elongatus, Trichodesmium erythraeum*, and *Saccharomyces cerevisiae*.

In a further aspect of the present invention, the nucleic acid sequences of the invention also encode peptides involved in intracellular localization, export, or post-translational modification.

In an embodiment of the present invention, exogenous genetic material encoding an LTT1 or fragment thereof is introduced into a plant with one or more additional genes. In one embodiment, preferred combinations of genes include a nucleic acid molecule of the present invention and one or more of the following genes: tyrA (e.g., WO 02/089561 and Xia et al., *J. Gen. Microbiol.*, 138:1309–1316, 1992), tocopherol cyclase (e.g., WO 01/79472), prephenate dehydrogenase, dxs (e.g., Lois et al., *Proc. Natl. Acad. Sci. (U.S.A.)*, 95(5):2105–2110, 1998), dxr (e.g., U.S. Publication 2002/0108814A and Takahashi et al., *Proc. Natl. Acad. Sci. (U.S.A.)*, 95 (17), 9879–9884, 1998), GGPPS (e.g., Bartley and Scolnik, *Plant Physiol.*, 104:1469–1470, 1994), HPPD (e.g., Norris et al., *Plant Physiol.*, 117:1317–1323, 1998; U.S. Pat. No. 6,087,563), GMT (e.g., U.S. patent appn. No. 10/219,810, filed Aug. 16, 2002; WO 03/016482), HPT (U.S. Pat. No. 6,541,259) (tMT2 (e.g., U.S. patent application No. 10/279,029, filed Oct. 24, 2002; WO 03/034812), AANT1 (e.g., WO 02/090506), IDI (E.C.:5.3.3.2; Blanc et al., In: *Plant Gene Register*, PRG96-036; and Sato et al., DNA Res., 4:215–230, 1997), GGH (Graβes et al., *Planta.*, 213–620, 2001), or a plant ortholog and an antisense construct for homogentisic acid dioxygenase (Kridl et al., *Seed Sci. Res.*, 1:209–219, 1991); Keegstra, *Cell*, 56(2):247–53, 1989); Nawrath, et al., *Proc. Natl. Acad. Sci. (U.S.A.)*, 91:12760–12764, 1994); Cyanobase, www.kazusa.or.jp/cyanobase; Smith et al., *Plant J.*, 11:83–92, 1997); WO 00/32757; ExPASy Molecular Biology Server, http://us.expasy.org/enzyme; MT1 (e.g., WO 00/10380); gcpE (e.g. WO 02/12478); Saint Guily et al., *Plant Physiol.*, 100(2):1069–1071, 1992); Sato et al., *J. DNA Res.*, 7(1): 31–63, 2000). In such combinations, in some crop plants, e.g. canola, a preferred promoter is a napin promoter and a preferred plastid targeting sequence is a CTP1 sequence. It is preferred that gene products are targeted to the plastid. Alternatively, one or more of the gene products can be localized in the cytoplasm. In a preferred aspect, the gene products of tyrA and HPPD are targeted to the plastids. In a second preferred embodiment, TyrA and HPPD are targeted to the cytoplasm. Such genes can be introduced, for example, on a single construct, introduced on different constructs but the same transformation event, or introduced into separate plants followed by one or more crosses to generate the desired combination of genes. In such combinations, a preferred promoter is a napin, 7S alpha promoter, the 7S alpha' promoter, the Arcelin 5 promoter, the USP88 promoter and a preferred plastid targeting sequence is a CTP1 sequence. It is preferred that gene products are targeted to the plastid.

In a preferred combination, a nucleic acid molecule of the present invention and a nucleic acid molecule encoding any of the following enzymes: tyrA, HPT slr1736, tocopherol cyclase, chlorophyllase, dxs, dxr, GGPPS, HPPD, tMT2, AANT1, slr1737, IDI, GGH or a plant ortholog and an antisense construct for homogentisic acid dioxygenase are introduced into a plant.

Such genetic material may be transferred into either monocotyledons or dicotyledons including, but not limited to canola, corn, soybean, Arabidopsis, Phaseolus, peanut, alfalfa, wheat, rice, oat, sorghum, rapeseed, rye, tritordeum, millet, fescue, perennial ryegrass, sugarcane, cranberry, papaya, banana, safflower, oil palms, flax, muskmelon, apple, cucumber, dendrobium, gladiolus, chrysanthemum, liliacea, cotton, eucalyptus, sunflower, *Brassica campestris*, oilseed rape, turfgrass, sugarbeet, coffee and dioscorea (Christou, In: *Particle Bombardment for Genetic Engineering of Plants*, Biotechnology Intelligence Unit. Academic Press, San Diego, Calif. (1996), with canola, corn, *Brassica campestris*, oilseed rape, rapeseed, soybean, crambe, mustard, castor bean, peanut, sesame, cottonseed, linseed, safflower, oil palm, flax, and sunflower preferred, and canola, rapeseed, corn, *Brassica campestris*, oilseed rape, soybean, sunflower, safflower, oil palms, and peanut preferred. In a preferred embodiment, the homolog is selected from the group consisting of maize, soybean, canola, cottonseed, sesame, flax, peanut, sunflower, safflower, and oil palm. In a more preferred embodiment, the genetic material is transferred into canola. In another more preferred embodiment, the genetic material is transferred into oilseed rape. In another particularly preferred embodiment, the genetic material is transferred into soybean.

Transfer of a nucleic acid molecule that encodes a protein can result in expression or overexpression of that polypeptide in a transformed cell or transgenic plant. One or more of the proteins or fragments thereof encoded by nucleic acid molecules of the invention may be overexpressed in a transformed cell or transformed plant. Such expression or overexpression may be the result of transient or stable transfer of the exogenous genetic material.

In a preferred embodiment, DNA constructs of the present invention comprising SEQ ID NOs: 1, 5, 17, or sequences having at least about 70, 80, 90, 95, 99% identity to such sequences provide in a transformed plant, relative to an untransformed plant with a similar genetic background, an increased level of tocopherols.

In a preferred embodiment, DNA constructs of the present invention comprising SEQ ID NOs: 1, 5, 17, or sequences having at least about 70, 80, 90, 95, 99% identity to such sequences provide in a transformed plant, relative to an untransformed plant with a similar genetic background, an increased level of α-tocopherols.

In a preferred embodiment, DNA constructs of the present invention comprising SEQ ID NOs: 1, 5, 17, or sequences having at least about 70, 80, 90, 95, 99% identity to such sequences provide in a transformed plant, relative to an untransformed plant with a similar genetic background, an increased level of γ-tocopherols.

In a preferred embodiment, DNA constructs of the present invention comprising SEQ ID NOs: 1, 5, 17, or sequences having at least about 70, 80, 90, 95, 99% identity to such sequences provide in a transformed plant, relative to an untransformed plant with a similar genetic background, an increased level of δ-tocopherols.

In a preferred embodiment, DNA constructs of the present invention comprising SEQ ID NOs: 1, 5, 17, or sequences having at least about 70, 80, 90, 95, 99% identity to such sequences provide in a transformed plant, relative to an untransformed plant with a similar genetic background, an increased level of β-tocopherols.

In a preferred embodiment, DNA constructs of the present invention comprising SEQ ID NOs: 1, 5, 17, or sequences having at least about 70, 80, 90, 95, 99% identity to such sequences provide in a transformed plant, relative to an untransformed plant with a similar genetic background, an increased level of tocotrienols.

In a preferred embodiment, DNA constructs of the present invention comprising SEQ ID NOs: 1, 5, 17, or sequences having at least about 70, 80, 90, 95, 99% identity to such sequences provide in a transformed plant, relative to an untransformed plant with a similar genetic background, an increased level of α-tocotrienols.

In a preferred embodiment, DNA constructs of the present invention comprising SEQ ID NOs: 1, 5, 17, or sequences having at least about 70, 80, 90, 95, 99% identity to such sequences provide in a transformed plant, relative to an untransformed plant with a similar genetic background, an increased level of γ-tocotrienols.

In a preferred embodiment, DNA constructs of the present invention comprising SEQ ID NOs: 1, 5, 17, or sequences having at least about 70, 80, 90, 95, 99% identity to such sequences provide in a transformed plant, relative to an untransformed plant with a similar genetic background, an increased level of δ-tocotrienols.

In a preferred embodiment, DNA constructs of the present invention comprising SEQ ID NOs: 1, 5, 17, or sequences having at least about 70, 80, 90, 95, 99% identity to such sequences provide in a transformed plant, relative to an untransformed plant with a similar genetic background, an increased level of β-tocotrienols.

In a preferred embodiment, DNA constructs of the present invention comprising SEQ ID NOs: 1, 5, 17, or sequences having at least about 70, 80, 90, 95, 99% identity to such sequences provide in a transformed plant, relative to an untransformed plant with a similar genetic background, an increased level of plastoquinols.

In a preferred embodiment, DNA constructs of the present invention comprising nucleic acid molecules encoding a phytol kinase polypeptide or polypeptide having phytol kinase activity provide in a transformed plant, relative to an untransformed plant with a similar genetic background, an increased level of tocopherols.

In a preferred embodiment, DNA constructs of the present invention comprising nucleic acid molecules encoding a phytol kinase polypeptide or a polypeptide having phytol kinase activity, provide in a transformed plant, relative to an untransformed plant with a similar genetic background, an increased level of α-tocopherols.

In a preferred embodiment, DNA constructs of the present invention comprising nucleic acid molecules encoding a phytol kinase polypeptide or a polypeptide having phytol kinase activity, provide in a transformed plant, relative to an untransformed plant with a similar genetic background, an increased level of γ-tocopherols.

In a preferred embodiment, DNA constructs of the present invention comprising nucleic acid molecules encoding a phytol kinase polypeptide or a polypeptide having phytol kinase activity, provide in a transformed plant, relative to an untransformed plant with a similar genetic background, an increased level of β-tocopherols.

In a preferred embodiment, DNA constructs of the present invention comprising nucleic acid molecules encoding a phytol kinase polypeptide or a polypeptide having phytol kinase activity, provide in a transformed plant, relative to an untransformed plant with a similar genetic background, an increased level of δ-tocopherols.

In a preferred embodiment, DNA constructs of the present invention comprising nucleic acid molecules encoding a phytol kinase polypeptide, or a polypeptide having phytol kinase activity, provide in a transformed plant, relative to an untransformed plant with a similar genetic background, an increased level of tocotrienols.

In a preferred embodiment, DNA constructs of the present invention comprising nucleic acid molecules encoding a phytol kinase polypeptide, or a polypeptide having phytol kinase activity, provide in a transformed plant, relative to an untransformed plant with a similar genetic background, an increased level of α-tocotrienols.

In a preferred embodiment, DNA constructs of the present invention comprising nucleic acid molecules encoding a phytol kinase polypeptide, or a polypeptide having phytol kinase activity, provide in a transformed plant, relative to an untransformed plant with a similar genetic background, an increased level of γ-tocotrienols.

In a preferred embodiment, DNA constructs of the present invention comprising nucleic acid molecules encoding a phytol kinase polypeptide or a polypeptide having phytol kinase activity, provide in a transformed plant, relative to an untransformed plant with a similar genetic background, an increased level of β-tocotrienols.

In a preferred embodiment, DNA constructs of the present invention comprising nucleic acid molecules encoding a phytol kinase polypeptide or a polypeptide having phytol kinase activity, provide in a transformed plant, relative to an untransformed plant with a similar genetic background, an increased level of δ-tocotrienols.

In a preferred embodiment, DNA constructs of the present invention comprising nucleic acid molecules encoding a polypeptide comprising an amino acid sequence selected from the group consisting of SEQ ID NOs: 20–41 and 53–68, provide in a transformed plant, relative to an untransformed plant with a similar genetic background, an increased level of tocopherols.

In a preferred embodiment, DNA constructs of the present invention comprising nucleic acid molecules encoding a polypeptide comprising an amino acid sequence selected from the group consisting of SEQ ID NOs: 20–41 and 53–68, provide in a transformed plant, relative to an untransformed plant with a similar genetic background, an increased level of α-tocopherols.

In a preferred embodiment, DNA constructs of the present invention comprising nucleic acid molecules encoding a polypeptide comprising an amino acid sequence selected from the group consisting of SEQ ID NOs: 20–41 and 53–68, provide in a transformed plant, relative to an untransformed plant with a similar genetic background, an increased level of γ-tocopherols.

In a preferred embodiment, DNA constructs of the present invention comprising nucleic acid molecules encoding a polypeptide comprising an amino acid sequence selected from the group consisting of SEQ ID NOs: 20–41 and 53–68, provide in a transformed plant, relative to an untransformed plant with a similar genetic background, an increased level of β-tocopherols.

In a preferred embodiment, DNA constructs of the present invention comprising nucleic acid molecules encoding a polypeptide comprising an amino acid sequence selected from the group consisting of SEQ ID NOs: 20–41 and 53–68, provide in a transformed plant, relative to an untransformed plant with a similar genetic background, an increased level of δ-tocopherols.

In a preferred embodiment, DNA constructs of the present invention comprising nucleic acid molecules encoding a polypeptide comprising an amino acid sequence selected from the group consisting of SEQ ID NOs: 20–41 and 53–68, provide in a transformed plant, relative to an untransformed plant with a similar genetic background, an increased level of tocotrienols.

In a preferred embodiment, DNA constructs of the present invention comprising nucleic acid molecules encoding a polypeptide comprising an amino acid sequence selected from the group consisting of SEQ ID NOs: 20–41 and 53–68, provide in a transformed plant, relative to an untransformed plant with a similar genetic background, an increased level of α-tocotrienols.

In a preferred embodiment, DNA constructs of the present invention comprising nucleic acid molecules encoding a polypeptide comprising an amino acid sequence selected from the group consisting of SEQ ID NOs: 20–41 and 53–68, provide in a transformed plant, relative to an untransformed plant with a similar genetic background, an increased level of γ-tocotrienols.

In a preferred embodiment, DNA constructs of the present invention comprising nucleic acid molecules encoding a polypeptide comprising an amino acid sequence selected from the group consisting of SEQ ID NOs: 20–41 and 53–68, provide in a transformed plant, relative to an untransformed plant with a similar genetic background, an increased level of β-tocotrienols.

In a preferred embodiment, DNA constructs of the present invention comprising nucleic acid molecules encoding a polypeptide comprising an amino acid sequence selected from the group consisting of SEQ ID NOs: 20–41 and 53–68, provide in a transformed plant, relative to an untransformed plant with a similar genetic background, an increased level of δ-tocotrienols.

In a preferred embodiment, DNA constructs of the present invention comprising nucleic acid molecules encoding polypeptides of the present invention provide in a transformed plant, relative to an untransformed plant with a similar genetic background, an increased level of plastoquinols.

In one embodiment, DNA constructs of the present invention comprising SEQ ID NO: 3 provide in a transformed plant, relative to an untransformed plant with a similar genetic background, a decreased level of tocopherols, α-tocopherols, γ-tocopherols, δ-tocopherols, β-tocopherols, tocotrienols, α-tocotrienols, γ-tocotrienols, δ-tocotrienols, β-tocotrienols, and/or plastoquinols.

In any of the embodiments described herein, an increase in γ-tocopherol, α-tocopherol, or both can lead to a decrease in the relative proportion of β-tocopherol, δ-tocopherol, or both. Similarly, an increase in γ-tocotrienol, α-tocotrienol, or both can lead to a decrease in the relative proportion of β-tocotrienol, δ-tocotrienol, or both.

In some embodiments, the levels of one or more products of the tocopherol biosynthesis pathway, including any one or more of tocopherols, α-tocopherols, γ-tocopherols, δ-tocopherols, β-tocopherols, tocotrienols, α-tocotrienols, γ-tocotrienols, δ-tocotrienols, β-tocotrienols are measurably increased. The levels of products may be increased throughout an organism such as a plant or localized in one or more specific organs or tissues of the organism. For example the levels of products may be increased in one or more of the tissues and organs of a plant including without limitation: roots, tubers, stems, leaves, stalks, fruit, berries, nuts, bark, pods, seeds and flowers. A preferred organ is a seed.

In a preferred embodiment, expression of enzymes involved in tocopherol, tocotrienol or plastoquinol synthesis in the seed will result in an increase in γ-tocopherol levels due to the absence of significant levels of GMT activity in those tissues. In another preferred embodiment, expression of enzymes involved in tocopherol, tocotrienol or plastoquinol synthesis in photosynthetic tissues will result in an increase in α-tocopherol due to the higher levels of GMT activity in those tissues relative to the same activity in seed tissue.

In another preferred embodiment, the expression of enzymes involved in tocopherol, tocotrienol or plastoquinol synthesis in the seed will result in an increase in the total tocopherol, tocotrienol or plastoquinol level in the plant.

In some embodiments, the levels of tocopherols or a species such as α-tocopherol may be altered. In some embodiments, the levels of tocotrienols may be altered. Such alteration can be compared to a plant with a similar genetic background but lacking the introduction of a nucleic acid sequence of the present invention.

In another embodiment, either the α-tocopherol level, α-tocotrienol level, or both of plants that natively produce high levels of either α-tocopherol, α-tocotrienol or both (e.g., sunflowers), can be increased by the introduction of a nucleic acid of the present invention.

As tocotrienols have their own health benefits, the nucleotide sequence of LTT1 and nucleotide sequences encoding phytol kinase polypeptides and polypeptides having phytol kinase activity can also be used to obtain transgenic seed that predominantly accumulate tocotrienols. Tocotrienols can be obtained in dicotyledone seed that carry seed-specific expression constructs for the prephenate dehydrogenase (tyrA) and the p-hydroxyphenylpyruvate dioxygenase (HPPD) (WO 02/089561). A higher purity of tocotrienols may be obtained in such seed by reducing the production of tocopherols while increasing the production of tocotrienols. Tocopherol biosynthesis can be reduced by a mutation in LTT1. Alternatively tocopherol biosynthesis may be reduced by downregulating LTT1 and other nucleotide sequences encoding phytol kinase polypeptides and polypeptides having phytol kinase activity. If it is desired to down-regulate the expression of a given gene, i.e., decrease the expression of a gene through any means, such as by about 25%, 50%, 75% or more at the mRNA or protein level, a nucleic acid molecule comprising (i.e., in the case of an RNA vector) or encoding (i.e., in the case of a DNA vector) an antisense nucleic acid molecule (see, e.g., Smith et al., Nature 334: 724–726 (1988)) to an RNA molecule transcribed from an aforementioned gene, for example, a dsRNAi molecule (see, e.g., Waterhouse et al., PNAS USA 95: 13959–13964 (1998)), a nucleic acid molecule, the expression of which results in the sense suppression (see, e.g., Napoli et al., Plant Cell 2: 279–289 (1989); U.S. Pat. Nos. 5,190,931; 5,107, 065; and 5,283,323; and international application publication No. WO 01/14538) of a gene encoding an LTT1 polypeptide or a nucleotide sequence encoding a phytol kinase polypeptide or a polypeptide having phytol kinase activity, or a nucleic acid molecule comprising a ribozyme to an RNA molecule transcribed from such a gene (see, for example, Senior, Biotech. Genet. Eng. Rev. 15: 79–119 (1998); Bird et al., Biotech. Genet. Eng. Rev. 9: 207–227 (1991); Matzke et al., Trends Genet. 11(1): 1–3 (1995); Baulcombe, Plant Mol. Biol. 32(1–2): 79–88 (1996); Castana Rev. Eukaryot. Gene Exp. 2(4): 331–357 (1992); Rossi, Trends Biotechnol. 13(8): 301–306 (1995); and WO 97/10328) can be utilized. Other techniques include promoter silencing (see, e.g., Park et al., Plant J. 9(2): 183–194 (1996)) and the use of DNA binding proteins (Beerli et al., PNAS USA 95: 14628–14633 (1997); and Liu et al., PNAS USA 94: 5525–5530 (1998)).

In antisense technology, the nucleic acid sequence generally is substantially identical to at least a portion, such as at least about 100 (or 125, 150, 175, 200, 225, 250, 275, 300, 325, 350, 375, 400, 425, 450, 475, 500, 750, 1,000, 1,500, 2,000 or more, up to the full-length of the gene, which is defined as a particular sequence of nucleotides along a molecule of DNA, which represents a functional unit of inheritance) contiguous nucleotides, of the endogenous gene or gene to be repressed, but need not be identical. The introduced sequence also need not be full-length relative to either of the primary transcription product or the fully processed mRNA. Generally, higher homology can be used to compensate for the use of a shorter sequence. Furthermore, the introduced sequence need not have the same intron or exon pattern, and homologous non-coding segments can be equally effective.

If desired, antisense nucleic acid molecules can be chemically synthesized or enzymatically ligated using procedures known in the art. For example, an antisense nucleic acid can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides.

Alternatively, the antisense nucleic acid can be produced biologically using an expression vector into which a nucleic acid has been subcloned in an antisense orientation and operably linked to a promoter. Preferably, production of antisense nucleic acids in plants occurs by means of a stably integrated transgene comprising a promoter operative in plants, an antisense oligonucleotide, and a terminator. The gene can be polycistronic, i.e., can comprise sequences from more than one gene, and can include sequences that correspond to a 5' UTR, a 3' UTR, an intron, and combinations thereof.

The plant cell, plant tissue, plant organ or plant is then contacted with the antisense nucleic acid molecules or with a construct encoding an antisense nucleic acid molecule such that the anti-sense strand of RNA is produced in vivo. In plant cells, it has been shown that anti-sense RNA inhibits gene expression (see, e.g., Sheehy et al., *PNAS USA* 85: 8805–8809 (1988); and U.S. Pat. Nos. 4,801,340 and 5,107, 065). The antisense molecules can bind to genomic DNA or cellular mRNA so as to inhibit transcription or translation. The hybridization can be by conventional nucleotide complementarity to form a stable duplex or by binding to DNA duplexes through specific interactions in the major groove of the double helix. Antisense nucleic acid molecules can be modified to target selected cells, i.e., via linking to a peptide or antibody (or antigenically reactive fragment thereof) that binds to a cell-surface molecule or receptor, and then administered systemically. Inhibition of expression of a given gene can be confirmed in a transformed plant cell by standard methods for measuring the presence and/or activity of a given protein. In this regard, it is important to point out that some plants contain two genes, i.e., "paralogs," encoding a given polypeptide. In such instances, a single antisense RNA molecule can be used to reduce and even block the expression of both paralogs, if so desired, depending on the antisense molecule utilized. However, in some instances, it may be desirable to down-regulate one paralog, but not the other.

dsRNA-dependent post-transcriptional gene silencing or RNAi is now used extensively in various diploid organisms. dsRNA-induced silencing phenomena are present in evolutionarily diverse organisms, including plants (see, e.g., U.S. Pat. No. 6,506,559; U.S. Pat. App. Pub. No. 2002/0168707; and int'l pat. app. pub. nos. WO 99/53050 and WO 99/61631), fungi, and metazoans (Hammond et al., Nat. Rev. Genet. 2: 110–119 (2001)). Stable silencing has been induced in model organisms by directed expression of long dsRNAs (Kennerdell et al., Nat. Biotechnol. 18: 896–898 (2000); Smith et al., Nature (London) 407: 319–320 (2000); and Tavernarakis et al., Nat. Genet. 24: 180–183 (2000)). dsRNAi constructs can comprise as few as 21 nucleotides in sense and antisense orientation, or as many as 50, 75, 100, 125, 150, 175, 200 or more nucleotides in sense and antisense orientation.

Another method of down-regulating an LTT1 gene or nucleotide sequences encoding phytol kinase polypeptides and polypeptides having phytol kinase activity is sense supression. Sense suppression is the reduction in expression levels, usually at the level of RNA, of a particular endogenous gene or gene family by the expression of a homologous sense construct that is capable of transcribing mRNA of the same strandedness as the transcript of the endogenous gene (Napoli et al., Plant Cell 2: 279–289 (1990); van der Krol et al., Plant Cell 2: 291–299 (1990)). Suppression can result from stable transformation with a single copy nucleic acid molecule that is homologous to a nucleic acid sequence found within the cell (Prolls et al., Plant J. 2: 465–475 (1992)) or with multiple copies of a nucleic acid molecule that is homologous to a nucleic acid sequence found within the cell (Mittlesten et al., Mol. Gen. Genet. 244: 325–330 (1994)). Genes, even though different, linked to homologous promoters can result in suppression of the linked genes (Vaucheret, C. R. Acad. Sci. III 316a: 1471–1483 (1993); Flavell, PNAS USA 91: 3490–3496 (1994); van Blokland et al., Plant J. 6: 861–877 (1994); Jorgensen, Trends Biotechnol. 8: 340–344 (1990); Meins et al., In: *Gene Activation and Homologous Recombination in Plants*, Paszkowski, ed., pp. 335–348, Kluwer Academic, Netherlands (1994); Kinney, Induced Mutations and Molecular Techniques for Crop Improvement, Proceedings of a Symposium (Jun. 19–23, 1995; jointly organized by IAEA and FA), pp. 101–113 (IAEA-SM 340–49); and Que et al., Dev. Genet. 22(1): 100–109 (1998), and Smyth, Curr. Biol. 7(12): R793–R795 (1997). In sense technology, the nucleic acid sequence generally is substantially identical to at least a portion, such as at least about 21 (or 50, 75, 100, 125, 150, 175, 200 or more) contiguous nucleotides, of the endogenous gene or gene to be repressed, but need not be identical.

Still yet another method is the use of a dominant negative mutant. For example, a dominant negative mutant of a polypeptide having phytol kinase activity as described herein can be generated by completely or partially deleting the C-terminal coding sequence, in particular all or part of the C-terminal coding sequence that is highly conserved among the polypeptides described herein. The resulting mutant can be operably linked to a promoter, such as an embryo-specific promoter from maize, for example, and cloned into a vector for introduction into a corn plant or part thereof. See, e.g., Jasinski et al., Plant Physiol. 130: 1871–1882 (2002)).

Ribozymes also have been reported to have use as a means to inhibit expression of endogenous plant genes (see, e.g., Merlo et al., Plant Cell 10(10): 1603–1622 (1998)). It is possible to design ribozymes that specifically pair with virtually any target RNA and cleave the phosphodiester backbone at a specific location, thereby functionally inactivating the target RNA. In carrying out this cleavage, the ribozyme is not itself altered and is, thus, capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., *Nature* 334: 585–591 (1988). Preferably, the ribozyme comprises at least about 20 continuous nucleotides complementary to the target sequence on each side of the active site of the ribozyme.

Alternatively, reverse genetics systems, which are well-known in the art, can be used to generate and isolate down-regulated or null mutants. One such system, the Trait Utility System for Corn, i.e., TUSC, is based on successful systems from other organisms (Ballinger et al., PNAS USA 86: 9402–9406 (1989); Kaiser et al., PNAS USA 87: 1686–1690 (1990); and Rushforth et al., Mol. Cell. Biol. 13: 902–910 (1993)). The central feature of the system is to identify Mu transposon insertions within a DNA sequence of interest in anticipation that at least some of these insertion alleles will be mutants. To develop the system in corn, DNA was collected from a large population of Mutator transposon stocks that were then self-pollinated to produce F2 seed. To find Mu transposon insertions within a specified DNA sequence, the collection of DNA samples is screened via PCR using a gene-specific primer and a primer that anneals to the inverted repeats of Mu transposons. A PCR product is expected only when the template DNA comes from a plant that contains a Mu transposon insertion within the target gene. Once such a DNA sample is identified, F2 seed from the corresponding plant is screened for a transposon insertion allele. Transposon insertion mutations of the an1 gene have been obtained via the TUSC procedure (Bensen et al., Plant Cell 7: 75–84 (1995)). This system is applicable to other plant species, at times modified as necessary in accordance with knowledge and skill in the art.

T-DNA insertional mutagenesis can be used to generate insertional mutations in one of the above-mentioned genes so as to affect adversely the expression of a given gene. T-DNA tagged lines of plants can be screened using PCR. For example, a primer can be designed for one end of the T-DNA and another primer can be designed for the gene of interest and both primers can be used in PCR. If no PCR product is obtained, then there is no insertion in the gene of interest. In contrast, if a PCR product is obtained, then there is an insertion in the gene of interest. Insertional mutations, however, often generate null alleles, which can be lethal. Alternatively, if there is more than one gene that encodes for a given enzyme, a mutation in one of the genes may not result in decreased expression of the enzyme encoded by the gene.

Another alternative method to decrease expression of a given gene is to use a compound that inhibits expression of one of the above-mentioned genes or that inhibits the activity of the protein encoded by one of the above-mentioned genes. In this regard, x-ray or gamma radiation can be used as can chemical mutagens, such as ethyl methyl sulfonate (EMS) or dimethyl butyric acid (DMB).

In addition to the above, gene replacement technology can be used to increase or decrease expression of a given gene.

Gene replacement technology is based upon homologous recombination (see, Schnable et al., Curr. Opinions Plant Biol. 1: 123 (1998)). The nucleic acid of the enzyme of interest can be manipulated by mutagenesis (e.g., insertions, deletions, duplications or replacements) to either increase or decrease enzymatic function. The altered sequence can be introduced into the genome to replace the existing, e.g., wild-type, gene via homologous recombination (Puchta and Hohn, Trends Plant Sci. 1: 340 (1996); Kempin et al., Nature 389: 802 (1997)).

Down regulating phytol kinase polypeptides and polypeptides having phytol kinase activity prevents the plant from recycling free phytol from chlorophyll degradation for tocopherol biosynthesis. Therefore, a seed with high tocotrienol content (preferably >75%) can be obtained by seed specific expression of tyrA, HPPD, and seed specific antisense or antisense with a constitutive promoter of LTT1. Additional seed-specific expression of other tocopherol genes such as HPT, TMT2, GMT, and tocopherol cyclase that express proteins with preference for tocotrienol precursors as substrates may even further enhance tocotrienol biosynthesis. Such enzymes may be found in monocotyledone plants such as oil palm, rice, corn, wheat and other monocotyledone plants that naturally accumulate large amounts of tocotrienols.

In a preferred aspect, a similar genetic background is a background where the organisms being compared share about 50% or greater of their nuclear genetic material. In a more preferred aspect a similar genetic background is a background where the organisms being compared share about 75% or greater, even more preferably about 90% or greater of their nuclear genetic material. In another even more preferable aspect, a similar genetic background is a background where the organisms being compared are plants, and the plants are isogenic except for any genetic material originally introduced using plant transformation techniques.

Exogenous genetic material may be transferred into a host cell by the use of a DNA vector or construct designed for such a purpose. Design of such a vector is generally within the skill of the art (See, *Plant Molecular Biology: A Laboratory Manual*, Clark (ed.), Springer, N.Y., 1997).

A construct or vector may include a plant promoter to express an mRNA that is translated into the polypeptide of choice. In a preferred embodiment, any nucleic acid molecules described herein can be operably linked to a promoter region which functions in a plant cell to cause the production of an mRNA molecule. For example, any promoter that functions in a plant cell to cause the production of an mRNA molecule, such as those promoters described herein, without limitation, can be used. In a preferred embodiment, the promoter is a plant promoter or a plant virus promoter.

A number of promoters that are active in plant cells have been described in the literature. These include the 7alpha' promoter, the USP88 promoter (U.S. patent application Ser. No. 10/429,516, filed May 5, 2003), the nopaline synthase (NOS) promoter (Ebert et al., *Proc. Natl. Acad. Sci.* (*U.S.A.*), 84:5745–5749, 1987), the octopine synthase (OCS) promoter (which is carried on tumor-inducing plasmids of *Agrobacterium tumefaciens*). Examples of constitutive promoters that are active in plant cells include, but are not limited to the nopaline synthase (P-NOS) promoters; the cauliflower mosaic virus (P-CaMV) 19S and 35S (P-CaMV35S, U.S. Pat. No. 5,858,642) and enhanced versions of the CaMV 35S promoter (P-CaMV35S-enh, U.S. Pat. No. 5,322,938; the figwort mosaic virus promoter (P-FMV35S, U.S. Pat. Nos. 6,051,753 and 6,018,100); and actin promoters, such as the rice actin promoter (P-Os.Act1, U.S. Pat. No. 5,641,876), the Adh promoter (Walker et al., *Proc. Natl. Acad. Sci.* (*U.S.A.*), 84:6624–6628, 1987), the sucrose synthase promoter (Yang et al., *Proc. Natl. Acad. Sci.* (*U.S.A.*), 87:4144–4148, 1990), the R gene complex promoter (Chandler et al., *The Plant Cell*, 1:1175–1183, 1989) and the chlorophyll a/b binding protein gene promoter, etc. These promoters have been used to create DNA constructs that have been expressed in plants. Promoters known or found to cause transcription of DNA in plant cells can be used in the invention. The sequences of the promoters disclosed in these referenced patents are herein incorporated by reference.

For the purpose of expression in source tissues of the plant, such as the leaf, seed, root or stem, it is preferred that the promoters utilized have relatively high expression in these specific tissues. Tissue-specific expression of a protein of the present invention is a particularly preferred embodiment. For this purpose, one may choose from a number of promoters for genes with tissue- or cell-specific or enhanced expression. Examples of such promoters reported in the literature include the chloroplast glutamine synthetase GS2 promoter from pea (Edwards et al., *Proc. Natl. Acad. Sci.* (*U.S.A.*), 87:3459–3463, 1990), the chloroplast fructose-1, 6-biphosphatase (FBPase) promoter from wheat (Lloyd et al., *Mol. Gen. Genet.*, 225:209–216, 1991), the nuclear photosynthetic ST-LS1 promoter from potato (Stockhaus et al., *EMBO J.*, 8:2445–2451, 1989), the serine/threonine kinase (PAL) promoter and the glucoamylase (CHS) promoter from *Arabidopsis thaliana*. Also reported to be active in photosynthetically active tissues are the ribulose-1,5-bisphosphate carboxylase (RbcS) promoter from eastern larch (*Larix laricina*), the promoter for the cab gene, cab6, from pine (Yamamoto et al., *Plant Cell Physiol.*, 35:773–778, 1994), the promoter for the Cab-1 gene from wheat (Fejes et al., *Plant Mol. Biol.*, 15:921–932, 1990), the promoter for the CAB-1 gene from spinach (Lubberstedt et al., *Plant Physiol.*, 104:997–1006, 1994), the promoter for the cab1R gene from rice (Luan et al., *Plant Cell.*, 4:971–981, 1992), the pyruvate, orthophosphate dikinase (PPDK) promoter from corn (Matsuoka et al., *Proc. Natl. Acad. Sci.* (*U.S.A.*), 90:9586–9590, 1993), the promoter for the tobacco Lhcb1*2 gene (Cerdan et al., *Plant Mol. Biol.*, 33:245–255, 1997), the *Arabidopsis thaliana* SUC2 sucrose-H+symporter promoter (Truernit et al., *Planta.*, 196:564–570, 1995) and the promoter for the thylakoid membrane proteins from spinach (psaD, psaF, psaE, PC, FNR, atpC, atpD, cab, rbcS). Other promoters for the chlorophyll a/b-binding proteins may also be utilized in the invention, such as the promoters for LhcB gene and PsbP gene from white mustard (*Sinapis alba*; Kretsch et al., *Plant Mol. Biol.*, 28:219–229, 1995).

For the purpose of expression in sink tissues of the plant, such as the tuber of the potato plant, the fruit of tomato, or the seed of corn, wheat, rice and barley, it is preferred that the promoters utilized in the invention have relatively high expression in these specific tissues. A number of promoters for genes with tuber-specific or tuber-enhanced expression are known, including the class I patatin promoter (Bevan et al., *EMBO J.*, 8:1899–1906, 1986); Jefferson et al., *Plant Mol. Biol.*, 14:995–1006, 1990), the promoter for the potato tuber ADPGPP genes, both the large and small subunits, the sucrose synthase promoter (Salanoubat and Belliard, *Gene*, 60:47–56, 1987), Salanoubat and Belliard, *Gene*, 84:181–185, 1989), the promoter for the major tuber proteins including the 22 kd protein complexes and protease inhibitors (Hannapel, *Plant Physiol.*, 101:703–704, 1993), the promoter for the granule-bound starch synthase gene (GBSS) (Visser et al., *Plant Mol. Biol.*, 17:691–699, 1991) and other class I and II patatins promoters (Koster-Topfer et al., *Mol. Gen. Genet.*, 219:390–396, 1989); Mignery et al., *Gene*, 62:27–44, 1988).

Other promoters can also be used to express a polypeptide in specific tissues, such as seeds or fruits. Indeed, in a preferred embodiment, the promoter used is a seed specific promoter. Examples of such promoters include the 5' regulatory regions from such genes as napin (Kridl et al., *Seed Sci. Res.* 1:209:219, 1991), phaseolin (Bustos, et al., *Plant Cell*, 1(9):839–853, 1989), soybean trypsin inhibitor (Riggs, et al., *Plant Cell*, 1(6):609–621, 1989ACP (Baerson, et al., *Plant Mol. Biol.*, 22(2):255–267, 1993), stearoyl-ACP desaturase (Slocombe, et al., *Plant Physiol.*, 104(4): 167–176, 1994), soybean a' subunit of β-conglycinin (Chen et al., *Proc. Natl. Acad. Sci.*, 83:8560–8564, 1986), and oleosin (see, for example, Hong, et al., *Plant Mol. Biol.*, 34(3):549–555, 1997). Further examples include the promoter for β-conglycinin (Chen et al., *Dev. Genet.*, 10:112–122, 1989). Also included are the zeins, which are a group of storage proteins, found in corn endosperm. Genomic clones for zein genes have been isolated (Pedersen et al., Cell 29:1015–1026, 1982), and Russell et al., *Transgenic Res.*, 6(2): 157–168, 1997) and the promoters from these clones, including the 15 kD, 16 kD, 19 kD, 22 kD, 27 kD and genes, could also be used. Other promoters known to function, for example, in corn include the promoters for the following genes: waxy, Brittle, Shrunken 2, Branching enzymes I and II, starch synthases, debranching enzymes, oleosins, glutelins and sucrose synthases. A particularly preferred promoter for corn endosperm expression is the promoter for the glutelin gene from rice, more particularly the Osgt-1 promoter (Zheng et al., *Mol. Cell Biol.*, 13:5829–5842, 1993). Examples of promoters suitable for expression in wheat include those promoters for the ADP-glucose pyrosynthase (ADPGPP) subunits, the granule bound and other starch synthase, the branching and debranching enzymes, the embryogenesis-abundant proteins, the gliadins and the glutenins. Examples of such promoters in rice include those promoters for the ADPGPP subunits, the granule bound and other starch synthase, the branching enzymes, the debranching enzymes, sucrose synthases and the glutelins. A particularly preferred promoter is the promoter for rice glutelin, Osgt-1. Examples of such promoters for barley include those for the ADPGPP subunits, the granule bound and other starch synthase, the branching enzymes, the debranching enzymes, sucrose synthases, the hordeins, the embryo globulins and the aleurone specific proteins.

The seed-specific promoters that include the 5' regulatory regions of the napin gene provide expression of transgenes in seed tissues (U.S. Pat. Nos. 5,420,034 and 6,459,018, herein incorporated by reference). In soybean, 7S refers to β-conglycinin, a major class of seed storage proteins. The trimeric β-conglycinin is comprised of the α, α' and β subunits. Expression of 7Sα' has been well studied by many researchers over the years. The 7α' subunit is expressed at mid to late stages of seed development. A transgene encoding the α'-subunit of soybean β-conglycinin showed seed-specific expression in petunia (Beachy et al., EMBO J. 4:3047–3053, 1985). Functional analysis of the regulatory elements indicated that a 900 bp upstream fragment of the 7Sα' promoter contains the necessary elements to produce seed-specific expression in transgenic petunia (Chen et al., Proc. Natl. Acad. Sci. 83:8560–8564, 1986). The ovule-specific promoter for BEL1 gene can also be used (Reiser et al. Cell 83:735–742, 1995, GenBank No. U39944; Ray et al, Proc. Natl. Acad. Sci. U.S.A. 91:5761–5765, 1994). The egg and central cell specific MEA (FIS1) and FIS2 promoters are also useful reproductive tissue-specific promoters (Luo et al., *Proc. Natl. Acad. Sci. (U.S.A.)*, 97:10637–10642, 2000; Vielle-Calzada, et al., Genes Dev. 13:2971–2982, 1999). Additional promoters useful for driving expression of a transgene in seed tissues are described in numerous references, for example, U.S. Pat. Nos. 6,437,220; 6,426,447; 6,342,6571 6,410,828; 5,767,363 and 5,623,067, herein incorporated by reference)

A preferred promoter for expression in the seed is a napin promoter. Another preferred promoter for expression is an Arcelin5 promoter (U.S. Patent Publication 2003/0046727). Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436.

Constructs or vectors may also include, with the coding region of interest, a nucleic acid sequence that acts, in whole or in part, to terminate transcription of that region. A number of such sequences have been isolated, including the Tr7 3' sequence and the NOS 3' sequence (Ingelbrecht et al., *The Plant Cell*, 1:671–680, 1989); Bevan et al., *Nucleic Acids Res.*, 11:369–385, 1983). Regulatory transcript termination regions can be provided in plant expression constructs of this invention as well. Transcript termination regions can be provided by the DNA sequence encoding the gene of interest or a convenient transcription termination region derived from a different gene source, for example, the transcript termination region that is naturally associated with the transcript initiation region. The skilled artisan will recognize that any convenient transcript termination region that is capable of terminating transcription in a plant cell can be employed in the constructs of the present invention, e.g., TML 3' from *Agrobacterium tumefaciens* Ti plasmid.

A vector or construct may also include regulatory elements. Examples of such include the Adh intron 1 (Callis et al., *Genes and Develop.*, 1:1183–1200, 1987), the sucrose synthase intron (Vasil et al., *Plant Physiol.*, 91:1575–1579, 1989) and the TMV omega element (Gallie et al., *The Plant Cell*, 1:301–311, 1989). These and other regulatory elements may be included when appropriate.

A vector or construct may also include a selectable marker. Selectable markers may also be used to select for plants or plant cells that contain the exogenous genetic material. Examples of such include, but are not limited to: a neo gene (Potrykus et al., *Mol. Gen. Genet.*, 199:183–188, 1985), which codes for kanamycin resistance and can be selected for using kanamycin, RptII, G418, hpt etc.; a bar gene which codes for bialaphos resistance; a mutant EPSP synthase gene (Hinchee et al., *Bio/Technology*, 6:915–922, 1988); Reynaerts et al., Selectable and Screenable Markers. In Gelvin and Schilperoort. Plant Molecular Biology Manual, Kluwer, Dordrecht (1988); Reynaerts et al., Selectable and screenable markers. In Gelvin and Schilperoort. Plant Molecular Biology Manual, Kluwer, Dordrecht (1988), and (Jones et al., *Mol. Gen. Genet.*, 1987), which encodes glyphosate resistance; a nitrilase gene which confers resistance to bromoxynil (Stalker et al., *J. Biol. Chem.* 263:6310–6314, 1988); a mutant acetolactate synthase gene (ALS) which confers imidazolinone or sulphonylurea resistance (European Patent Application 154,204 (Sep. 11, 1985), ALS (D'Halluin et al., *Bio/Technology*, 10:309–314, 1992), and a methotrexate resistant DHFR gene (Thillet et al., *J. Biol. Chem.* 263:12500–12508, 1988).

A vector or construct may also include a screenable marker. Screenable markers may be used to monitor expression. Exemplary screenable markers include: a β-glucuronidase or uidA gene (GUS) which encodes an enzyme for which various chromogenic substrates are known (Jefferson, *Plant Mol. Biol, Rep.,* 5:387–405, 1987); Jefferson et al., *EMBO J.,* 6:3901–3907, 1987); an R-locus gene, which encodes a product that regulates the production of anthocyanin pigments (red color) in plant tissues (Dellaporta et al., Stadler Symposium, 11:263–282, 1988); a β-lactamase gene (Sutcliffe et al., *Proc. Natl. Acad. Sci. (U.S.A.),* 75:3737–3741, 1978), a gene which encodes an enzyme for which various chromogenic substrates are known (e.g., PADAC, a chromogenic cephalosporin); a luciferase gene (Ow et al., *Science,* 234:856–859, 1986); a xylE gene (Zukowsky et al., *Proc. Natl. Acad. Sci. (U.S.A.),* 80:1101–1105, 1983) which encodes a catechol dioxygenase that can convert chromogenic catechols; an ox-amylase gene (Ikatu et al., *Bio/Technol.,* 8:241–242, 1990); a tyrosinase gene (Katz et al., *J. Gen. Microbiol.,* 129:2703–2714, 1983) which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes that encode a secretable marker whose secretion can be detected as a means of identifying or selecting for transformed cells. Examples include markers that encode a secretable antigen that can be identified by antibody interaction, or even secretable enzymes that can be detected catalytically. Secretable proteins fall into a number of classes, including small, diffusible proteins that are detectable, (e.g., by ELISA), small active enzymes that are detectable in extracellular solution (e.g., α-amylase, β-lactamase, phosphinothricin transferase), or proteins that are inserted or trapped in the cell wall (such as proteins that include a leader sequence such as that found in the expression unit of extension or tobacco PR-S). Other possible selectable and/or screenable marker genes will be apparent to those of skill in the art.

In a preferred embodiment of the invention, a transgenic plant expressing the desired protein is to be produced. Various methods for the introduction of a desired polynucleotide sequence encoding the desired protein into plant cells are available and known to those of skill in the art and include, but are not limited to: (1) physical methods such as microinjection, electroporation, and microprojectile mediated delivery (biolistics or gene gun technology); (2) virus mediated delivery methods; and (3) Agrobacterium-mediated transformation methods.

The most commonly used methods for transformation of plant cells are the Agrobacterium-mediated DNA transfer process and the biolistics or microprojectile bombardment mediated process (i.e., the gene gun). Typically, nuclear transformation is desired but where it is desirable to specifically transform plastids, such as chloroplasts or amyloplasts, plant plastids may be transformed utilizing a microprojectile-mediated delivery of the desired polynucleotide.

Agrobacterium-mediated transformation is achieved through the use of a genetically engineered soil bacterium belonging to the genus Agrobacterium. A number of wild type and disarmed strains of *Agrobacterium tumefaciens* and *Agrobacterium rhizogenes* harboring Ti or Ri plasmids can be used for gene transfer into plants. Gene transfer is done via the transfer of a specific DNA known as "T-DNA" that can be genetically engineered to carry any desired piece of DNA into many plant species.

Agrobacterium-mediated genetic transformation of plants involves several steps. The first step, in which the virulent Agrobacterium and plant cells are first brought into contact with each other, is generally called "inoculation". Following the inoculation, the, Agrobacterium and plant cells/tissues are permitted to be grown together for a period of several hours to several days or more under conditions suitable for growth and T-DNA transfer. This step is termed "co-culture". Following co-culture and T-DNA delivery, the plant cells are treated with bactericidal or bacteriostatic agents to kill the Agrobacterium remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, one or more "selection" steps typically follow it.

With respect to microprojectile bombardment (U.S. Pat. Nos. 5,550,318; 5,538,880; and 5,610,042; each of which is specifically incorporated herein by reference in its entirety), particles are coated with nucleic acids and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, CA), which can be used to propel particles coated with DNA or cells through a screen, such as a stainless steel or Nytex screen, onto a filter surface covered with monocot plant cells cultured in suspension.

Microprojectile bombardment techniques are widely applicable, and may be used to transform virtually any plant species. Examples of species that have been transformed by microprojectile bombardment include monocot species such as maize (PCT Publication WO 95/06128), barley, wheat (U.S. Pat. No. 5,563,055, incorporated herein by reference in its entirety), rice, oat, rye, sugarcane, and sorghum; as well as a number of dicots including tobacco, soybean (U.S. Pat. No. 5,322,783, incorporated herein by reference in its entirety), sunflower, peanut, cotton, tomato, and legumes in general (U.S. Pat. No. 5,563,055, incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin (and neomycin, G418, bleomycin); methotrexate (and trimethoprim); chloramphenicol; kanamycin and tetracycline.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, Physiol. Plant, 15:473–497, 1962) or N6-based media (Chu et al., *Scientia Sinica* 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

Any of the nucleic acid molecules of the invention may be introduced into a plant cell in a permanent or transient manner in combination with other genetic elements such as vectors, promoters, enhancers, etc. Further, any of the nuclcic acid molecules of the invention may be introduced into a plant cell in a manner that allows for expression or overexpression of the protein or fragment thereof encoded by the nucleic acid molecule.

The present invention also provides for parts of the plants, particularly reproductive or storage parts, of the present invention. Plant parts, without limitation, include seed, endosperm, ovule and pollen. In a particularly preferred embodiment of the present invention, the plant part is a seed. In one embodiment the seed (or grain) is a constituent of animal feed.

In another embodiment, the plant part is a fruit, more preferably a fruit with enhanced shelf life. In another preferred embodiment, the fruit has increased levels of a tocopherol. In another preferred embodiment, the fruit has increased levels of a tocotrienol.

Any of the plants or parts thereof of the present invention may be processed to produce a feed, meal, protein, or oil preparation, including oil preparations high in total tocopherol content and oil preparations high in any one or more of each tocopherol component listed herein. A particularly preferred plant part for this purpose is a seed. In a preferred embodiment the feed, meal, protein or oil preparation is designed for livestock animals or humans, or both. Methods to produce feed, meal, protein and oil preparations are known in the art. See, for example, U.S. Pat. Nos. 4,957,748; 5,100,679; 5,219,596; 5,936,069; 6,005,076; 6,146,669; and 6,156,227. In a preferred embodiment, the protein preparation is a high protein preparation. Such a high protein preparation preferably has a protein content of greater than about 5% w/v, more preferably 10% w/v, and even more preferably 15% w/v. In a preferred oil preparation, the oil preparation is a high oil preparation with an oil content derived from a plant or part thereof of the present invention of greater than 5% w/v, more preferably 10% w/v, and even more preferably 15% w/v. In a preferred embodiment the oil preparation is a liquid and of a volume greater than about 1, 5, 10 or 50 liters. The present invention provides for oil produced from plants of the present invention or generated by a method of the present invention. Such an oil may exhibit enhanced oxidative stability. Also, such oil may be a minor or major component of any resultant product. Moreover, such oil may be blended with other oils. In a preferred embodiment, the oil produced from plants of the present invention or generated by a method of the present invention constitutes greater than about 0.5%, 1%, 5%, 10%, 25%, 50%, 75% or 90% by volume or weight of the oil component of any product. In another embodiment, the oil preparation may be blended and can constitute greater than about 10%, 25%, 35%, 50% or 75% of the blend by volume. Oil produced from a planit of the present invention can be admixed with one or more organic solvents or petroleum distillates.

Descriptions of breeding methods that are commonly used for different traits and crops can be found in one of several reference books (e.g., Hayward, *Plant Breeding: Principles and Prospects*, Vol 1, Chapman & Hall; ISBN: 0412433907 (1993); Richards, A. J., *Plant Breeding Systems*, Stanley Thornes Pub Ltd; 2nd ed., ISBN: 0412574500 (1997); Allard, R. W., *Principles of Plant Breeding*, 2nd ed., John Wiley & Sons, ISBN: 0471023094 (1999)

A transgenic plant of the present invention may also be reproduced using apomixis. Apomixis is a genetically controlled method of reproduction in plants where the embryo is formed without union of an egg and a sperm. Apomixis is economically important, especially in transgenic plants, because it causes any genotype, no matter how heterozygous, to breed true. Thus, with apomictic reproduction, heterozygous transgenic plants can maintain their genetic fidelity throughout repeated life cycles. Methods for the production of apomictic plants are known in the art, e.g., U.S. Pat. No. 5,811,636.

Other Organisms

A nucleic acid of the present invention may be introduced into any cell or organism such as a mammalian cell, mammal, fish cell, fish, bird cell, bird, algae cell, algae, fungal cell, fungi, or bacterial cell. A protein of the present invention may be produced in an appropriate cell or organism. Preferred host and transformants include: fungal cells such as Aspergillus, yeasts, mammals, particularly bovine and porcine, insects, bacteria, and algae. Particularly preferred bacteria are Agrobacteruim tumefaciens and *E. coli*.

Methods to transform such cells or organisms are known in the art (EP 0 238 023; Yelton et al., *Proc. Natl. Acad. Sci. (U.S.A.)*, 81:1470–1474, 1984); Malardier et al., *Gene*, 78:147–156, 1989); Becker and Guarente, In: Abelson and Simon (eds.), *Guide to Yeast Genetics and Molecular Biology, Method Enzymol.*, 194:182–187, Academic Press, Inc., New York; Ito et al., *J. Bacteriology*, 153:163, 1983) Hinnen et al., *Proc. Natl. Acad. Sci. (U.S.A.)*, 75:1920, 1978); Bennett and LaSure (eds.), *More Gene Manipulations in fungi*, Academic Press, CA (1991). Methods to produce proteins of the present invention are also known (Kudla et al., *EMBO*, 9:1355–1364, 1990); Jarai and Buxton, *Current Genetics*, 26:2238–2244 (1994); Verdier, *Yeast*, 6:271–297, 1990; MacKenzie et al., *Journal of Gen. Microbiol.*, 139: 2295–2307, 1993); Hartl et al., *TIBS*, 19:20–25, 1994);

Bergenron et al., *TIBS*, 19:124–128, 1199); Dermolder et al., *J. Biotechnology*, 32:179–189, 1994); Craig, *Science*, 260: 1902–1903, 1993); Gething and Sambrook, *Nature*, 355: 33–45, 1992); Puig and Gilbert, *J. Biol. Chem.*, 269:7764–7771, 1994); Wang and Tsou, *FASEB Journal*, 7:1515–1517, 1993); Robinson et al., *Bio/Technology*, 1:381–384, 1994); Enderlin and Ogrydziak, *Yeast*, 10:67–79, 1994); Fuller et al., *Proc. Natl. Acad. Sci. (U.S.A.)*, 86:1434–1438, 1989); Julius et al., *Cell*, 37:1075–1089, 1984); Julius et al., *Cell*, 32:839–852, 1983).

In a preferred embodiment, DNA constructs of the present invention comprising SEQ ID NOs: 1, 5, 17, or sequences having at least about 70, 80, 90, 95, or 99% identity to such sequences, provide in a transformed cell, relative to an untransformed cell with a similar genetic background, an increased level of tocopherols.

In a preferred embodiment, DNA constructs of the present invention comprising SEQ ID NOs: 1, 5, 17, or sequences having at least about 70, 80, 90, 95, or 99% identity to such sequences, provide in a transformed cell, relative to an untransformed cell with a similar genetic background, an increased level of α-tocopherols.

In a preferred embodiment, DNA constructs of the present invention comprising SEQ ID NOs: 1, 5, 17, or sequences having at least about 70, 80, 90, 95, or 99% identity to such sequences, provide in a transformed cell, relative to an untransformed cell with a similar genetic background, an increased level of γ-tocopherols.

In a preferred embodiment, DNA constructs of the present invention comprising SEQ ID NOs: 1, 5, 17, or sequences having at least about 70, 80, 90, 95, or 99% identity to such sequences, provides in a transformed cell, relative to an untransformed cell with a similar genetic background, an increased level of β-tocopherols.

In a preferred embodiment, DNA constructs of the present invention comprising SEQ ID NOs: 1, 5, 17, or sequences having at least about 70, 80, 90, 95, or 99% identity to such sequences, provides in a transformed cell, relative to an untransformed cell with a similar genetic background, an increased level of δ-tocopherols.

In a preferred embodiment, DNA constructs of the present invention comprising SEQ ID NOs: 1, 5, 17, or sequences having at least about 70, 80, 90, 95, or 99% identity to such sequences, provide in a transformed cell, relative to an untransformed cell with a similar genetic background, an increased level of tocotrienols.

In a preferred embodiment, DNA constructs of the present invention comprising SEQ ID NOs: 1, 5, 17, or sequences having at least about 70, 80, 90, 95, or 99% identity to such sequences, provide in a transformed cell, relative to an untransformed cell with a similar genetic background, an increased level of α-tocotrienols.

In a preferred embodiment, DNA constructs of the present invention comprising SEQ ID NOs: 1, 5, 17, or sequences having at least about 70, 80, 90, 95, or 99% identity to such sequences, provide in a transformed cell, relative to an untransformed cell with a similar genetic background, an increased level of γ-tocotrienols.

In a preferred embodiment, DNA constructs of the present invention comprising SEQ ID NOs: 1, 5, 17, or sequences having at least about 70, 80, 90, 95, or 99% identity to such sequences, provides in a transformed cell, relative to an untransformed cell with a similar genetic background, an increased level of δ-tocotrienols.

In a preferred embodiment, DNA constructs of the present invention comprising SEQ ID NOs: 1, 5, 17, or sequences having at least about 70, 80, 90, 95, or 99% identity to such sequences, provides in a transformed cell, relative to an untransformed cell with a similar genetic background, an increased level of β-tocotrienols.

In a preferred embodiment, DNA constructs of the present invention comprising nucleic acid molecules encoding a phytol kinase polypeptide or polypeptide having phytol kinase activity provide in a transformed cell, relative to an untransformed cell with a similar genetic background, an increased level of tocopherols.

In a preferred embodiment, DNA constructs of the present invention comprising nucleic acid molecules encoding a phytol kinase polypeptide or a polypeptide having phytol kinase activity, provide in a transformed cell, relative to an untransformed cell with a similar genetic background, an increased level of α-tocopherols.

In a preferred embodiment, DNA constructs of the present invention comprising nucleic acid molecules encoding a phytol kinase polypeptide or a polypeptide having phytol kinase activity, provide in a transformed cell, relative to an untransformed cell with a similar genetic background, an increased level of γ-tocopherols.

In a preferred embodiment, DNA constructs of the present invention comprising nucleic acid molecules encoding a phytol kinase polypeptide or a polypeptide having phytol kinase activity, provide in a transformed cell, relative to an untransformed cell with a similar genetic background, an increased level of β-tocopherols.

In a preferred embodiment, DNA constructs of the present invention comprising nucleic acid molecules encoding a phytol kinase polypeptide or a polypeptide having phytol kinase activity, provide in a transformed cell, relative to an untransformed cell with a similar genetic background, an increased level of δ-tocopherols.

In a preferred embodiment, DNA constructs of the present invention comprising nucleic acid molecules encoding a phytol kinase polypeptide, or a polypeptide having phytol kinase activity, provide in a transformed cell, relative to an untransformed cell with a similar genetic background, an increased level of tocotrienols.

In a preferred embodiment, DNA constructs of the present invention comprising nucleic acid molecules encoding a phytol kinase polypeptide, or a polypeptide having phytol kinase activity, provide in a transformed cell, relative to an untransformed cell with a similar genetic background, an increased level of α-tocotrienols.

In a preferred embodiment, DNA constructs of the present invention comprising nucleic acid molecules encoding a phytol kinase polypeptide, or a polypeptide having phytol kinase activity, provide in a transformed cell, relative to an untransformed cell with a similar genetic background, an increased level of γ-tocotrienols.

In a preferred embodiment, DNA constructs of the present invention comprising nucleic acid molecules encoding a phytol kinase polypeptide or a polypeptide having phytol kinase activity, provide in a transformed cell, relative to an untransformed cell with a similar genetic background, an increased level of β-tocotrienols.

In a preferred embodiment, DNA constructs of the present invention comprising nucleic acid molecules encoding a phytol kinase polypeptide or a polypeptide having phytol kinase activity, provide in a transformed cell, relative to an untransformed cell with a similar genetic background, an increased level of δ-tocotrienols.

In a preferred embodiment, DNA constructs of the present invention comprising nucleic acid molecules encoding a polypeptide comprising an amino acid sequence selected from the group consisting of SEQ ID NOs: 20–41 and 53–68, provide in a transformed cell, relative to an untransformed cell with a similar genetic background, an increased level of tocopherols.

In a preferred embodiment, DNA constructs of the present invention comprising nucleic acid molecules encoding a polypeptide comprising an amino acid sequence selected from the group consisting of SEQ ID NOs: 20–41 and 53–68, provide in a transformed cell, relative to an untransformed cell with a similar genetic background, an increased level of α-tocopherols.

In a preferred embodiment, DNA constructs of the present invention comprising nucleic acid molecules encoding a polypeptide comprising an amino acid sequence selected from the group consisting of SEQ ID NOs: 20–41 and 53–68, provide in a transformed cell, relative to an untransformed cell with a similar genetic background, an increased level of γ-tocopherols.

In a preferred embodiment, DNA constructs of the present invention comprising nucleic acid molecules encoding a polypeptide comprising an amino acid sequence selected from the group consisting of SEQ ID NOs: 20–41 and 53–68, provide in a transformed cell, relative to an untransformed cell with a similar genetic background, an increased level of β-tocopherols.

In a preferred embodiment, DNA constructs of the present invention comprising nucleic acid molecules encoding a polypeptide comprising an amino acid sequence selected from the group consisting of SEQ ID NOs: 20–41 and 53–68, provide in a transformed cell, relative to an untransformed cell with a similar genetic background, an increased level of δ-tocopherols.

In a preferred embodiment, DNA constructs of the present invention comprising nucleic acid molecules encoding a polypeptide comprising an amino acid sequence selected from the group consisting of SEQ ID NOs: 20–41 and 53–68, provide in a transformed cell, relative to an untransformed cell with a similar genetic background, an increased level of tocotrienols.

In a preferred embodiment, DNA constructs of the present invention comprising nucleic acid molecules encoding a polypeptide comprising an amino acid sequence selected from the group consisting of SEQ ID NOs: 20–41 and 53–68, provide in a transformed cell, relative to an untransformed cell with a similar genetic background, an increased level of α-tocotrienols.

In a preferred embodiment, DNA constructs of the present invention comprising nucleic acid molecules encoding a polypeptide comprising an amino acid sequence selected from the group consisting of SEQ ID NOs: 20–41 and 53–68, provide in a transformed cell, relative to an untransformed cell with a similar genetic background, an increased level of γ-tocotrienols.

In a preferred embodiment, DNA constructs of the present invention comprising nucleic acid molecules encoding a polypeptide comprising an amino acid sequence selected from the group consisting of SEQ ID NOs: 20–41 and 53–68, provide in a transformed cell, relative to an untransformed cell with a similar genetic background, an increased level of β-tocotrienols.

In a preferred embodiment, DNA constructs of the present invention comprising nucleic acid molecules encoding a polypeptide comprising an amino acid sequence selected from the group consisting of SEQ ID NOs: 20–41 and 53–68, provide in a transformed cell, relative to an untransformed cell with a similar genetic background, an increased level of δ-tocotrienols.

In a preferred embodiment, DNA constructs of the present invention comprising nucleic acid molecules encoding polypeptides of the present invention provide in a transformed cell, relative to an untransformed cell with a similar genetic background, an increased level of plastoquinols.

Any of a variety of methods may be used to obtain one or more of the above-described nucleic acid molecules (Zamechik et al., *Proc. Natl. Acad. Sci. (U.S.A.)*, 83:4143–4146, 1986); Goodchild et al., *Proc. Natl. Acad. Sci. (U.S.A.)*, 85:5507–5511, 1988); Wickstrom et al., *Proc. Natl. Acad. Sci. (U.S.A.)*, 85:1028–1032, 1988); Holt et al., *Molec. Cell. Biol.*, 8:963–973, 1988); Gerwirtz et al., *Science*, 242: 1303–1306, 1988); Anfossi et al., *Proc. Natl. Acad. Sci. (U.S.A.)*, 86:3379–3383, 1989); Becker et al., *EMBO J.*, 8:3685–3691, 1989). Automated nucleic acid synthesizers may be employed for this purpose. In lieu of such synthesis, the disclosed nucleic acid molecules may be used to define a pair of primers that can be used with the polymerase chain reaction (Mullis et al., *Cold Spring Harbor Symp. Quant. Biol.*, 51:263–273, 1986); Erlich et al., European Patent 50,424; European Patent 84,796; European Patent 258,017; European Patent 237,362; Mullis, European Patent 201,184; Mullis et al., U.S. Pat. No. 4,683,202; Erlich, U.S. Pat. No. 4,582,788; and Saiki et al., U.S. Pat. No. 4,683,194) to amplify and obtain any desired nucleic acid molecule or fragment.

Promoter sequences and other genetic elements, including but not limited to transcriptional regulatory flanking sequences, associated with one or more of the disclosed nucleic acid sequences can also be obtained using the disclosed nucleic acid sequence provided herein. In one embodiment, such sequences are obtained by incubating nucleic acid molecules of the present invention with members of genomic libraries and recovering clones that hybridize to such nucleic acid molecules thereof. In a second embodiment, methods of "chromosome walking," or inverse PCR may be used to obtain such sequences (Frohman et al., *Proc. Natl. Acad. Sci. (U.S.A.)*, 85:8998–9002, 1988); Ohara et al., *Proc. Nati. Acad. Sci. (U.S.A.)*, 86:5673–5677, 1989); Pang et al., *Biotechniques*, 22:1046–1048, 1977); Huang et al., *Methods Mol. Biol.*, 69:89–96, 1997); Huang et al., *Method Mol. Biol.*, 67:287–294, 1997); Benkel et al., *Genet. Anal.*, 13:123–127, 1996); Hartl et al., *Methods Mol. Biol.*, 58:293–301, 1996). The term "chromosome walking" means a process of extending a genetic map by successive hybridization steps.

Another subset of the nucleic acid molecules of the invention includes nucleic acid molecules that are markers. The markers can be used in a number of conventional ways in the field of molecular genetics. Such markers include nucleic acid molecules homologous or complementary to SEQ ID NOs: 1, 5, or 17 and fragments thereof that can act as markers and other nucleic acid molecules of the present invention that can act as markers.

It is understood that one or more of the nucleic acid molecules of the invention may be used as molecular markers. It is also understood that one or more of the protein molecules of the invention may be used as molecular markers.

In an aspect of the present invention, one or more of the nucleic molecules of the present invention are used to determine the level of expression (i.e., the concentration of mRNA in a sample, etc.) in a plant (preferably canola, corn, *Brassica campestris*, oilseed rape, rapeseed, soybean, crambe, mustard, castor bean, peanut, sesame, cottonseed, linseed, safflower, oil palm, flax or sunflower) or pattern (i.e., the kinetics of expression, rate of decomposition, stability profile, etc.) of the expression of a protein encoded in part or whole by one or more of the nucleic acid molecule of the present invention A number of methods can be used to compare the expression between two or more samples of cells or tissue. These methods include hybridization assays, such as northerns, RNAse protection assays, and in situ hybridization. Alternatively, the methods include PCR-type assays. In a preferred method, the expression response is compared by hybridizing nucleic acids from the two or more samples to an array of nucleic acids. The array contains a plurality of suspected sequences known or suspected of being present in the cells or tissue of the samples.

Having now generally described the invention, the same will be more readily understood through reference to the following examples that are provided by way of illustration, and are not intended to be limiting of the present invention, unless specified.

EXAMPLE 1

This example sets forth the identification and characterization of the *Arabidopsis thaliana* LTT1 mutant. Mutagenized ($M_2$) seeds of *Arabidopsis thaliana*, ecotypes Columbia and Lansberg were obtained both by purchase from Lehle Seeds (Round Rock, Tex., U.S.A.) and by standard ethane methyl sulfonate (EMS) (a.k.a. Ethyl methanesulfonate, Sigma-Aldrich, St. Louis, Mo., U.S.A.) mutagenesis methodology. The $M_2$ plants were grown from the $M_2$ seeds in greenhouse conditions with one plant per 2.5 inch pot. The resulting $M_3$ seeds were collected from individual $M_2$ plants and analyzed for tocopherol levels.

Approximately 10,000 $M_3$ seeds of *Arabidopsis thaliana*, ecotypes Landsberg and Columbia, were analyzed for individual tocopherol levels using the following procedure. Five milligrams of seeds from individual plants were ground to a fine powder and then extracted with 200 microliter (µl) of a 1% pyrogallol (Sigma-Aldrich, St. Louis, Mo., U.S.A.) in ethanol solution. This mixture was allowed to incubate at 4° C. for 60 minutes prior to filtering (Whatman UniFilter® plate, PVDF 0.45 µm, Whatman, Scarborough, Me., U.S.A.). The filtrate was then analyzed for tocopherol content and composition by fractionating the mixture using a Waters model 2790 high performance liquid chromatography (HPLC) system (Waters Corporation, Milford, Mass., U.S.A.) equipped with a 4.6×250 mm Zorbax silica reversed phase column (Agilent Technologies, U.S.A.). Tocopherol and metabolites were detected using a Waters model 474 fluorescence detector with excitation set at 290 nanometer (nm), emittance at 336 nm, and bandpass and slits set at 30 nm. The elution program used an isocratic flow of 10% methyl-tert-butyl-ether (MTBE) (Sigma-Aldrich, St. Louis, Mo., U.S.A.) in hexane at a rate of 1.5 milliliter (ml)/minute for 12 minutes. Prior to each injection, a clean up run of 75% MTBE in hexane was performed for 3 minutes, followed by a re-equilibration step of 10% MTBE in hexane for 3 minutes.

Individual plant lines with total tocopherol levels lower than wild type were reanalyzed in the next generation (M4) to confirm their heritability. One Arabidopsis LTT mutant line was identified and designated LTT1. The LTT1 mutant line produced 127 ng total tocopherol/mg seed versus 438 nanogram (ng) total tocopherol/milligram (mg) seed observed in the non-mutagenized Arabidopsis wild type control. This equates to about a 75% reduction in total seed tocopherol levels.

EXAMPLE 2

This example sets forth the identification and sequencing of the mutant LTT1 gene in the *Arabidopsis thaliana* low total tocopherol mutants. The mutant LT71 gene was mapped between markers T32M21_29601 and T32M21_66646 on chromosome V. This region contains seven open reading frames. This entire 37 kilobase (kb) region was sequenced, using polymerase chain reaction (PCR) techniques well known in the art, from the LTT1 mutant line described in EXAMPLE 1 and compared to the wild type nucleic acid sequence for this region. Analysis of this region in the LTT1 mutant line revealed that one of the open reading frames, T32M21_90 (SEQ ID NO: 3) contained a point mutation resulting in the conversion of the amino acid tryptophan to a stop codon at amino acid position 227, relative to the ATG (SEQ ID NO: 4). The corresponding wild type polynucleic acid sequence for LTT1 was SEQ ID NO: 1 which encodes the LTT1 polypeptide SEQ ID NO: 2.

EXAMPLE 3

This example describes the identification of the LTT1-r gene from *Arabidopsis thaliana*. The LTT1-r polypeptide sequence (SEQ ID NO: 6) (NCBI General Identifier gi: 15237702) was identified in the NCBI database by a BLAST [blastp] and BLAST[PSI] alignment searches (NCBI) using the LTT1 polypeptide sequence (SEQ ID NO: 2) (gi: 15238184) as the query sequence. Like the LTT1 polypeptide (SEQ ID NO: 2), the LTT1-r polypeptide (SEQ ID NO: 6) also contains six transmembrane domains and a chloroplast target peptide and shares 38% identity with LTT1.

EXAMPLE 4

Figure 2:
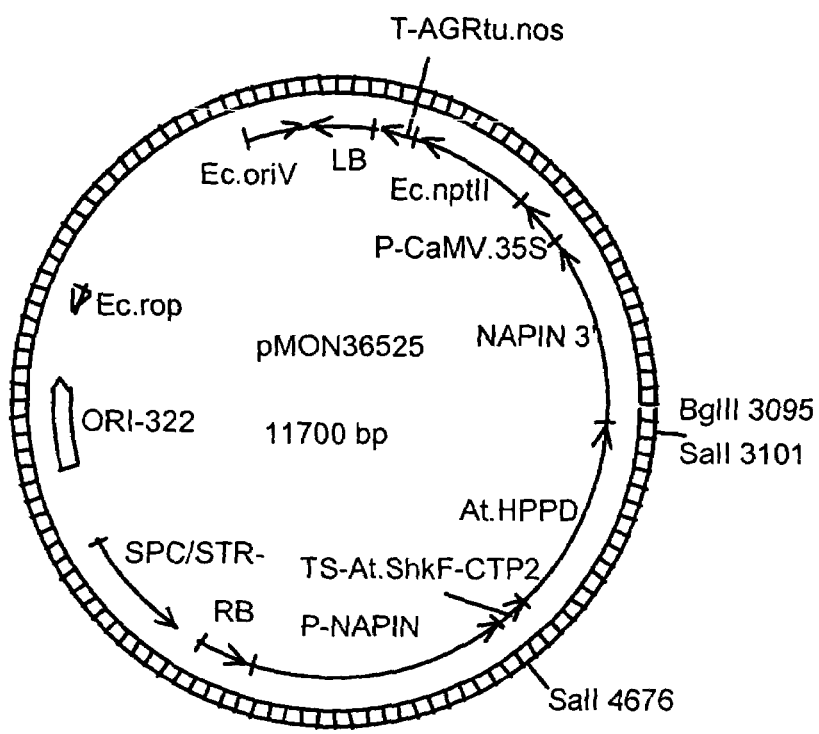
FIG. 2 illustrates the plasmid map of pMON36525.
Figure 3:
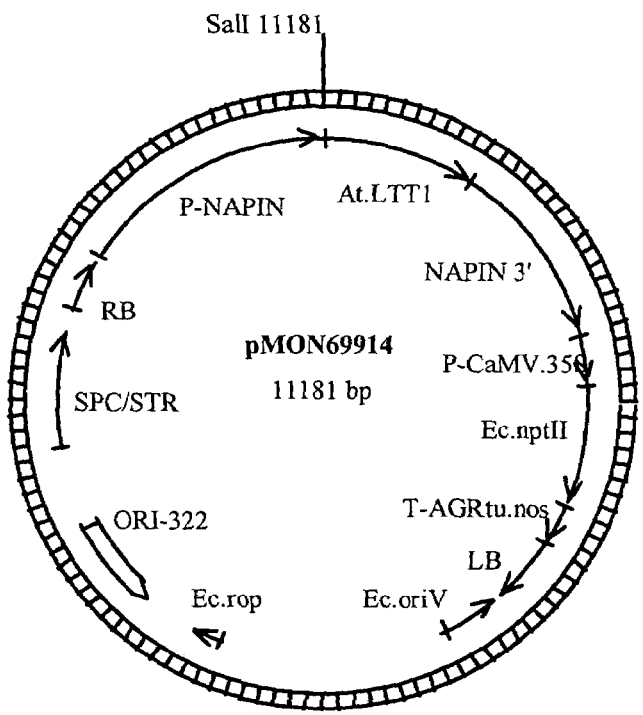
FIG. 3 illustrates the plasmid map of pMON69914.

This example sets forth the transformation and expression of a wild type Arabidopsis LTT1 gene in *Arabidopsis thialiana*. The LTT1 (SEQ ID NO: 1) full-length cDNA was excised from an EST clone, CPR208415, with SalI and BamHI restriction enzymes and operably linked to the napin promoter and napin 3' termination sequences at SalI and BglII restriction sites in sense orientation with respect to the napin promoter in pMON36525 (FIG. 2) to generate a recombinant binary vector pMON69914 (FIG. 3). The sequence of the LTT1 (SEQ ID NO: 1) cDNA was confirmed by sequencing with napin 5'-sense (SEQ ID NO: 7) and napin 3'-antisense (SEQ ID NO: 8) nucleic acid primers using standard sequencing methodology.

The plant binary vector pMON69914 (FIG. 3) was used in *Arabidopsis thaliana* plant transformation to direct the expression of the LLT1 (SEQ ID NO: 1) in the embryo. The binary vector was transformed into ABI strain Agrobacterium cells by electroporation (Bio-Rad electroprotocol manual, Dower et al., *Nucleic Acids Res.* 16:6127–6145, 1988). Transgenic *Arabidopsis thaliana* plants were obtained by Agrobacterinum-mediated transformation as described by Valverkens et al., *Proc. Nat. Acad. Sci.* 85:5536–5540,1988), Bent et al., *Science*, 265:1856–1860, 1994), and Bechtold et al., *C. R. Acad. Sci., Life Sciences* 316:1194–1199, 1993). Transgenic plants were selected by sprinkling the transformed $T_1$ seeds onto the selection plates containing MS basal salts (4.3 g/L), Gamborg'a B-5, 500X (2.0 g/L), sucrose (10 g/L), MES (0.5 g/L), phytagar (8 g/L), carbenicillin (250 mg/L), cefotaxime (100 mg/L), plant preservation medium (2 ml/L), and kanamycin (60 mg/L) and then vernalizing them at 4° C. in the absence of light for 2–4 days. The seeds were transferred to 23° C., and 16/8 hours light/dark cycle for 5–10 days until seedlings emerge. After one set of true leaves were formed on the kanamycin resistant seedlings, they were transferred to soil and grown to maturity. The $T_2$ seed harvested from the transformants was analyzed for tocopherol content. The plant binary vector pMON69914 (FIG. 3) was also transformed into the LTT1 mutant lines of Arabidopsis thaliana by the same plant transformation method described above.

EXAMPLE 5

This example sets forth the results of expressing a wild type Arabidopsis LTT1 gene (SEQ ID NO: 1) in wild type or LTT1 mutant Arabidopsis plants. A binary vector pMON69914 (FIG. 3) carrying a P-napin::Arabidopsis LTT1::napin 3' expression cassette was transformed into wild type Columbia Arabidopsis and LTT1 mutant Arabidopsis lines as described in Example 4, and seeds from the transgenic Arabidopsis lines were analyzed for seed total tocopherol levels. As shown in Table 2, the over expression of Arabidopsis LTT1 (SEQ ID NO: 1) in transgenic wild type Arabidopsis increases seed total tocopherol levels in all lines tested. In one case (Col-0 LTT1-1), the tocopherol level was significantly greater than the empty vector control as determined using the Tukey-Kramer HSD statistical test set at a 95% confidence level (alpha=0.05) (JMP statistical software, SAS Institute, Cary, N.C., U.S.A.). Wild type empty vector control seed produced a mean total tocopherol level of 448.3 ng/mg seed. The transgenic Arabidopsis LTT1 mutant lines carrying the pnapin::Arabidopsis LTT1::napin 3' expression cassette produced mean seed total tocopherol levels that ranged from 454.0 to 477.0 ng/mg.

TABLE 2

Total seed tocopherol levels in T3 Arabidopsis seed lines expressing the LTT1 (SEQ ID NO: 1) gene.

| Line | N | Mean Total Seed Tocopherol level (ng/mg) | Std Error | | |
|---|---|---|---|---|---|
| Col-0 LTT1-1 | 12 | 477.0 | 5.4 | A | |
| Col-0 LTT1-2 | 10 | 453.0 | 5.9 | | B |
| Col-0 LTT1-3 | 12 | 461.1 | 5.4 | A | B |
| Col-0 LTT1-4 | 12 | 469.0 | 5.4 | A | B |
| Col-0 LTT1-5 | 8 | 454.0 | 6.6 | A | B |
| Empty vector control | 7 | 448.3 | 7.0 | | B |

Lines not designated by same letter (either A or B) are significantly different from one another.

Comparisons for all Pairwise Combinations Using Tukey-Kramer HSD, Alpha=0.05

Over expression of the LTT1 gene (SEQ ID NO: 1) in the LTT1 mutant line restored wild type levels of seed tocopherols (Table 3). Both the LTT1 mutant line and the LTT1 mutant line transformed with an empty vector control produced tocopherol levels of approximately 90 ng/mg. When expressed in the mutant LTT1 background, the functional wild type LTT1 lines produced seed total tocopherol levels of approximately 365 ng/mg. The tocopherol levels observed in the wild type LTT1 (SEQ ID NO: 1) line was significantly greater than that observed in both the empty vector and LTT1 mutant lines as determined using the Tukey-Kramer HSD test set at a 95% confidence level (alpha=0.05) (JMP statistical software, SAS Institute, Cary, N.C., U.S.A.).

TABLE 3

Total seed tocopherol levels in mutant LTT1 Arabidopsis seed lines expressing the LTT1 (SEQ ID NO: 1) gene

| Line | N | Mean Total Seed Tocopherol level (ng/mg) | Std Dev | | |
|---|---|---|---|---|---|
| LTT1 (SEQ ID NO: 1) | 20 | 364.5 | 38.7 | A | |
| Empty vector control | 4 | 86.6 | 1.2 | | B |
| LTT1 Mutant | 2 | 91.2 | 6.5 | | B |

Lines not designated by same letter (either A or B) are significantly different from one another.

Comparisons for all Pairs Using Tukey-Kramer HSD, Alpha=0.05.

EXAMPLE 6

Figure 8:
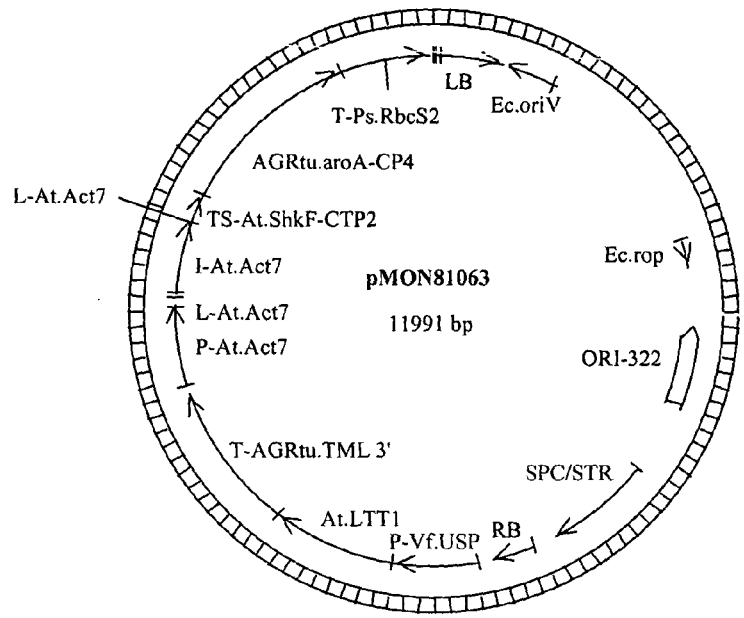
FIG. 8 illustrates the plasmid map of pMON81063.
Figure 9:
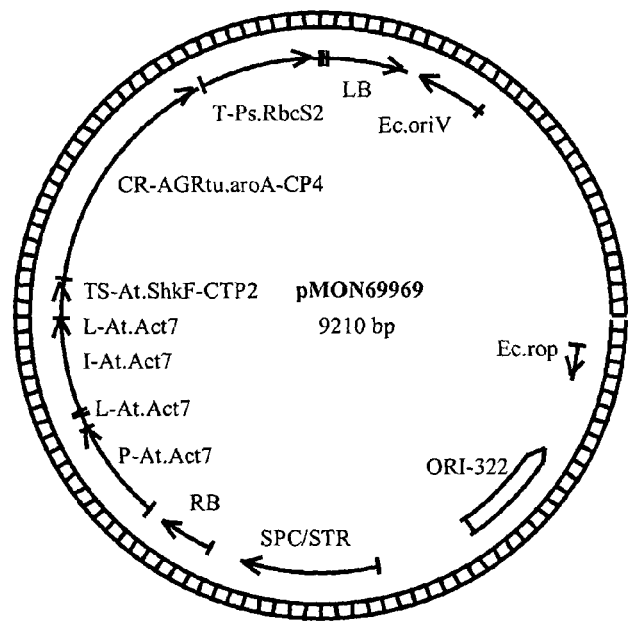
FIG. 9 illustrates the plasmid map of pMON69969

This example sets forth the transformation and expression of a wild type Arabidopsis LTT1 gene in soybean plants to increase total seed tocopherol levels. To direct the expression of Arabidopsis LTT1gene (SEQ ID NO: 1) in soybean seed, a binary construct with LTT1 operably linked to a seed-specific USP88 (seed protein from Vicia faba) promoter and operably linked to a 3' TML termination sequence is prepared (pMON81063) (FIG. 8). Other soybean seed-specific promoters such as 7Sα, 7Sα' and arcelin-5 can also be used. Other termination sequences such as pea rubisco small subunit 3' (T-Ps.RbcS) and arcelin 3' can also be used. Vector construction for the LTT1 construct is performed using standard cloning techniques well established in the art and described in lab manuals such as Sambrook et al., 2001. The control vector (pMON69969) (FIG. 9) contains a T-DNA with a selectable marker cassette. Finally, an assortment of transformation strategies, such as co-transformation and re-transformation, all well known in the art, can be employed to direct these genes in an assortment of combinations into the soybean plant.

Transgenic soybean seeds generated with the LTT1 constructs are analyzed for total seed tocopherol and tocotrienol levels as described in Example 1. Total seed tocopherol and tocotrienol levels are significantly higher in the LTT1 (SEQ ID NO: 1) transformed plant lines than those of the empty vector control lines as determined using statistical tests such as the Tukey-Kramer HSD test set at a 95% confidence level (alpha=0.05) (JMP statistical software, SAS Institute, Cary, N.C., U.S.A.).

EXAMPLE 7

Figure 4:
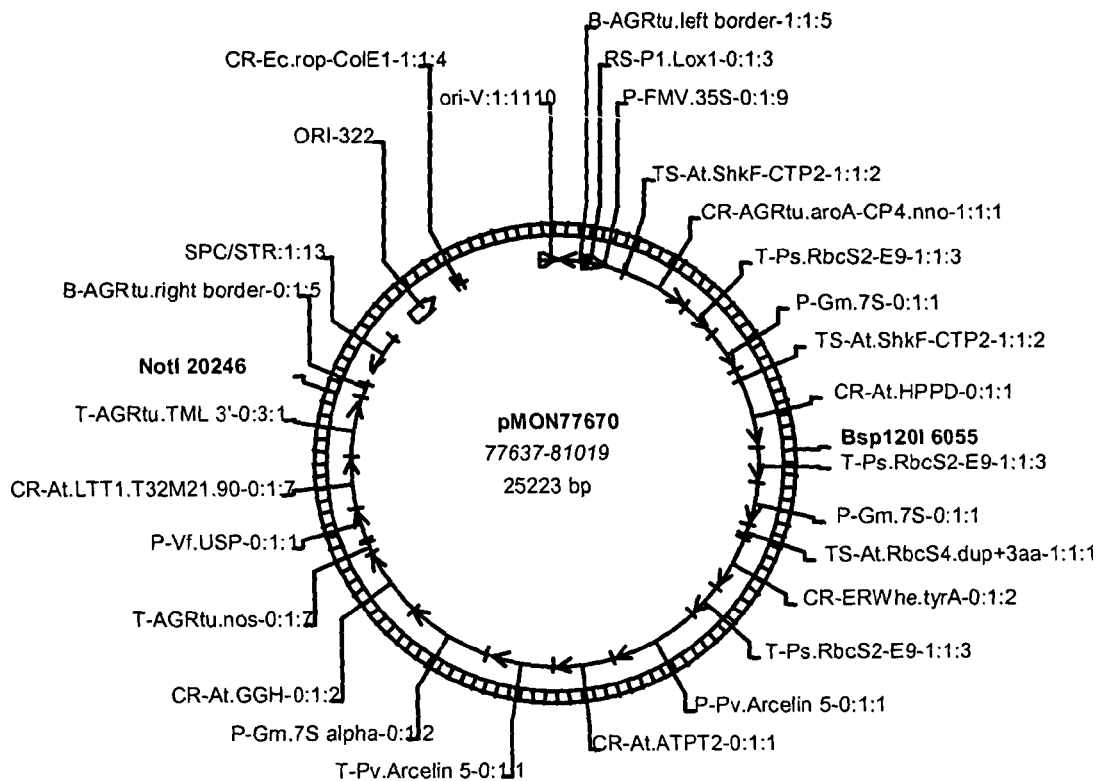
FIG. 4 illustrates the plasmid map of pMON77670.

This example sets forth the transformation and expression of a wild type Arabidopsis LTT1 gene (SEQ ID NO: 1) in combination with other tocopherol pathway genes in soybean plants to increase total seed tocopherol levels. To demonstrate the in planta performance of the LTT1 nucleic acid sequence with other tocopherol pathway genes, a soybean binary vector (pMON77670) (FIG. 4) containing the LTT1 gene (SEQ ID NO: 1) driven by a USP promoter and a 3' TML termination sequence is prepared to direct the expression of LTT1 in soybean seeds, an Arabidopsis geranylgeranyl hydrogenase ($GGH_{At}$) (SEQ ID NO: 13), an Arabidopsis homogentisate phytyltransferase (HPTAt) (SEQ ID NO: 15), an Arabidopsis p-hydroxyphenylpyruvate dioxygenase ($HPPD_{At}$)(SEQ ID NO: 14) and an Erwinia herbicola prephenate dehydrogenase ($tyrA_{Eh}$)(SEQ ID NO: 16). The specific nucleic acid sequences selected and used herein are examples only. Other GGH, HPT, HPPD and TyrA sequences are known and can be used. The Synechocystis LTT1 (SEQ ID NO: 17) or other nucleic acids (N-terminally fused to CTP, if needed) of the present invention could be substituted for SEQ ID NO: 1.

Figure 5:
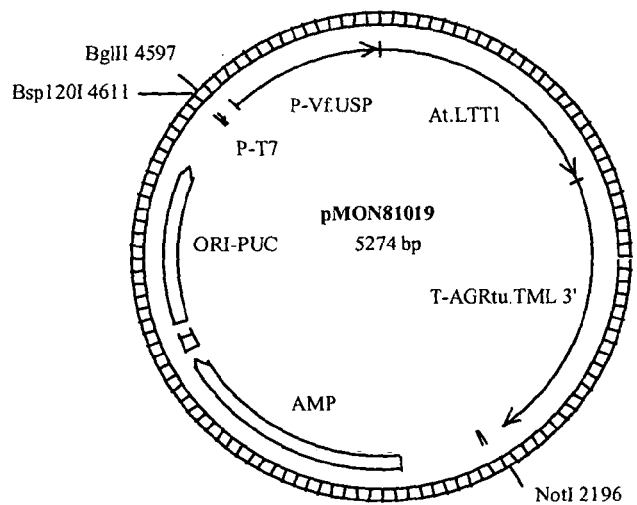
FIG. 5 illustrates the plasmid map of pMON81019.
Figure 6:
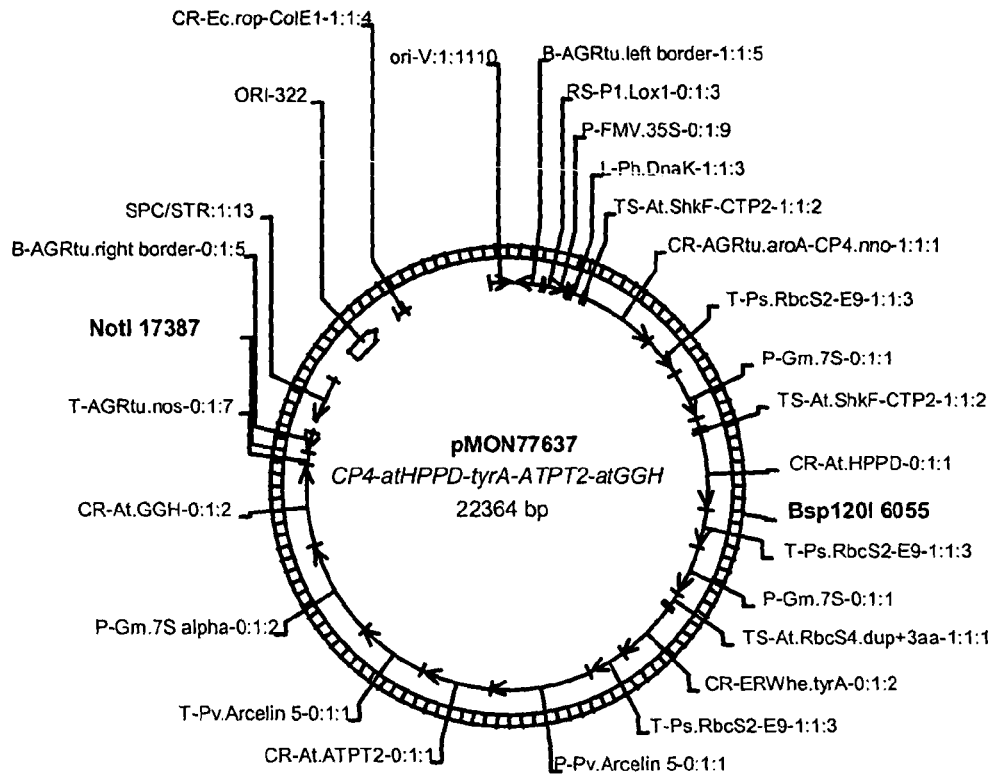
FIG. 6 illustrates the plasmid map of pMON77637.

Construction of the 5-gene vector (pMON77670) (FIG. 4), as well as the control vector (pMON77637), is performed using standard cloning techniques well established in the art (Sambrook et al., 2001). The LTT1 gene construct (pMON81019) (FIG. 5) is digested with Bsp120I and NotI restriction enzymes and the resulting nucleic acid fragment is inserted into the NotI site of the 4-gene vector (pMON77637) (FIG. 6) containing expression cassettes for a 7Salpha promoter::(GGHAt)::E9 3'-termination sequence, an arcelin-5 promoter::(HPTAt)::arcelin-3'sequence, a 7Salpha' promoter::CTP1::HPPDAt::E9-3' termination sequence, and a 7Salpha' promoter::CTP2::TyrAEh::E9-3' termination sequence. The 4-gene vector pMON77637 serves as the control vector for measuring the effects of LTT1 on seed total tocopherol levels.

Tocopherol pathway genes that are useful for optimal tocopherol biosynthesis, such as GGH, HPPD, tyrA, GGPPS, HPT, DXS, DXR GMT, TMT2, and LTT1 can be prepared by codon optimization to optimally express in soybean or any other commercially important transgenic crop to further boost the tocopherol production in oil seeds. For codon opimization references, see, e.g., GenBank, National Center Biotechnology Information, USA; see U.S. Pat. No. 5,689,052), and FindPatterns (Genetics Computer Group, Inc., USA), which is a database of 20 known 5–6 nucleotide long motifs that are known to be associated with mRNA instability (i.e., premature polyadenylation signals).

Finally, an assortment of transformation strategies, such as co-transformation and re-transformation, all well known in the art, can be employed to direct these genes in an assortment of combinations into the soybean plant.

Total seed tocopherol and tocotrienol levels are significantly higher in plant lines transformed with the aforementioned tocopherol pathway genes than those of the LTT1 minus control lines as determined using statistical tests such as the Tukey-Kramer HSD test set at a 95% confidence level (alpha=0.05) (JMP statistical software, SAS Institute, Cary, N.C., U.S.A.).

EXAMPLE 8

Figure 7:
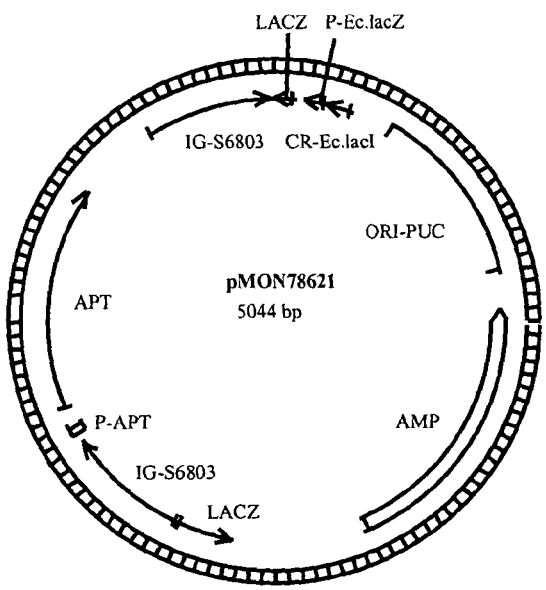
FIG. 7 illustrates the plasmid map of pMON78621.

This example sets forth the identification and characterization of a Synechocystis LTT1 homolog. A BLASTP search (National Center for Biotechnology Information, NIH, U.S.A.) of a Synechocystis PCC6803 genomic nucleic acid sequence database using the Arabidopsis LTT1 nucleotide sequence (SEQ ID: 1) as the query sequence identified a nucleic acid sequence, slr1652 (SEQ ID NO: 17), as an Arabidopsis LTT1 homolog (E value of $5 \times 10^{-11}$, with 29% identity over a 237 residue stretch). A Synechocystis mutant cyanobacteria colony was created by inactivating the slr1652 gene to show that slr1652 functions in tocopherol synthesis and accumulation. Four nucleic acid PCR primer pairs, designated SEQ ID NO: 9, SEQ ID NO: 10, SEQ ID NO: 11, and SEQ ID NO: 12, were designed based on the Synechocystis genomic nucleic acid sequence including and flanking the slr1652 gene. Using standard PCR amplification protocols (Sambrook et al., 2001) and Synechocystis PCC6803 genomic DNA and SEQ ID NO: 9 and SEQ ID NO: 10, and separately, SEQ ID NO: 11 and SEQ ID NO: 12, nucleic acid primer sequences, two PCR products of approximately 0.45 kb, corresponding to sequences surrounding the upstream and downstream regions of the slr1652 nucleic acid sequence, were produced. The PCR products were successively cloned as NotI/BamHI and BamHI/XhoI restriction fragments into a pBluescriptII KS(+) plasmid (Stratagene, Calif., U.S.A.), to recreate an approximately 0.9 kb region encompassing the slr1652 gene, with a unique BamHI site marking the deletion of approximately 236 bp within the slr1652 coding region. A 1.25 kb kanamycin resistance cassette from a pKISS plasmid (Pharmacia Corporation, St. Louis, Mo., U.S.A.) was cloned as an Ecl136II restriction fragment into the slr1652 BamHI site after blunting with T4 DNA polymerase. Plasmid pMON78621 (FIG. 7) with the kanamycin cassette oriented in the same direction as the internally truncated slr1652 gene was obtained and confirmed by nucleic acid sequencing.

Chromosomal knock-out mutants of the slr1652 gene were obtained by the transformation of pMON78621 into Synechocystis PCC6803 and selection of transconjugants on medium supplemented with 5 mg/L kanamycin, as described in (Williams, *Methods Enzymology,* 167:766–778 (1988). The medium for the growth of cells was BG-11 (Sigma-Aldrich Inc., St. Louis, Mo., U.S.A.), supplemented with 5 mM TES (N-[Tris(hyrdoxymethyl)methyl]-2-aminoethanesulfonic acid) (Sigma-Aldrich, St. Louis, Mo., U.S.A.) pH 8.0. Kanamycin-resistant transconjugants were sub-cultured by re-streaking on kanamycin containing medium 4–5 times, and two single colony isolates were established and designated as strains 1652-KO-1 and 1652-KO-2. When partially purified genomic DNA from these two strains, as well as the wild type parent were used as templates for PCR using the primers SEQ ID NO: 9 and SEQ ID NO: 12, an amplified product of ~1.1 kb was produced from the wild type DNA. Strains 1652-KO-1 and 1652-KO-2 yielded a product of ~2.1 kb and none of the ~1.1 kb product. PCR analysis clearly showed that the slr1652 genomic region had been faithfully deleted by homologous recombination in both mutants, and wild type copies of the gene were no longer present. The growth rate of both mutants was not significantly different from the wild type parent, showing that slr1652 function is not essential for Synechocystis growth and development.

Liquid cultures of wild type Synechocystis PCC6803 and both mutants were grown under light in BG-11 medium+5 mM TES (+5 mg/lit kanamycin for the mutants) with shaking at 30° C. to a final density of ~2.0–2.5 as measured by absorbance at 730 nm (an absorbance of 1.0 correspond to a cell density of ~$4 \times 10^8$ cells/mL). Cells corresponding to 10.0 $A_{730}$ units were harvested, extracted and analyzed for their tocopherol content as described in EXAMPLE 1. The wild type and 1652-KO-1 and 1652-KO-2 strains had a total tocopherol content of 80.5, 42.0 and 21.0 ng/$A_{730}$ units, respectively (n=2). The 50–75% reduction of total tocopherol in the slr1652 knock-out mutants is similar to the phenotype seen in the Arabidopsis LTT1 mutants described in EXAMPLE 2 demonstrating that LTT1 and slr1652 are homologs that perform the same function in plants and cyanobacteria.

EXAMPLE 9

This example sets forth the transformation and expression of an LTT1 (SEQ ID NO: 1) or LTT1-r (SEQ ID NO: 5) gene in combination with a Synechocystis chlorophyllase gene (SEQ ID NO: 18 or SEQ ID NO: 19) to increase total seed tocopherol levels in Synechosystis.

Pfam analysis (Pfam version 9.0 (May 2003), Washington University, St. Louis, Mo., USA; Pfam is a large collection of multiple sequence alignments and hidden Markov models covering many common protein families) of LTT1 revealed that LTT1 and LTT1-r are members of the DUF56 gene family of putative integral membrane proteins. While the function of the DUF56 family is unknown, members of the family include a dolichol kinase (EC:2.7.1.108) termed Sec59, and a phosphatidate cytidylyltransferase (EC: 2.7.7.41), termed CDS, also known as CDP-diacylglycerol synthase, both isolated from yeast.

CDS is the enzyme that catalyzes the synthesis of CDP-diacylglycerol from CTP and phosphatidate (PA). CDS is a membrane-bound enzyme, and contains the N-terminal consensus sequence S-x-[LIVMF]-K-R-x (4)-K-D-x-[GSA]-x (2)-[LIF]-[PG]-x-H-G-G[LIVMF]-x-D-R-[LIVMFT]-D (SeqLab®, GCG Wisconsin Package, 2001–2003 Accelrys Inc.). LTT1 and LTT1-r are not cytidyltransferases since they lack the CDS consensus sequence.

Based on multiple sequence alignments as well as an examination of key structural and phylogenic motifs, e.g., substrate and consensus recognition sequences, LTT1 and LTT1-r are not functional homologs of Sec59, rhodopsin or CDS in Arabidopsis. LTT1 is a novel enzyme of the DUF56 gene family. The likely substrate for LTT1 and LTT1-r is phytol, a molecule that is structurally similar to retinol and dolichol. The likely primary function of LTT1 is to phosphorylate phytol. This function is consistent with the low tocopherol phenotype observed in the Arabidopsis and Synechocystis LTT1 mutant lines based on a model in which a portion of the phytoldiphosphate used for tocopherol biosynthesis is provided by phytol liberated from metabolized chlorophyll rather than directly from geranylgeranyldiphosphate reduction to phytoldiphosphate. This position is supported by the fact that there is an inverse relationship between chlorophyll degradation and tocopherol synthesis in, for example, canola; as the concentration of chlorophyll goes down the concentration of tocopherol increases.

To increase phytoldiphosphate availability in a seed, the LTT1 gene (SEQ ID NO: 1) from *A. thaliana* or its homolog from Synechocystis (SEQ ID NO: 17) (which is operably linked 3' to a chloroplast target peptide such as the Arabidopsis ribulose bisphosphate carboxylase small subunit (CTP1)), are operably linked to a seed-specific promoter, such as the 7S alpha promoter or the napin promoter, which is in turn operably linked to a 3' sequence such as the Nos 3' sequence, the E9 3' sequence, or the napin 3' sequence. This expression cassette is combined with a seed-specific expression cassette for a chlorophyllase, such as the Arabidopsis chlorophyllase 1 (gi:30912637) (SEQ ID NO: 18), or the Arabidopsis chlorophyllase 2 (gi:30912739, gi:6729677) (SEQ ID NO: 19). The chlorophyllase is expressed using the 7S alpha' promoter, the USP88 promoter, or the napin promoter and an appropriate 3' sequence such as the TML 3' sequence, or the E9 3' sequence. These two expression cassettes are transformed into a plant binary vector (e.g., a soy binary vector, see FIG. 3) and further transformed via Agrobacterium mediated transformation into soybean. Transgenic seed are analyzed for changes in tocopherol content and composition as described in Example 1.

Total seed tocopherol and tocotrienol levels are significantly higher in plant lines transformed with the aforementioned tocopherol pathway genes than those of the empty vector control lines as determined using statistical tests such as the Tukey-Kramer HSD test set at a 95% confidence level (alpha=0.05) (JMP statistical software, SAS Institute, Cary, N.C., U.S.A.).

EXAMPLE 10

This example describes an assay which can be used to determine the amount of phytol in tissue extracts. This method determines phytol levels in liquid extracts of various biological materials, such as plants, by use of gas chromatography coupled with a time of flight mass spectrometer. The quantification was accomplished using an external standard curve constructed by using a unique mass that represents phytol and using the retention time of the phytol eluting from the gas chromatograph. The identity of the phytol was further confirmed by comparing the mass spectra at this retention time with the reference standard. The detection limit of the instrument was 0.05 nanograms per microliter. The method detection limit depends on the extract solution and the amount of noise created by the extract sample itself. Thus, method detection limits were determined on a sample-by-sample basis. The analysis time was less than 4 minutes per sample.

The gas chromatograph was an Agilent 6890 chromatograph (Agilent Technologies, U.S.A.). The gas chromatograph column was a DB5. The dimensions of the column were 10 meters in length, with an internal diameter of 180 microns, and a film thickness of 0.18. The carrier gas was helium and flowed through the column at a rate of 1.5 mL/minute. A constant flow was maintained throughout the programmed temperature ramp of the chromatograph. The initial temperature of the column was 130° C. with no hold time. The temperature was increased at a rate of 30° C. per minute until the column reaches 270° C. and was held at 270° C. for 2 minutes. One microliter of extract was injected into the injection port of the gas chromatograph. The mode of injection was splitless. The temperature of the injector was 250° C.

The mass of the phytol molecules was determined using a Pegasus® III (LECO Corporation, U.S.A.) time of flight mass spectrometer (TOFMS). The outlet of the Agilent gas chromatograph column was placed through a heated transfer line (250° C.) into the TOFMS. The instrument was operated in electron impact mode with ionzation energy of 70 electron volts. The source was operated at a temperature of 200° C. and the detector voltage was 1600 volts. The mass to charge range was set to be between 45 and 305 units.

The standard curve was constructed using commercial standards (Sigma-Aldrich, St. Louis, Mo., U.S.A.). The standard curve was an external curve and ranged in concentration from 7 nanograms per microliter to 0.14 nanograms per microliter. The R squared value for the curve was 0.9993. The mass to charge used for quantification was 71. The retention time was 178 seconds for the cis isomer and 183 seconds for the trans isomer.

EXAMPLE 11

This example illustrates the increase in phytol levels resulting from inactivation of the *Arabidopsis thaliana* LTT1 (SEQ ID NO: 1) gene or the Synechocystis LTT1 (SEQ ID NO: 17) gene. As shown in FIG. 1, Geranylgeranioldiphosphate can serve as a substrate for chlorophyll synthase to form geranylated chlorophyll (Grassl et al., Planta 213:620–628, 2001). Geranylated chlorophyll is then reduced to phytylated chlorophyll in a reaction catalyzed by geranylgeranioldiphosphate reductase (chlP). Phytylated chlorophyll accounts for the majority of chlorophyll in plants. When phytylated chlorophyll is degraded by chlorophyllase, free phytol is released. As chlorophyll degradation increases post anthesis, the level of phytol increases and the phytol is activated by phytol kinase (LTT1) to produce phytyl pyrophosphate (Phytyl-PP), which is a substrate for HPT. The increase in Phytyl-PP substrate leads to an increase in tocopherol production. If the activity of LTT1 is blocked, the result is an increase in cell phytol levels. This effect is illustrated for *Arabidopsis thaliana* LTT1 mutant seed and Synechocystis LTT1 mutant cells in Table 4. These results show that seed phytol levels increase from 0.203 ng/mg to 0.595 ng/mg when *Arabidopsis thaliana* LTT1 (SEQ ID NO: 1) is inactivated. Similarly, when Synechocystis LTT1 (SEQ ID NO: 17) is inactivated, cell phytol levels increase from undetectable levels to 0.482 ng/mg.

TABLE 4

Phytol levels in wild type and mutant *Arabidopsis thaliana* seeds and Synechocystis cells

| Sample ID | N | Phytol Content | Std. Dev. |
| --- | --- | --- | --- |
| *A thaliana* wild type seed | 2 | 101.7 | 9.1 |
| *A thaliana* LTT1 mutant seed | 2 | 297.4 | 34.2 |
| Synechocystis wild type cells | 2 | Not detectable | Not detectable |
| Synechocystis LTT1 mutant cells | 4 | 241.0 | 17.1 |

The phytol content in *Arabidopsis thaliana* is expressed as ng/mg.
The phytol content in Synechocystis cells is expressed as ng per OD unit at 730 nm.

EXAMPLE 12

This example sets forth the transformation and expression of a wild type Arabidopsis LTT1 gene in combination with a chlorophyllase gene and other tocopherol pathway genes in soybean to increase total seed tocopherol levels. As illustrated in EXAMPLE 11, chlorophyll degradation by the chlorophyllase can increase seed phytol levels. When used in combination with LTT1 (SEQ ID NO: 1) and other tocopherol pathway genes, total seed tocopherol levels are increased. To demonstrate the in planta performance of the LTT1 nucleic acid sequence in combination with a chlorophyllase gene and other tocopherol pathway genes, a soybean binary vector (pMON77670) (FIG. 4) containing the LTT1 gene (SEQ ID NO: 1) driven by a USP promoter and a 3' TML termination sequence is prepared to direct the expression of LTT1 in soybean seeds in combination with an Arabidopsis chlorophyllase (SEQ ID NO: 18 or SEQ ID NO: 19), an Arabidopsis geranylgeranyl hydrogenase ($GGH_{At}$) (SEQ ID NO: 13), an Arabidopsis homogentisate phytyltransferase (HPTAt) (SEQ ID NO: 15), an Arabidopsis p-hydroxyphenylpyruvate dioxygenase ($HPPD_{At}$) (SEQ. ID NO: 14) and an *Erwinia herbicola* prephenate dehydrogenase ($tyrA_{Eh}$) (SEQ ID NO: 16). The specific nucleic acid sequences selected and used herein are examples only. Other GGH, HPT, HPPD and tyrA sequences are known and can be used. Similarly, other chlorophyllases can be used, preferably those with native CTPs. The Synechocystis LTT1 (SEQ ID NO: 17) or other nucleic acids (N-terminally fused to CTP, if needed) of the present invention could be substituted for SEQ ID NO: 1.

Construction of the 5-gene vector (pMON77670) (FIG. 4), as well as the control vector (pMON77637), is performed using standard cloning techniques well established in the art (Sambrook et al., 2001). The LTT1 gene construct (pMON81019) (FIG. 5) is digested with Bsp120I and NotI restriction enzymes and the resulting nucleic acid fragment is inserted into the NotI site of the 4-gene vector (pMON77637) (FIG. 6) containing expression cassettes for a 7Salpha promoter::(GGHAt)::E9 3'-termination sequence, an arcelin-5 promoter::(HPTAt)::arcelin-3' sequence, a 7Salpha' promoter::CTP1::HPPDAt::E9-3' termination sequence, and a 7Salpha' promoter::CTP2::TyrAEh::E9-3' termination sequence. A seed specific expression cassette for a plastid targeted chlorophyllase is added to pMON77670 using standard cloning techniques. The 4-gene vector pMON77637 serves as a control vector for measuring the effects of LTT1 on seed total tocopherol levels. Other controls include the 5-gene vector pMON77670 and the vector resulting from the combination of an expression cassette for a plastid targeted chlorophyllase with pMON77670.

As explained in Example 7, tocopherol pathway genes that are useful for optimal tocopherol expression, such as GGH, HPPD, tyrA, GGPPS, HPT, DXS, DXR GMT, TMT2, chlorophyllase, and LTT1 can be prepared by codon optimization to optimally express in soybean or any other commercially important transgenic crop to further boost the tocopherol production in oil seeds.

Co-transformation and re-transformation strategies are used to incorporate 4 to 8 or more tocopherol pathway genes to create transgenic lines expressing multiple tocopherol pathway genes.

Total seed tocopherol and tocotrienol levels are significantly higher in plant lines transformed with chlorophyllase, LTT1 (SEQ ID NO: 1) and the aforementioned tocopherol pathway genes when compared to control lines transformed with a similar vector lacking LTT1 and chlorophyllase as determined using statistical tests such as the Tukey-Kramer HSD test set at a 95% confidence level (alpha=0.05) (JMP statistical software, SAS Institute, Cary, N.C., U.S.A.).

EXAMPLE 13

This example sets forth methods used to analyze LTT1 (SEQ ID NO: 2) and LTT1-r (SEQ ID NO: 6) amino acid sequences from a variety of biological sources in order to identify common structural motifs and sequence homologs contained therein. A variety of cDNA and genomic databases were searched and the data extracted from them analyzed using a suite of sequence search programs available from NCBI (National Center For Biotechnology Information, U.S.A.).

cDNA sequences from soybean (*Glycine max*), *Arabidopsis thaliana*, Corn (*Zea mays*), Leek (*Allium porrum*), wheat (*Triticum aestivum*), and rice (*Oryza sativa*) that were found to be homologous to *Arabidopsis thaliana* LTT1 were identified by searching EST (Expressed Sequence Tags) databases using the TBLASTN program (NCBI) and an E value criterion of $1e^{-5}$ or lower. The identities of these ESTs were confirmed by searching non-redundant databases using BLAST[blastx] (NCBI). ESTs with top blast hits to LTT1 or LTT1-r were extracted from the databases. Full insert sequences of the cDNA clones from the different EST sequences that aligned with the 5' region of LTIT and LTT1-r were determined. The full insert sequence of the cDNA which covered the most 5' region of LTT1 and LTT1-r cDNAs was translated using in-house software and the encoded amino acid sequences were determined (SEQ ID NOs: 37–68).

Rice homologues (SEQ ID NOs: 46–52) of LTT1 (SEQ ID NO: 2) and LTT1-r ((SEQ ID NO: 6) were identified by searching an in-house rice genomic database using BLAST [blastp] (NCBI).

Figure 10:
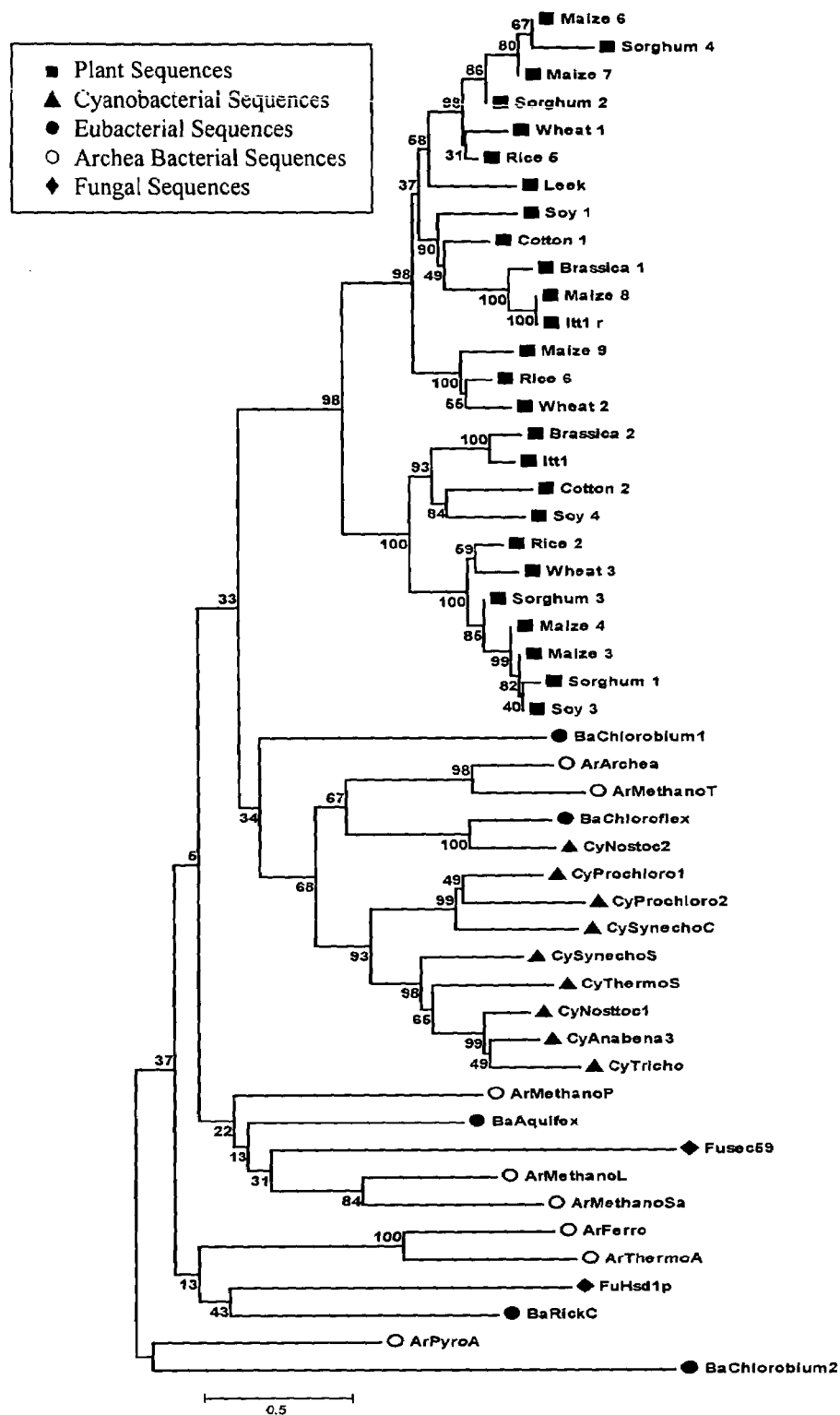
FIG. 10 illustrates a phylogenetic tree.

Cyanobacterial, Eubacterial and Archea amino acid sequences (SEQ ID NOs: 20–35, and 79) were obtained from GenBank® (NCBI). Yeast sequences sec59 (SEQ ID NO: 35) and Hsd1 (SEQ ID NO: 36) were also obtained from GenBank®. To show the relationship among these sequences (SEQ ID NOs: 2, 6, 20–35, 37–68, and 79) a phylogenetic tree was constructed (FIG. 10). Sequences (representing SEQ ID NOs: 2, 6, 20–35, 37–68, and 79) were aligned with one another using the ClustalX multiple sequence alignment software (Jeanmougin et al., *Trends Biochem. Sci.*, 23:403–405, 1998; Thompson et al., *Nucleic Acids Research*, 24:4876–4882,1997). The multiple alignments of the protein sequences were visualized and edited using GeneDoc (Indiana University, Ind., USA; Nicholas et al., *Embnew.News*, 4:14, 1997). Portions of the sequences from yeast sec59 (SEQ ID NO: 35), yeast Hsd1 (SEQ ID NO: 36) and BaProchloro2 (SEQ ID NO: 28), which introduced gaps in the amino acid sequence, were deleted from the multiple alignment. Portions of the N terminal sequence, which did not align or were missing from several sequences, were also removed. The resulting optimized alignment was used to construct a phylogenetic tree using MEGA version 2.1 software (http:H/www.megasoftware.net/(Kumar et al., (2001) MEGA2: Molecular Evolutionary Genetics Analysis software, Arizona State University, Ariz., USA.). The phylogenetic tree was refined using the gamma distance model with pair wise deletion. Bootstrapping was used to test the accuracy of the tree (1000 replications). The phylogenetic tree with the bootstrap values is shown in (FIG. 10). All plant amino acid sequences split into two major groups (clades) exemplified by LTT1 (SEQ ID NO: 2) and LTT1-r (SEQ ID NO: 6). All the cyanobacterial sequences clustered together in a separate lade. Yeast sequences clustered separately in a yet another lade along with the Archea sequences.

From the multiple alignments, five plant phytol kinase motifs (SEQ ID NOs: 74–78) and five cyanobacterial phytol kinase motifs (SEQ ID NOs: 69–73) were used to identify plant and cyanobacterial phytol kinases. Plant motifs 1, 2, 3, 4 and 5 correspond to amino acids 101–122, 131–175, 187–122, 225 to 254 and 267–285 of Arabidopsis LTT1 (SEQ ID NO:2), respectively. Cyanobacterial motifs 1, 2, 3, 4 and 5 correspond to amino acids 43–66, 89–118, 129–144, 156–174, and 203–219, respectively of Synechocystis LTT1 homolog (SEQ ID NO: 79). The specificity of these motifs was tested using a Hidden Markov Model (HMM) that was built using an HMMER software package (Washington University, Mo., USA; Eddy, *Bioinformatics*, 14:755–763, 1998). The non-redundant amino acid database from Genbank (NCBI), which contains more than 1.45 million protein sequences, was searched using HMM and the aforementioned motifs. Plant motifs 1, 4 and 5 (FIGS. 16, 19, and 20, SEQ ID NOs: 74, 77, and 78) are specific to plant phytol kinase sequences at an E value cut off of 1.0. Cyanobacterial motifs 3, 4, and 5 (SEQ ID NOs: 71, 72, and 73) are specific to Cyanobacterial sequences. Cyano motifs 4 and 5 are specific to cyanobacterial phytol kinases at an E value cut off of 1.0 and motif 3 is specific at an E value cutoff of 0.001.

EXAMPLE 14

This example sets forth a Phytol kinase assay. Phytol kinase activity is assayed according to a modified procedure of Inoue et al., *Phytochemistry* 40:377–381, 1995. The pH of the assay mixture is adjusted to pH 7.6, and tritiated phytol (Moravek Biochemicals, Inc., Brea, Calif., U.S.A.) is used in place of farnesol. Ribonucleotide triphosphates such as CTP, ATP, GTP, or TTP are provided as phosphor donors. Additional cations such as Ca++ can be added as required. The enzyme reaction is terminated by the addition of a 2-fold volume of chloroform/methanol (2:1). The assay mixture is centrifuged at 3000×g for 15 min for phase separation. Aliquots of the aqueous and the organic layer are analyzed by HPLC. Samples of approximately 20 microliters are separated on a HP1100 series HPLC system (Hewlett-Packard, Agilent Technologies, U.S.A.) consisting of HP G1329A Auto Sampler, HP G1311A Quaternary Pump, HP G1315A Diode Array Detector, HP G1321A Fluorescence Detector, Packard Radiomatic 500TR Flow Scintillation Analyzer, connected to a 4.6×250 mm (5 µm) Vydac model 201TP54 C18 HPLC column (VYDAC, Hesperia, Calif., U.S.A.). Phytol derivatives are monitored via the radiation emitted by the tritium label. The mobile phase used on the C18 column is a gradient consisting of two solvents. Solvent A is 25 mM $NaHCO_3$ in water, and solvent B is 100% acetonitrile (ACN). The gradient is initiated using a solvent mix of 70/30 A/B and increased to a solvent mix of 0/100 A/B over a 20-minute time period. From 20 to 39 minutes the gradient is maintained at 0/100 A/B. From 39 to 40 minutes the gradient ratio is shifted to 70/30 A/B. Retention times for metabolites are given in Table 5.

TABLE 5

| Retention times (minutes) for metabolites fractionated be a C18 HPLC column | |
|---|---|
| Metabolite | Retention Time (Minutes) |
| Gerranylgeranyl diphosphate | 8.6 |
| Phytyl diphosphate | 10.2 |
| Gerranylgeraniol | 21.1 |
| Phytol | 26.4 |
| Chlorophyll a | 29.5 |
| Chlorophyll b | 31.5 |

EXAMPLE 15

This example sets forth the drought tolerance test that shows that *A. thaliana* plants transformed with a phytol kinase gene (LTT1; SEQ ID NO: 1) are tolerant to drought relative to control plants that were not transformed with the LTT1 gene. The study design for this stress assay is a single factor design, with the LTT1 construct being the factor, where all experimental plants are exposed to a period of drought stress during flowering.

Seeds were stratified in 0.1% phytagar at 4° C. in the dark for 3 days and then sown in flats filled with Metro-Mix® 200 (The Scotts® Company, U.S.A.). Humidity domes were then added to each flat and flats were assigned locations and placed in climate-controlled growth chambers. Plants were grown under a temperature regime of 22° C. day and 20° C. night, with a photoperiod of 16 hours and average light intensity of 170 µmol/m²/s.

After the first true leaves appeared, humidity domes were removed and the plants were sprayed with BASTA™ herbicide in Silwet™ L-77 (OSI Specialties Inc., U.S.A.) at a mixture rate of 8.28 mL BASTA™ containing 18.2% active ingredient and 1 mL Silwet diluted to 20 L. After spraying, plants were put back in the growth chamber for 3 additional days. Flats were watered for 1 hour the week following the BASTA™ treatment. Watering was continued every seven days until the flower bud primordia became apparent (growth stage 5.10), at which time plants were watered for the last time. After the last watering, plants were covered with ARACON® (DuPont Company, U.S.A.) sleeves and placed on growth chamber drying racks.

Beginning ten days after the last watering, plants were examined daily until 4 plants/line had wilted. The proportions of wilted and non-wilted LTT1 transgenic and control plants were compared over each of the next six days and an overall log rank test was performed to compare the two survival curves using S-PLUS statistical software (S-PLUS 6, Guide to statistics, Insightful, Seattle, Wash., U.S.A.). The results of that analysis (TABLE 6) show that the LTT1 (SEQ ID NO: 1) plants were significantly more tolerant to drought than the wild type control plants, which were not transformed with the LTT1 gene (p=0.0336). The mean number of days from last watering until wilting for the LTT1 transformed plants was 5.73 days and for the wild type controls was 4.71 days. At the end of the experiment, 86.4% of the LTT1 plants had wilted as compared to 100% of the wild type controls.

TABLE 6

Results of a log rank test for drought stress

| line | Time To Wilting (days) | Mean days to wilting | p-value |
|---|---|---|---|
| LTT1-1 | 3, 6, 6, 6, 6+ | 5.73 | 0.034 |
| LTT1-2 | 6, 6, 6, 6+ | | |
| LTT1-3 | 6, 6, 6, 6, 6+ | | |
| LTT1-4 | 6, 6, 6, 6 | | |
| LTT1-5 | 3, 6, 6, 6 | | |

TABLE 6-continued

Results of a log rank test for drought stress

| line | Time To Wilting (days) | Mean days to wilting | p-value |
|---|---|---|---|
| Wild type control | 3, 3, 3, 6, 6, 6, 6 | 4.71 | |

Log rank test (S-PLUS 6).
A "+" score signifies that the plant was not wilted at the conclusion of the test.
p-value is the probability that the difference in the LTT1 and Control survival curves is not due merely to chance.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

What is claimed is:

1. A substantially purified nucleic acid molecule selected from the group consisting of:

(a) a nucleic acid molecule encoding a polypeptide comprising an amino acid sequence of SEQ ID NO:2;

(b) a nucleic acid molecule encoding a polypeptide having phytol kinase activity and comprising a sequence with at least 99% identity to the nucleic acid sequence of SEQ ID NO:1; and (c) a nucleic acid molecule comprising the nucleic acid sequence of SEQ ID NO:1.

2. A DNA construct comprising a heterologous promoter that functions in plants operably linked to the nucleic acid molecule of claim 1.

3. A transformed plant comprising the nucleic acid molecule of claim 1.

4. The transformed plant of claim 3, wherein said plant is selected from the group consisting of alfalfa, *Arabidopsis thaliana*, barley, *Brassica campestris*, oilseed rape, broccoli, cabbage, citrus, canola, cotton, garlic, oat, *Allium*, flax, an ornamental plant, peanut, pepper, potato, rapeseed, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, chick peas, corn, *Phaseolus*, crambe, mustard, castor bean, sesame, cottonseed, linseed, safflower, and oil palm.

5. The transformed plant of claim 3, wherein said plant is selected from the group consisting of canola, oilseed rape, and soybean.

6. A transformed plant comprising the DNA construct of claim 2.

7. The transformed plant of claim 6, wherein said plant is selected from the group consisting of alfalfa, *Arabidopsis thaliana*, barley, *Brassica campestris*, oilseed rape, broccoli, cabbage, citrus, canola, cotton, garlic, oat, *Allium*, flax, an ornamental plant, peanut, pepper, potato, rapeseed, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, chick peas, corn, *Phaseolus*, crambe, mustard, castor bean, sesame, cottonseed, linseed, safflower, and oil palm.

8. The transformed plant of claim 6, wherein said plant is selected from the group consisting of oilseed rape, soybean and canola.

9. A method for transforming a plant comprising introducing into the plant DNA construct of claim 2.

10. The method of claim 9, wherein said plant is selected from the group consisting of alfalfa, *Arabidopsis thaliana*, barley, *Brassica campestris*, oilseed rape, broccoli, cabbage, citrus, canola, cotton, garlic, oat, *Allium*, flax, an ornamental plant, peanut, pepper, potato, rapeseed, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, chick peas, corn, *Phaseolus*, crambe, mustard, castor bean, sesame, cottonseed, linseed, safflower, and oil palm.

11. The method of claim 9, wherein said plant is selected from the group consisting of oilseed rape, soybean and canola.

12. Seed from the plant of claim 6 comprising the DNA construct.

13. The transformed plant of claim 6, further comprising an introduced second nucleic acid molecule encoding an enzyme selected from the group consisting of MT1, tMT2, GMT, tyrA, HPT, tocopherol cyclase, chlorophyllase, dxs, dxr, GGPPS, HPPD, AANT1, IDI, and GGH.

14. The method of claim 9, further comprising transforming the plant with an introduced second nucleic acid molecule encoding an enzyme selected from the group consisting of MT1, tMT2, GMT, tyrA, HPT, tocopherol cyclase, chlorophyllase, dxs, dxr, GGPPS, HPPD, AANT1, IDI, and GGH.

15. The nucleic acid molecule of claim 1, wherein the nucleic acid molecule encodes a polypeptide comprising the amino acid sequence of SEQ ID NO: 2.

16. The nucleic acid molecule of claim 1, wherein the nucleic acid molecule comprises SEQ ID NO: 1.

17. The transformed plant of claim 13, wherein the second introduced nucleic acid molecule comprises one or more of SEQ ID NOs: 13–16, and 18 or 19.

* * * * *